US012559534B2

(12) United States Patent
Yan et al.

(10) Patent No.: US 12,559,534 B2
(45) Date of Patent: Feb. 24, 2026

(54) MODIFIED IL-2 PROTEINS, PEG CONJUGATES, AND USES THEREOF

(71) Applicant: CSPC MEGALITH BIOPHARMACEUTICAL CO., LTD., Hebei (CN)

(72) Inventors: Zhe Yan, Sacramenta, CA (US); Lixin Feng, Sacramenta, CA (US); Yingui Li, Sacramenta, CA (US)

(73) Assignee: CSPC MEGALITH BIOPHARMACEUTICAL CO., LTD., Hebei (CN)

( * ) Notice: Subject to any disclaimer, the term of this patent is extended or adjusted under 35 U.S.C. 154(b) by 1100 days.

(21) Appl. No.: 17/620,894

(22) PCT Filed: Jun. 18, 2020

(86) PCT No.: PCT/US2020/038537

§ 371 (c)(1),
(2) Date: Dec. 20, 2021

(87) PCT Pub. No.: WO2020/257525

PCT Pub. Date: Dec. 24, 2020

(65) Prior Publication Data

US 2022/0324932 A1 Oct. 13, 2022

Related U.S. Application Data

(60) Provisional application No. 62/864,372, filed on Jun. 20, 2019.

(51) Int. Cl.

| | |
|---|---|
| ***C07K 14/55*** | (2006.01) |
| ***A61K 47/60*** | (2017.01) |
| ***A61P 35/00*** | (2006.01) |

(52) U.S. Cl.

CPC .............. *C07K 14/55* (2013.01); *A61K 47/60* (2017.08); *A61P 35/00* (2018.01)

(58) Field of Classification Search

CPC ....... C07K 14/55; C07K 1/1077; A61P 35/00; A61K 38/2013

See application file for complete search history.

(56) References Cited

U.S. PATENT DOCUMENTS

2006/0269515 A1* 11/2006 Denis-Mize ....... G01N 33/5047 435/69.52

FOREIGN PATENT DOCUMENTS

| | | | | |
|---|---|---|---|---|
| EP | 0785276 | * | 7/1997 | .............. C12P 21/02 |
| EP | 0785276 | A1 | 7/1997 | |
| WO | 2005/007121 | A2 | 1/2005 | |
| WO | 2019/028419 | A1 | 2/2019 | |
| WO | 2019/125732 | A1 | 6/2019 | |

OTHER PUBLICATIONS

Liao et al. Immunity. Jan. 24, 2013;38(1):13-25. (Year: 2013).*
Mizui Clin Immunol. Sep. 2019;206:63-70. Epub Nov. 8, 2018. (Year: 2018).*

* cited by examiner

*Primary Examiner* — Jeffrey Stucker
*Assistant Examiner* — Sarah Cooper Patterson
(74) *Attorney, Agent, or Firm* — NKL Law; Bin Lu; Allen Xue

(57) ABSTRACT

The present application provides a modified interleukin-2 (IL-2) protein comprising an engineered glutamine (Q) residue. The present application also provides a modified IL-2 protein-polyethylene glycol (PEG) conjugate comprising a modified IL-2 protein comprising an engineered Q residue and a PEG moiety, wherein the PEG moiety is conjugated to the modified IL-2 protein via the engineered Q residue. Pharmaceutical compositions, kits, methods of making, and methods of treatment (e.g., for cancer) are also provided.

15 Claims, 28 Drawing Sheets

Specification includes a Sequence Listing.

PTSSSTKKTQLQLEHLLLDLQMILNGINNYKNPKLTRMLTFKFYMPKKATELKHLQCLEEELKPLEEVLN cccccccchhhhhhhhhhhhhhhhcccccccccceeeeeeeeeecccccchhhhhhhhhhhhhhhhhhhh

LAQSKNFHLRPRDLISNINVIVLEILKGSETTFMCEYADETATIVEF*LNRWITFSQSIISTLT* (SEQ ID NO: 1)

hhhhcccccccccccchhhhhhhccccceeeeecccccchhhhhccccccccceeeeeec

FIG. 2

```
(SEQ ID NO: 3) IL-2(A2)          PTSSSTKKTQLQLEHLLLDLQMILNGINNYKNPKLTRMLTFKQTYPKKATELKHLQCLEE   60
(SEQ ID NO: 8) IL-2(A8)          PTSSSTKKTQLQLEHLLLDLQMILNGINNYKNPKLTQMLTFKFQMPKKATELKHLQCLEE   60
(SEQ ID NO: 7) IL-2(A6)          PTSSSTKKTQLQLEHLLLDLQMILNGINNYKNPKLTRMLTFKFQMPKKATELKHLQCLEE   60
(SEQ ID NO: 6) IL-2(A5)          PTSSSTKKTQLQLEHLLLDLQMILNGINNYKNPKLTRMLTFQFYMPKKATELKHLQCLEE   60
(SEQ ID NO: 5) IL-2(A4)          PTSSSTKKTQLQLEHLLLDLQMILNGINNYKNPKLTRMLTQKFYMPKKATELKHLQCLEE   60
(SEQ ID NO: 4) IL-2(A3)          PTSSSTKKTQLQLEHLLLDLQMILNGINNYKNPKLTQMLTFKFYMPKKATELKHLQCLEE   60
(SEQ ID NO: 1) IL-2(Aldesleukin) PTSSSTKKTQLQLEHLLLDLQMILNGINNYKNPKLTRMLTFKFYMPKKATELKHLQCLEE   60
(SEQ ID NO: 2) IL-2(A1)          PTSSSTKKTQLQLEHLLLDLQMILNGINNYKNPKLTRMLTFKQYMPKKATELKHLQCLEE   60
                                 ************************************:**  :   ***************

(SEQ ID NO: 3) IL-2(A2)          ELKPLEEVLNLAQSKNFHLRPRDLISNINVIVLELKGSETTFMCEYADETATIVEFLNRW   120
(SEQ ID NO: 8) IL-2(A8)          ELKPLEEVLNLAQSKNFHLRPRDLISNINVIVLELKGSETTFMCEYADETATIVEFLNRW   120
(SEQ ID NO: 7) IL-2(A6)          ELKPLEEVLNLAQSKNFHLRPRDLISNINVIVLELKGSETTFMCEYADETATIVEFLNRW   120
(SEQ ID NO: 6) IL-2(A5)          ELKPLEEVLNLAQSKNFHLRPRDLISNINVIVLELKGSETTFMCEYADETATIVEFLNRW   120
(SEQ ID NO: 5) IL-2(A4)          ELKPLEEVLNLAQSKNFHLRPRDLISNINVIVLELKGSETTFMCEYADETATIVEFLNRW   120
(SEQ ID NO: 4) IL-2(A3)          ELKPLEEVLNLAQSKNFHLRPRDLISNINVIVLELKGSETTFMCEYADETATIVEFLNRW   120
(SEQ ID NO: 1) IL-2(Aldesleukin) ELKPLEEVLNLAQSKNFHLRPRDLISNINVIVLELKGSETTFMCEYADETATIVEFLNRW   120
(SEQ ID NO: 2) IL-2(A1)          ELKPLEEVLNLAQSKNFHLRPRDLISNINVIVLELKGSETTFMCEYADETATIVEFLNRW   120
                                 ************************************************************

(SEQ ID NO: 3) IL-2(A2)          ITFSQSIISTLT   132
(SEQ ID NO: 8) IL-2(A8)          ITFSQSIISTLT   132
(SEQ ID NO: 7) IL-2(A6)          ITFSQSIISTLT   132
(SEQ ID NO: 6) IL-2(A5)          ITFSQSIISTLT   132
(SEQ ID NO: 5) IL-2(A4)          ITFSQSIISTLT   132
(SEQ ID NO: 4) IL-2(A3)          ITFSQSIISTLT   132
(SEQ ID NO: 1) IL-2(Aldesleukin) ITFSQSIISTLT   132
(SEQ ID NO: 2) IL-2(A1)          ITFSQSIISTLT   132
                                 ************
```

1. Expression of IL-2A1 in *E. coli*
2. Purified IL-2A1 inclusion body
3. Purified IL-2A1 (DP006A)
4. Purified IL-2A2

1. IL-2A1 (DP006A)
2. 20kDa PEGylation of IL-2A1 (DP006-A-20)
3. 20kDa PEGylation of parent IL-2 (Aldesleukin)
4. Parent IL-2 (Aldesleukin)

| | EC50 (ng/mL IL-2) | EC50 (nM) | Reduced Folds to IL-2 Aldesleukin |
| --- | --- | --- | --- |
| ● IL-2 Aldesleukin | 3.7 | 242.0 | 1 |
| (DP006A) ▲ IL-2A1 | 13.6 | 889.4 | 4 |
| (DP006-A-20) ◆ 20k PEG-IL-2A1 | 40.4 | 2642.2 | 11 |
| ■ IL-2A2 | 182.8 | 11955.1 | 49 |
| ▼ 20k PEG-IL-2A2 | 150.4 | 9836.2 | 41 |

FIG. 6B
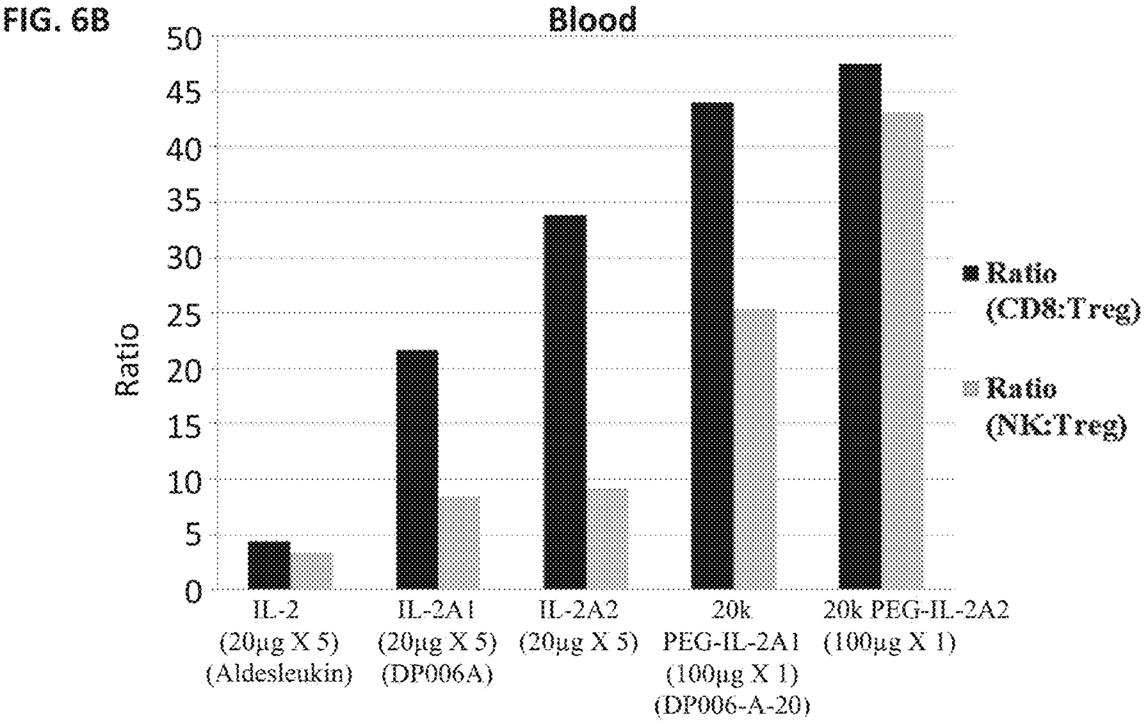
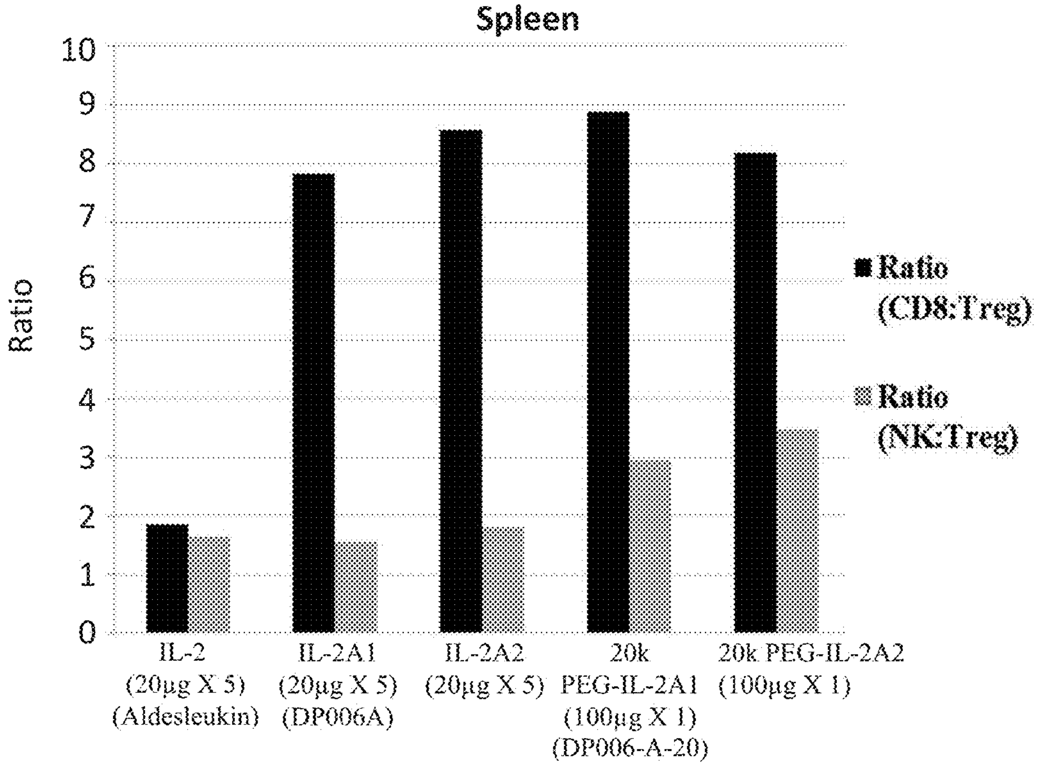

| Group | PEG size | | $C_{max}$ (µg/mL) | $T_{max}$ (hr)[a] | $C_{last}$ (µg/mL) | $T_{last}$ (hr) | $AUC_{0-t}$ (µg*hr/mL) | $t_{1/2}$ (hr) |
|---|---|---|---|---|---|---|---|---|
| 2 | 20KDa | Mean | 42.5 | 0.30 | 0.005 | 96 | 133.6 | 11.9 |
| | | SD | 9.2 | 0.39 | 0.001 | NA | 35.6 | 2.5 |
| | | N | 3 | | | | | |
| | | | | | | | | |
| 3 | 30KDa | Mean | 26.6 | 0.08 | 0.011 | 96 | 121.5 | 14.0 |
| | | SD | 14.2 | 0.00 | 0.006 | NA | 19.6 | 4.3 |
| | | N | 3 | | | | | |
| | | | | | | | | |
| 4 | 40KDa | Mean | 80.0 | 0.30 | 0.1 | 96 | 404.6 | 19.4 |
| | | SD | 44.4 | 0.39 | 0.03 | NA | 97.7 | 8.1 |
| | | N | 3 | | | | | |

| Group | PEG size | | $C_{max}$ (µg/mL) | $T_{max}$ (hr)[a] | $C_{last}$ (µg/mL) | $T_{last}$ (hr) | $AUC_{0-t}$ (µg*hr/mL) | $t_{1/2}$ (hr) |
|---|---|---|---|---|---|---|---|---|
| 2 | 20KDa | Mean | 0.49 | 8.0 | 0.004 | 120 | 15.0 | 15.6 |
| | | SD | 0.17 | 0.0 | 0 | NA | 4.5 | 3.6 |
| | | N | 3 | | | | | |
| | | | | | | | | |
| 3 | 30KDa | Mean | 0.66 | 8.0 | 0.009 | 120 | 21.0 | 17.2 |
| | | SD | 0.28 | 0 | 0.001 | NA | 4.8 | 1.4 |
| | | N | 3 | | | | | |
| | | | | | | | | |
| 4 | 40KDa | Mean | 1.00 | 13.3 | 0.034 | 120 | 38.8 | 22.0 |
| | | SD | 0.40 | 9.2 | 0.007 | NA | 9.3 | 3.1 |
| | | N | 3 | | | | | |

Binding Curves to IL-2Rα

Binding Curves to IL-2Rα

Binding Curves to IL-2Rα

Binding Curves to IL-2Rβ

Binding Curves to IL-2Rβ

Binding Curves to IL-2Rβ

Serum DP630a(DP006-A-30) Concentration-time Profile Following
a Single IV Bolus Injection of DP630a(DP006-A-30) in SD rats Serum DP630a(DP006-A-30) Concentration-time Profile Following
a Single SC Injection of DP630a(DP006-A-30) in SD rats FIG. 19 Sequence coverage for DP006-A and DP006-A-30 with Trypsin digestion by database searching
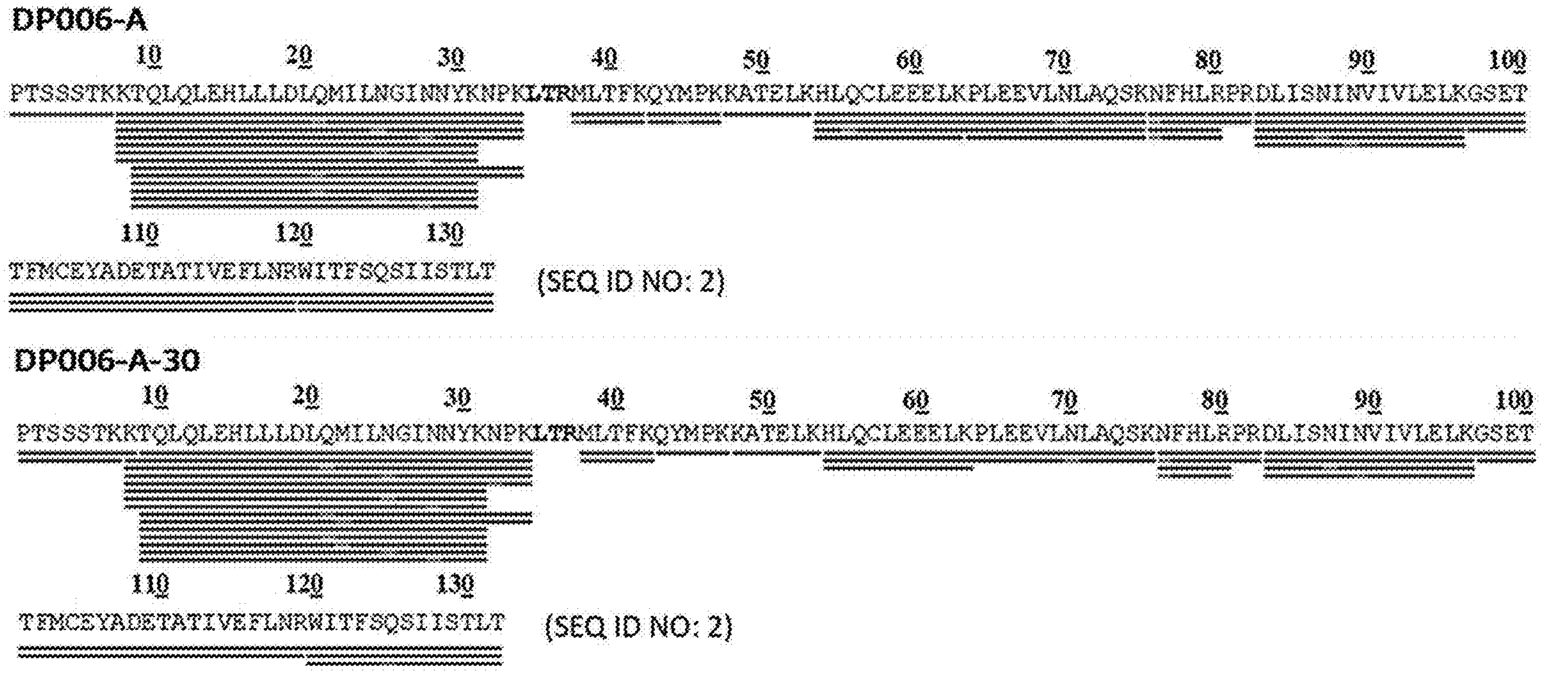

FIG. 20 Base Peak Chromatography for DP006-A and DP006-A-30 with Trypsin Digestion
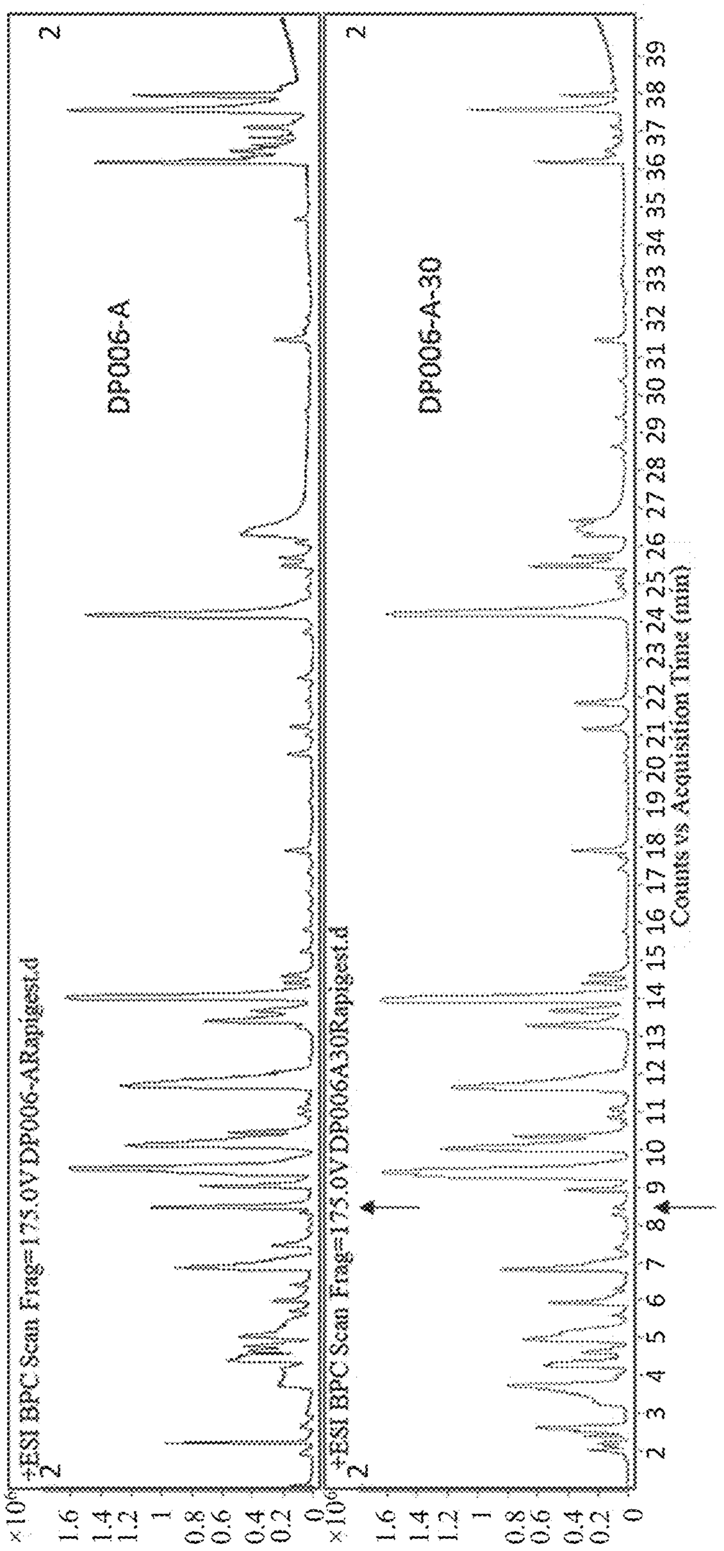

FIG. 21 EIC of PEGylated P43-47 in DP006-A-30
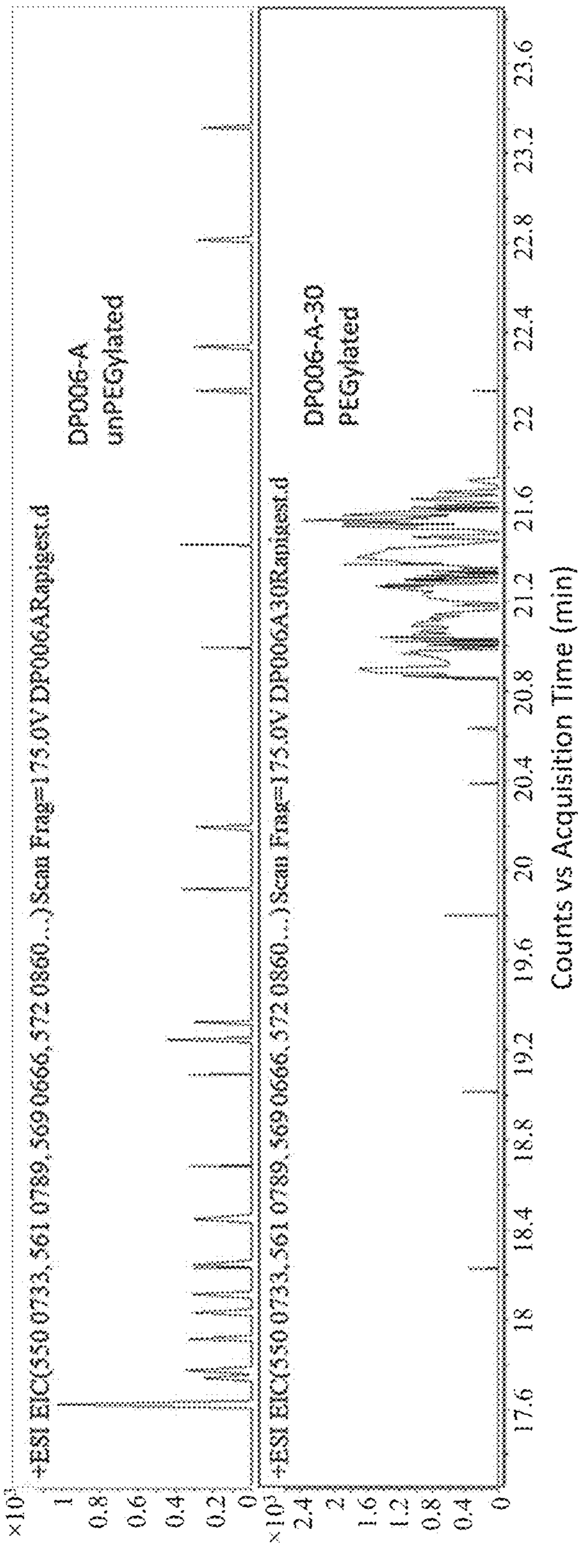

FIG. 22 MS1 and MS/MS Spectra of *m/z* at 539.0666 (z=4)
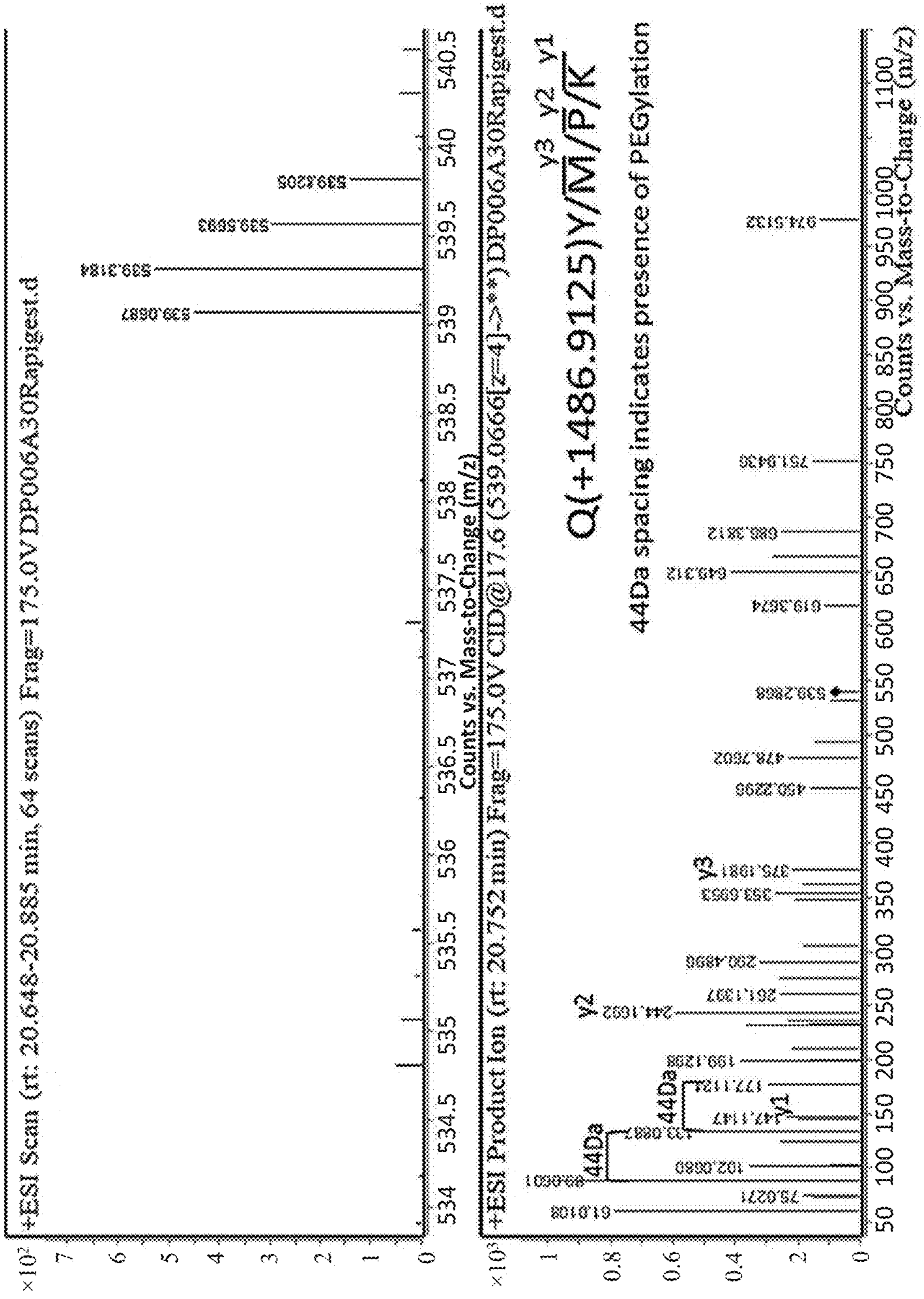

FIG. 23 MS1 and MS/MS Spectra of $m/z$ at 550.0738 ($z$=4)
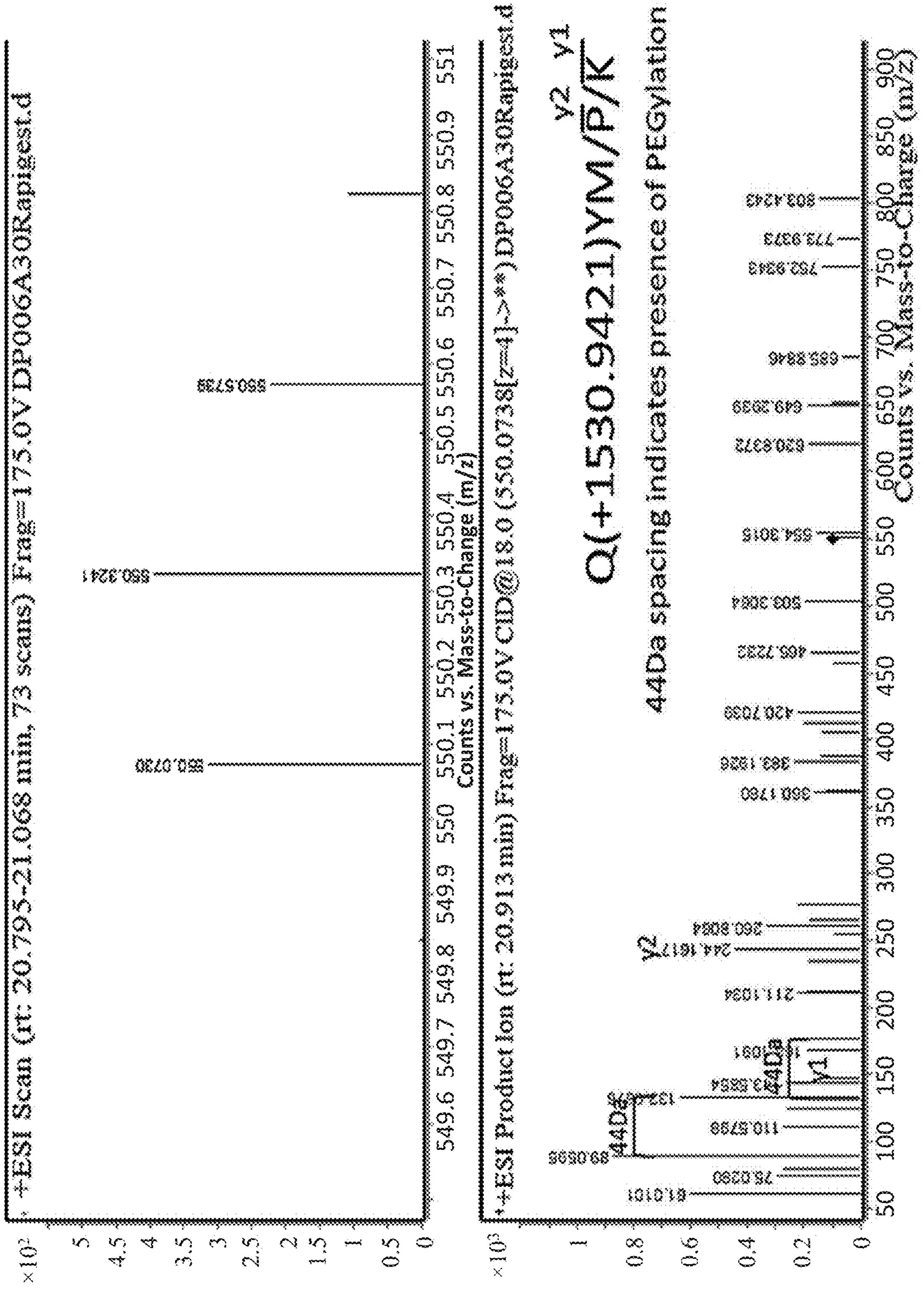

FIG. 24 Sequence coverage for DP006-A and DP006-A-30 with Glu-C digestion by database searching
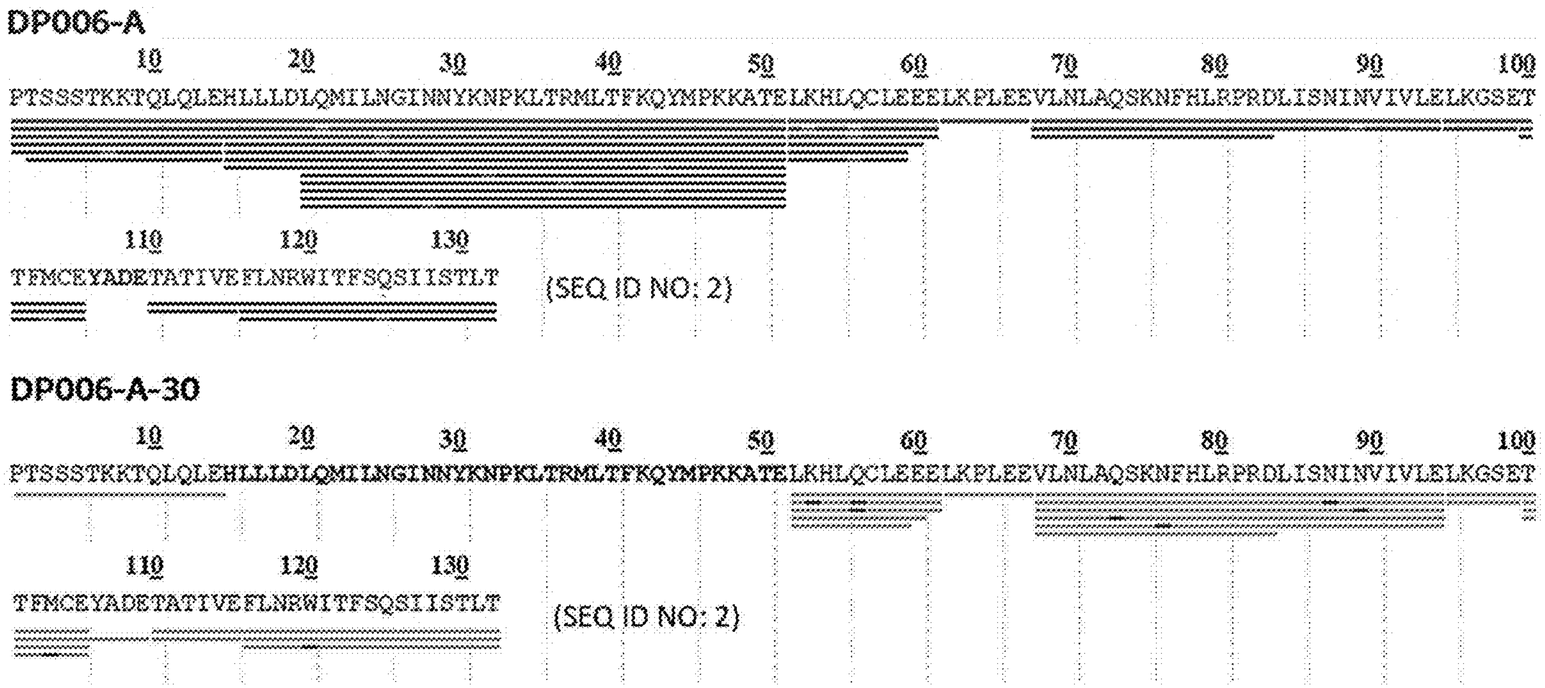

FIG. 25 Base Peak Chromatography for DP006-A and DP006-A-30 with Glu-C Digestion
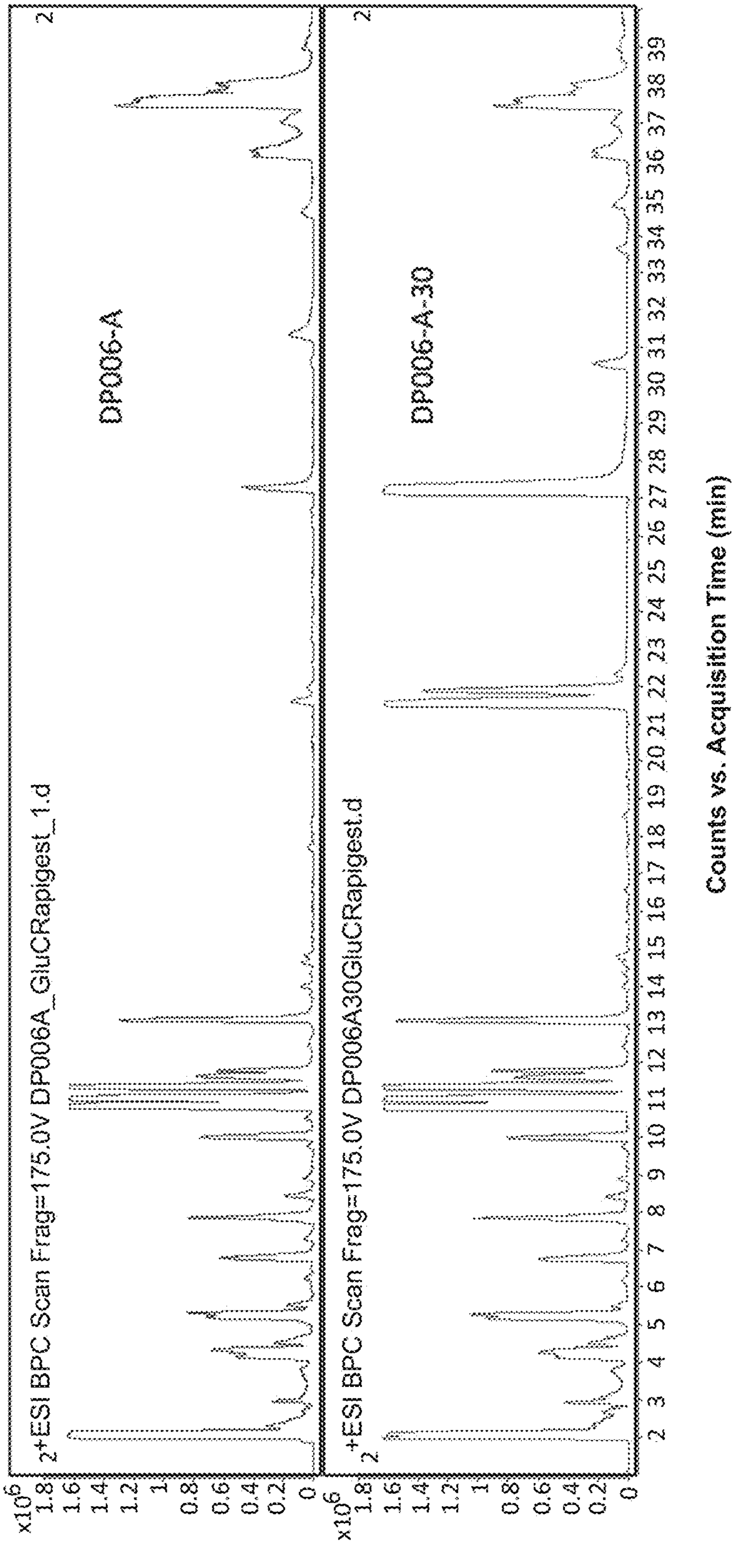

SEQUENCE LISTING

<160> NUMBER OF SEQ ID NOS: 51

<210> SEQ ID NO 1
<211> LENGTH: 132
<212> TYPE: PRT
<213> ORGANISM: Artificial Sequence
<220> FEATURE:
<223> OTHER INFORMATION: synthesized

<400> SEQUENCE: 1

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80
```

```
Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 2
<211> LENGTH: 132
<212> TYPE: PRT
<213> ORGANISM: Artificial Sequence
<220> FEATURE:
<223> OTHER INFORMATION: synthesized

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Gln Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 3
<211> LENGTH: 132
<212> TYPE: PRT
<213> ORGANISM: Artificial Sequence
<220> FEATURE:
<223> OTHER INFORMATION: synthesized

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Ile Phe Lys Gln Thr Tyr Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
```

-continued

```
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 4
<211> LENGTH: 132
<212> TYPE: PRT
<213> ORGANISM: Artificial Sequence
<220> FEATURE:
<223> OTHER INFORMATION: synthesized

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Gln Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 5
<211> LENGTH: 132
<212> TYPE: PRT
<213> ORGANISM: Artificial Sequence
<220> FEATURE:
<223> OTHER INFORMATION: synthesized

<400> SEQUENCE: 5

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Gln Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125
```

```
Ser Thr Leu Thr
    130


<210> SEQ ID NO 6
<211> LENGTH: 132
<212> TYPE: PRT
<213> ORGANISM: Artificial Sequence
<220> FEATURE:
<223> OTHER INFORMATION: synthesized

<400> SEQUENCE: 6

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Gln Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 7
<211> LENGTH: 132
<212> TYPE: PRT
<213> ORGANISM: Artificial Sequence
<220> FEATURE:
<223> OTHER INFORMATION: synthesized

<400> SEQUENCE: 7

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Gln Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 8
```

<211> LENGTH: 132
<212> TYPE: PRT
<213> ORGANISM: Artificial Sequence
<220> FEATURE:
<223> OTHER INFORMATION: synthesized

<400> SEQUENCE: 8

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Gln Met Leu Thr Phe Lys Phe Gln Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 9
<211> LENGTH: 6
<212> TYPE: PRT
<213> ORGANISM: Artificial Sequence
<220> FEATURE:
<223> OTHER INFORMATION: synthesized

<400> SEQUENCE: 9

```
Leu Glu Glu Gln Ala Ala
1               5
```

<210> SEQ ID NO 10
<211> LENGTH: 6
<212> TYPE: PRT
<213> ORGANISM: Artificial Sequence
<220> FEATURE:
<223> OTHER INFORMATION: synthesized

<400> SEQUENCE: 10

```
Ile Phe Lys Gln Thr Tyr
1               5
```

<210> SEQ ID NO 11
<211> LENGTH: 6
<212> TYPE: PRT
<213> ORGANISM: Artificial Sequence
<220> FEATURE:
<223> OTHER INFORMATION: synthesized

<400> SEQUENCE: 11

```
Pro Lys Glu Gln Lys Tyr
1               5
```

<210> SEQ ID NO 12
<211> LENGTH: 5
<212> TYPE: PRT
<213> ORGANISM: Artificial Sequence
<220> FEATURE:
<223> OTHER INFORMATION: synthesized

<400> SEQUENCE: 12

Val Ile Gln Gly Val
1 5

<210> SEQ ID NO 13
<211> LENGTH: 6
<212> TYPE: PRT
<213> ORGANISM: Artificial Sequence
<220> FEATURE:
<223> OTHER INFORMATION: synthesized

<400> SEQUENCE: 13

Arg Glu Glu Gln Phe Asn
1 5

<210> SEQ ID NO 14
<211> LENGTH: 6
<212> TYPE: PRT
<213> ORGANISM: Artificial Sequence
<220> FEATURE:
<223> OTHER INFORMATION: synthesized

<400> SEQUENCE: 14

Gly Leu Leu Gln Gly Ala
1 5

<210> SEQ ID NO 15
<211> LENGTH: 132
<212> TYPE: PRT
<213> ORGANISM: Artificial Sequence
<220> FEATURE:
<223> OTHER INFORMATION: synthesized

<400> SEQUENCE: 15

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Leu Glu Glu Gln Ala Ala Pro Lys Lys
35 40 45

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 16
<211> LENGTH: 132
<212> TYPE: PRT
<213> ORGANISM: Artificial Sequence
<220> FEATURE:
<223> OTHER INFORMATION: synthesized

<400> SEQUENCE: 16

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Phe Lys Phe Tyr Met Pro Lys Glu
35 40 45

Gln Lys Tyr Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 17
<211> LENGTH: 132
<212> TYPE: PRT
<213> ORGANISM: Artificial Sequence
<220> FEATURE:
<223> OTHER INFORMATION: synthesized

<400> SEQUENCE: 17

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Val Ile Gln Gly Val Pro Lys Lys
35 40 45

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 18
<211> LENGTH: 132
<212> TYPE: PRT
<213> ORGANISM: Artificial Sequence
<220> FEATURE:
<223> OTHER INFORMATION: synthesized

<400> SEQUENCE: 18

Pro Thr Ser Ser Ser Thr Lys Lys Thr Gln Leu Gln Leu Glu His Leu
1 5 10 15

```
Leu Leu Asp Leu Gln Met Ile Leu Asn Gly Ile Asn Asn Tyr Lys Asn
            20                  25                  30

Pro Lys Leu Thr Arg Met Leu Arg Glu Glu Gln Phe Asn Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 19
<211> LENGTH: 132
<212> TYPE: PRT
<213> ORGANISM: Artificial Sequence
<220> FEATURE:
<223> OTHER INFORMATION: synthesized

<400> SEQUENCE: 19

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Gly Leu Leu Gln Gly Ala Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 20
<211> LENGTH: 331
<212> TYPE: PRT
<213> ORGANISM: Strep Ladakanum

<400> SEQUENCE: 20

Asp Ser Asp Glu Arg Val Thr Pro Pro Ala Glu Pro Leu Asp Arg Met
1               5                   10                  15

Pro Asp Pro Tyr Arg Pro Ser Tyr Gly Arg Ala Glu Thr Ile Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
```

```
    50                  55                  60

Val Gly Val Thr Trp Val Asn Ser Gly Gln Tyr Pro Thr Asn Arg Leu
65                  70                  75                  80

Ala Phe Ala Phe Phe Asp Glu Asp Lys Tyr Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Asp Ser Phe Asp Glu Ala Lys Gly Phe Gln Arg Ala Arg Asp
        115                 120                 125

Val Ala Ser Val Met Asn Lys Ala Leu Glu Asn Ala His Asp Glu Gly
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Asp Arg Asn Gly Gly Asn His Asp Pro Ser Lys
            180                 185                 190

Met Lys Ala Val Ile Tyr Ser Lys His Phe Trp Ser Gly Gln Asp Arg
        195                 200                 205

Ser Gly Ser Ser Asp Lys Arg Lys Tyr Gly Asp Pro Glu Ala Phe Arg
    210                 215                 220

Pro Asp Arg Gly Thr Gly Leu Val Asp Met Ser Arg Asp Arg Asn Ile
225                 230                 235                 240

Pro Arg Ser Pro Thr Ser Pro Gly Glu Ser Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Asp Gly Tyr Ser Asp
    290                 295                 300

Phe Asp Arg Gly Ala Tyr Val Val Thr Phe Val Pro Lys Ser Trp Asn
305                 310                 315                 320

Thr Ala Pro Asp Lys Val Thr Gln Gly Trp Pro
                325                 330


<210> SEQ ID NO 21
<211> LENGTH: 342
<212> TYPE: PRT
<213> ORGANISM: Artificial Sequence
<220> FEATURE:
<223> OTHER INFORMATION: synthesized

<400> SEQUENCE: 21

Pro Asp Ser Asp Glu Arg Val Thr Pro Pro Ala Glu Pro Leu Asp Arg
1               5                   10                  15

Met Pro Asp Pro Tyr Arg Pro Ser Tyr Gly Arg Ala Glu Thr Ile Val
            20                  25                  30

Asn Asn Tyr Ile Arg Lys Trp Gln Gln Val Tyr Ser His Arg Asp Gly
        35                  40                  45

Arg Lys Gln Gln Met Thr Glu Glu Gln Arg Glu Trp Leu Ser Tyr Gly
    50                  55                  60

Cys Val Gly Val Thr Trp Val Asn Ser Gly Gln Tyr Pro Thr Asn Arg
65                  70                  75                  80

Leu Ala Phe Ala Phe Phe Asp Glu Asp Lys Tyr Lys Asn Glu Leu Lys
```

-continued

```
                85                  90                  95

Asn Gly Arg Pro Arg Ser Gly Glu Thr Arg Ala Glu Phe Glu Gly Arg
            100                 105                 110

Val Ala Lys Asp Ser Phe Asp Glu Ala Lys Gly Phe Gln Arg Ala Arg
        115                 120                 125

Asp Val Ala Ser Val Met Asn Lys Ala Leu Glu Asn Ala His Asp Glu
    130                 135                 140

Gly Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
                165                 170                 175

Asn Thr Pro Ser Phe Lys Asp Arg Asn Gly Gly Asn His Asp Pro Ser
            180                 185                 190

Lys Met Lys Ala Val Ile Tyr Ser Lys His Phe Trp Ser Gly Gln Asp
        195                 200                 205

Arg Ser Gly Ser Ser Asp Lys Arg Lys Tyr Gly Asp Pro Glu Ala Phe
    210                 215                 220

Arg Pro Asp Arg Gly Thr Gly Leu Val Asp Met Ser Arg Asp Arg Asn
225                 230                 235                 240

Ile Pro Arg Ser Pro Thr Ser Pro Gly Glu Ser Phe Val Asn Phe Asp
                245                 250                 255

Tyr Gly Trp Phe Gly Ala Gln Thr Glu Ala Asp Ala Asp Lys Thr Val
            260                 265                 270

Trp Thr His Gly Asn His Tyr His Ala Pro Asn Gly Ser Leu Gly Ala
        275                 280                 285

Met His Val Tyr Glu Ser Lys Phe Arg Asn Trp Ser Asp Gly Tyr Ser
    290                 295                 300

Asp Phe Asp Arg Gly Ala Tyr Val Val Thr Phe Val Pro Lys Ser Trp
305                 310                 315                 320

Asn Thr Ala Pro Asp Lys Val Thr Gln Gly Trp Pro Leu Glu His His
                325                 330                 335

His His His His His His
            340


<210> SEQ ID NO 22
<211> LENGTH: 331
<212> TYPE: PRT
<213> ORGANISM: Strep Mobaraensis

<400> SEQUENCE: 22

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110
```

```
Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 23
<211> LENGTH: 153
<212> TYPE: PRT
<213> ORGANISM: Homo sapiens

<400> SEQUENCE: 23

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 24
<211> LENGTH: 133
<212> TYPE: PRT
<213> ORGANISM: Homo sapiens

<400> SEQUENCE: 24

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 25
<211> LENGTH: 6
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: (1)..(6)
<223> OTHER INFORMATION: Xaa = Any Amino Acid

<400> SEQUENCE: 25

```
Xaa Xaa Xaa Xaa Gln Xaa
1               5
```

<210> SEQ ID NO 26
<211> LENGTH: 6
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: (2)..(6)
<223> OTHER INFORMATION: Xaa = Any Amino Acid

<400> SEQUENCE: 26

```
Gln Xaa Xaa Xaa Xaa Xaa
1               5
```

<210> SEQ ID NO 27
<211> LENGTH: 6
<212> TYPE: PRT
<213> ORGANISM: Artificial Sequence
<220> FEATURE:
<223> OTHER INFORMATION: synthesized

<400> SEQUENCE: 27

Asn Tyr Lys Asn Pro Lys
1 5

<210> SEQ ID NO 28
<211> LENGTH: 3
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: (1)..(3)
<223> OTHER INFORMATION: Xaa = Any Amino Acid

<400> SEQUENCE: 28

Xaa Xaa Xaa
1

<210> SEQ ID NO 29
<211> LENGTH: 3
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: (2)..(3)
<223> OTHER INFORMATION: Xaa = Any Amino Acid

<400> SEQUENCE: 29

Gln Xaa Xaa
1

<210> SEQ ID NO 30
<211> LENGTH: 6
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: (2)..(6)
<223> OTHER INFORMATION: Xaa = Any Amino Acid

<400> SEQUENCE: 30

Gln Xaa Xaa Xaa Gln Xaa
1 5

<210> SEQ ID NO 31
<211> LENGTH: 7
<212> TYPE: PRT
<213> ORGANISM: Artificial Sequence
<220> FEATURE:
<223> OTHER INFORMATION: synthesized

<400> SEQUENCE: 31

Pro Thr Ser Ser Ser Thr Lys
1 5

<210> SEQ ID NO 32
<211> LENGTH: 26
<212> TYPE: PRT
<213> ORGANISM: Artificial Sequence
<220> FEATURE:
<223> OTHER INFORMATION: synthesized

<400> SEQUENCE: 32

Thr Gln Leu Gln Leu Glu His Leu Leu Leu Asp Leu Gln Met Ile Leu 1 5 10 15

Asn Gly Ile Asn Asn Tyr Lys Asn Pro Lys
20 25

<210> SEQ ID NO 33
<211> LENGTH: 3
<212> TYPE: PRT
<213> ORGANISM: Artificial Sequence
<220> FEATURE:
<223> OTHER INFORMATION: synthesized

<400> SEQUENCE: 33

Leu Thr Arg
1

<210> SEQ ID NO 34
<211> LENGTH: 5
<212> TYPE: PRT
<213> ORGANISM: Artificial Sequence
<220> FEATURE:
<223> OTHER INFORMATION: synthesized

<400> SEQUENCE: 34

Met Leu Thr Phe Lys
1 5

<210> SEQ ID NO 35
<211> LENGTH: 5
<212> TYPE: PRT
<213> ORGANISM: Artificial Sequence
<220> FEATURE:
<223> OTHER INFORMATION: synthesized

<400> SEQUENCE: 35

Gln Tyr Met Pro Lys
1 5

<210> SEQ ID NO 36
<211> LENGTH: 6
<212> TYPE: PRT
<213> ORGANISM: Artificial Sequence
<220> FEATURE:
<223> OTHER INFORMATION: synthesized

<400> SEQUENCE: 36

Lys Ala Thr Glu Leu Lys
1 5

<210> SEQ ID NO 37
<211> LENGTH: 22
<212> TYPE: PRT
<213> ORGANISM: Artificial Sequence
<220> FEATURE:
<223> OTHER INFORMATION: synthesized

<400> SEQUENCE: 37

His Leu Gln Cys Leu Glu Glu Glu Leu Lys Pro Leu Glu Glu Val Leu
1 5 10 15

Asn Leu Ala Gln Ser Lys
20

<210> SEQ ID NO 38
<211> LENGTH: 7
<212> TYPE: PRT
<213> ORGANISM: Artificial Sequence
<220> FEATURE:

<223> OTHER INFORMATION: synthesized

<400> SEQUENCE: 38

Asn Phe His Leu Arg Pro Arg
1               5

<210> SEQ ID NO 39
<211> LENGTH: 14
<212> TYPE: PRT
<213> ORGANISM: Artificial Sequence
<220> FEATURE:
<223> OTHER INFORMATION: synthesized

<400> SEQUENCE: 39

Asp Leu Ile Ser Asn Ile Asn Val Ile Val Leu Glu Leu Lys
1               5                   10

<210> SEQ ID NO 40
<211> LENGTH: 23
<212> TYPE: PRT
<213> ORGANISM: Artificial Sequence
<220> FEATURE:
<223> OTHER INFORMATION: synthesized

<400> SEQUENCE: 40

Gly Ser Glu Thr Thr Phe Met Cys Glu Tyr Ala Asp Glu Thr Ala Thr
1               5                   10                  15

Ile Val Glu Phe Leu Asn Arg
            20

<210> SEQ ID NO 41
<211> LENGTH: 13
<212> TYPE: PRT
<213> ORGANISM: Artificial Sequence
<220> FEATURE:
<223> OTHER INFORMATION: synthesized

<400> SEQUENCE: 41

Trp Ile Thr Phe Ser Gln Ser Ile Ile Ser Thr Leu Thr
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthesized

<400> SEQUENCE: 42

Pro Thr Ser Ser Ser Thr Lys Lys Thr Gln Leu Gln Leu Glu
1               5                   10

<210> SEQ ID NO 43
<211> LENGTH: 37
<212> TYPE: PRT
<213> ORGANISM: Artificial Sequence
<220> FEATURE:
<223> OTHER INFORMATION: synthesized

<400> SEQUENCE: 43

His Leu Leu Leu Asp Leu Gln Met Ile Leu Asn Gly Ile Asn Asn Tyr
1               5                   10                  15

Lys Asn Pro Lys Leu Thr Arg Met Leu Thr Phe Lys Gln Tyr Met Pro
            20                  25                  30

Lys Lys Ala Thr Glu

35

<210> SEQ ID NO 44
<211> LENGTH: 10
<212> TYPE: PRT
<213> ORGANISM: Artificial Sequence
<220> FEATURE:
<223> OTHER INFORMATION: synthesized

<400> SEQUENCE: 44

Leu Lys His Leu Gln Cys Leu Glu Glu Glu
1 5 10

<210> SEQ ID NO 45
<211> LENGTH: 6
<212> TYPE: PRT
<213> ORGANISM: Artificial Sequence
<220> FEATURE:
<223> OTHER INFORMATION: synthesized

<400> SEQUENCE: 45

Leu Lys Pro Leu Glu Glu
1 5

<210> SEQ ID NO 46
<211> LENGTH: 27
<212> TYPE: PRT
<213> ORGANISM: Artificial Sequence
<220> FEATURE:
<223> OTHER INFORMATION: synthesized

<400> SEQUENCE: 46

Val Leu Asn Leu Ala Gln Ser Lys Asn Phe His Leu Arg Pro Arg Asp
1 5 10 15

Leu Ile Ser Asn Ile Asn Val Ile Val Leu Glu
20 25

<210> SEQ ID NO 47
<211> LENGTH: 5
<212> TYPE: PRT
<213> ORGANISM: Artificial Sequence
<220> FEATURE:
<223> OTHER INFORMATION: synthesized

<400> SEQUENCE: 47

Leu Lys Gly Ser Glu
1 5

<210> SEQ ID NO 48
<211> LENGTH: 6
<212> TYPE: PRT
<213> ORGANISM: Artificial Sequence
<220> FEATURE:
<223> OTHER INFORMATION: synthesized

<400> SEQUENCE: 48

Thr Thr Phe Met Cys Glu
1 5

<210> SEQ ID NO 49
<211> LENGTH: 4
<212> TYPE: PRT
<213> ORGANISM: Artificial Sequence
<220> FEATURE:
<223> OTHER INFORMATION: synthesized

<400> SEQUENCE: 49

-continued

```
Tyr Ala Asp Glu
1


<210> SEQ ID NO 50
<211> LENGTH: 6
<212> TYPE: PRT
<213> ORGANISM: Artificial Sequence
<220> FEATURE:
<223> OTHER INFORMATION: synthesized

<400> SEQUENCE: 50

Thr Ala Thr Ile Val Glu
1               5


<210> SEQ ID NO 51
<211> LENGTH: 17
<212> TYPE: PRT
<213> ORGANISM: Artificial Sequence
<220> FEATURE:
<223> OTHER INFORMATION: synthesized

<400> SEQUENCE: 51

Phe Leu Asn Arg Trp Ile Thr Phe Ser Gln Ser Ile Ile Ser Thr Leu
1               5                   10                  15

Thr
```

MODIFIED IL-2 PROTEINS, PEG CONJUGATES, AND USES THEREOF

CROSS REFERENCE TO RELATED APPLICATIONS

This application claims priority benefit from U.S. Provisional Application No. 62/864,372 filed on Jun. 20, 2019, the content of which is incorporated herein by reference in its entirety.

INCORPORATION OF SEQUENCE LISTING

This application contains a sequence listing in Computer Readable Form (CRF). The CFR file containing the sequence listing entitled "PBA4085080-SequenceListing.txt", which was created on Dec. 16, 2021, and is 34,463 bytes in size. The information in the sequence listing is incorporated herein by reference in entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720692000440SEQLIST.TXT, date recorded: Jun. 16, 2020, size: 33 KB).

FIELD OF THE PRESENT APPLICATION

The present application relates to a modified interleukin-2 (IL-2) protein comprising an engineered glutamine (Q) residue. The present application also relates to a modified IL-2 protein-polyethylene glycol (PEG) conjugate comprising a modified IL-2 protein comprising an engineered Q residue and a PEG moiety, wherein the PEG moiety is conjugated to the modified IL-2 protein via the engineered Q residue. Also provided are pharmaceutical compositions, kits, methods of making, and methods of treatment.

BACKGROUND OF THE PRESENT APPLICATION

The immune system of healthy individuals can discriminate between healthy cells and non-healthy cells, such as cancerous cells, the latter will typically be eliminated by immune response. When the immune system is compromised, it cannot differentiate and eliminate cancer cells. By administering immunomodulatory proteins to cancer patients, the patient's immune system may be at least partially brought back to normal for cancer elimination. Interleukin-2 (IL-2) is one of such immunomodulatory proteins used for cancer immunotherapy.

Wild-type IL-2 is a cytokine signaling molecule of about 15-16 kDa. It regulates the activities of white blood cells (leukocytes, often lymphocytes) of the immune system. IL-2 is involved in body's natural response to microbial infection and discriminating between "self" and "non-self". It mediates its effects by binding to IL-2 receptors (IL-2R) expressed on lymphocytes. IL-2R is a heterotrimer complex consisting of three chains (subunits), IL-2Rα (p55, CD25), IL-2Rβ (p75, CD122), and 7c (common gamma chain, IL-2Rγ, p65, CD132). IL-2 is essential for the rapid expansion, differentiation, and survival of antigen-selected T cell clones during an immune response, as well as normal functions of B cells, natural killer (NK) cells, and regulatory T cells ($T_{reg}$).

IL-2 has been suggested for treating acute myeloid leukemia (AML), non-Hodgkin's lymphoma (NHL), cutaneous T-cell lymphoma (CTCL), breast cancer, and bladder cancer. Aldesleukin (Proleukin®) is a commercially available unglycosylated human recombinant IL-2 (hrIL-2), and has been approved by the FDA for treating metastatic renal cell carcinoma (mRCC) and metastatic melanoma (mM). However, severe side effects, including capillary leak syndrome (CLS) and impaired neutrophil function, have been reported for Aldesleukin treatment even at its recommended doses. Further, due to the requirement of frequent intravenous infusion over multiple doses, administration of Aldesleukin occurs within a clinical setting. For more prevalent application in the future, toxicity and short half-life concerns of IL-2 need to be addressed.

The disclosures of all publications, patents, patent applications and published patent applications referred to herein are hereby incorporated herein by reference in their entirety.

BRIEF SUMMARY OF THE PRESENT APPLICATION

The present application provides modified IL-2 proteins comprising an engineered Q residue. The present application also provides modified IL-2 protein-PEG conjugates comprising a modified IL-2 protein comprising an engineered Q residue and a PEG moiety, wherein the PEG moiety is conjugated to the modified IL-2 protein via the engineered Q residue. Any modified IL-2 proteins described herein can be used to make modified IL-2 protein-PEG conjugates, such as any of modified IL-2 protein-PEG conjugates described herein. Further provided are pharmaceutical compositions, kits, methods of making, and methods of treatment.

In one aspect, there is provided a modified IL-2 protein comprising an engineered Q residue. In some embodiments, the engineered Q residue is within the IL-2 Receptor alpha (IL-2Rα) subunit binding domain. In some embodiments, the engineered Q residue is between about 1 and about 3 (such as 1, 2, or 3) amino acid residues outside of the IL-2Rα subunit binding domain.

In some embodiments according to any one of the modified IL-2 protein described above, the modified IL-2 protein comprises one engineered Q residue.

In some embodiments according to any one of the modified IL-2 protein described above, the modified IL-2 protein comprises two or more engineered Q residues.

In some embodiments according to any one of the modified IL-2 protein described above, the engineered Q residue is (e.g., results from) a single amino acid mutation relative to a parent IL-2 protein, such as a parent IL-2 protein (e.g., wild-type IL-2, or IL-2 Aldesleukin). In some embodiments, the parent IL-2 comprises an amino acid sequence of SEQ ID NO: 1. In some embodiments, the single amino acid mutation is selected from the group consisting of F43Q, R37Q, F41Q, K42Q, Y44Q, T36Q, M38Q, and any combinations thereof. In some embodiments, the modified IL-2 protein comprises an amino acid sequence of any of SEQ ID NOs: 2 and 4-8.

In some embodiments according to any one of the modified IL-2 protein described above, the engineered Q residue is part of an exogenous patch sequence suitable for Transglutaminase (TGase) reaction. In some embodiments, the modified IL-2 protein comprises the exogenous patch sequence, and the engineered Q residue is one of the amino acid residues within the patch sequence. In some embodiments, the exogenous patch sequence replaces a portion of a parent IL-2 protein (e.g., wild-type IL-2 protein, or IL-2 Aldesleukin). In some embodiments, the parent IL-2 protein comprises an amino acid sequence of SEQ ID NO: 1. In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the modified IL-2 protein comprises an amino acid sequence of any of SEQ ID NOs: 3 and 15-19.

In some embodiments according to any one of the modified IL-2 protein described above, the modified IL-2 protein further comprises one or more additional amino acid mutations that are not engineered Q residues.

In some embodiments according to any one of the modified IL-2 protein described above, the modified IL-2 protein comprises an amino acid sequence having at least about 95% (such as at least about any of 95%, 96%, 97%, 98%, or 99%) identity to a parent IL-2 protein comprising an amino acid sequence of SEQ ID NO: 1.

In some embodiments according to any one of the modified IL-2 protein described above, the $K_D$ of the binding between the modified IL-2 protein and an IL-2Rα subunit is about 2 to about 800 times (e.g., about 2 to about 50 times, about 400 to about 500 times, or about 476 times) of the $K_D$ of the binding between a parent IL-2 protein (e.g., wild-type IL-2, human IL-2, or IL-2 Aldesleukin) and an IL-2Rα subunit.

In some embodiments according to any one of the modified IL-2 protein described above, the $K_D$ of the binding between the modified IL-2 protein and an IL-2Rβ subunit is similar to (e.g., equal to) or about 1 to about 30 times (e.g., about 1 to about 10 times, about 10 to about 20 times, or about 16 times) of the $K_D$ of the binding between a parent IL-2 protein (e.g., wild-type IL-2, human IL-2, or IL-2 Aldesleukin) and an IL-2Rβ subunit.

In some embodiments according to any one of the modified IL-2 protein described above, the modified IL-2 protein is capable of activating an immune cell selected from the group consisting of a killer T cell (Tc, cytotoxic T lymphocyte, or CTL), a helper T cell (Th), a regulatory T cells (Treg), a γδ T cell, a natural killer T (NKT) cell, and a natural killer (NK) cell. In some embodiments, the modified IL-2 protein has about 2 to about 50 folds (e.g., about 2 to about 10 folds) reduced ability to activate a Treg cell compared to a parent IL-2 protein (e.g., wild-type IL-2, human IL-2, or IL-2 Aldesleukin). In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein has similar (e.g., equal) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

In another aspect, there is provided a modified IL-2 protein-polyethylene glycol (PEG) conjugate comprising any one of the modified IL-2 proteins described above and a PEG moiety, wherein the PEG moiety is conjugated to the modified IL-2 protein via the engineered Q residue. In some embodiments, the PEG moiety is linear. In some embodiments, the PEG moiety is branched.

In some embodiments according to any one of the modified IL-2 protein-PEG conjugates described above, the PEG moiety has a molecular weight of between about 10 kDa and about 40 kDa, such as about 20 kDa, about 30 kDa, or about 40 kDa.

In some embodiments according to any one of the modified IL-2 protein-PEG conjugates described above, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine.

In some embodiments according to any one of the modified IL-2 protein-PEG conjugates described above, the modified IL-2 protein comprises two or more engineered Q residues, and wherein at least one of the two or more engineered Q residues is each conjugated with a PEG moiety.

In some embodiments according to any one of the modified IL-2 protein-PEG conjugates described above, the conjugation of the PEG moiety is mediated via a TGase, such as a microbial TGase (mTGase). In some embodiments, the TGase is a wild-type TGase, such as a wild-type TGase comprising an amino acid sequence of SEQ ID NO: 20. In some embodiments, the TGase is an engineered TGase, such as an engineered TGase comprising an amino acid sequence having at least about 80% (such as at least about any of 80%, 85%, 90%, 95%, 96%, 97%, 98%, or 99%) identity to SEQ ID NO: 20. In some embodiments, the TGase has a purity of at least about 90% (such as at least about any of 90%, 95%, 96%, 97%, 98%, or 99%).

In some embodiments according to any one of the modified IL-2 protein-PEG conjugates described above, the $K_D$ of the binding between the modified IL-2 protein-PEG conjugate and an IL-2Rα subunit is about 10 to about 2000 times of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit.

In some embodiments according to any one of the modified IL-2 protein-PEG conjugates described above, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and an IL-2Rβ subunit.

In some embodiments according to any one of the modified IL-2 protein-PEG conjugates described above, the modified IL-2 protein-PEG conjugate is capable of activating an immune cell selected from the group consisting of a killer T cell (Tc, cytotoxic T lymphocyte, or CTL), a helper T cell (Th), a regulatory T cells (Treg), a γδ T cell, a natural killer T (NKT) cell, and a natural killer (NK) cell. In some embodiments, the modified IL-2 protein-PEG conjugate has about 2 to about 5000 folds reduced ability to activate a Treg cell compared to a parent IL-2 protein (e.g., wild-type IL-2, human IL-2, or IL-2 Aldesleukin). In some embodiments, the modified IL-2 protein-PEG conjugate has similar or about 1 to about 50 folds reduced ability to activate a CTL or a NK cell compared to a parent IL-2 protein (e.g., wild-type IL-2, human IL-2, or IL-2 Aldesleukin). In some embodiments, the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein-PEG conjugate has similar or preferential activation on CTL and/or NK cells over Treg cells, compared to a parent IL-2 protein (e.g., wild-type IL-2, human IL-2, or IL-2 Aldesleukin), such as similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

Also provided are isolated nucleic acids encoding any of the modified IL-2 proteins described above, vectors comprising such isolated nucleic acids, and host cells comprising such isolated nucleic acids or such vectors.

Further provided are pharmaceutical compositions comprising any one of the modified IL-2 proteins described above, or any of the modified IL-2 protein-PEG conjugates described above, and an optional pharmaceutically acceptable carrier.

In another aspect, there is provided a method of treating a disease (such as cancer) in an individual (such as human), comprising administering to the individual an effective amount of any one of the pharmaceutical compositions described above. In some embodiments, the pharmaceutical composition is administered intravenously, intratumorally, intraperitoneally, or subcutaneously. In some embodiments, the pharmaceutical composition is administered at about 1 μg/kg to about 100 μg/kg (e.g., about 1 μg/kg to about 50 μg/kg). In some embodiments, the pharmaceutical composition is administered once per month, once every 3 weeks, once every 2 weeks, once a week, twice a week, once every other day, or daily. In some embodiments, the disease is a cancer, such as renal cell carcinoma, metastatic melanoma, acute myeloid leukemia (AML), non-Hodgkin's lymphoma (NHL), cutaneous T-cell lymphoma (CTCL), breast cancer, or bladder cancer.

In another aspect, there is provided a method of making a modified IL-2 protein-PEG conjugate comprising a modified IL-2 protein comprising an engineered Q residue specifically conjugated to a PEG moiety, wherein the method comprises: contacting any one of the modified IL-2 proteins described above with the PEG moiety in the presence of a TGase under a condition that is sufficient to generate the modified IL-2 protein-PEG conjugate, wherein the PEG moiety is conjugated to the modified IL-2 protein via the engineered Q residue. In some embodiments, the method further comprises generating the modified IL-2 protein comprising the engineered Q residue.

In another aspect, there is provided a method of making a modified IL-2 protein-PEG conjugate comprising a modified IL-2 protein comprising an engineered Q residue specifically conjugated to a PEG moiety, wherein the method comprises: a) contacting any one of the modified IL-2 proteins described above with a small molecule handle in the presence of a TGase under a condition that is sufficient to generate an intermediate conjugate comprising the modified IL-2 protein specifically conjugated to the small molecule handle via the engineered Q residue, and b) contacting the intermediate conjugate with the PEG moiety thereby obtaining the modified IL-2 protein-PEG conjugate, wherein the PEG moiety is conjugated via the small molecule handle. In some embodiments, the method further comprises generating the modified IL-2 protein comprising the engineered Q residue.

In another aspect, there is provided a method of making a modified IL-2 protein-PEG conjugate comprising a modified IL-2 protein comprising an engineered Q residue specifically conjugated to a PEG moiety, wherein the method comprises: contacting a composition comprising a plurality of any one of the modified IL-2 proteins described above with the PEG moiety in the presence of a TGase under a condition that is sufficient to generate the modified IL-2 protein-PEG conjugate, wherein at least about 30% (e.g., at least about any of 30%, 40%, 50%, 60%, 70%, 80%, 90%, or 95%) of the modified IL-2 protein within the composition is conjugated with the PEG moiety via the engineered Q residue. In some embodiments, the method further comprises generating the composition comprising the plurality of modified IL-2 protein comprising the engineered Q residue. In some embodiments, at least about 70% (such as at least about any of 70%, 80%, 90%, or 95%) of the modified IL-2 protein within the composition is conjugated with the PEG moiety via the engineered Q residue.

In another aspect, there is provided a method of making a modified IL-2 protein-PEG conjugate comprising a modified IL-2 protein comprising an engineered Q residue specifically conjugated to a PEG moiety, wherein the method comprises: a) contacting a composition comprising a plurality of any one of the modified IL-2 proteins described above with a small molecule handle in the presence of a TGase under a condition that is sufficient to generate an intermediate conjugate comprising the modified IL-2 protein specifically conjugated to the small molecule handle, wherein at least about 30% (e.g., at least about any of 30%, 40%, 50%, 60%, 70%, 80%, 90%, or 95%) of the modified IL-2 protein within the composition is conjugated with the small molecule handle via the engineered Q residue, and b) contacting the intermediate conjugate with the PEG moiety thereby obtaining the modified IL-2 protein-PEG conjugate, wherein at least about 30% (e.g., at least about any of 30%, 40%, 50%, 60%, 70%, 80%, 90%, or 95%) of the intermediate conjugate within the composition is conjugated with the PEG moiety via the small molecule handle. In some embodiments, the method further comprises generating the composition comprising the plurality of modified IL-2 protein comprising the engineered Q residue. In some embodiments, at least about 70% (such as at least about any of 70%, 80%, 90%, or 95%) of the modified IL-2 protein within the composition is conjugated with the PEG moiety via the engineered Q residue.

In another aspect, there is provided a method of increasing the circulating half-life $t_{1/2}$ or overall exposure $AUC_{0\text{-}inf}$ of an IL-2 protein, comprising: a) introducing an engineered Q residue into the IL-2 protein to generate a modified IL-2 protein of any one of the modified IL-2 proteins described above; b) contacting the modified IL-2 protein with a PEG moiety in the presence of a TGase under a condition sufficient to conjugate the PEG moiety to the modified IL-2 protein via the engineered Q residue; and wherein the PEG moiety is of a length sufficient to increase the circulating half-life or overall exposure $AUC_{0\text{-}inf}$ of the PEG conjugated modified IL-2 protein compared to the IL-2 protein. In some embodiments, the circulating half-life of the PEG conjugated modified IL-2 protein is at least about 1.5 times (e.g., at least about any of 2, 3, 4, 5, 6, 7, 8, 9, 10, 15, 20, 25, or 30 times) longer than the IL-2 protein. In some embodiments, the overall exposure ($AUC_{0\text{-}inf}$) of the PEG conjugated modified IL-2 protein is at least about 5 times (e.g., at least about any of 10, 15, 20, 25, 30, 35, 40, 45, 50, or 100 times) larger than the IL-2 protein, such as after a single intravenous or a single subcutaneous administration.

In another aspect, there is provided a method of increasing the circulating half-life or overall exposure $AUC_{0\text{-}inf}$ of an IL-2 protein, comprising: a) introducing an engineered Q residue into the IL-2 protein to generate a modified IL-2 protein of any one of the modified IL-2 proteins described above; b) contacting the modified IL-2 protein with a small molecule handle in the presence of a TGase under a condition that is sufficient to generate an intermediate conjugate comprising the modified IL-2 protein specifically conjugated to the small molecule handle via the engineered Q residue; and c) contacting the intermediate conjugate with a PEG moiety under a condition sufficient to conjugate the PEG moiety to the intermediate conjugate via the small molecule handle; and wherein the PEG moiety is of a length sufficient to increase the circulating half-life of the PEG conjugated modified IL-2 protein compared to the IL-2 protein. In some embodiments, the circulating half-life of the PEG conjugated modified IL-2 protein is at least about 1.5 times (e.g., at least about any of 2, 3, 4, 5, 6, 7, 8, 9, 10, 15, 20, 25, or 30 times) longer than the IL-2 protein. In some embodiments, the overall exposure ($AUC_{0\text{-}inf}$) of the PEG conjugated modified IL-2 protein is at least about 5 times (e.g., at least about any of 10, 15, 20, 25, 30, 35, 40, 45, 50, or 100 times) larger than the IL-2 protein, such as after a single intravenous or a single subcutaneous administration.

In another aspect, there is provided a method of increasing the circulating half-life or overall exposure $AUC_{0\text{-}inf}$ of an IL-2 protein, comprising: a) introducing an engineered Q residue into the IL-2 protein to generate a composition comprising a plurality of modified IL-2 protein comprising an engineered Q residue, such as a composition comprising any one of the modified IL-2 proteins described above; b) contacting the composition with a PEG moiety in the presence of a TGase under a condition sufficient to conjugate the PEG moiety to the modified IL-2 protein via the engineered Q residue; wherein at least about 30% (e.g., at least about any of 30%, 40%, 50%, 60%, 70%, 80%, 90%, or 95%) of the modified IL-2 protein within the composition is conjugated with the PEG moiety via the engineered Q residue; and wherein the PEG moiety is of a length sufficient to increase the circulating half-life or overall exposure $AUC_{0\text{-}inf}$ of the PEG conjugated modified IL-2 protein compared to the IL-2 protein. In some embodiments, at least about 70% (e.g., at least about any of 70%, 80%, 90%, or 95%) of the modified IL-2 protein within the composition is conjugated with the PEG moiety via the engineered Q residue. In some embodiments, the circulating half-life of the PEG conjugated modified IL-2 protein is at least about 1.5 times (e.g., at least about any of 2, 3, 4, 5, 6, 7, 8, 9, 10, 15, 20, 25, or 30 times) longer than the IL-2 protein. In some embodiments, the overall exposure ($AUC_{0\text{-}inf}$) of the PEG conjugated modified IL-2 protein is at least about 5 times (e.g., at least about any of 10, 15, 20, 25, 30, 35, 40, 45, 50, or 100 times) larger than the IL-2 protein, such as after a single intravenous or a single subcutaneous administration.

In another aspect, there is provided a method of increasing the circulating half-life or overall exposure $AUC_{0\text{-}inf}$ of an IL-2 protein, comprising: a) introducing an engineered Q residue into the IL-2 protein to generate a composition comprising a plurality of modified IL-2 protein comprising an engineered Q residue, such as a composition comprising any one of the modified IL-2 proteins described above; b) contacting the composition with a small molecule handle in the presence of a TGase under a condition sufficient to conjugate the small molecule handle to the modified IL-2 protein via the engineered Q residue, wherein at least about 30% (e.g., at least about any of 30%, 40%, 50%, 60%, 70%, 80%, 90%, or 95%) of the modified IL-2 protein within the composition is conjugated with the small molecule handle via the engineered Q residue; and c) contacting the composition comprising the intermediate conjugate with a PEG moiety thereby obtaining a modified IL-2-protein-PEG conjugate, wherein at least about 30% (e.g., at least about any of 30%, 40%, 50%, 60%, 70%, 80%, 90%, or 95%) of the intermediate conjugate within the composition is conjugated with the PEG moiety via the small molecule handle; and wherein the PEG moiety is of a length sufficient to increase the circulating half-life or overall exposure $AUC_{0\text{-}inf}$ of the PEG conjugated modified IL-2 protein compared to the IL-2 protein. In some embodiments, at least about 70% (e.g., at least about any of 70%, 80%, 90%, or 95%) of the modified IL-2 protein within the composition is conjugated with the PEG moiety via the engineered Q residue. In some embodiments, the circulating half-life of the PEG conjugated modified IL-2 protein is at least about 1.5 times (e.g., at least about any of 2, 3, 4, 5, 6, 7, 8, 9, 10, 15, 20, 25, or 30 times) longer than the IL-2 protein. In some embodiments, the overall exposure ($AUC_{0\text{-}inf}$) of the PEG conjugated modified IL-2 protein is at least about 5 times (e.g., at least about any of 10, 15, 20, 25, 30, 35, 40, 45, 50, or 100 times) larger than the IL-2 protein, such as after a single intravenous or a single subcutaneous administration.

The present invention further provides kits and articles of manufacture that are useful for the methods described herein.

BRIEF DESCRIPTION OF THE DRAWINGS

FIG. 1 shows amino acid sequence and structure of an exemplary parent IL-2 protein (IL-2 Aldesleukin). IL-2Rα subunit binding domains are underlined, IL-2Rβ subunit binding domains are squared, $\gamma_c$ bindin domain is italicized. Exemplary residues to be mutated to glutamine (Q) are bolded. Secondary structure a helix (h), random coil (c), and extended strand (e) are also shown.

FIG. 2 shows amino acid sequence alignment of exemplary modified IL-2 proteins and parent IL-2 protein (Aldesleukin, e.g., Proleukin®). Engineered Q residues are shaded.

FIGS. 6A-6B demonstrates proliferation of lymphocytes in blood and spleen in mice after injecting parent IL-2 (Aldesleukin), exemplary modified IL-2 proteins (IL-2A1, IL-2A2), and exemplary modified IL-2 protein-PEG conjugates (PEG-20K-IL-2A1, PEG-20K-IL-2A2). Parent IL-2 (unmodified) and modified IL-2 proteins (IL-2A1, IL-2A2) were intraperitoneally (i.p.) injected, once per day for 5 days, 20 μg/mouse/day. Modified IL-2 protein-PEG conjugates were subcutaneously (s.c.) injected for a single dose, 100 μg/mouse.

FIG. 19 shows sequence coverage for DP006-A and DP006-A-30 with trypsin digestion by database searching.

FIG. 20 shows base peak chromatography for DP006-A and DP006-A-30 with trypsin digestion.

FIG. 21 shows extracted ion chromatogram (EIC) of PEGylated P43-47 in DP006-A-30.

FIG. 22 shows MS1 and MS/MS Spectra of m/z at 539.0666 (z=4).

FIG. 23 shows MS1 and MS/MS Spectra of m/z at 550.0738 (z=4).

FIG. 24 shows sequence coverage for DP006-A and DP006-A-30 with Glu-C digestion by database searching.

FIG. 25 shows base peak chromatography for DP006-A and DP006-A-30 with Glu-C digestion.

DETAILED DESCRIPTION OF THE PRESENT APPLICATION

Figure 3:
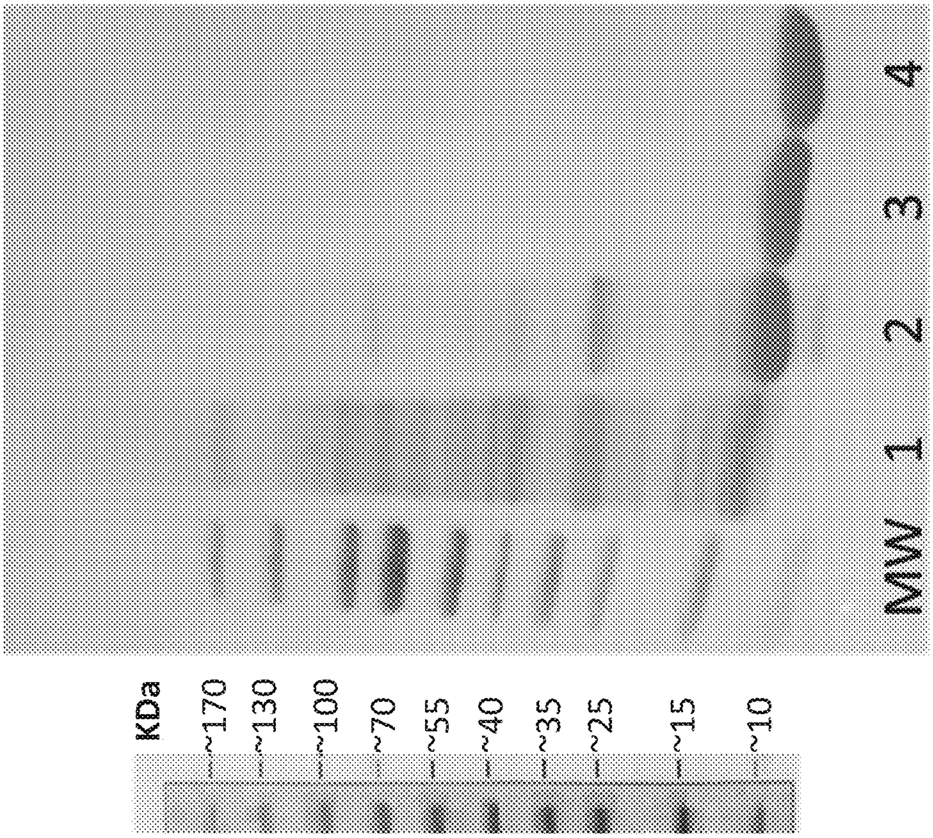
FIG. 3 shows SDS-PAGE analysis of expression and purification of exemplary modified IL-2 proteins (IL-2A1, IL-2A2). Ladder is shown on the left.

IL-2 is a useful therapeutic agent for cancer immunotherapy. However, due to the severe side effects such as capillary leak syndrome (CLS) and impaired neutrophil function, and the requirement of frequent intravenous infusion over multiple doses, the use of IL-2 is limited and of certain concern in cancer treatment. Inventors of the present application generated a modified IL-2 protein comprising an engineered Q residue, and a modified IL-2 protein-PEG conjugate, which shows significantly improved circulating half-life and overall exposure ($AUC_{0-inf}$) (PEG conjugates) and bioactivity in vivo, leading to reduced dosing frequency. The modified IL-2 proteins in some embodiments have reduced binding affinity to IL-2Rα subunit while retain or only suffer from slightly affected binding affinity to IL-2Rβ and/or $\gamma_c$ subunit, by way of introducing an engineered Q residue within the IL-2Rα subunit binding domain. The PEG moiety conjugated to the modified IL-2 protein via the engineered Q residue was found to further tune IL-2R subunits binding and T cell/NK cell activation, and improve pharmacokinetic profiles of modified IL-2 protein, such as extending IL-2 serum circulating half-life, and enhancing overall exposure ($AUC_{0-inf}$). The modified IL-2 proteins and modified IL-2 protein-PEG conjugates described herein may selectively activate NK cells and effector T cells (CD8+ T cells) without inducing Treg expansion (or induce much lower Treg activation compared to NK cell/effector T cell activation) compared to unmodified IL-2 proteins, in order to avoid or reduce immunosuppressive activities and toxicities.

The present application provides, in one aspect, a modified IL-2 protein comprising an engineered Q residue (hereinafter also referred to as "modified IL-2 protein"). In another aspect, the present invention also provides a modified IL-2 protein-PEG conjugate comprising a modified IL-2 protein comprising an engineered Q residue and a PEG moiety, wherein the PEG moiety is conjugated to the modified IL-2 protein via the engineered Q residue (hereinafter also referred to as "modified IL-2 protein-PEG conjugate", "PEG-modified IL-2", "PEGylated modified IL-2" or "PEG conjugate of modified IL-2 protein"). In some embodiments, the modified IL-2 protein described herein can be used to make any of the modified IL-2 protein-PEG conjugates described herein. In some embodiments, the modified IL-2 protein-PEG conjugate described herein may comprise any of the modified IL-2 protein described herein. In some embodiments, the modified IL-2 protein has two or more (such as two) engineered Q residues, and at least one engineered Q residue is conjugated with one PEG moiety. In some embodiments, each of the engineered Q residue(s) of the modified IL-2 protein is conjugated with one PEG moiety. In some embodiments for a population of modified IL-2 proteins comprising an engineered Q residue, at least about 90% (such as at least any of about 91%, 92%, 93%, 94%, 95%, 96%, 97%, 98%, 99%, or 100%) of the modified IL-2 proteins are conjugated with a PEG moiety via the engineered Q residue (such as one PEG moiety conjugated to at least one of the engineered Q residues, or each engineered Q residue is conjugated with one PEG moiety). Also provided are isolated nucleic acids encoding the modified IL-2 proteins described herein; vectors comprising such isolated nucleic acids; host cells comprising such isolated nucleic acids or vectors; pharmaceutical compositions comprising the modified IL-2 proteins and/or modified IL-2 protein-PEG conjugates described herein; methods of treatment using such pharmaceutical compositions, any modified IL-2 proteins described herein, and/or any modified IL-2 protein-PEG conjugates described herein; and methods of making the modified IL-2 proteins and/or modified IL-2 protein-PEG conjugates described herein. Kits and article of manufacture are also provided.

I. Definitions

"Transglutaminase," used interchangeably herein with "TGase," refers to an enzyme capable of carrying out transglutamination reactions. The term "transglutamination" as used herein refers to a reaction where the 7-glutaminyl of an acceptor glutamine residue (e.g. engineered Q residue) from a protein/peptide (e.g., modified IL-2) is transferred to an amine group, such as a primary amine or the ε-amino group of lysine.

The term "acceptor glutamine residue," when referring to an amino acid residue of a polypeptide or protein, refers to a glutamine residue (such as an engineered Q residue described herein) that, under suitable conditions, is recognized by a TGase and can be crosslinked to a conjugate moiety comprising a donor amine group by a TGase through a reaction between the glutamine and a donor amine group (such as lysine or a structurally related primary amine such as amino pentyl group).

An "endogenous acceptor glutamine residue on an IL-2 protein" or "endogenous Q residue" used herein refers to a naturally occurring acceptor glutamine residue in an IL-2 protein, rather than the engineered Q residue described herein.

"Engineered Q residue" used herein refers to non-naturally occurring acceptor glutamine residue in a parent IL-2 protein (e.g., wild-type IL-2, or IL-2 Aldesleukin) and is (e.g., results from) a manmade mutation (such as insertion or replacement). See "Engineered Q residue" subsection below for examples.

The term "amine donor group" as used herein refers to a reactive group containing one or more reactive amines (e.g., primary amines). For example, a PEG moiety can comprise an amine donor group (e.g., primary amine $-NH_2$), an optional linker, and a PEG molecule. The amine donor group in some embodiments is a primary amine ($-NH_2$) that provides a substrate for transglutaminase to allow conjugation of the PEG molecule to the modified IL-2 protein via the engineered Q residue. Accordingly, the linkage between the engineered Q residue and the amine donor group can be of the formula $-CH_2-CH_2-CO-NH-$. The PEG moiety can also be a polymer containing a reactive Lys residue.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "$-(OCH_2CH_2)_n-$" where (n) is integer of 2 to 4000. As used herein, PEG also includes "$-CH_2CH_2-O(CH_2CH_2O)_n-CH_2CH_2-$" and "$-(OCH_2CH_2)_nO-$," depending upon whether or not the terminal oxygens have been displaced, e.g., during a synthetic transformation. The term "PEG" includes structures having various terminal or "end capping" groups and so forth. The term "PEG" also means a polymer that contains a majority, that is to say, greater than about 50%, of $-OCH_2CH_2-$ repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or end-point of a polymer having an end-capping moiety.

"Non-naturally occurring" with respect to a polymer as described herein, such as a PEG moiety, means a polymer that in its entirety is not found in nature. A non-naturally occurring polymer may, however, contain one or more monomers or segments of monomers that are naturally occurring, so long as the overall polymer structure is not found in nature.

The terms "spacer moiety," "linkage" and "linker" are used herein to refer to a bond or an atom or a collection of atoms optionally used to link interconnecting moieties. The spacer moiety may be hydrolytically stable or may include a physiologically hydrolysable or enzymatically degradable linkage. Unless the context clearly dictates otherwise, a spacer moiety optionally exists between any two elements of a compound (e.g., the provided conjugates comprising modified IL-2 with engineered Q residue and PEG moiety can be attached directly or indirectly through a spacer or linker moiety).

"Optional" or "optionally" means that the subsequently described circumstance may or may not occur, so that the description includes instances where the circumstance occurs and instances where it does not.

"Substantially" means nearly totally or completely, for instance, satisfying one or more of the following: greater than 50%, 51% or greater, 75% or greater, 80% or greater, 90% or greater, and 95% or greater of the condition.

As use herein, the term "specifically binds," "specifically recognizes," or is "specific for" refers to measurable and reproducible interactions such as binding between a ligand (e.g., IL-2) and its corresponding receptor (or receptor subunit, e.g., IL-2R), which is determinative of the presence of the ligand in the presence of a heterogeneous population of molecules including biological molecules. For example, a ligand (e.g., IL-2) that specifically binds its corresponding receptor (or receptor subunit, e.g., IL-2R) is a ligand that binds this receptor with greater affinity, avidity, more readily, and/or with greater duration than it binds other receptors. In some embodiments, the extent of binding of a ligand (e.g., IL-2) to an unrelated receptor is less than about 10% of the binding of the ligand (e.g., IL-2) to its corresponding receptor (e.g., IL-2R) as measured, e.g., by a radioimmunoassay (RIA) or surface plasmon resonance (SPR). In some embodiments, a ligand (e.g., IL-2) that specifically binds its corresponding receptor (or receptor subunit, e.g., IL-2R) has a dissociation constant (Kd) of ≤100 μM, ≤10 μM, ≤1 μM, ≤100 nM, ≤10 nM, ≤1 nM, ≤0.1 nM, or ≤0.01 nM. In some embodiments, a ligand (e.g., IL-2) specifically binds its corresponding receptor (or receptor subunit, e.g., IL-2R) that is conserved among the protein from different species. In some embodiments, specific binding can include, but does not require exclusive binding.

The term "specificity" refers to selective recognition of a ligand (e.g., IL-2) for its corresponding receptor (or receptor subunit, e.g., IL-2R).

"Binding affinity" generally refers to the strength of the sum total of non-covalent interactions between a single binding site of a molecule (e.g., a ligand such as IL-2, or its binding domains) and its binding partner (e.g., a receptor such as IL-2R, or its subunits). Unless indicated otherwise, as used herein, "binding affinity" refers to intrinsic binding affinity that reflects a 1:1 interaction between members of a binding pair (e.g., ligand and receptor, or ligand binding domain and receptor subunit). The affinity of a molecule X (or a binding site of X) for its partner Y (or a corresponding recognition site of Y) can generally be represented by the dissociation constant (Kd). Molecules (e.g., modified IL-2) with low-affinity generally bind its binding partner (e.g., IL-2R, or its subunits) slowly and tend to dissociate readily, whereas molecules with high-affinity generally bind its binding partner faster and tend to remain bound longer. A variety of methods of measuring binding affinity are known in the art, any of which can be used for purposes of the present application. Specific illustrative and exemplary embodiments for measuring binding affinity are described in the following. Any suitable ligand binding assays or antibody/antigen binding assays known in the art can be used to measure binding affinity, e.g., RIA, SPR, Biacore assay, Octet analysis, etc.

"Percent (%) amino acid sequence identity" and "homology" with respect to a peptide or polypeptide sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule (e.g., encoding a modified IL-2 protein) described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human. A "patient" as used herein includes any human who is afflicted with a disease (e.g., cancer). The terms "subject," "individual," and "patient" are used interchangeably herein.

The term "effective amount" used herein refers to an amount of an agent, such as a modified IL-2 protein or modified IL-2 protein-PEG conjugate described herein, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the agent (e.g., a modified IL-2 protein or modified IL-2 protein-PEG conjugate) or composition (such as pharmaceutical composition) may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. In some embodiments, the therapeutically effective amount is an amount that extends the survival of a patient.

As used herein, "delaying" the development of a disease means to defer, hinder, slow, retard, stabilize, and/or postpone development of the disease (e.g., cancer). This delay can be of varying lengths of time, depending on the history of the disease and/or individual being treated.

As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex.

Further, the stimulation event may activate a cell and upregulate or downregulate expression or secretion of a molecule. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cellular responses.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process. The term "activated T cells" indicates T cells that are currently undergoing cell division, cytokine production, performance of regulatory or cytolytic effector functions, and/or has recently undergone the process of "activation."

"Bioactivity or "biological activity" include but are not limited to the ability of a molecule (e.g., IL-2) in specifically binding to its corresponding receptor (e.g., IL-2R), properly inducing downstream signal transduction, such as inducing cellular proliferation, differentiation, cytokine production and/or performance of regulatory or cytolytic effector functions.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X."

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Modified IL-2 Proteins and Modified IL-2 Protein-PEG (Polyethylene Glycol) Conjugates In one aspect, the present invention provides a modified IL-2 protein comprising an engineered Q residue. The present invention in another aspect also provides a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue. In some embodiments, the modified IL-2 protein described herein can be used to make any of the modified IL-2 protein-PEG conjugate described herein. In some embodiments, the modified IL-2 protein-PEG conjugate described herein may comprise any of the modified IL-2 protein described herein.

In some embodiments, there is also provided antibodies or antigen binding fragments thereof specifically recognizing any of the modified IL-2 protein described herein. In some embodiments, there is also provided antibodies or antigen binding fragments thereof specifically recognizing any of the modified IL-2 protein-PEG conjugates described herein. In some embodiments, these antibodies or antigen binding fragments thereof can be used to detect or measure protein concentration (e.g., in ELISA) of any of the modified IL-2 protein or modified IL-2 protein-PEG conjugates described herein.

In some embodiments, the engineered Q residue is within the IL-2Rα subunit binding domain. In some embodiments, the engineered Q residue is between about 1 and about 3 amino acid residues (such as any of 1, 2, or 3 amino acid residues) outside of the IL-2Rα subunit binding domain.

Thus in some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, and wherein the engineered Q residue is within the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, and wherein the engineered Q residue is between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is within the IL-2Rα subunit binding domain. In some embodiments, there is provided a modified IL-2 protein comprising an engineered Q residue, wherein the engineered Q residue is between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues. In some embodiments, the engineered Q residue is (e.g., results from) a single amino acid mutation (e.g., insertion, substitution) relative to a parent IL-2 protein (e.g., wild-type IL-2, human IL-2, or IL-2 Aldesleukin). In some embodiments, the single amino acid mutation (e.g., substitution) is selected from the group consisting of F43Q, R37Q, F41Q, K42Q, Y44Q, T36Q, M38Q, and any combinations thereof, wherein the amino acid position is relative to a parent IL-2 protein (e.g., IL-2 Aldesleukin). In some embodiments, the parent IL-2 protein is IL-2 Aldesleukin, which comprises an amino acid sequence of SEQ ID NO: 1. In some embodiments, the modified IL-2 protein comprises an amino acid sequence of any of SEQ ID NOs: 2 and 4-8. In some embodiments, the engineered Q residue is part of an exogenous patch sequence suitable for TGase reaction (when a modified IL-2 protein comprises an engineered Q residue that is part of an exogenous patch sequence, the modified IL-2 protein comprises the exogenous patch sequence, and the engineered Q residue is one of the amino acid residues within the patch sequence). In some embodiments, the exogenous patch sequence replaces a portion of a parent IL-2 protein (e.g., wild-type IL-2, human IL-2, or IL-2 Aldesleukin). In some embodiments, the parent IL-2 protein is Aldesleukin, which comprises an amino acid sequence of SEQ ID NO: 1. In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the modified IL-2 protein comprises an amino acid sequence of any of SEQ ID NOs: 3 and 15-19. In some embodiments, the modified IL-2 protein further comprises one or more additional amino acid mutations that are not engineered Q residues. In some embodiments, the modified IL-2 protein comprises an amino acid sequence having at least about 95% (such as at least any of about 96%, about 97%, about 98%, about 99%, or about 100%) identity to a parent IL-2 protein (e.g., wild-type IL-2, human IL-2, or IL-2 Aldesleukin) comprising the amino acid sequence of SEQ ID NO: 1. In some embodiments, the $K_D$ of the binding between the modified IL-2 protein and an IL-2Rα subunit is about 2 to about 800 times (e.g., about 2 to about 10 times, about 10 to about 50 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and an IL-2Rα subunit. In some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, or about 16 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein is capable of activating an immune cell selected from the group consisting of a killer T cell (Tc, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein has about 2 to about 50 folds (e.g., about 2 to about 10 folds) reduced ability to activate a Treg cell compared to a parent IL-2 protein. In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the PEG moiety is linear. In some embodiments, the PEG moiety is branched. In some embodiments, the PEG moiety has a molecular weight of between about 10 kDa and about 40 kDa, such as about 20 kDa, about 30 kDa, or about 40 kDa. In some embodiments, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine. In some embodiments, the modified IL-2 protein-PEG conjugate comprises a modified IL-2 protein comprising one engineered Q residue, wherein one PEG moiety is conjugated to the modified IL-2 protein via the one engineered Q residue. In some embodiments, the modified IL-2 protein comprises two or more engineered Q residues, wherein each of the two or more engineered Q residues is each conjugated with one PEG moiety. In some embodiments, the modified IL-2 protein comprises two or more engineered Q residues, wherein at least one of the two or more engineered Q residues is each conjugated with one PEG moiety. In some embodiments, the conjugation of the PEG moiety is mediated via a TGase, such as a microbial TGase (mTGase). In some embodiments, the TGase is a wild-type TGase, such as comprising an amino acid sequence of SEQ ID NO: 20. In some embodiments, the TGase is an engineered TGase. In some embodiments, the engineered TGase comprises an amino acid sequence having at least about 80% (such as at least about any of 80%, 85%, 90%, 95%, 96%, 97%, 98%, or 99%) identity to a wild-type TGase, such as a wild-type TGase comprising an amino acid sequence of SEQ ID NO: 20. In some embodiments, the TGase has a purity of at least about 90% (such as at least about any of 90%, 91%, 92%, 93%, 94%, 95%, 96%, 97%, 98%, 99%, or 100%). In some embodiments, the $K_D$ of the binding between the modified IL-2 protein-PEG conjugate and an IL-2Rα subunit is about 10 to about 2000 times (e.g., about 10 to about 50 times, or about 100 to about 2000 times) of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit. In some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein-PEG conjugate is capable of activating an immune cell selected from the group consisting of a killer T cell ($T_c$, cytotoxic T lymphocyte, or CTL), a helper T cell (Th), a regulatory T cells (Treg), a γδ T cell, a natural killer T (NKT) cell, and a natural killer (NK) cell. In some embodiments, the modified IL-2 protein-PEG conjugate has about 2 to about 5000 folds reduced ability to activate a Treg cell compared to a parent IL-2 protein (e.g., wild-type IL-2, human IL-2, or IL-2 Aldesleukin). In some embodiments, the modified IL-2 protein-PEG conjugate has similar or about 1 to about 50 folds reduced ability to activate a CTL or a NK cell compared to a parent IL-2 protein (e.g., wild-type IL-2, human IL-2, or IL-2 Aldesleukin). In some embodiments, the modified IL-2 protein and/or the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein and/or the modified IL-2 protein-PEG conjugate has similar or preferential activation on CTL and/or NK cells over Treg cells, compared to a parent IL-2 protein (e.g., wild-type IL-2, human IL-2, or IL-2 Aldesleukin), such as similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

In some embodiments, the engineered Q residue is (e.g., results from) a single amino acid mutation (e.g., insertion, substitution) relative to a parent IL-2 protein (e.g., wild-type IL-2, human IL-2, or IL-2 Aldesleukin). In some embodiments, the parent IL-2 protein is Aldesleukin, comprises an amino acid sequence of SEQ ID NO: 1. In some embodiments, the single amino acid mutation is selected from the group consisting of F43Q, R37Q, F41Q, K42Q, Y44Q, T36Q, M38Q, and any combinations thereof, wherein the amino acid residue position is relative to parent IL-2 protein comprising an amino acid sequence of SEQ ID NO: 1.

Thus in some embodiments, there is provided a modified IL-2 protein comprising an engineered Q residue, wherein the engineered Q residue is (e.g., results from) a single amino acid mutation (e.g., insertion, substitution) relative to a parent IL-2 protein (such as IL-2 protein Aldesleukin comprising an amino acid sequence of SEQ ID NO: 1). In some embodiments, there is provided a modified IL-2 protein comprising an engineered Q residue, wherein the engineered Q residue is (e.g., results from) a single amino acid mutation (e.g., insertion, substitution) relative to a parent IL-2 protein (such as IL-2 protein Aldesleukin comprising an amino acid sequence of SEQ ID NO: 1), and wherein the engineered Q residue is within the IL-2Rα subunit binding domain. In some embodiments, there is provided a modified IL-2 protein comprising an engineered Q residue, wherein the engineered Q residue is (e.g., results from) a single amino acid mutation (e.g., insertion, substitution) relative to a parent IL-2 protein (such as IL-2 protein Aldesleukin comprising an amino acid sequence of SEQ ID NO: 1), and wherein the engineered Q residue is between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is (e.g., results from) a single amino acid mutation (e.g., insertion, substitution) relative to a parent IL-2 protein comprising an amino acid sequence of SEQ ID NO: 1, and wherein the single amino acid mutation is selected from the group consisting of F43Q, R37Q, F41Q, K42Q, Y44Q, T36Q, M38Q, and any combinations thereof. In some embodiments, the modified IL-2 protein comprises one engineered Q residue. In some embodiments, the modified IL-2 protein comprises two or more (such as two) engineered Q residues. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, human IL-2, or IL-2 Aldesleukin), such as a parent IL-2 protein comprising an amino acid sequence of SEQ ID NO: 1. In some embodiments, there is provided a modified IL-2 protein comprising an engineered Q residue of F34Q relative to a parent IL-2 protein comprising an amino acid sequence of SEQ ID NO: 1. In some embodiments, there is provided a modified IL-2 protein comprising an engineered Q residue of R37Q relative to a parent IL-2 protein comprising an amino acid sequence of SEQ ID NO: 1. In some embodiments, there is provided a modified IL-2 protein comprising an engineered Q residue of F41Q relative to a parent IL-2 protein comprising an amino acid sequence of SEQ ID NO: 1. In some embodiments, there is provided a modified IL-2 protein comprising an engineered Q residue of K42Q relative to a parent IL-2 protein comprising an amino acid sequence of SEQ ID NO: 1. In some embodiments, there is provided a modified IL-2 protein comprising an engineered Q residue of Y44Q relative to a parent IL-2 protein comprising an amino acid sequence of SEQ ID NO: 1. In some embodiments, there is provided a modified IL-2 protein comprising a first engineered Q residue of R37Q and a second engineered Q residue of Y44Q relative to a parent IL-2 protein comprising an amino acid sequence of SEQ ID NO: 1. In some embodiments, there is provided a modified IL-2 protein comprising an amino acid sequence of any of SEQ ID NOs: 2 and 4-8. In some embodiments, the modified IL-2 protein has reduced binding to IL-2Rα subunit compared to a parent IL-2 protein (e.g., wild-type IL-2, human IL-2, or IL-2 Aldesleukin). In some embodiments, the $K_D$ of the binding between the modified IL-2 protein and an IL-2Rα subunit is about 2 to about 800 times (e.g., about 2 to about 10 times, about 10 to about 50 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and an IL-2Rα subunit. In some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, or about 16 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein has about 2 to about 50 folds (e.g., about 2 to about 10 folds) reduced ability to activate a Treg cell compared to a parent IL-2 protein (e.g., wild-type IL-2, human IL-2, or IL-2 Aldesleukin). In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 protein preferentially activates IL-2Rβ subunit over IL-2Rα subunit, compared to parent IL-2 protein (e.g., wild-type IL-2, human IL-2, or IL-2 Aldesleukin).

In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, and wherein the engineered Q residue is (e.g., results from) a single amino acid mutation (e.g., insertion, substitution) relative to a parent IL-2 protein (such as IL-2 Aldesleukin comprising an amino acid sequence of SEQ ID NO: 1). In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation (e.g., insertion, substitution) relative to a parent IL-2 protein (such as IL-2 Aldesleukin comprising an amino acid sequence of SEQ ID NO: 1), and wherein the engineered Q residue is within the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation (e.g., insertion, substitution) relative to a parent IL-2 protein (such as IL-2 Aldesleukin comprising an amino acid sequence of SEQ ID NO: 1), and wherein the engineered Q residue is between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation (e.g., insertion, substitution) relative to a parent IL-2 protein comprising an amino acid sequence of SEQ ID NO: 1, and wherein the single amino acid mutation is selected from the group consisting of F43Q, R37Q, F41Q, K42Q, Y44Q, T36Q, M38Q, and any combinations thereof. In some embodiments, the modified IL-2 protein comprises one engineered Q residue. In some embodiments, the modified IL-2 protein comprises two or more (such as two) engineered Q residues. In some embodiments, the modified IL-2 protein-PEG conjugate comprises a modified IL-2 protein comprising one engineered Q residue, wherein one PEG moiety is conjugated to the modified IL-2 protein via the one engineered Q residue. In some embodiments, the modified IL-2 protein comprises two or more engineered Q residues, wherein each of the two or more engineered Q residues is each conjugated with one PEG moiety. In some embodiments, the modified IL-2 protein comprises two or more engineered Q residues, wherein at least one of the two or more engineered Q residues is each conjugated with one PEG moiety. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (such as a wild-type IL-2, human IL-2 protein, or IL-2 Aldesleukin). In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation F43Q relative to a parent IL-2 protein comprising an amino acid sequence of SEQ ID NO: 1. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation R37Q relative to a parent IL-2 protein comprising an amino acid sequence of SEQ ID NO: 1. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation F41Q relative to a parent IL-2 protein comprising an amino acid sequence of SEQ ID NO: 1. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation K42Q relative to a parent IL-2 protein comprising an amino acid sequence of SEQ ID NO: 1. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation Y44Q relative to a parent IL-2 protein comprising an amino acid sequence of SEQ ID NO: 1. In some embodiments, there is provided a modified IL-2 protein-PEG conjugate comprising a modified IL-2 protein comprising two engineered Q residues and one PEG moiety (e.g., methoxy-PEG-amine), wherein the PEG moiety is conjugated to the modified IL-2 protein via one of the engineered Q residues, wherein the engineered Q residues are (e.g., result from) single amino acid mutations R37Q and Y44Q relative to a parent IL-2 protein comprising an amino acid sequence of SEQ ID NO: 1. In some embodiments, there is provided a modified IL-2 protein-PEG conjugate comprising a modified IL-2 protein comprising two engineered Q residues and two PEG moieties (e.g., methoxy-PEG-amine), wherein each engineered Q residue is conjugated with one PEG moiety, wherein the engineered Q residues are (e.g., result from) single amino acid mutations R37Q and Y44Q relative to a parent IL-2 protein comprising an amino acid sequence of SEQ ID NO: 1. In some embodiments, the two PEG moieties are the same. In some embodiments, the two PEG moieties are different. In some embodiments, the modified IL-2 protein comprises an amino acid sequence of any of SEQ ID NOs: 2 and 4-8. Thus in some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is (e.g., results from) a single amino acid mutation relative to a parent IL-2 protein comprising an amino acid sequence of SEQ ID NO: 1, and wherein the modified IL-2 protein comprises an amino acid sequence of any of SEQ ID NOs: 2 and 4-8. In some embodiments, the PEG moiety is linear. In some embodiments, the PEG moiety is branched. In some embodiments, the PEG moiety has a molecular weight of between about 10 kDa and about 40 kDa, such as about 20 kDa, about 30 kDa, or about 40 kDa. In some embodiments, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine. In some embodiments, the conjugation of the PEG moiety is mediated via a TGase, such as a microbial TGase (mTGase). In some embodiments, the TGase is a wild-type TGase, such as comprising an amino acid sequence of SEQ ID NO: 20. In some embodiments, the TGase is an engineered TGase. In some embodiments, the engineered TGase comprises an amino acid sequence having at least about 80% (such as at least about any of 85%, 90%, 95%, 96%, 97%, 98%, or 99%) identity to a wild-type TGase, such as a wild-type TGase comprising an amino acid sequence of SEQ ID NO: 20. In some embodiments, the TGase has a purity of at least about 90% (such as at least about any of 90%, 91%, 92%, 93%, 94%, 95%, 96%, 97%, 98%, 99%, or 100%). In some embodiments, the $K_D$ of the binding between the modified IL-2 protein-PEG conjugate and an IL-2Rα subunit is about 10 to about 2000 times (e.g., about 10 to about 50 times, or about 10 to about 100 times) of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit. In some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein-PEG conjugate is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein-PEG conjugate has about 2 to about 5000 folds reduced ability to activate a Treg cell compared to a parent IL-2 protein (e.g., wild-type IL-2, human IL-2, or IL-2 Aldesleukin). In some embodiments, the modified IL-2 protein-PEG conjugate has similar to (e.g., equal to) or about 1 to about 50 folds reduced ability to activate a CTL or a NK cell compared to a parent IL-2 protein (e.g., wild-type IL-2, human IL-2, or IL-2 Aldesleukin). In some embodiments, the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein-PEG conjugate has similar or preferential activation on CTL and/or NK cells over Treg cells, compared to a parent IL-2 protein (e.g., wild-type IL-2, human IL-2, or IL-2 Aldesleukin), such as similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

In some embodiments, the engineered Q residue is part of an exogenous patch sequence suitable for TGase reaction. When a modified IL-2 protein comprises an engineered Q residue that is part of an exogenous patch sequence, the modified IL-2 protein comprises the exogenous patch sequence, and the engineered Q residue is one of the amino acid residues within the patch sequence. In some embodiments, the exogenous patch sequence replaces a portion of a parent IL-2 protein (e.g., wild-type IL-2, human IL-2, or IL-2 Aldesleukin) sequence. In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the parent IL-2 protein comprises an amino acid sequence of SEQ ID NO: 1. In some embodiments, the modified IL-2 protein and/or the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin).

Thus in some embodiments, there is provided a modified IL-2 protein comprising an engineered Q residue, wherein the engineered Q residue is part of an exogenous patch sequence suitable for TGase reaction. In some embodiments, there is provided a modified IL-2 protein comprising an engineered Q residue, wherein the engineered Q residue is part of an exogenous patch sequence suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence suitable for TGase reaction, and wherein the exogenous patch sequence replaces a portion of a parent IL-2 protein (such as a parent IL-2 protein comprising an amino acid sequence of SEQ ID NO: 1). In some embodiments, there is provided a modified IL-2 protein comprising an engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), and wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, there is provided a modified IL-2 protein comprising an engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, human IL-2, or IL-2 Aldesleukin). In some embodiments, the modified IL-2 protein comprises an amino acid sequence of any of SEQ ID NOs: 3 and 15-19. In some embodiments, the modified IL-2 protein has reduced binding to IL-2Rα subunit compared to a parent IL-2 protein (e.g., wild-type IL-2, human IL-2, or IL-2 Aldesleukin). In some embodiments, the $K_D$ of the binding between the modified IL-2 protein and an IL-2Rα subunit is about 2 to about 800 times (e.g., about 2 to about 10 times, about 10 to about 50 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and an IL-2Rα subunit. In some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, or about 16 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein is capable of activating an immune cell selected from the group consisting of a killer T cell (Tc, cytotoxic T lymphocyte, or CTL), a helper T cell (Th), a regulatory T cells (Treg), a γδ T cell, a natural killer T (NKT) cell, and a natural killer (NK) cell. In some embodiments, the modified IL-2 protein has about 2 to about 50 folds (e.g., about 2 to about 10 folds) reduced ability to activate a Treg cell compared to a parent IL-2 protein (e.g., wild-type IL-2, or IL-2 Aldesleukin). In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 protein preferentially activates IL-2Rβ subunit over IL-2Rα subunit, compared to parent IL-2 protein (e.g., wild-type IL-2, human IL-2, or IL-2 Aldesleukin).

In some embodiments, there is provided a modified IL-2 protein comprising an engineered Q residue, wherein the engineered Q residue is part of an exogenous patch sequence LEEQAA (SEQ ID NO: 9) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence IFKQTY (SEQ ID NO: 10) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence PKEQKY (SEQ ID NO: 11) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence VIQGV (SEQ ID NO: 12) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence REEQFN (SEQ ID NO: 13) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence GLLQGA (SEQ ID NO: 14) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence LEEQAA (SEQ ID NO: 9) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence IFKQTY (SEQ ID NO: 10) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence PKEQKY (SEQ ID NO: 11) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence VIQGV (SEQ ID NO: 12) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence REEQFN (SEQ ID NO: 13) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein comprising an engineered Q residue, wherein the engineered Q residue is part of an exogenous patch sequence GLLQGA (SEQ ID NO: 14) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, human IL-2, or IL-2 Aldesleukin). In some embodiments, there is provided a modified IL-2 protein comprising an engineered Q residue, wherein the engineered Q residue is part of an exogenous patch sequence suitable for TGase reaction, wherein the exogenous patch sequence replaces a portion of a parent IL-2 protein comprising an amino acid sequence of SEQ ID NO: 1, and wherein the modified IL-2 protein comprises an amino acid sequence of any of SEQ ID NOs: 3 and 15-19. In some embodiments, the $K_D$ of the binding between the modified IL-2 protein and an IL-2Rα subunit is about 2 to about 800 times (e.g., about 2 to about 10 times, about 10 to about 50 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and an IL-2Rα subunit. In some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, or about 16 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein has about 2 to about 50 folds (e.g., about 2 to about 10 folds) reduced ability to activate a Treg cell compared to a parent IL-2 protein (e.g., wild-type IL-2, or IL-2 Aldesleukin). In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 protein preferentially activates IL-2Rβ subunit over IL-2Rα subunit, compared to parent IL-2 protein (e.g., wild-type IL-2, human IL-2, or IL-2 Aldesleukin).

In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, and wherein the engineered Q residue is part of an exogenous patch sequence suitable for TGase reaction. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, and wherein the engineered Q residue is within the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, and wherein the engineered Q residue is between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, and wherein the exogenous patch sequence replaces a portion of a parent IL-2 protein (such as a parent IL-2 protein comprising an amino acid sequence of SEQ ID NO: 1). In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is within the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, and wherein the exogenous patch sequence replaces a portion of a parent IL-2 protein (such as a parent IL-2 protein comprising an amino acid sequence of SEQ ID NO: 1), and wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof, and wherein the engineered Q residue is within the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, wherein the exogenous patch sequence replaces a portion of a parent IL-2 protein (such as a parent IL-2 protein comprising an amino acid sequence of SEQ ID NO: 1), wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof, and wherein the engineered Q residue is between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (such as a wild-type IL-2, human IL-2 protein, IL-2 Aldesleukin). In some embodiments, the modified IL-2 protein-PEG conjugate comprises a modified IL-2 protein comprising one engineered Q residue, wherein one PEG moiety is conjugated to the modified IL-2 protein via the one engineered Q residue. In some embodiments, the modified IL-2 protein comprises two or more (e.g., two) engineered Q residues, wherein each of the two or more engineered Q residues is each conjugated with one PEG moiety. In some embodiments, the modified IL-2 protein comprises two or more engineered Q residues, wherein at least one of the two or more engineered Q residues is each conjugated with one PEG moiety. In some embodiments, the modified IL-2 protein comprises an amino acid sequence of any of SEQ ID NOs: 3 and 15-19. In some embodiments, the PEG moiety is linear. In some embodiments, the PEG moiety is branched. In some embodiments, the PEG moiety has a molecular weight of between about 10 kDa and about 40 kDa, such as about 20 kDa, about 30 kDa, or about 40 kDa. In some embodiments, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine. In some embodiments, the conjugation of the PEG moiety is mediated via a TGase, such as a microbial TGase (mTGase). In some embodiments, the TGase is a wild-type TGase, such as comprising an amino acid sequence of SEQ ID NO: 20. In some embodiments, the TGase is an engineered TGase. In some embodiments, the engineered TGase comprises an amino acid sequence having at least about 80% (such as at least about any of 85%, 90%, 95%, 96%, 97%, 98%, or 99%) identity to a wild-type TGase, such as a wild-type TGase comprising an amino acid sequence of SEQ ID NO: 20. In some embodiments, the TGase has a purity of at least about 90% (such as at least about any of 90%, 91%, 92%, 93%, 94%, 95%, 96%, 97%, 98%, 99%, or 100%). In some embodiments, the $K_D$ of the binding between the modified IL-2 protein-PEG conjugate and an IL-2Rα subunit is about 10 to about 2000 times (e.g., about 10 to about 50 times, or about 50 to about 500 times) of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit. In some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein-PEG conjugate is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein-PEG conjugate has about 2 to about 5000 folds (e.g., about 2 to about 50 folds) reduced ability to activate a Treg cell compared to a parent IL-2 protein (e.g., wild-type IL-2, human IL-2, or IL-2 Aldesleukin). In some embodiments, the modified IL-2 protein-PEG conjugate has similar to (e.g., equal to) or about 1 to about 50 folds reduced ability to activate a CTL or a NK cell compared to a parent IL-2 protein (e.g., wild-type IL-2, human IL-2, or IL-2 Aldesleukin). In some embodiments, the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein-PEG conjugate has similar or preferential activation on CTL and/or NK cells over Treg cells, compared to a parent IL-2 protein (e.g., wild-type IL-2, human IL-2, or IL-2 Aldesleukin), such as similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

Thus in some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence LEEQAA (SEQ ID NO: 9) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence IFKQTY (SEQ ID NO: 10) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence PKEQKY (SEQ ID NO: 11) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence VIQGV (SEQ ID NO: 12) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence REEQFN (SEQ ID NO: 13) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence GLLQGA (SEQ ID NO: 14) suitable for TGase reaction, and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence LEEQAA (SEQ ID NO: 9) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence IFKQTY (SEQ ID NO: 10) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence PKEQKY (SEQ ID NO: 11) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence VIQGV (SEQ ID NO: 12) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence REEQFN (SEQ ID NO: 13) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence GLLQGA (SEQ ID NO: 14) suitable for TGase reaction, wherein the exogenous patch sequence replaces a portion of a parent IL-2 protein (such as a parent IL-2 protein comprising an amino acid sequence of SEQ ID NO: 1), and wherein the engineered Q residue is (a) within the IL-2Rα subunit binding domain; or (b) between about 1 and about 3 amino acid residues (such as any of 1, 2, or 3 amino acid residues) outside of the IL-2Rα subunit binding domain. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, human IL-2, or IL-2 Aldesleukin). In some embodiments, there is provided a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue, wherein the engineered Q residue is part of an exogenous patch sequence suitable for TGase reaction, wherein the exogenous patch sequence replaces a portion of a parent IL-2 protein (Aldesleukin) comprising an amino acid sequence of SEQ ID NO: 1, and wherein the modified IL-2 protein comprises an amino acid sequence of any of SEQ ID NOs: 3 and 15-19. In some embodiments, the PEG moiety is linear. In some embodiments, the PEG moiety is branched. In some embodiments, the PEG moiety has a molecular weight of between about 10 kDa and about 40 kDa, such as about 20 kDa, about 30 kDa, or about 40 kDa. In some embodiments, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine. In some embodiments, the conjugation of the PEG moiety is mediated via a TGase, such as a microbial TGase (mTGase). In some embodiments, the TGase is a wild-type TGase, such as comprising an amino acid sequence of SEQ ID NO: 20. In some embodiments, the TGase is an engineered TGase. In some embodiments, the engineered TGase comprises an amino acid sequence having at least about 80% (such as at least about any of 85%, 90%, 95%, 96%, 97%, 98%, or 99%) identity to a wild-type TGase, such as a wild-type TGase comprising an amino acid sequence of SEQ ID NO: 20. In some embodiments, the TGase has a purity of at least about 90% (such as at least about any of 90%, 91%, 92%, 93%, 94%, 95%, 96%, 97%, 98%, 99%, or 100%). In some embodiments, the $K_D$ of the binding between the modified IL-2 protein-PEG conjugate and an IL-2Rα subunit is about 10 to about 2000 times (e.g., about 10 to about 50 times, or about 50 to about 500 times) of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit. In some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and an IL-2Rβ subunit. In some embodiments, the modified IL-2 protein-PEG conjugate is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 protein-PEG conjugate has about 2 to about 5000 folds (e.g., about 2 to about 50 folds) reduced ability to activate a Treg cell compared to a parent IL-2 protein (e.g., wild-type IL-2, human IL-2, or IL-2 Aldesleukin). In some embodiments, the modified IL-2 protein-PEG conjugate has similar to (e.g., equal to) or about 1 to about 50 folds reduced ability to activate a CTL or a NK cell compared to a parent IL-2 protein (e.g., wild-type IL-2, human IL-2, or IL-2 Aldesleukin). In some embodiments, the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein-PEG conjugate has similar or preferential activation on CTL and/or NK cells over Treg cells, compared to a parent IL-2 protein (e.g., wild-type IL-2, human IL-2, or IL-2 Aldesleukin), such as similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

Modified IL-2 Proteins Comprising an Engineered Glutamine (Q) Residue

In some embodiments, there is provided a modified IL-2 protein comprising an engineered Q residue. In some embodiments, the modified IL-2 protein has reduced binding affinity to IL-2Rα subunit unit, while retain or have slightly affected binding affinity to IL-2Rβ subunit, compared to parent IL-2 protein (e.g., wild-type IL-2, human IL-2, or IL-2 Aldesleukin). In some embodiments, the modified IL-2 protein preferentially activates IL-2Rβ subunit over IL-2Rα subunit, compared to parent IL-2 protein (e.g., wild-type IL-2, human IL-2, or IL-2 Aldesleukin). The modified IL-2 proteins can be used directly, or be conjugated with another moiety (e.g., PEG) to generate modified IL-2 protein conjugates, such as any of the modified IL-2 protein-PEG conjugates described herein. The description of the modified IL-2 proteins in this section is also applicable to the modified IL-2 protein contained within the PEG-modified IL-2 protein throughout the application.

Thus in some embodiments, there is provided a modified IL-2 protein comprising an engineered Q residue. In some embodiments, the engineered Q residue is within the IL-2 Receptor alpha (IL-2Rα) subunit binding domain. In some embodiments, the engineered Q residue is between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues. In some embodiments, the engineered Q residue is (e.g., results from) a single amino acid mutation (e.g., insertion, substitution) relative to a parent IL-2 protein (e.g., wild-type IL-2, human IL-2, or IL-2 Aldesleukin). In some embodiments, the parent IL-2 protein is Aldesleukin, comprises an amino acid sequence of SEQ ID NO: 1. In some embodiments, the single amino acid mutation (e.g., substitution) is selected from the group consisting of F43Q, R37Q, F41Q, K42Q, Y44Q, T36Q, M38Q, and any combinations thereof, wherein the amino acid position is relative to a parent IL-2 protein comprising an amino acid sequence of SEQ ID NO: 1. In some embodiments, the modified IL-2 protein comprises an amino acid sequence of any of SEQ ID NOs: 2 and 4-8. In some embodiments, the engineered Q residue is part of an exogenous patch sequence suitable for Transglutaminase (TGase) reaction. In some embodiments, the exogenous patch sequence replaces a portion of a parent IL-2 protein (e.g., wild-type IL-2, human IL-2, or IL-2 Aldesleukin). In some embodiments, the parent IL-2 protein is Aldesleukin, comprises an amino acid sequence of SEQ ID NO: 1. In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the modified IL-2 protein comprises an amino acid sequence of any of SEQ ID NOs: 3 and 15-19. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, human IL-2, or IL-2 Aldesleukin). In some embodiments, the modified IL-2 protein has about 2 to about 800 folds (e.g., about 2 to about 10 folds, about 5 to about 50 folds, about 2 to about 50 folds, about 400 to about 500 folds, or about 476 folds) reduced binding to an IL-2Rα subunit compared to a parent IL-2 protein (e.g., wild-type IL-2, human IL-2, or IL-2 Aldesleukin). In some embodiments, the $K_D$ of the binding between the modified IL-2 protein and an IL-2Rα subunit is about 2 to about 800 times (e.g., about 2 to about 10 times, about 5 to about 50 times, about 10 to about 50 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and the IL-2Rα subunit. In some embodiments, the modified IL-2 protein has similar (e.g., equal) or about 1 to about 30 folds (such as equal to, about 1 to about 1.1 folds, about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 folds, about 1 to about 10 folds, about 10 to about 20 folds, or about 16 folds) reduced binding to an IL-2Rβ subunit compared to a parent IL-2 protein (e.g., wild-type IL-2, human IL-2, or IL-2 Aldesleukin). In some embodiments, the $K_D$ of the binding between the modified IL-2 protein and a IL-2Rβ subunit is similar to (e.g., equal to) or about 1 to about 30 times (such as equal to, about 1 to about 1.1 times, or about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 times, about 1 to about 10 times, about 10 to about 20 times, or about 16 times) of the $K_D$ of the binding between a parent IL-2 protein (e.g., wild-type IL-2, human IL-2, or IL-2 Aldesleukin) and the IL-2Rβ subunit. In some embodiments, the $K_D$ of the binding between the modified IL-2 protein and an IL-2Rα subunit is about 50 nM to about 100 μM (e.g., about 50 nM to about 600 nM, about 50 nM to about 1 μM, about 1 μM to about 100 μM, about 1 μM to about 30 PM, or about 17 μM). In some embodiments, the $K_D$ of the binding between the modified IL-2 protein and an IL-2Rβ subunit is about 400 nM to about 50 μM (e.g., about 400 nM to about 3000 nM, about 1 μM to about 50 μM, about 1 μM to about 10 μM, or about 8.39 μM). In some embodiments, the modified IL-2 protein is capable of activating an immune cell, such as a killer T cell (TC, cytotoxic T lymphocyte, or CTL), a helper T cell (Th), a regulatory T cell (Treg), a γδ T cell, a natural killer T (NKT) cell, or a natural killer (NK) cell. In some embodiments, the modified IL-2 protein has about 2 to about 50 folds (e.g., about 2 to about 10 folds) reduced ability to activate a Treg cell compared to a parent IL-2 protein (e.g., wild-type IL-2, human IL-2, or IL-2 Aldesleukin). In some embodiments, the modified IL-2 protein has similar or about 1 to about 5 folds (such as equal, about 1 to about 1.1 folds, or any of about 1, 2, 3, 4, or 5 folds) reduced ability to activate a CTL compared to a parent IL-2 protein (e.g., wild-type IL-2, human IL-2, or IL-2 Aldesleukin).

Parent IL-2 Protein

Interleukin-2 (IL-2) is a cytokine signaling molecule of about 15-16 kDa. It is found in vivo in variably glycosylated forms. IL-2 regulates the activities of white blood cells (leukocytes, often lymphocytes) of the immune system. It is involved in body's natural response to microbial infection and discriminating between "self" and "non-self". It mediates its effects by binding to IL-2 receptors (IL-2R) expressed on lymphocytes. IL-2 is essential for the rapid expansion, differentiation, and survival of antigen-selected T cell clones during an immune response, as well as normal functions of B cells, natural killer (NK) cells, and regulatory T cells ($T_{reg}$). IL-2R is a heterotrimer complex consisting of three chains (subunits), IL-2Rα (p55, CD25), IL-2Rβ (p75, CD122), and 7c (common gamma chain, IL-2Rγ, p65, CD132). The 7 chain is shared by all members of the cytokine family including IL-2, IL-4, IL-7, IL-9, IL-15 and IL-21. The three IL-2R subunits are expressed separately and differently on various cell types. Due to the different combinations of IL-2R subunit assembly, low, intermediate, and high affinity IL-2 receptors can be generated. The IL-2R α chain binds IL-2 with low affinity ($K_d$~$10^{-8}$M), IL-2Rα subunit is thus also known as "low affinity" IL-2 receptor. Binding of IL-2 to cells expressing only the IL-2Rα subunit does not lead to any detectable biologic response. R and 7 chains together form a complex that binds IL-2 with intermediate affinity ($K_d$~$10^{-9}$ M), primarily on memory T cells and NK cells. All three receptor chains form a complex that binds IL-2 with high affinity (Kd~$10^{-11}$ M, or ~10 pM) on activated T cells and regulatory T cells (Tregs). Such high affinity binding is due to a rapid rate of association ($k_{on}$≈$10^7$ $M^{-1}\cdot s^{-1}$) but relatively slow dissociation rate ($k_{off}$≈$10^{-4}$ $s^{-1}$) (D J Stauber et al., *Proc Natl Acad Sci USA.* 103(8):2788-2793. Epub Feb. 13, 2006). Most cells (e.g., resting T cells) only express the IL-2Rβ and the IL-2Rγ, which have low affinity for IL-2, thus are not responsive to IL-2. Upon stimulation, resting T cells express the relatively high affinity IL-2Rα. Binding of IL-2 to the IL-2Rα causes this receptor to sequentially engage the IL-2Rβ and the IL-2Rγ, leading to T cell activation. The intermediate (βγ) and high affinity (αβγ) receptor forms are functional and cause changes in the cell upon IL-2 binding. The IL-2R α chain is not involved in signaling. The β chain is complexed with Janus kinase 1 (JAK1). The 7 chain is complexed with JAK3. Upon IL-2 binding to IL-2R, JAK1 and JAK3 are activated and capable of adding phosphate groups to molecules, thus initiating three intracellular signaling pathways: the MAP kinase pathway, the Phosphoinositide 3-kinase (PI3K) pathway, and the JAK-STAT pathway.

"IL-2 protein" or "IL-2" described herein refers to IL-2 full length protein, fragment thereof, or variant thereof, that has IL-2 bioactivities, such as inducing effector T cell (CTL) expansion. The term "fragment" means any protein or polypeptide having the amino acid sequence of a portion or fragment of an IL-2 protein, and which has the biological activity of IL-2. Fragments include proteins or polypeptides produced by proteolytic degradation of an IL-2 protein as well as proteins or polypeptides produced by chemical synthesis by methods routine in the art.

"Parent IL-2 protein" or "parent IL-2" described herein refers to IL-2 protein reference sequence from which the modified IL-2 protein is engineered/modified. In some embodiments, the parent IL-2 protein is a wild-type IL-2 protein. In some embodiments, the parent IL-2 protein is derived from a mammal, including, but not limited to, human, bovine, horse, feline, canine, rodent, rabbit, or primate. In some embodiments, the parent IL-2 protein is a human IL-2 protein. In some embodiments, the parent IL-2 protein is a wild-type IL-2 protein, e.g., wild-type human IL-2 protein. In some embodiments, the parent IL-2 protein is a precursor IL-2 form. In some embodiments, the parent IL-2 protein is a mature IL-2 form. In some embodiments, the parent IL-2 protein is a human precursor IL-2 (SEQ ID NO: 23). In some embodiments, the parent IL-2 protein is can be found under Genbank under accession locator NP 000577.2. In some embodiments, the parent IL-2 protein is a human mature IL-2, In some embodiments, the parent IL-2 protein comprises amino acid sequence of SEQ ID NO: 24.

In some embodiments, the parent IL-2 protein is Aldesleukin (e.g., Proleukin®; SEQ ID NO: 1). Aldesleukin (desalanyl-1, serine-125 human interleukin-2) is an antineoplastic (anti-cancer) biologic response modifier approved by the FDA. It has a molecular weight of approximately 15,300 Daltons, and synonym recombinant interleukin-2 human, Interleukin-2 aldesleukin, 125-L-serine-2-133-interleukin 2 (human reduced), or Interleukin-2 (2-133), 125-ser. Hereinafter referred to as "IL-2 Aldesleukin." Aldesleukin is a recombinant IL-2, it differs from native IL-2 in the following ways: a) Aldesleukin is not glycosylated because it is produced from *E. coli*; b) Aldesleukin has no N-terminal alanine (A); c) Aldesleukin has a cysteine to serine substitution at position 125 (C125S); and d) the aggregation state of Aldesleukin is likely different from that of native IL-2. Thus in some embodiments, the parent IL-2 protein comprises a cysteine to serine substitution at position 125 (C125S) from the IL-2 mature form. In some embodiments, an unglycosylated parent human IL-2 has a molecular weight of about 15.3 kDa, FIG. 1 shows the sequence and structure of an exemplary IL-2 protein (Aldesleukin, SEQ ID NO: 1). In some embodiments, the parent IL-2 protein comprises an amino acid sequence of SEQ ID NO: 1. In some embodiments, the IL-2 protein is a protein or polypeptide substantially homologous to amino acid sequence of SEQ ID NO: 1, e.g., having at least about 85% (such as at least about any of 90%, 91%, 92%, 93%, 94%, 95%, 96%, 97%, 98%, 99%, or 100%) amino acid sequence identity to SEQ ID NO; 1.

The parent IL-2 protein can also be analogs contain from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The parent IL-2 protein can be natural or recombinantly produced. In some embodiments, the parent and/or modified IL-2 protein are glycosylated. In some embodiments, the parent and/or modified IL-2 protein are unglycosylated. In some embodiments, the parent and/or modified IL-2 protein contain other post-translational modification.

In some embodiments, the parent IL-2 protein is a mutant IL-2, such as IL-2 proteins comprising one or more of insertion(s), deletion(s), point mutation(s), and/or rearrangement(s), wherein the mutation is not the engineered Q residue. The mutant IL-2, or modified IL-2 proteins described herein, may comprise a mutation (e.g., non-naturally occurring mutation) in one or more domains or motifs selected from IL-2Rα binding domain, IL-2Rβ binding domain, $\gamma_c$ binding domain, amino acids in-between these binding domains, a helix region, random coil region, extended strand region, and any combinations thereof, wherein the mutation is not the engineered Q residue (see, e.g., FIG. 1). Parent IL-2 protein can be truncated versions, hybrid variants, peptide mimetics, biologically active fragments, deletion variants, substitution variants or addition variants that maintain at least some degree of IL-2 activity.

The parent IL-2 protein can be derived from human sources, animal sources, and plant sources. In some embodiments, the parent IL-2 protein or the modified IL-2 protein can be derived from recombinant methods. See, for example, U.S. Pat. No. 5,614,185, the disclosure and the Experiments provided herein. In some embodiments, the parent IL-2 protein is a recombinant IL-2 having comparable biological activity to native IL-2 prepared by recombinant DNA techniques as described, e.g., by Taniguchi et al., Nature, 302:305-310 (1983) and Devos, Nucleic Acids Research, 11:4307-4323 (1983). In general, the gene coding for modified IL-2 protein is constructed by PCR-mediated mutagenesis or general molecular cloning method, or in vitro synthesized, and inserted into a cloning vector to be cloned and then into an expression vector, which is used to transform a host organism, such as microorganism, e.g., *E. coli.*, or mammalian cells such as CHO cells. The host organism expresses the foreign gene to produce modified IL-2 protein under expression conditions.

Substantial identity of amino acid sequences means the sequences are identical or differ by one or more amino acid alterations (additions, substitutions) which do not cause an adverse functional dissimilarity between the synthetic protein and native human IL-2.

In some embodiments, the modified IL-2 protein is conjugated with an active moiety. In some embodiments, the active moiety is a non-IL-2 peptide or polypeptide. In some embodiments, the active moiety is a biocompatible polymer. In some embodiments, the active moiety is a cytotoxic agent, an immunosuppressive agent, or an imaging agent (e.g., a fluorophore). In some embodiments, the cytotoxic agent is a chemotherapeutic agent. In some embodiments, the active a moiety is any one of: a moiety that improves the pharmacokinetic property of the modified IL-2 protein, a therapeutic moiety, and a diagnostic moiety. In some embodiments, the active moiety is a small molecule. Examples of a cytotoxic agent include, but are not limited to, an anthracycline, an auristatin, a dolastatin, CC-1065, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof. Examples of an immunosuppressive agent include, but are not limited to, gancyclovier, etanercept, tacrolimus, sirolimus, voclosporin, cyclosporine, rapamycin, cyclophosphamide, azathioprine, mycophenolgate mofetil, methotrextrate, and glucocorticoid and its analogs. In some embodiments, the active moiety is an imaging agent (e.g., a fluorophore), such as fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). In some embodiments, the active moiety comprises a label such as a radioisotope. Examples of a radioisotope or other labels include, but are not limited to, 3H, 14C, 15N, 355, 18F, 32P, 33P, 64Cu, 68Ga, 89Zr, 90Y, 99Tc, 123I, 124I, 125I, 131I, 111In, 131In, 153Sm, 186Re, 188Re, 211At, 212Bi, and 153Pb.

Engineered Q Residue

In some embodiments, the engineered Q residue is within the IL-2Rα subunit binding domain. In some embodiments, the engineered Q residue is between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues.

The DNA sequence encoding the modified IL-2 protein comprising the engineered Q residue described herein can be constructed using PCR-assisted mutagenesis technique, regular molecular cloning techniques such as digestion and ligation, or by chemical synthesis.

In some embodiments, the engineered Q residue is (e.g., results from) a single amino acid mutation (insertion or substitution) relative to a parent IL-2 protein, such as IL-2 Aldesleukin comprising an amino acid sequence of SEQ ID NO: 1. In some embodiments, the engineered Q residue is within the IL-2Rα subunit binding domain, see underlined portion in FIG. 1. In some embodiments, the single amino acid mutation is (e.g., results from) a single amino acid substitution to Q. Any of the amino acid residue(s) within the IL-2Rα subunit binding domain can be mutated (substituted) to a Q residue. In some embodiments, the single amino acid mutation is an insertion of a Q residue. The insertion of a Q residue can be at any position(s) within the IL-2Rα subunit binding domain. For example, for IL-2 in FIG. 1, a Q residue can be inserted at any position within the underlined domain boundary. In some embodiments, the modified IL-2 protein comprises only one single amino acid mutation (insertion or substitution). In some embodiments, the modified IL-2 protein comprises two or more (such as two) single amino acid mutations (insertions, substitutions, or a combination thereof). For example, in some embodiments, two or more Q residues are inserted within the IL-2Rα subunit binding domain. In some embodiments, two or more amino acid residues within the IL-2Rα subunit binding domain (including the domain boundary) are substituted into Q residues. In some embodiments, the modified IL-2 protein comprises one or more Q residue(s) inserted within the IL-2Rα subunit binding domain, and one or more original amino acid residue(s) within the IL-2Rα subunit binding domain (including the domain boundary) substituted into a Q residue. In some embodiments, the engineered Q residue (single amino acid insertion or substitution) is proximal to the IL-2Rα subunit binding domain, such as between about 1 and about 3 amino acid residues (such as any of 1, 2, or 3 amino acid residues) outside of the IL-2Rα subunit binding domain. For example, in some embodiments, the modified IL-2 protein comprises one or more engineered Q residue (insertion or substitution) within the IL-2Rα subunit binding domain (including substitution on the domain boundary), and one or more engineered Q residue(s) (insertion or substitution) between about 1 and about 3 amino acid residues (e.g., any of 1, 2, or 3 amino acid residues) outside of the IL-2Rα subunit binding domain either on the N-terminal or C-terminal end. In some embodiments, the two or more engineered Q residues (insertion or substitution) are continuous. In some embodiments, the two or more engineered Q residues (insertion or substitution) are not continuous, such as interspersed by one or more original amino acid residues of the IL-2 protein.

In some embodiments, the single amino acid mutation of engineered Q residue is selected from the group consisting of F43Q, R37Q, F41Q, K42Q, Y44Q, T36Q, M38Q, and any combinations thereof, wherein the amino acid position is relative to a parent IL-2 protein comprising an amino acid sequence of SEQ ID NO: 1, e.g., IL-2 Aldesleukin. Thus in some embodiments, the modified IL-2 protein comprises a single amino acid mutation (substitution) of F43Q. In some embodiments, the modified IL-2 protein comprises an amino acid sequence of SEQ ID NO: 2. In some embodiments, the modified IL-2 protein comprises a single amino acid mutation (substitution) of R37Q. In some embodiments, the modified IL-2 protein comprises an amino acid sequence of SEQ ID NO: 4. In some embodiments, the modified IL-2 protein comprises a single amino acid mutation (substitution) of F41Q. In some embodiments, the modified IL-2 protein comprises an amino acid sequence of SEQ ID NO: 5. In some embodiments, the modified IL-2 protein comprises a single amino acid mutation (substitution) of K42Q. In some embodiments, the modified IL-2 protein comprises an amino acid sequence of SEQ ID NO: 6. In some embodiments, the modified IL-2 protein comprises a single amino acid mutation (substitution) of Y44Q. In some embodiments, the modified IL-2 protein comprises an amino acid sequence of SEQ ID NO: 7. In some embodiments, the modified IL-2 protein comprises a first single amino acid mutation (substitution) of R37Q, and a second single amino acid mutation (substitution) of Y44Q. In some embodiments, the modified IL-2 protein comprises an amino acid sequence of SEQ ID NO: 8.

In some embodiments, the engineered Q residue is part of an exogenous patch sequence suitable for Transglutaminase (TGase) reaction. For the purpose of this application, when a modified IL-2 protein comprises an engineered Q residue that is part of an exogenous patch sequence, the modified IL-2 protein comprises the exogenous patch sequence, and the engineered Q residue is one of the amino acid residues within the patch sequence. "Suitable for TGase reaction" as used herein means that with the introduction of the exogenous patch sequence comprising the engineered Q residue, a TGase is capable of catalyzing, for example, the formation of an isopeptide bond between γ-carboxamide groups (—(C═O)$NH_2$) of a protein/peptide (such as IL-2) bound Q residue side chain and a primary amine (R—$NH_2$, such as a PEG molecule containing a primary amine), with subsequent release of ammonia ($NH_3$). See exemplary Formula I.

Formula I

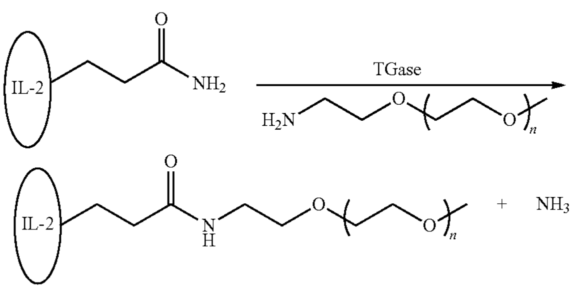

In some embodiments, the exogenous patch sequence comprising the engineered Q residue replaces a portion of a parent IL-2 protein sequence, such as wild-type IL-2, or IL-2 Aldesleukin comprising an amino acid sequence of SEQ ID NO: 1. In some embodiments, the exogenous patch sequence comprising the engineered Q residue is inserted into the a parent IL-2 protein sequence (such as IL-2 Aldesleukin of SEQ ID NO: 1). In some embodiments, the exogenous patch sequence comprising the engineered Q residue is introduced completely within the IL-2Rα subunit binding domain, either via insertion, or replacing a portion of the IL-2Rα subunit binding domain sequence. In some embodiments, after introducing into the IL-2 protein (insertion or replacement), the exogenous patch sequence comprising the engineered Q residue contains amino acid residue(s) (such as about 1, 2, 3, 4, or 5 amino acid residues) that are outside of the IL-2Rα subunit binding domain. For example, in some embodiments, an exogenous patch sequence of 6 amino acids long (e.g., XXXXQX (SEQ ID NO: 25), or QXXXXX (SEQ ID NO: 26), X can be any amino acid residue) replaces the "NYKNPK" sequence (SEQ ID NO: 27) in hIL-2 of SEQ ID NO: 1 (see FIG. 1), the 3 amino acids on the N-terminus of the exogenous patch sequence (e.g., XXX (SEQ ID NO: 28) or QXX (SEQ ID NO: 29)) will be outside of the IL-2Rα subunit binding domain. In some embodiments, after introducing the exogenous patch sequence comprising an engineered Q residue (insertion or replacement) into the IL-2 protein, the engineered Q residue is within the IL-2Rα subunit binding domain (including the domain boundary, such as the XXXXQX example above (SEQ ID NO: 25)). In some embodiments, after introducing the exogenous patch sequence comprising an engineered Q residue (insertion or replacement) into the IL-2 protein, the engineered Q residue is between about 1 to about 3 amino acids (such as about 1, 2, or 3 amino acids) outside of the IL-2Rα subunit binding domain (such as the QXXXXX example above (SEQ ID NO: 26)). In some embodiment, the exogenous patch sequence comprises two or more (such as two) engineered Q residues (e.g., QXXXQX (SEQ ID NO: 30), X can be any amino acid residue), after introducing the exogenous patch sequence (insertion or replacement) into the IL-2 protein, one or more engineered Q residue can be within the IL-2Rα subunit binding domain (including the domain boundary), and one or more engineered Q residue can be between about 1 to about 3 amino acids (such as about 1, 2, or 3 amino acids) outside of the IL-2Rα subunit binding domain. In some embodiments, the exogenous patch sequence is introduced outside (insertion or replacement, without overlap) of the IL-2Rα subunit binding domain, but the engineered Q residue contained therein is between about 1 to about 3 amino acids (such as about 1, 2, or 3 amino acids) outside of the IL-2Rα subunit binding domain.

In some embodiments, the modified IL-2 protein comprises one engineered Q residue that is part of one exogenous patch sequence. In some embodiments, the modified IL-2 protein comprises two or more (such as two) engineered Q residues that are part of one exogenous patch sequence. In some embodiments, the modified IL-2 protein comprises two or more (such as two) engineered Q residues, each is part of a different exogenous patch sequence. In some embodiments, the two or more (such as two) engineered Q residues within one exogenous patch sequence are continuous. In some embodiments, the two or more (such as two) engineered Q residues within one exogenous patch sequence are interspersed by other amino acid residues. In some embodiments, the modified IL-2 protein comprises two or more (such as two) exogenous patch sequences each comprising engineered Q residue(s). In some embodiments, the two or more (such as two) exogenous patch sequences are continuous (right next to each other). In some embodiments, the two or more (such as two) exogenous patch sequences are interspersed by other amino acid residues.

The exogenous patch sequence can be of any length between about 3 to about 10 amino acids (such as about any of 3, 4, 5, 6, 7, 8, 9, or 10 amino acids long). In some embodiments, the exogenous patch sequence comprising an engineered Q residue has a length of about 3 to about 9 amino acids, about 3 to about 8 amino acids, about 3 to about 7 amino acids, about 3 to about 6 amino acids, about 3 to about 5 amino acids, about 4 to about 9 amino acids, about 5 to about 8 amino acids, about 5 to about 7 amino acids, or about 6 amino acids.

The exogenous patch sequence can comprise one or more engineered Q residues (such as 1, 2, or 3 engineered Q residues) along the entire length of the exogenous patch sequence. In some embodiments, the exogenous patch sequence comprises 1 or 2 engineered Q residues. The engineered Q residue(s) can be at any position(s) of the exogenous patch sequence, such as on the N' terminus, C' terminus, and/or any position(s) in between. In some embodiments, the exogenous patch sequence is identical to the corresponding replacing portion of a parent IL-2 except for the engineered Q residue (substitution to Q or insertion of a Q). In some embodiments, the exogenous patch sequence comprises other mutations (e.g., insertion, deletion, or substitution) besides the engineered Q residue.

In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the exogenous patch sequence is LEEQAA (SEQ ID NO: 9). In some embodiments, the modified IL-2 protein comprises an amino acid sequence of SEQ ID NO: 15. In some embodiments, the exogenous patch sequence is IFKQTY (SEQ ID NO: 10). In some embodiments, the modified IL-2 protein comprises an amino acid sequence of SEQ ID NO: 3. In some embodiments, the exogenous patch sequence is PKEQKY. In some embodiments, the modified IL-2 protein comprises an amino acid sequence of SEQ ID NO: 16. In some embodiments, the exogenous patch sequence is VIQGV (SEQ ID NO: 12). In some embodiments, the modified IL-2 protein comprises an amino acid sequence of SEQ ID NO: 17. In some embodiments, the exogenous patch sequence is REEQFN (SEQ ID NO: 13). In some embodiments, the modified IL-2 protein comprises an amino acid sequence of SEQ ID NO: 18. In some embodiments, the exogenous patch sequence is GLLQGA (SEQ ID NO: 14). In some embodiments, the modified IL-2 protein comprises an amino acid sequence of SEQ ID NO: 19.

In some embodiments, the modified IL-2 protein comprises one or more engineered Q residue as single amino acid mutation (insertion or substitution), and one or more engineered Q residue that is part of an exogenous patch sequence.

In some embodiments, the modified IL-2 protein only consists an engineered Q residue mutation described herein, without any other mutations compared to parent IL-2 (e.g., wild-type IL-2, or IL-2 Aldesleukin). In some embodiments, the modified IL-2 protein described herein may further comprise one or more additional amino acid mutations (e.g., non-naturally occurring mutation, such as insertion, deletion, point mutation(s), and/or rearrangement) that are not engineered Q residues. The additional one or more mutations can be in one or more domains or motifs selected from IL-2Rα binding domain, IL-2Rβ binding domain, $\gamma_c$ binding domain, any amino acids in-between, a helix structure region, random coil structure region, extended strand structure region, and any combinations thereof. In some embodiments, the additional one or more mutations do not affect TGase reaction on the engineered Q residue.

In some embodiments, the modified IL-2 protein comprises an amino acid sequence having at least about 85% (such as at least about any of 86%, 87%, 88%, 89%, 90%, 91%, 92%, 93%, 94%, 95%, 96%, 97%, 98%, or 99%) identity to the parent IL-2 protein, such as a wild-type IL-2, or IL-2 Aldesleukin of SEQ ID NO: 1.

In some embodiments, the modified IL-2 protein can be further modified to include attachment of a functional group (other than through addition of a functional group-containing amino acid residue). For example, in some embodiments, the modified IL-2 protein can be further modified to include a thiol group. In some embodiments, the modified IL-2 protein can be further modified to include an N-terminal alpha carbon. In some embodiments, the modified IL-2 protein can be further modified to include one or more carbohydrate moieties. In some embodiments, the modified IL-2 protein can be further modified to include an aldehyde group. In some embodiments, the modified IL-2 protein can be further modified to include a ketone group.

In some embodiments, the modified IL-2 protein will be in a "monomer" form, wherein a single expression of the corresponding peptide is organized into a discrete unit. In other instances, the modified IL-2 protein will be in the form of a "dimer" (e.g., a dimer of recombinant IL-2) wherein two monomer forms of the protein are associated (e.g., by disulfide bonding) to each other. For example, in the context of a dimer of recombinant human IL-2, the dimer may be in the form of two monomers associated to each other by a disulfide bond formed from each monomer's Cys125 residue.

Binding Affinity to IL-2R Subunits of Modified IL-2 Protein Comprising an Engineered Q Residue Binding affinity can be indicated by $K_D$, $K_{off}$, $K_{on}$, or $K_a$. The term "$K_{off}$" of "$k_{off}$", as used herein, is intended to refer to the off rate constant for dissociation of a molecule (e.g., IL-2) from the molecule/binding partner complex (e.g., IL-2/IL-2R complex, or IL-2/IL-2R subunit complex), as determined from a kinetic selection set up. The term "$K_{on}$" or "$k_{on}$", as used herein, is intended to refer to the on rate constant for association of a molecule (e.g., IL-2) to its binding partner (e.g., IL-2R or subunits thereof) to form the molecule/binding partner complex (e.g., IL-2/IL-2R complex, or IL-2/IL-2R subunit complex). The term equilibrium dissociation constant "$K_D$" or "$K_d$", as used herein, refers to the dissociation constant of a particular molecule/binding partner interaction (e.g., IL-2/IL-2R interaction, or IL-2/IL-2R subunit interaction), and describes the concentration of a molecule (e.g., IL-2) required to occupy one half of all of the binding domains present in a solution of binding partner (e.g., IL-2R or subunits thereof) at equilibrium, and is equal to $K_{off}/K_{on}$. The measurement of $K_D$ presupposes that all binding agents are in solution. In the case where the binding partner (e.g., IL-2R) is tethered to a cell wall, e.g., in a yeast expression system, the corresponding equilibrium rate constant is expressed as EC50, which gives a good approximation of $K_D$. The affinity constant, $K_a$, is the inverse of the dissociation constant, $K_D$. Any suitable ligand binding assays or antibody/antigen binding assays known in the art can be used to measure binding affinity, e.g., RIA, SPR, Biacore assay, Octet analysis, etc. Also see Example 7.

The dissociation constant ($K_D$) is used as an indicator showing affinity of a molecule (e.g., IL-2) to its binding partner (e.g., IL-2R or subunits thereof). For example, easy analysis is possible by using IL-2 or IL-2R (or subunits thereof) marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols). An IL-2 that specifically binds to IL-2R (or subunits thereof) may have a dissociation constant ($K_D$) of, for example, $\leq 10^{-5}$ M (10 μM), $\leq 10^{-6}$ M (1 μM), $\leq 10^{-7}$ M (100 nM), $\leq 10^{-8}$ M (10 nM), $\leq 10^{-9}$ M (1 nM), $\leq 10^{-10}$ M (100 μM), or $\leq 10^{-11}$ M (10 μM).

Binding affinity of a molecule (e.g., IL-2) and its binding partner (e.g., IL-2R or subunits thereof) can be determined experimentally by methods known in the art. Such methods comprise, but are not limited to Western blots, ELISA-, RIA-, ECL-, IRMA-, EIA-, BIAcore-tests, Surface Plasma Resonance (SPR), Octet, and peptide scans. Also see Example 1 for exemplary binding affinity measuring method using SPR (Biacore T-200). Briefly, anti-human antibody is coupled to the surface of a CM-5 sensor chip using EDC/NHS chemistry. Then either human IL-2Rα-Fc or IL-2RP-Fc fusion protein is used as the captured ligand over this surface. Serial dilutions of modified IL-2 protein (or parent IL-2 as control) are allowed to bind to the ligands, and the response units (RU) bound is plotted against IL-2 concentration to determine EC50 values. The affinities of each test IL-2 protein to each IL-2R subunit are calculated as fold change relative to those of parent IL-2 protein (e.g., wild-type IL-2, or IL-2 Aldesleukin).

In some embodiments, the $K_D$ of the binding between a parent IL-2 (e.g., a wild-type IL-2 or IL-2 Aldesleukin) and an IL-2Rα subunit is about 10 nM to about 50 nM, such as about 10 nM to about 20 nM, about 20 nM to about 40 nM, about 10 nM to about 15 nM, about 36.1 nM, about 14.5 nM, or about 10 nM. In some embodiments, the $K_D$ of the binding is measured by SPR.

In some embodiments, the modified IL-2 protein has reduced binding affinity to IL-2Rα subunit compared to a parent IL-2 protein (e.g., wild-type IL-2, human IL-2, or IL-2 Aldesleukin), such as about 2 to about 800 folds (e.g., about 2 to about 50 folds) reduction. Thus in some embodiments, the $K_D$ of the binding between the modified IL-2 protein and an IL-2Rα subunit is about 2 to about 800 times (e.g., about 5-6 times, about 38-39 times, about 2 to about 50 times, about 400 to about 500 times, or about 476 times) of the $K_D$ of the binding between a parent IL-2 protein (e.g., wild-type IL-2, human IL-2, or IL-2 Aldesleukin) and the IL-2Rα subunit, such as any of about 2 to about 50 times, about 2 to about 10 times, about 10 to about 50 times, about 20 to about 45 times, about 30 to about 40 times, about 40 to about 50 times, about 50 to about 100 times, about 100 to about 500 times, about 100 to about 800 times, about 200 to about 700 times, about 300 to about 600 times, about 400 to about 500 times, or about 450 to about 500 times of the $K_D$ of the binding between parent IL-2 protein (e.g., wild-type IL-2, human IL-2, or IL-2 Aldesleukin) and IL-2Rα subunit. In some embodiments, the $K_D$ of the binding between the modified IL-2 protein and an IL-2Rα subunit is about 20 nM to about 100 μM, such as any of about 20 nM to about 1000 nM, about 50 nM to about 100 PM, about 1 μM to about 100 μM, about 1 μM to about 10 μM, about 10 μM to about 100 μM, about 1 μM to about 50 μM, about 10 μM to about 20 μM, about 17.2 μM, about 20 nM to about 100 nM, about 100 nM to about 1000 nM, about 200 nM to about 900 nM, about 300 nM to about 800 nM, about 200 nM to about 600 nM, about 400 nM to about 700 nM, about 500 nM to about 1000 nM, about 500 nM to about 600 nM, about 560 nM, or about 81 nM. In some embodiments, the $K_D$ of the binding is measured by SPR.

In some embodiments, the modified IL-2 protein also has reduced binding affinity to the IL-2R complex formed by all three subunits ("IL-2R αβγ complex") compared to a parent IL-2 (e.g., wild-type IL-2, or IL-2 Aldesleukin). In some embodiments, the modified IL-2 protein has both reduced binding affinity to an IL-2Rα subunit (e.g., about 2 to about 800 folds reduction) and an IL-2R αβγ complex compared to a parent IL-2 (e.g., wild-type IL-2, or IL-2 Aldesleukin).

In some embodiments, the $K_D$ of the binding between a parent IL-2 protein (e.g., wild-type IL-2, or IL-2 Aldesleukin) and an IL-2Rβ subunit is about 100 nM to about 20 PM, such as any of about 100 nM to about 500 nM, about 400 nM to about 20 PM, about 500 nM to about 1000 nM, about 1 μM to about 20 μM, about 1 μM to about 10 μM, about 100 nM to about 200 nM, about 300 nM to about 500 nM, about 200 nM to about 400 nM, about 536 nM, about 144 nM, or about 410 nM.

In some embodiments, the modified IL-2 protein has similar (e.g., equal) or about 1 to about 30 folds (e.g., about 1 to about 10 times, about 10 to about 20 times, or about 16 times) reduced binding affinity to an IL-2Rβ subunit compared to a parent IL-2 (e.g., wild-type IL-2, human IL-2, or IL-2 Aldesleukin). Thus in some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, about 16 times, about 1.4 times, or about 6.7 times) of the $K_D$ of the binding between parent IL-2 (e.g., wild-type IL-2, or IL-2 Aldesleukin) and IL-2Rβ subunit, such as identical to, about 1 to about 1.1 times, about 1 time to about 2 times, about 2 times to about 30 times, about 2 times to about 10 times, about 10 to about 20 times, about 16 times, the $K_D$ of the binding between a parent IL-2 (e.g., wild-type IL-2, human IL-2, or IL-2 Aldesleukin) and IL-2Rβ subunit. Thus in some embodiments, the $K_D$ of the binding between the modified IL-2 protein and an IL-2Rβ subunit is about 100 nM to about 50 μM, such as about 400 nM to about 50 μM, about 400 nM to about 3000 nM, about 1 μM to about 50 μM, about 10 μM to about 50 μM, about 1 μM to about 10 μM, about 100 nM to about 800 nM, about 400 nM to about 1000 nM, about 1000 nM to about 3000 nM, about 2000 nM to about 5000 nM, about 400 nM to about 3000 nM, about 8.39 μM, about 579 nM, or about 2751 nM.

In some embodiments, the modified IL-2 protein has reduced binding affinity to an IL-2Rα subunit (e.g., about 2 to about 800 folds or about 2 to about 50 folds reduction), but has similar (e.g., equal) or about 1 to about 30 folds (e.g., about 1 to about 10 folds) reduced binding affinity to an IL-2Rβ subunit compared to a parent IL-2 (e.g., wild-type IL-2, or IL-2 Aldesleukin). Thus in some embodiments, the $K_D$ of the binding between the modified IL-2 protein and an IL-2Rα subunit is about 2 to about 800 times (e.g., about 2 to about 50 times, about 400 to about 500 times, or about 476 times, about 5 to about 6 times, or about 38 to about 39 times) of the $K_D$ of the binding between a parent IL-2 protein (e.g., wild-type IL-2, or IL-2 Aldesleukin) and the IL-2Rα subunit, and the $K_D$ of the binding between the modified IL-2 protein and an IL-2Rβ subunit is similar to (e.g., equal to) or about 1 to about 30 times (such as identical to, about 1 to about 1.1 times, about 1 time to about 2 times, about 2 times to about 10 times, about 2 times to about 30 times, about 10 to about 20 times, or about 16 times) of the $K_D$ of the binding between a parent IL-2 protein (e.g., wild-type IL-2, or IL-2 Aldesleukin) and IL-2Rβ subunit.

Bioactivity of Modified IL-2 Protein Comprising an Engineered Q Residue

Resting T cells and NK cells only express the IL-2Rβ and the IL-2Rγ. Activated T cells and Treg cells express IL-2Rα, IL-2Rβ, and IL-2Rγ, and have high affinity to IL-2. The intermediate (βγ) and high affinity (αβγ) receptor forms are functional and cause changes in the cell upon IL-2 binding. The β chain is complexed with Janus kinase 1 (JAK1). The 7 chain is complexed with JAK3. Upon IL-2 binding to IL-2R, JAK1 and JAK3 are activated and capable of adding phosphate groups to molecules, thus initiating three intracellular signaling pathways: the MAP kinase pathway, the Phosphoinositide 3-kinase (PI3K) pathway, and the JAK-STAT pathway.

Various methods for determining the in vitro IL-2 activity are described in the art. An exemplary approach is the CTTL-2 cell proliferation assay described below (also see Example 3). CTLL-2 is C57BL/6 mouse cytotoxic T lymphocyte cell line with high expression of IL-2Rα on cell surface. Briefly, CTTL-2 cells are cultured, then incubated with various concentrations of modified IL-2 proteins or modified IL-2 protein-PEG conjugates described herein. Parent IL-2 (e.g., wild-type IL-2, or IL-2 Aldesleukin) serves as control. Following sufficient (e.g., 44 hr) incubation, Resazurin is added into each well of reaction and allowed for incubation. Luminescence is then recorded at an integration time of one second/well. The EC50 values (concentration of test compounds required to exhibit 50% of maximal response) for cell proliferation can then be obtained from non-linear regression analysis of dose-response curves. Another exemplary approach is described in Moreau et al. (1995) Mol. Immunol. 32:1047-1056). Briefly, in a non-specific binding assay, modified IL-2 protein or modified IL-2 protein-PEG conjugate described herein is allowed to pre-incubate for one hour at 4° C. in the presence of a cell line bearing a receptor of IL-2 (e.g., CTTL-2). Thereafter, $^{125}$I-labelled IL-2 is allowed to incubate in the system for three hours at 4° C. Data is expressed as % inhibitory capacity of the proposed IL-2 moiety activity versus parent IL-2 (e.g., wild-type IL-2, or IL-2 Aldesleukin). Other methodologies known in the art can also be used to assess IL-2 function, including electrometry, spectrophotometry, chromatography, and radiometric methodologies.

STAT5 and ERK1/2 signaling can also be measured to reflect IL-2 bioactivity, for example, by phosphorylation of STAT5 and ERK1/2 using any suitable method known in the art. For example, STAT5 and ERK1/2 phosphorylation can be measured using antibodies specific for the phosphorylated version of these molecules in combination with flow cytometry analysis. For example, freshly isolated PBMCs are incubated for 20 min at 37° C. with modified IL-2 protein. After incubation, cells are immediately fixed with Cytofix buffer (BD Bioscience) for 10 min at 37° C. to preserve the phosphorylation status and permeabilized with Phosflow Perm buffer III (BD Bioscience) for 30 min at 4° C. The cells are stained with antibodies against phosphorylated STAT5 or ERK1/2, e.g., Alexa647 conjugated anti-STAT5 pY694 (BD Biosciences, San Jose, Calif.), or Alexa488-conjugated anti-ERK1/2 pT202/pY204 (BD Biosciences), and analyzed by flow cytometry. Alternatively, IL-2 test samples (e.g., modified IL-2 protein or modified IL-2 protein-PEG conjugate described herein) can be injected i.p. into mice, then total splenocytes can be isolated, immediately fixed using BD Phosphoflow™ Lyse/Fix buffer, washed twice with ice cold PBS, stained using anti-CD4 and anti-CD25 antibodies (Biolegend), and then permeabilized using BD PhosFlow Perm Buffer III for 30 min on ice in the dark. Cells are then washed twice with ice-cold FACS buffer, stained with anti-FoxP3 per the manufacturer's protocol (eBioscience), washed twice with ice-cold FACS buffer, and stained with anti-phospho-STAT5-PE (1:30) (BD) at room temperature for 30 min in the dark. Cells are washed three times with FACS buffer, then data can be acquired on a FACS Canto flow cytometer (BD) and analyzed using FlowJo (Tree Star).PI 3-kinase signaling can be measured using any suitable method known in the art to reflect IL-2 bioactivity, too. For example, PI 3-kinase signaling can be measured using antibodies that are specific for phospho-S6 ribosomal protein in conjunction with flow cytometry analysis.

IL-2 bioactivity can also be reflected by in vivo or ex vivo experiments, for example, by measuring the proliferation of CD8+ and/or NK cells relative to Tregs after administering or incubating with IL-2 test sample (e.g., modified IL-2 protein or modified IL-2 protein-PEG conjugate described herein); or by measuring tumor volume reduction in tumor xenograft mice after injecting IL-2 test sample (e.g., modified IL-2 protein or modified IL-2 protein-PEG conjugate described herein). Also see Examples 4 and 5.

In some embodiments, the modified IL-2 protein described herein is capable of activating an immune cell. "Capable of activating an immune cell" described herein refer to the ability of inducing IL-2 dependent immune cell proliferation (e.g., NK cell, CD8+ T cell), and/or the ability of activating immune cells such as inducing STAT5 phosphorylation, ERK1/2 phosphorylation, or stimulating PI 3-kinase signaling. In some embodiments, the immune cell is selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 proteins have reduced ability (such as about 2 to about 50 folds or about 2 to about 15 folds reduced ability) in activating a Treg compared to a parent IL-2 protein (e.g., wild-type IL-2, or IL-2 Aldesleukin). In some embodiments, the modified IL-2 protein has similar (e.g., equal) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 proteins have reduced ability (such as about 2 to about 50 folds or about 2 to about 15 folds reduced ability) in activating a Treg compared to a parent IL-2 protein (e.g., wild-type IL-2, or IL-2 Aldesleukin), and have similar (e.g., equal to) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 protein described herein has an enhanced capability to induce the proliferation of CD8+ T cells and/or NK cells relative to that of Treg cells, compared to parent IL-2 (e.g., wild-type IL-2. hIL-2, or IL-2 Aldesleukin). See FIG. 6B for example. In some embodiments, the modified IL-2 protein described herein has an enhanced capability to induce differentiation of Tregs compared to parent IL-2 (e.g., wild-type IL-2. hIL-2, or IL-2 Aldesleukin).

In some embodiments, the bioactivity of modified IL-2 proteins and modified IL-2 protein-PEG conjugates described herein is measured by IL-2 dependent CTLL-2 cell proliferation assay. See, e.g., Example 3. In some embodiments, the EC50 of parent IL-2 protein (e.g., wild-type IL-2, or IL-2 Aldesleukin) is about 65.4 nM to about 654 nM, such as about 100 nM to about 500 nM, about 200 nM to about 400 nM, or about 242 nM. In some embodiments, the EC50 of modified IL-2 proteins is about 200 nM to about 2000 nM, such as about 200 nM to about 1000 nM, about 400 nM to about 1500 nM, about 1000 nM to about 2000 nM, about 500 nM to about 900 nM, or about 889 nM.

In some embodiments, the modified IL-2 protein described herein has a reduced capability (e.g., about 1 to about 200 folds reduced capability) to stimulate STAT5 phosphorylation in an IL-2Rα+ T cell (e.g., Treg cell) as compared to parent IL-2 (e.g., wild-type IL-2. hIL-2, or IL-2 Aldesleukin). In some embodiments, the modified IL-2 protein described herein has a reduced capability (e.g., about 1 to about 200 folds reduced capability) to stimulate the pERK1/ERK2 signaling in an IL-2Rα+ T cell (e.g., Treg cell) as compared to parent IL-2 (e.g., wild-type IL-2. hIL-2, or IL-2 Aldesleukin). In some embodiments, the IL-2Rα+ T cell is a Treg cell.

Pharmacokinetic Profiles of Modified IL-2 Protein

Pharmacokinetics (PK) refers to the absorption, distribution, metabolism, and excretion of a drug (e.g., modified IL-2 protein, or pegylated modified IL-2 protein) once it has been administered to a subject. Pharmacokinetic parameters that may be useful in determining clinical utility include but are not limited to serum concentration, serum concentration over time, maximum serum concentration ($C_{max}$), time to reach maximum concentration ($T_{max}$), elimination half-life ($t_{1/2}$), area under concentration time curve within the dosing interval ($AUC_\tau$), etc.

Techniques for obtaining a PK curve of a drug, such as modified IL-2 proteins or pegylated modified IL-2 proteins described herein, or a reference drug (e.g., IL-2 Aldesleukin), are known in the art. See, e.g., Heller et al., *Annu Rev Anal Chem,* 11, 2018; and Ghandforoush-Sattari et al., *J Amino Acids*, Article ID 346237, Volume 2010. In some embodiments, the PK curves of the modified IL-2 proteins or pegylated modified IL-2 proteins described herein in the individual is measured in a blood, plasma, or serum sample from the individual. In some embodiments, the PK curves of the modified IL-2 proteins or modified IL-2 protein-PEG conjugates described herein in the individual is measured using a mass spectrometry technique, such as LC-MS/MS, or ELISA. PK analysis on PK curves can be conducted by any methods known in the art, such as non-compartmental analysis, e.g., using PKSolver V2 software (Zhang Y. et al., "PKSolver: An add-in program for pharmacokinetic and pharmacodynamic data analysis in Microsoft Excel," Comput Methods Programs Biomed. 2010; 99(3):306-1). Also see Examples 6 and 8 for exemplary methods.

"C" denotes the concentration of drug (e.g., modified IL-2 protein, or pegylated modified IL-2 protein) in blood plasma, serum, or in any appropriate body fluid or tissue of a subject, and is generally expressed as mass per unit volume, for example nanograms per milliliter. For convenience, the concentration of drug in serum is referred to herein as "serum concentration." The serum concentration at any time following drug administration (e.g., modified IL-2 protein, or pegylated modified IL-2 protein, such as i.v. or s.c. administration) is referenced as $C_{time}$ or $C_t$. The maximum serum drug concentration during the dosing period is referenced as $C_{max}$, while $C_{min}$ refers to the minimum serum drug concentration at the end of a dosing interval; and Cave refers to an average concentration during the dosing interval.

The term "bioavailability" refers to an extent to which- and sometimes rate at which the drug (e.g., modified IL-2 protein, or pegylated modified IL-2 protein) enters systemic circulation, thereby gaining access to the site of action.

"AUC" is the area under the serum concentration-time curve and is considered to be the most reliable measure of bioavailability, such as area under concentration time curve within the dosing interval ($AUC_t$), "overall exposure" or "total drug exposure across time" ($AUC_{0\text{-}last}$ or $AUC_{0\text{-}inf}$), area under concentration time curve at time t post-administration ($AUC_{0\text{-}t}$), etc.

Serum concentration peak time ($T_{max}$) is the time when peak serum concentration ($C_{max}$) is reached after administration of a drug (e.g., modified IL-2 protein, or pegylated modified IL-2 protein).

Half-life ($t_{1/2}$) is the amount of time required for the drug concentration (e.g., modified IL-2 protein, or pegylated modified IL-2 protein) measured in plasma or serum (or other biological matrices) to be reduced to exactly half of its concentration or amount at certain time point. After IV dosing, the drug concentrations in plasma or serum decline due to both distribution and elimination. In a plasma or serum profile of drug concentration over time post-IV doing, the first phase or rapid decline is considered to be primarily due to distribution, while the later phase of decline is usually slower and considered to be primarily due to elimination, although both processes occur in both phases. Distribution is assumed to be complete after sufficient time. In general, the elimination half-life is determined from the terminal or elimination (dominant) phase of the plasma/serum concentration versus time curve. See, e.g., Michael Schrag and Kelly Regal, "Chapter 3—Pharmacokinetics and Toxicokinetics" of "A Comprehensive Guide to Toxicology in Preclinical Drug Development", 2013.

In some embodiments, the modified IL-2 protein described herein has a half-life (e.g., elimination half-life or distribution half-life) of about 0.1 hr to about 10 hrs, such as about 0.1 hr to about 1 hr, about 0.5 hr to about 5 hrs, about 1 hr to about 10 hrs, or about 3 hrs to about 10 hrs. In some embodiments, the half-life of the modified IL-2 protein described herein is about 7.3 hrs, or about 0.1 hr to about 0.5 hr. In some embodiments, the modified IL-2 protein described herein is administered in a single intravenous injection (e.g., at about 2 mg/kg). In some embodiments, the circulating half-life of the parent IL-2 protein and/or modified IL-2 protein described herein is about 80 min.

In some embodiments, the modified IL-2 protein described herein when administered in a single intravenous injection provides for a $T_{max}$ shorter than that when administered in a single subcutaneous injection.

In some embodiments, the modified IL-2 protein described herein when administered in a single intravenous injection or a single subcutaneous injection (e.g., at about 2 mg/kg) provides for a maximum serum concentration ($C_{max}$) of between about 0.05 μg/mL to about 100 μg/mL, such as about 1 μg/mL to about 10 μg/mL, or about 10 μg/mL to about 100 μg/mL. In some embodiments, the modified IL-2 protein described herein when administered in a single intravenous injection provides for a $C_{max}$ higher than that when administered in a single subcutaneous injection.

In some embodiments, the modified IL-2 protein described herein when administered in a single intravenous injection (e.g., at about 2 mg/kg) provides for an $AUC_{0\text{-}last}$ or $AUC_{0\text{-}inf}$ of between about 0.5 hr·μg/mL to about 20 hr·μg/mL, such as about 0.5 hr·μg/mL to about 5 hr·μg/mL, about 1 hr·μg/mL to about 10 hr·μg/mL, or about 5 hr·μg/mL to about 20 hr·μg/mL.

In some embodiments, $AUC_{0\text{-}last}$ or $AUC_{0\text{-}inf}$ of the modified IL-2 protein described herein is about 5.3 hr·μg/mL. In some embodiments, the modified IL-2 protein described herein when administered in a single intravenous injection provides for an overall exposure ($AUC_{0\text{-}last}$) bigger than that when administered in a single subcutaneous injection.

Modified IL-2 Proteins Conjugated with a Polyethylene Glycol (PEG) Moiety

In some embodiments, the modified IL-2 protein described herein is conjugated with a PEG moiety via the engineered Q residue (also referred to as "modified IL-2 protein-PEG conjugate"). The description of the modified IL-2 proteins above is also applicable to the modified IL-2 protein contained within the PEG-modified IL-2 protein described herein. In some embodiments, the modified IL-2 protein-PEG conjugate has reduced binding affinity to IL-2Rα subunit unit, while retain or have slightly affected binding affinity to IL-2Rβ subunit, compared to parent IL-2 protein (e.g., wild-type IL-2, human IL-2, or IL-2 Aldesleukin). In some embodiments, the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin).

In some embodiments, all engineered Q residues of the modified IL-2 protein are each conjugated with one PEG moiety. In some embodiments, the modified IL-2 protein comprises two or more (e.g., 2) engineered Q residues, but not all engineered Q residues are each conjugated with one PEG moiety. In some embodiments, at least about 50% (such as at least about any of 60%, 70%, 80%, 90%, 95%, 96%, 97%, 98%, or 99%) of the engineered Q residues are each conjugated with one PEG moiety. In some embodiments, the molar ratio of the PEG moiety and the engineered Q residue on the PEG-modified IL-2 is about 1:1, about 1:2, about 1:3, about 1:4, about 1:6, about 1:6, about 1:7, about 1:8, about 1:9, or about 1:10. In some embodiments, the PEGylation (i.e., conjugation of a PEG moiety to the modified IL-2 protein) only occurs between a PEG moiety and the engineered Q residue. In some embodiments, the PEGylation also occurs on endogenous Q residue of the modified IL-2 protein. In some preferred embodiments, the modified IL-2 protein-PEG conjugate comprises a PEG moiety conjugated to the modified IL-2 protein only via the engineered Q residue but not endogenous Q residue of the modified IL-2 protein.

Polyethylene Glycol (PEG) Moiety

PEG is a non-antigenic, inert polymer that significantly prolongs the length of time a protein circulates in the body. This allows the protein to be effective for a longer period of time. Covalent modification of proteins with PEG has proven to be a useful method to extend the circulating half-lives of proteins in the body (Abuchowski et al., 1984; Hershfield, 1987; Meyers et al., 1991). Covalent attachment of PEG to a protein increases the protein's effective size and reduces its rate of clearance rate from the body. PEGs are commercially available in several sizes, allowing the circulating half-lives of PEG-modified proteins to be tailored for individual indications through use of different size PEGs. Other benefits of PEG modification include an increase in protein solubility, an increase in vivo protein stability and a decrease in protein immunogenicity (Katre et al., 1987; Katre, 1990).

PEG described herein encompass any nonpeptidic water-soluble poly(ethylene oxide). Typically, PEGs for use in accordance with the invention comprise the following structure "$-(OCH_2CH_2)_n-$" where (n) is 2 to 4000. As used herein, PEG also includes "$-CH_2CH_2-O(CH_2CH_2O)_n-CH_2CH_2-$" and "$-(OCH_2CH_2)_nO-$," depending upon whether or not the terminal oxygens have been displaced, e.g., during a synthetic transformation.

Without wishing to be bound by any theory or mechanism of action, the long, chain-like PEG polymer is believed to be heavily hydrated and in rapid motion when in an aqueous medium. This rapid motion is believed to cause the PEG to sweep out a large volume and prevents the approach and interference of other molecules. As a result, when attached to another chemical entity (such as a polypeptide), PEG polymer chains can protect such chemical entity from immune response and other clearance mechanisms. As a result, pegylation (i.e., covalent addition of PEG) can lead to improved drug efficacy and safety by optimizing pharmacokinetics, increasing bioavailability, and decreasing immunogenicity and dosing frequency. "PEGylation" refers in the customary sense to conjugation (i.e., chemical bonding) of a PEG molecule with another compound (e.g., modified IL-2 protein). For example, attachment of PEG has been shown to protect proteins against proteolysis. See e.g., Blomhoff, H. K. et al., 1983, *Biochim Biophys Acta,* 757:202-208. Unless expressly indicated to the contrary, the terms "PEG," "polyethylene glycol polymer" and the like refer to polyethylene glycol polymer and derivatives thereof, including methoxy-PEG (mPEG).

Typically, PEG is activated to possess a reactive group (e.g., amine) appropriate for coupling to a desired site on the modified IL-2 (e.g., the engineered Q residue). Methods for conjugating PEG to a reactive group is known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) Advanced Drug Reviews 16:157-182. In some embodiments, the "PEG moiety" can comprise an amine donor group (e.g., primary amine $-NH_2$), an optional linker, and a PEG molecule. In some embodiments, the PEG moiety is amino-(optional linker)-$(CH_2CH_2O)_n$, wherein n is an integer of at least 1. The amine donor group in some embodiments is a primary amine ($-NH_2$) that provides a substrate for transglutaminase to allow conjugation of the PEG molecule to the modified IL-2 protein via the engineered Q residue. Accordingly, the linkage between the engineered Q residue and the amine donor group can be of the formula $-CH_2-CH_2-CO-NH-$. In some embodiments, the PEG moiety can be $NH_2$-(linker)-PEG, $NH_2-NH$-(linker)-PEG, or $NH_2-O$-(linker)-PEG. In some embodiments, the PEG moiety is methoxy-PEG-amine (mPEG-amine). Other exemplary amine donor group-linkers include, but are not limited to, Ac-Lys-Gly, aminocaproic acid, Ac-Lys-beta-Ala, Ac-Lys-Val (valine)-Cit (citrulline)-PABC (p-aminobenzyloxycarbonyl), aminocaproyl-Val-Cit-PABC, putrescine, and Ac-Lys-putrescine.

In some embodiments, the linker is a non-cleavable linker. In some embodiments, the linkers include, but are not limited to, $NH_2-R$-PEG, $NH_2NH-R$-PEG, and $NH_2-O-R$-PEG. In some embodiments, R is alkyl. In some embodiments, the PEG molecule and the engineered Q residue are linked through a cleavable linker. Suitable cleavable linkers include, but are not limited to Lys-Phe-PEG or Lys-Val-Cit-PABC-PEG. PABC refers to p-aminobenzyloxycarbonyl. Cit refers to citrulline.

In some embodiments, the PEG moiety is linked to the acceptor glutamine residue via a $-NH-(C)_n-$ linker, wherein the $(C)_n$ is a substituted or unsubstituted alkyl or heteroalkyl chain, wherein n is an integer from about 1 to about 60. In some embodiments, the carbon of the chain is substituted with an alkoxyl, hydroxyl, alkylcarbonyloxy, alkyl-S-, thiol, alkyl-C(O)S—, amine, alkylamine, amide, or alkylamide. In some embodiments, n is about 2 to about 20.

In some embodiments, the optional linker is branched. In some embodiments, the linker is linear. In some embodiments, the optional linker has more than one (such as 2, 3, 4, 5, 6, 7, 8, 9, 10, 11, 12, 13, 14, 15, 16, 17, 18, 19, 20, or more) attachment sites for the attachment of a PEG moiety. These active moieties can be the same or different from each other. For example, the PEG moiety may comprise a polyacetal- or polyacetal derivative-based polymer linked to a plurality of PEG molecules.

In some embodiments, when a two-step conjugation method is performed as described herein (e.g., see FIG. 9 and "Conjugation of a PEG moiety to an engineered Q residue" subsection below), the PEG moiety comprises a linker and a PEG molecule, wherein the linker is a binding partner to the R ligand within the small molecule handle $NH_2$—R (see "small molecule handle" subsection below). This allows attachment of any PEG moiety that contains the binding partner. Suitable ligand/binding partner pairs include, but are not limited to, antibody/antigen, antigen/antibody, avidin/biotin, biotin/avidin, streptavidin/biotin, biotin/streptavidin, glutathione/GST, GST/glutathione, maltose binding protein/amylose, amylose/maltose binding protein, cellulose binding protein and cellulose, cellulose/cellulose binding protein, etc.

In some embodiments, the PEG moiety comprises between about 2 to about 300 termini. In some embodiments, the PEG moiety is end capped, e.g., alkoxy PEG or a bifunctional PEG. In some embodiments, the PEG moiety is linear. In some embodiments, the PEG moiety is branched or multi-armed (e.g., forked PEG or PEG attached to a polyol core), a dendritic (or star) architecture, each with or without one or more degradable linkages. The internal structure of the PEG moiety can be organized in any number of different repeat patterns and can be selected from the group consisting of homopolymer, alternating copolymer, random copolymer, block copolymer, alternating tripolymer, random tripolymer, and block tripolymer.

In some embodiments, PEG moiety is terminally capped with an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer (e.g., the end-capping moiety "methoxy" in $CH_3O(CH_2CH_2O)_n$— and $CH_3(OCH_2CH_2)_n$—). In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin. The end-capping group may also include a targeting moiety, such that the polymer—as well as anything, e.g., modified IL-2 protein, attached thereto—can preferentially localize in an area of interest. In some embodiments, the end-capping moiety is methoxy. In some embodiments, the PEG moiety is methoxy-PEG-amine. In some embodiments, the PEG moiety is methoxy-PEG-amine of about 20 kDa, about 30 kDa, or about 40 kDa. In some embodiments, the PEG moiety is X-$(PEG)_n$-$NH_2$, wherein n is an integer of 5-100, X is a functional group selected from methoxy group, acetaldehyde, aminooxy, propionaldehyde, N-hydroxysuccinimide, thiol, maleimide, iodoacetamide, azide, alkyne, DBCO, etc.

As customary in the art, the size of a PEG moiety is indicated by reference to the nominal molecular weight, typically provided in kilo Daltons (kDa). The molecular weight is calculated in a variety of ways known in the art, including number, weight, viscosity and "Z" average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention, e.g. PEG moieties, are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03. It is understood that polymers, such as PEG and the like, exist as a distribution of molecule weights about a nominal average value. Exemplary of the terminology for molecular weight for PEGs, the term "PEG20KD" or "20 kDa PEG" refers to a polyethylene glycol polymer having a nominal molecular weight of 20 kilo Daltons. Similarly for 30 kDa PEG or 40 kDa PEG.

In some embodiments, the PEG moiety has a molecular weight in the range of about 5 kDa to about 50 kDa, such as any of about 6 kDa to about 40 kDa, about 7 kDa to about 30 kDa, about 8 kDa to about 25 kDa, about 9 kDa to about 20 kDa, about 10 kDa to about 15 kDa, about 10 kDa to about 20 kDa, about 10 kDa to about 30 kDa about 10 kDa to about 40 kDa, about 20 kDa to about 40 kDa, or about 10 kDa to about 50 kDa. In some embodiments, the PEG moiety has a molecular weight of about any of 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, or about 50 kDa. In some embodiments, the PEG moiety has a molecular weight of about 20 kDa or about 40 kDa.

When used as the polymer, PEGs will typically comprise a number of $(OCH_2CH_2)$ monomers (or $(CH_2CH_2O)$ monomers, depending on how the PEG is defined). As used throughout the description, the number of repeating units is identified by the subscript "n" in "$(OCH_2CH_2)_n$." Thus, the value of (n) typically falls within about 50 to about 2000, such as any of about 60 to about 1800, about 70 to about 1500, about 80 to about 1500, about 100 to about 1500, about 500 to about 1200, about 500 to about 1000, about 100 to about 1000, about 100 to about 500, about 50 to about 100, or about 600 to about 800.

Binding Affinity to IL-2R Subunits of Modified IL-2 Protein-PEG Conjugates

The binding affinity of modified IL-2 protein-PEG conjugates described herein can be measured by any methods described in the above "binding affinity to IL-2R subunits of modified IL-2 protein comprising an engineered Q residue" section.

In some embodiments, PEGylation (conjugation of a PEG moiety) reduces or slightly affects the binding of the modified IL-2 protein-PEG conjugate to IL-2Rα subunit compared to the same modified IL-2 protein without PEGylation. In some embodiments, PEGylation reduces or slightly affects the binding of the modified IL-2 protein-PEG conjugate to IL-2Rα subunit compared to a parent IL-2 protein (e.g., wild-type IL-2, or IL-2 Aldesleukin). In some embodiments, PEGylation does not affect or only slightly affects the binding of the modified IL-2 protein-PEG conjugate to IL-2Rβ subunit and/or 7c subunit compared to the same modified IL-2 protein without PEGylation. In some embodiments, PEGylation does not affect or only slightly affects the binding of the modified IL-2 protein-PEG conjugate to IL-2Rβ subunit and/or $\gamma_c$ subunit compared to a parent IL-2 protein (e.g., wild-type IL-2, or IL-2 Aldesleukin).

In some embodiments, the binding affinity between a modified IL-2 protein-PEG conjugate and an IL-2Rα subunit reduced about 10 to about 2000 folds compared to that between a parent IL-2 protein (e.g., wild-type IL-2, human IL-2, or IL-2 Aldesleukin) and the IL-2Rα subunit. Thus in some embodiments, the $K_D$ of the binding between the modified IL-2 protein-PEG conjugate and an IL-2Rα subunit is about 10 to about 2000 times of the $K_D$ of the binding between a parent IL-2 protein (e.g., wild-type IL-2, or IL-2 Aldesleukin) and the IL-2Rα subunit, such as any of about 10 to about 50 times, about 10 to about 100 times, about 100 to about 500 times, about 100 to about 1000 times, about 500 to about 1000 times, about 200 to about 1500 times, about 400 to about 1200 times, about 600 to about 800 times, or about 1000 to about 2000 times, the $K_D$ of the binding between a parent IL-2 protein (e.g., wild-type IL-2, or IL-2 Aldesleukin) and the IL-2Rα subunit. Thus in some embodiments, the $K_D$ of the binding between the modified IL-2 protein-PEG conjugate and an IL-2Rα subunit is about 100 nM to about 40,000 nM, such as any of about 100 nM to about 500 nM, about 500 nM to about 1000 nM, about 100 nM to about 1000 nM, about 1000 nM to about 5000 nM, about 5000 nM to about 10000 nM, about 10000 nM to about 40000 nM, about 500 nM to about 30000 nM, or about 1000 nM to about 20000 nM. In some embodiments, the $K_D$ of the binding between the modified IL-2 protein-PEG conjugate and an IL-2Rα subunit is about 100 nM to about 1000 nM, such as about 245 nM or about 835 nM. In some embodiments, the modified IL-2 protein-PEG conjugate does not bind or cannot be detected (e.g., by SPR) to bind an IL-2Rα subunit.

In some embodiments, the $K_D$ of the binding between the modified IL-2 protein-PEG conjugate and an IL-2Rα subunit is similar to (e.g., equal to, or about 1 to about 2 times) or about 2 to about 500 times of the $K_D$ of the binding between the same modified IL-2 protein without PEGylation and IL-2Rα subunit, such as identical to, about 1 to about 1.1 times, about 1 to about 2 times, about 2 to about 400 times, about 10 to about 300 times, about 50 to about 250 times, or about 100 to about 200 times, of the $K_D$ of the binding between the same modified IL-2 protein without PEGylation and the IL-2Rα subunit.

In some embodiments, the modified IL-2 protein-PEG conjugate also has reduced binding affinity to an IL-2R αβγ complex compared to a parent IL-2 protein (e.g., wild-type IL-2, or IL-2 Aldesleukin). In some embodiments, the modified IL-2 protein-PEG conjugate also has reduced binding affinity to an IL-2R αβγ complex compared to the same modified IL-2 protein without PEGylation.

In some embodiments, the binding affinity between the modified IL-2 protein-PEG conjugate and an IL-2Rβ subunit is similar (e.g., equal) or reduced about 1 to about 30 folds (e.g., about 1 to about 10 folds) compared to that between a parent IL-2 protein (e.g., wild-type IL-2, human IL-2, or IL-2 Aldesleukin) and the IL-2Rβ subunit. Thus in some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, human IL-2, or IL-2 Aldesleukin) and the IL-2Rβ subunit, such as identical to, about 1 to about 1.1 times, about 1 to about 2 times, about 2 to about 9 times, about 3 to about 8 times, about 4 to about 7 times, about 1 to about 10 times, about 8 to about 11 times, about 10 to about 30 times, about 5 to about 20 times, about 6 to about 15 times, or about 5 to about 6 times, the $K_D$ of the binding between a parent IL-2 protein (e.g., wild-type IL-2, or IL-2 Aldesleukin) and the IL-2Rβ subunit. Thus in some embodiments, the $K_D$ of the binding between the modified IL-2 protein-PEG conjugate and an IL-2Rβ subunit is about 100 nM to about 10 μM, such as any of about 100 nM to about 5000 nM, about 100 nM to about 500 nM, about 100 nM to about 1000 nM, about 500 nM to about 1000 nM, about 200 nM to about 3500 nM, about 1000 nM to about 5000 nM, about 1000 nM to about 4000 nM, about 2000 nM to about 4000 nM, about 1 μM to about 10 μM, about 1 μM to about 9 μM, about 2 μM to about 8 μM, about 3 μM to about 7 μM, about 4 μM to about 6 μM, or about 1500 nM to about 3500 nM. In some embodiments, the $K_D$ of the binding between the modified IL-2 protein-PEG conjugate and an IL-2Rβ subunit is about 200 nM to about 4000 nM (e.g., about 1000 nM to about 4000 nM), or about 4 μM to about 6 μM.

In some embodiments, the $K_D$ of the binding between the modified IL-2 protein-PEG conjugate and an IL-2Rβ subunit is similar to (e.g., equal to) or about 1 to about 10 times of the $K_D$ of the binding between the same modified IL-2 protein without PEGylation and the IL-2Rβ subunit, such as identical to, about 1 to about 1.1 times, about 1 to about 2 times, about 2 to about 9 times, about 3 to about 8 times, about 4 to about 7 times, or about 5 to about 6 times, the $K_D$ of the binding between the same modified IL-2 protein without PEGylation and the IL-2Rβ subunit.

In some embodiments, the $K_D$ of the binding between the modified IL-2 protein and an IL-2Rβ subunit is similar to (e.g., equal to) or about 1 to about 10 times of the $K_D$ of the binding between the same modified IL-2 protein with PEGylation (i.e., modified IL-2 protein-PEG conjugate) and the IL-2Rβ subunit, such as identical to, about 1 to about 1.1 times, about 1.4 to about 1.9 times, about 1 to about 2 times, about 2 to about 9 times, about 3 to about 8 times, about 4 to about 7 times, or about 5 to about 6 times, the $K_D$ of the binding between the same modified IL-2 protein with PEGylation and the IL-2Rβ subunit.

In some embodiments, the binding affinity of a modified IL-2 protein-PEG conjugate to IL-2Rα and/or IL-2Rβ subunit decreases as the size of PEG moiety increases. See, e.g., DP006-A-20, DP006-A-30, DP006-A-40 in Example 7.

Bioactivity of Modified IL-2 Protein-PEG Conjugates

The bioactivity of modified IL-2 protein-PEG conjugates described herein can be measured by any methods described in the above "bioactivity of modified IL-2 protein comprising an engineered Q residue" section.

In some embodiments, the modified IL-2 protein-PEG conjugate is capable of activating immune cells, such as inducing IL-2 dependent immune cell proliferation, and/or inducing STAT5 phosphorylation. In some embodiments, the immune cell is selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell.

The modified IL-2 protein-PEG conjugate (as opposed to the same/parent modified IL-2 protein without PEGylation) may or may not possess a measurable degree of IL-2 activity. That is to say, a modified IL-2 protein-PEG conjugate in accordance with the invention may possess anywhere from about 0.1% to about 100% of the bioactivity of the parent modified IL-2 protein without PEGylation. In some embodiments, the modified IL-2 protein-PEG conjugate may have greater than 100% (e.g., greater than about any of 105%, 110%, 120%, 130%, 140%, 150%, 200%, 250%, 300%, or 400%) bioactivity of the unPEGylated parent modified IL-2 protein. In some embodiments, modified IL-2 protein-PEG conjugates are characterized as having a bioactivity satisfying one or more of the following percentages relative to that of the unPEGylated parent modified IL-2 protein: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, or at least about 97% (when measured in a suitable model, such as those well known in the art). Preferably, modified IL-2 protein-PEG conjugate possesses at least some degree of the bioactivity of the unPEGylated parent modified IL-2 protein.

In some embodiments, the modified IL-2 protein-PEG conjugate has similar (e.g., equal) or about 2 to about 200 folds reduced ability in activating (e.g., inducing proliferation) a Treg compared to the same modified IL-2 protein without PEGylation, such as identical ability, or reduced ability of any of about 1 to about 1.1 folds, about 1 to about 2 folds, about 2 to about 10 folds, about 2 to about 20 folds, about 5 to about 50 folds, about 10 to about 100 folds, about 100 to about 200 folds, about 50 to about 150 folds, to activate a Treg compared to the same modified IL-2 protein without PEGylation. In some embodiments, the modified IL-2 protein-PEG conjugate has similar (e.g., equal) or about 1 to about 10 folds reduced ability to activate a CTL/a NK cell compared to the same modified IL-2 protein without PEGylation, such as identical ability, or reduced ability of any of about 1 to about 1.1 folds, about 1 to about 2 folds, about 2 to about 10 folds, about 3 to about 9 folds, about 4 to about 8 folds, about 5 to about 7 folds, or about 4 to about 6 folds, to activate a CTL/a NK cell compared to the same modified IL-2 protein without PEGylation. In some embodiments, the modified IL-2 protein has similar (e.g., equal) or about 1 to about 10 folds reduced ability to activate a CTL/a NK cell compared to the same modified IL-2 protein with PEGylation (i.e., modified IL-2 protein-PEG conjugates), such as identical ability, or reduced ability of any of about 1 to about 1.1 folds, about 1 to about 2 folds, about 2 to about 10 folds, about 3 to about 9 folds, about 4 to about 8 folds, about 5 to about 7 folds, or about 4 to about 6 folds, to activate a CTL/a NK cell compared to the same modified IL-2 protein with PEGylation.

In some embodiments, the modified IL-2 protein-PEG conjugate has similar (e.g., equal) or about 2 to about 200 folds reduced ability in activating a Treg compared to the same modified IL-2 protein without PEGylation, and has similar (e.g., equal) or about 1 to about 10 folds reduced ability in activating a CTL cell and/or a NK cell compared to the same modified IL-2 protein without PEGylation. In some embodiments, the modified IL-2 protein-PEG conjugate has similar (e.g., equal, or about 1 to about 2 folds) or about 2 to about 200 folds reduced ability in activating a Treg compared to the same modified IL-2 protein without PEGylation, and has similar (e.g., equal) or about 1 to about 20 folds (e.g., about 1 to about 10 folds) higher ability in activating a CTL cell and/or a NK cell compared to the same modified IL-2 protein without PEGylation. In some embodiments, the modified IL-2 protein-PEG conjugate has enhanced ability in activating an NK cell and/or a CTL relative to a Treg cell, compared to the parent modified IL-2 protein without PEGylation. See, e.g., FIG. 6B. In some embodiments, the modified IL-2 protein-PEG conjugate activates an NK cell and/or a CTL with little or no activation in a Treg cell.

In some embodiments, the modified IL-2 protein-PEG conjugate has about 2 to about 5000 folds reduced ability to activate a Treg cell compared to a parent IL-2 protein (e.g., wild-type IL-2, or IL-2 Aldesleukin), such as reduced ability of any of about 2 to about 20 folds, about 2 to about 100 folds, about 100 to about 500 folds, about 500 to about 1000 folds, about 1000 to about 2000 folds, about 100 to about 1000 folds, about 1000 to about 5000 folds, about 2000 to about 3000 folds, about 3000 to about 4000 folds, or about 4000 to about 5000 folds, to activate a Treg cell compared to a parent IL-2 protein (e.g., wild-type IL-2, or IL-2 Aldesleukin). In some embodiments, the modified IL-2 protein-PEG conjugate has similar (e.g., equal) or about 1 to about 50 folds reduced ability to activate a CTL (or NK) cell compared to a parent IL-2 protein (e.g., wild-type IL-2, or IL-2 Aldesleukin), such as identical ability, reduced ability of any of about 1 to about 1.1 folds, about 1 to about 2 folds, about 2 to about 10 folds, about 10 to about 50 folds, about 20 to about 40 folds, about 20 to about 30 folds, or about 30 to about 50 folds, to activate a CTL (or NK) cell compared to a parent IL-2 protein (e.g., wild-type IL-2, or IL-2 Aldesleukin). In some embodiments, the modified IL-2 protein-PEG conjugate has similar (e.g., equal) or about 1 to about 20 folds (e.g., about 1 to about 10 folds) higher ability to activate a CTL (or NK) cell compared to a parent IL-2 protein (e.g., wild-type IL-2, or IL-2 Aldesleukin), such as identical ability, higher ability of any of about 1 to about 1.1 folds, about 1 to about 2 folds, about 2 to about 10 folds, or about 5 to about 20 folds, to activate a CTL (or NK) cell compared to a parent IL-2 protein (e.g., wild-type IL-2, or IL-2 Aldesleukin).

In some embodiments, the modified IL-2 protein-PEG conjugate has about 2 to about 5000 folds reduced ability to activate a Treg cell compared to a wild-type IL-2 protein, and has similar (e.g., equal) or about 1 to about 50 folds reduced ability in activating a CTL cell and/or a NK cell compared to a parent IL-2 protein (e.g., wild-type IL-2, or IL-2 Aldesleukin). In some embodiments, the modified IL-2 protein-PEG conjugate has about 2 to about 5000 folds reduced ability to activate a Treg cell compared to a wild-type IL-2 protein, and has similar (e.g., equal) or about 1 to about 20 folds (e.g., about 1 to about 10 folds) higher ability in activating a CTL cell and/or a NK cell compared to a parent IL-2 protein (e.g., wild-type IL-2, or IL-2 Aldesleukin). In some embodiments, the modified IL-2 protein-PEG conjugate has similar (e.g., equal) or preferential activation on CTL and/or NK cells over Treg cells, compared to a parent IL-2 protein (e.g., wild-type IL-2, human IL-2, or IL-2 Aldesleukin), such as similar (e.g., equal) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

In some embodiments, the bioactivity of modified IL-2 protein-PEG conjugate described herein is measured by IL-2 dependent CTLL-2 cell proliferation assay. In some embodiments, the EC50 of modified IL-2 protein-PEG conjugate is about 1000 nM to about 15000 nM, such as about 1000 nM to about 5000 nM, about 5000 nM to about 10000 nM, about 10000 nM to about 15000 nM, about 2000 nM to about 4000 nM, or about 2642 nM.

In some embodiments, the modified IL-2 protein-PEG conjugate described herein has a reduced capability (e.g., about 1 to about 200 folds reduced capability) to stimulate STAT5 phosphorylation in an IL-2Rα+ T cell (e.g., Treg cell) as compared to parent IL-2 (e.g., wild-type IL-2. hIL-2, or IL-2 Aldesleukin). In some embodiments, the modified IL-2 protein-PEG conjugate described herein has a reduced capability (e.g., about 1 to about 200 folds reduced capability) to stimulate the pERK1/ERK2 signaling in an IL-2Rα+ T cell (e.g., Treg cell) as compared to parent IL-2 (e.g., wild-type IL-2. hIL-2, or IL-2 Aldesleukin). In some embodiments, the IL-2Rα+ T cell is a Treg cell.

In some embodiments, the bioactivity (e.g., ability to activate a CTL or NK cell, or preferentially activate CTL and/or NK cells over Treg cells) of a modified IL-2 protein-PEG conjugate decreases as the size of PEG moiety increases. In some embodiments, the bioactivity (e.g., ability to activate a CTL or NK cell, or preferentially activate CTL and/or NK cells over Treg cells) of a modified IL-2 protein-PEG conjugate increases as the size of PEG moiety increases.

Pharmacokinetic Profiles of Modified IL-2 Protein-PEG Conjugates

PEG moiety may improve pharmacokinetic and/or biological characteristics of polypeptides, e.g., to increase serum half-life and bioactivity, to enhance $C_{max}$ (the maximum serum drug concentration during the dosing period), to increase $AUC_{0\text{-}inf}$ (the total area under the curve or the overall drug exposure over time after dosing), and/or to extend in vivo half-lives.

In some embodiments, the modified IL-2 protein-PEG conjugates described herein has a half-life (e.g., elimination half-life or distribution half-life) of about 1 hr to about 30 hrs, such as about 1 hr to about 10 hrs, about 4 hrs to about 30 hrs, about 5 hrs to about 20 hrs, about 10 hrs to about 30 hrs, about 8 hrs to about 25 hrs, about 2 hrs to about 10 hrs, about 20 hrs to about 30 hrs, or about 10 hrs to about 20 hrs. In some embodiments, the half-life of the modified IL-2 protein-PEG conjugates described herein is about 11.7 hrs, or about 18.1 hrs. In some embodiments, the modified IL-2 protein described herein is administered in a single intravenous injection (e.g., at about 2 mg/kg), or a single subcutaneous injection (e.g., at about 2 mg/kg). In some embodiments, the serum half-life of a modified IL-2 protein-PEG conjugate increases as the size of PEG moiety increases, e.g., see Examples 6 and 8.

In some embodiments, the modified IL-2 protein-PEG conjugates described herein when administered in a single intravenous injection provides for a $T_{max}$ shorter than that when administered in a single subcutaneous injection, such as about 5 minutes to about 1000 minutes shorter, or about 50 minutes to 100 minutes shorter.

In some embodiments, the modified IL-2 protein-PEG conjugates described herein when administered in a single intravenous injection or a single subcutaneous injection (e.g., at about 2 mg/kg) provides for a maximum serum concentration ($C_{max}$) of between about 0.05 μg/mL to about 100 μg/mL, such as about 1 μg/mL to about 10 μg/mL, or about 10 μg/mL to about 100 μg/mL. In some embodiments, the modified IL-2 protein-PEG conjugates described herein when administered in a single intravenous injection provides for a $C_m$ax higher than that when administered in a single subcutaneous injection, such as about 5 times to about 500 times higher, or about 90 times to 100 times higher.

In some embodiments, the modified IL-2 protein-PEG conjugates described herein when administered in a single intravenous injection or a single subcutaneous injection (e.g., at about 2 mg/kg) provides for an $AUC_{0\text{-}last}$ or $AUC_{0\text{-}inf}$ of between about 1 hr·μg/mL to about 500 hr·μg/mL, such as about 1 hr·μg/mL to about 50 hr·μg/mL, about 10 hr·μg/mL to about 100 hr·μg/mL, about 5 hr·μg/mL to about 20 hr·μg/mL, about 50 hr·μg/mL to about 200 hr·μg/mL, about 100 hr·μg/mL to about 500 hr·μg/mL, or about 100 hr·μg/mL to about 300 hr·μg/mL. In some embodiments, $AUC_{0\text{-}last}$ or $AUC_{0\text{-}inf}$ of the modified IL-2 protein described herein is about 200 hr·μg/mL to about 300 hr·μg/mL, such as about 227.5 hr·μg/mL (e.g., following a single intravenous injection). In some embodiments, $AUC_{0\text{-}last}$ or $AUC_{0\text{-}inf}$ of the modified IL-2 protein described herein is about 10 hr·μg/mL to about 20 hr·μg/mL, such as about 16.9 hr·μg/mL (e.g., following a single subcutaneous injection). In some embodiments, the modified IL-2 protein-PEG conjugates described herein when administered in a single intravenous injection provides for an overall exposure ($AUC_{0\text{-}last}$) bigger than that when administered in a single subcutaneous injection, such as about 2 times to about 200 times higher, or about 5 times to 20 times higher.

In some embodiments, the circulating half-life of the modified IL-2 protein-PEG conjugate is at least about 1.5 times longer, such as at least about any of 1.6 times, 1.7 times, 1.8 times, 1.9 times, 2 times, 3 times, 4 times, 5 times, 6 times, 7 times, 8 times, 9 times, 10 times, 15 times, 20 times, 30 times, or 40 times longer than that of the same modified IL-2 protein without the PEG moiety and/or a parent IL-2 protein (e.g., wild-type IL-2, or IL-2 Aldesleukin). In some embodiments, the circulating half-life of the modified IL-2 protein-PEG conjugate is about 1.5 to about 2 times, about 1.5 to about 5 times, about 3 to about 20 times, about 10 to about 20 times, about 15 to about 30 times, about 10 to about 15 times, about 3 to about 10 times, about 6 to about 18 times, about 8 to about 15 times, or about 10 to about 12 times, longer than the same modified IL-2 protein without the PEG moiety and/or a parent IL-2 protein (e.g., wild-type IL-2, or IL-2 Aldesleukin). In some embodiments, the circulating half-life of the parent IL-2 protein and/or modified IL-2 protein described herein is about 80 min.

In some embodiments, the overall exposure ($AUC_{0\text{-}last}$ or $AUC_{0\text{-}inf}$) of the modified IL-2 protein-PEG conjugate is at least about 1.5 times higher, such as at least about any of 2 times, 3 times, 4 times, 5 times, 6 times, 7 times, 8 times, 9 times, 10 times, 15 times, 20 times, 30 times, 40 times, 50 times, 60 times, 100 times, or higher than that of the same modified IL-2 protein without the PEG moiety and/or a parent IL-2 protein (e.g., wild-type IL-2, or IL-2 Aldesleukin). In some embodiments, the overall exposure ($AUC_{0\text{-}last}$ or $AUC_{0\text{-}inf}$) of the modified IL-2 protein-PEG conjugate is about 1.5 to about 5 times, about 2 to about 10 times, about 5 to about 20 times, about 10 to about 100 times, about 20 to about 50 times, or about 43 times, higher than that of the same modified IL-2 protein without the PEG moiety and/or a parent IL-2 protein (e.g., wild-type IL-2, or IL-2 Aldesleukin).

The pharmacokinetic properties of the modified IL-2 protein-PEG conjugate can be determined as follows (also see, e.g., Examples 6 and 8). For example, pairs of rats or mice can receive an intravenous bolus injection of the test proteins. Circulating levels of the proteins are measured over the course of 24 h by removing a small sample of blood from the animals at desired time points. Circulating levels of the test proteins can be quantitated using ELISA assays. Additional experiments can be performed using the subcutaneous route to administer the proteins. Similar experiments should be performed with the non-PEGylated protein to serve as a control. These experiments will reveal whether attachment of a PEG reagent to the protein alters its pharmacokinetic properties. Covalent modification of the protein with PEG should increase the protein's circulating half-life relative to the unPEGylated protein. Larger PEG molecules and/or attachment of multiple PEG molecules should lengthen the circulating half-life longer than smaller PEG molecules.

III. Methods of Producing Modified IL-2 Proteins and Modified IL-2 Protein-PEG Conjugates The present application provides methods of making any of the modified IL-2 proteins described herein, as well as methods of making any of the modified IL-2 protein-PEG conjugates described herein. The modified IL-2 protein comprising an engineered Q residue described herein, or a composition thereof, can be produced by any recombinant-based methods for preparing proteins, such as any methods described in recombinant production of modified IL-2 proteins subsections below, or see Example 1.

Thus in some embodiments, there is provided a method of making a modified IL-2 protein comprising an engineered Q residue described herein. In some embodiments, there is provided a method of making a composition comprising a plurality of modified IL-2 protein comprising an engineered Q residue described herein. In some embodiments, there is provided a method of making a modified IL-2 protein-PEG conjugate, comprising contacting a modified IL-2 protein comprising an engineered Q residue described herein with a PEG moiety in the presence of a TGase under a condition sufficient to conjugate the PEG moiety to the modified IL-2 protein via the engineered Q residue. In some embodiments, the method further comprises generating the modified IL-2 protein comprising an engineered Q residue described herein. In some embodiments, of a composition comprising a plurality of modified IL-2 proteins described herein, only some (e.g., at least about any of 70%, 80%, 90%, 95%, 96%, 97%, 98%, 99%) of the modified IL-2 proteins are conjugated with a PEG moiety via the engineered Q residue. In some embodiments, all modified IL-2 proteins within a composition are conjugated with a PEG moiety via the engineered Q residue. Thus in some embodiments, there is provided a method of making a modified IL-2 protein-PEG conjugate, comprising contacting a composition comprising a plurality of modified IL-2 protein comprising an engineered Q residue described herein with a PEG moiety in the presence of a TGase under a condition sufficient to conjugate the PEG moiety to the modified IL-2 protein via the engineered Q residue. In some embodiments, the method further comprises generating the composition comprising the plurality of modified IL-2 protein comprising the engineered Q residue. In some embodiments, at least about 70% (e.g., at least about any of 75%, 80%, 90%, or 95%) of the modified IL-2 protein within the composition is conjugated with the PEG moiety via the engineered Q residue. In some embodiments, at least about 90% (e.g., at least about any of 91%, 92%, 93%, 94%, 95%, 96%, 97%, 98%, or 99%) of the modified IL-2 protein within the composition is conjugated with the PEG moiety via the engineered Q residue. In some embodiments, the composition contains a homogenous population of modified IL-2 proteins described herein. In some embodiments, the composition contains a heterogeneous population of modified IL-2 proteins described herein, i.e., the modified IL-2 proteins contain different engineered Q residues.

The present application also provides isolated nucleic acids and vectors for cloning and expressing any one of modified IL-2 proteins described herein, host cells comprising such nucleic acids or vectors. Modified IL-2 proteins and modified IL-2 protein-PEG conjugates can be prepared using any methods known in the art or as described herein. See, e.g., Examples 1-2.

In some embodiments, IL-2 protein (e.g., wt IL-2, IL-2 Aldesleukin, or modified IL-2 protein) can be expressed in bacterial (e.g., *E. coli*, see, for example Fischer et al. (1995) Biotechnol. Appl. BioIL-2m. 21(3):295-311), mammalian (see, for example, Kronman et al. (1992) Gene 121:295-304), yeast (e.g., *Pichia pastoris*, see, for example, Morel et al. (1997) Biochem. J. 328(1): 121-129), and plant (see, for example, Mor et al. (2001) Biotechnol. Bioeng. 75(3):259-266) expression systems. The expression can occur via exogenous expression (when the host cell naturally contains the desired genetic coding) or via endogenous expression.

Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art.

In some embodiments, the vector is suitable for replication and integration in eukaryotic cells, such as mammalian cells (e.g., CHO cells). In some embodiments, the vector is a viral vector. Examples of viral vectors include, but are not limited to, adenoviral vectors, adeno-associated virus vectors, lentiviral vector, retroviral vectors, herpes simplex viral vector, and derivatives thereof. In some embodiments, the vector is suitable for replication and expression in prokaryotic cells, such as *E. coli*. Molecular cloning technology and vectors are well known in the art and is described, for example, in Sambrook et al. (2001, Molecular Cloning: A Laboratory Manual, Cold Spring Harbor Laboratory, New York), and in other molecular biology manuals.

In some embodiments, polypeptides of the present invention are synthetic, or are produced by expression of a recombinant nucleic acid molecule. In the event the polypeptide is a chimera (e.g., a fusion protein containing at least a modified IL-2 protein described herein and a heterologous polypeptide), it can be encoded by a hybrid nucleic acid molecule containing one sequence that encodes all or part of the modified IL-2 protein, and a second sequence that encodes all or part of the heterologous polypeptide. For example, the modified IL-2 proteins described herein may be fused to a hexa-histidine tag to facilitate purification of bacterially expressed protein, or to a hemagglutinin tag to facilitate purification of protein expressed in eukaryotic cells.

Methods for constructing a DNA sequence encoding the modified IL-2 proteins described herein and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A DNA oligomer containing a nucleotide sequence coding for modified IL-2 proteins can be synthesized. For example, several small oligonucleotides coding for portions of the desired polypeptide can be synthesized and then ligated. The individual oligonucleotides typically contain 5' or 3' overhangs for complementary assembly.

In addition to generating modified IL-2 proteins via expression of nucleic acid molecules that have been altered by recombinant molecular biological techniques, subject modified IL-2 proteins can be chemically synthesized. Chemically synthesized polypeptides are routinely generated by those of skill in the art.

Once assembled (by synthesis, site-directed mutagenesis or another method), the DNA sequences encoding a modified IL-2 protein will be inserted into an expression vector and operatively linked to an expression control sequence appropriate for expression of the modified IL-2 protein in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the modified IL-2 protein, whether prepared by site directed mutagenesis, chemical synthesis or other methods, can also include DNA sequences that encode a signal sequence. Such signal sequence, if present, should be one recognized by the cell chosen for expression of the modified IL-2 protein. It can be prokaryotic, eukaryotic or a combination of the two. It can also be the signal sequence of native IL-2. The inclusion of a signal sequence depends on whether it is desired to secrete the modified IL-2 protein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

Recombinant Production of Modified IL-2 Proteins in Prokaryotic Cells a) Vector Construction Polynucleic acid sequences encoding the modified IL-2 proteins of the present application can be obtained using standard recombinant techniques. Desired polynucleic acid sequences may be isolated and sequenced from IL-2 producing cells such as T cells. Alternatively, polynucleotides can be synthesized using nucleotide synthesizer or PCR techniques, e.g., site-directed mutation. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the modified IL-2 protein by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the—galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the modified IL-2 protein using linkers or adaptors to supply any required restriction sites.

In one aspect, each cistron within the recombinant vector comprises a secretion signal sequence component that directs translocation of the expressed polypeptides across a membrane.

In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments, the signal sequences are STII signal sequences or variants thereof.

In some embodiments, the production of the modified IL-2 protein according to the present application can occur in the cytoplasm of the host cell, and therefore does not require the presence of secretion signal sequences within each cistron. In some embodiments, polypeptide components are expressed, folded and assembled to form functional IL-2 within the cytoplasm. Certain host strains (e.g., the *E. coli* trxB$^-$ strains) provide cytoplasm conditions that are favorable for disulfide bond formation, thereby permitting proper folding and assembly of expressed protein subunits. Proba and Pluckthun Gene, 159:203 (1995).

b) Prokaryotic Host Cells

Prokaryotic host cells suitable for expressing the modified IL-2 proteins of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In some embodiments, gram-negative cells are used. In some embodiments, *E. coli* cells are used as hosts for the invention. Examples of *E. coli* strains include strain W3110 and derivatives thereof, including strain 33D3 having genotype W3110 AfhuA (AtonA) ptr3 lac Iq lacL8 AompT A(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. It is generally necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon.

Typically, the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the modified IL-2 proteins of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium. A variety of other inducers may be used, according to the vector construct employed, as is known in the art.

The expressed modified IL-2 proteins of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermenters use agitator impellers to distribute oxygen and nutrients, especially glucose (the preferred carbon/energy source). Small scale fermentation refers generally to fermentation in a fermenter that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the modified IL-2 proteins of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof.

*E. coli* strains deficient for proteolytic enzymes and transformed with plasmids overexpressing one or more chaperone proteins may be used as host cells in the expression system encoding the modified IL-2 proteins of the present application.

d) Protein Purification

The modified IL-2 proteins produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Recombinant Production of Modified IL-2 Proteins in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

a) Vectors

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the modified IL-2 protein coding sequence can be packaged with protocols known in the art. The resulting lentiviral vectors can be used to transduce a mammalian cell (such as CHO cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector is a non-viral vector. In some embodiments, the vector is a transposon, such as a Sleeping Beauty (SB) transposon system, or a PiggyBac transposon system. In some embodiments, the vector is a polymer-based non-viral vector, including for example, poly (lactic-co-glycolic acid) (PLGA) and poly lactic acid (PLA), poly(ethylene imine) (PEI), and dendrimers. In some embodiments, the vector is a cationic-lipid based non-viral vector, such as cationic liposome, lipid nanoemulsion, and solid lipid nanoparticle (SLN). In some embodiments, the vector is a peptide-based gene non-viral vector, such as poly-L-lysine. Any of the known non-viral vectors suitable for genome editing can be used for introducing the modified IL-2-encoding nucleic acid to the host cell (e.g., T cell). See, for example, Yin H. et al. *Nature Rev. Genetics* (2014) 15:521-555; Aronovich E L et al. "The Sleeping Beauty transposon system: a non-viral vector for gene therapy." *Hum. Mol. Genet.* (2011) R1: R14-20; and Zhao S. et al. "PiggyBac transposon vectors: the tools of the human gene editing." *Transl. Lung Cancer Res.* (2016) 5(1): 120-125, which are incorporated herein by reference. In some embodiments, any one or more of the nucleic acids encoding the modified IL-2 proteins described herein is introduced to the host cells (e.g., T cell) by a physical method, including, but not limited to electroporation, sonoporation, photoporation, magnetofection, hydroporation.

In some embodiments, the vector (e.g., viral vector such as lentiviral vector) comprises any one of the nucleic acids encoding the modified IL-2 proteins described herein. The nucleic acid can be cloned into the vector using any known molecular cloning methods in the art, including, for example, using restriction endonuclease sites and one or more selectable markers.

In some embodiments, the nucleic acid is operably linked to a promoter. Varieties of promoters have been explored for gene expression in mammalian cells, and any of the promoters known in the art may be used in the present invention.

The host cell described herein (e.g., CHO cell) may comprise any number (such as any of 1, 2, 3, 4, 5, 10, 50, 100, 1000, or more) of the nucleic acid encoding the modified IL-2 protein described herein.

The nucleic acids described herein can be present in a heterologous gene expression cassette, which comprises one or more protein-coding sequences and optionally one or more promoters. In some embodiments, the heterologous gene expression cassette comprises a single protein-coding sequence. In some embodiments, the heterologous gene expression cassette comprises two or more protein-coding sequences driven by a single promoter (i.e., polycistronic). In some embodiments, the heterologous gene expression cassette further comprises one or more regulatory sequences (such as 5'UTR, 3'UTR, enhancer sequence, IRES, transcription termination sequence), recombination sites, one or more selection markers (such as antibiotic resistance gene, reporter gene, etc.), signal sequence, or combinations thereof.

The nucleic acid encoding the modified IL-2 proteins described herein may be transiently or stably incorporated in the host cell (e.g., CHO cell). In some embodiments, the nucleic acid is transiently expressed in the host cell. For example, the nucleic acid may be present in the nucleus of the host cell (e.g., CHO cell) in an extrachromosomal array comprising the heterologous gene expression cassette. Heterologous nucleic acids may be introduced into the host cell (e.g., CHO cell) using any transfection or transduction methods known in the art, including viral or non-viral methods. Exemplary non-viral transfection methods include, but are not limited to, chemical-based transfection, such as using calcium phosphate, dendrimers, liposomes, or cationic polymers (e.g., DEAE-dextran or polyethylenimine); non-chemical methods, such as electroporation, cell squeezing, sonoporation, optical transfection, impalefection, protoplast fusion, hydrodynamic delivery, or transposons; particle-based methods, such as using a gene gun, magnectofection or magnet assisted transfection, particle bombardment; and hybrid methods, such as nucleofection. In some embodiments, the nucleic acid is a DNA. In some embodiments, the nucleic acid is an RNA. In some embodiments, the nucleic acid is linear. In some embodiments, the nucleic acid is circular.

In some embodiments, the nucleic acid encoding the modified IL-2 protein described herein is present in the genome of the host cell (e.g., CHO cell). For example, the nucleic acid may be integrated into the genome of the host cell (e.g., CHO cell) by any methods known in the art, including, but not limited to, virus-mediated integration, random integration, homologous recombination methods, and site-directed integration methods, such as using site-specific recombinase or integrase, transposase, Transcription activator-like effector nuclease (TALEN®), CRISPR/Cas9, and zinc-finger nucleases. In some embodiments, the nucleic acid is integrated in a specifically designed locus of the genome of the host cell (e.g., CHO cell). In some embodiments, the nucleic acid is integrated in an integration hotspot of the genome of the host cell (e.g., CHO cell). In some embodiments, the nucleic acid is integrated in a random locus of the genome of the host cell (e.g., CHO cell).

b) Signal Sequence Component

In general, signal peptides are peptide sequences that target a polypeptide to the desired site in a cell. In some embodiments, the signal peptide targets the modified IL-2 proteins to the secretory pathway of the cell and will allow for secretion outside of the host cell. Signal peptides including signal sequences of naturally occurring proteins or synthetic, non-naturally occurring signal sequences, which are compatible for use in the modified IL-2 proteins described herein will be evident to one of skill in the art.

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the modified IL-2 protein of the present application.

c) Origin of Replication

Generally, the origin of replication component is not needed for mammalian expression vectors (the SV40 origin may typically be used only because it contains the early promoter).

d) Selection Gene Component

In some embodiments, the vector contains a selectable marker gene or a reporter gene to select cells expressing the modified IL-2 proteins described herein from the population of host cells transfected through vectors (e.g., lentiviral vectors). Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the modified IL-2 proteins of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

e) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. At the 3' end of most eukaryotic is an AATAAA sequence that may be the signal for addition of the poly A tail to the 3' end of the coding sequence. All of these sequences may be inserted into eukaryotic expression vectors.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

In some embodiments, the nucleic acid encoding the modified IL-2 protein described herein is operably linked to a constitutive promoter. Constitutive promoters allow heterologous genes (also referred to as transgenes) to be expressed constitutively in the host cells. Exemplary promoters contemplated herein include, but are not limited to, cytomegalovirus iinimediate-early promoter (CMV), human elongation factors-1alpha (hEF1α), ubiquitin C promoter (UbiC), phosphoglycerokinase promoter (PGK), simian virus 40 early promoter (SV40), chicken β-Actin promoter coupled with CMV early enhancer (CAGG), a Rous Sarcoma Virus (RSV) promoter, a polyoma enhancer/herpes simplex thymidine kinase (MC1) promoter, a beta actin (β-ACT) promoter, a "myeloproliferative sarcoma virus enhancer, negative control region deleted, d1587rev primer-binding site substituted (MND)" promoter. The efficiencies of such constitutive promoters on driving transgene expression have been widely compared in a huge number of studies. For example, Michael C. Milone et al. compared the efficiencies of CMV, hEF1α, UbiC and PGK in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the modified IL-2 protein described herein is operably linked to a hEF1α promoter or a PGK promoter. In some embodiments, the promoter is selected from the group consisting of an EF-1 promoter, a CMV IE gene promoter, an EF-la promoter, an ubiquitin C promoter, a phosphoglycerate kinase (PGK) promoter, a Rous Sarcoma Virus (RSV) promoter, an Simian Virus 40 (SV40) promoter a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), a simian virus 40 promoter (SV40), and a myeloproliferative sarcoma virus enhancer, negative control region deleted, d1587rev primer-binding site substituted (MND) promoter, an NFAT promoter, a TETON® promoter, and an NFκB promoter.

In some embodiments, the nucleic acid encoding the modified IL-2 protein described herein is operably linked to an inducible promoter. Inducible promoters belong to the category of regulated promoters. The inducible promoter can be induced by one or more conditions, such as a physical condition, microenvironment of the host cell, or the physiological state of the host cell, an inducer (i.e., an inducing agent), or a combination thereof. In some embodiments, the inducing condition does not induce the expression of endogenous genes in the host cell, and/or in the subject that receives the pharmaceutical composition comprising such host cells. In some embodiments, the inducing condition is selected from the group consisting of: inducer, irradiation (such as ionizing radiation, light), temperature (such as heat), redox state, tumor environment, and the activation state of the host cell. In some embodiments, the inducible promoter can be an NFAT promoter, a TETON® promoter, or an NFκB promoter.

f) Enhancer Element Component

Transcription of a DNA encoding the modified IL-2 protein of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (100-270 bp), the cytomegalovirus early promoter enhancer, the polyoma enhancer on the late side of the replication origin, and adenovirus enhancers. The enhancer may be spliced into the vector at a position 5' or 3' to the polypeptide encoding sequence, but is preferably located at a site 5' from the promoter.

g) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

h) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for modified IL-2 protein production and cultured in conventional nutrient media modified as appropriate for inducing promoters, selecting transformants, or amplifying the genes encoding the desired sequences.

Physical methods for introducing a polynucleotide into a host cell (e.g., CHO cell) include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human, cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In some embodiments, RNA molecules encoding the modified IL-2 proteins described herein may be prepared by a conventional method (e.g., in vitro transcription) and then introduced into the host cell (e.g., CHO cells) via known methods such as mRNA electroporation. See, e.g., Rabinovich et al., Human Gene Therapy 17:1027-1035.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In some embodiments, the transduced or transfected host cells (e.g., CHO cells) are propagated ex vivo after introduction of the vector or isolated nucleic acid described herein. In some embodiments, the transduced or transfected host cells (e.g., CHO cells) are cultured to propagate for at least about any of 1 day, 2 days, 3 days, 4 days, 5 days, 6 days, 7 days, 10 days, 12 days, or 14 days. In some embodiments, the transduced or transfected host cells (e.g., CHO cells) are further evaluated or screened to select the engineered host cells.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

i) Culturing the Host Cells

The host cells used to produce the modified IL-2 proteins of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. The media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

j) Protein Purification

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first miming a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art. In some embodiments, the modified IL-2 protein is not in the form of a fusion protein.

When using recombinant techniques, the protein can be produced intracellularly, in the periplasmic space, or directly secreted into the medium. If the protein is produced intracellularly, as a first step, the particulate debris, either host cells or lysed fragments, are removed, for example, by centrifugation or ultrafiltration. Briefly, cell paste is thawed in the presence of sodium acetate (pH 3.5), EDTA, and phenylmethylsulfonylfluoride (PMSF) over about 30 min. Cell debris can be removed by centrifugation. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, affinity chromatography, or Cation Exchange Chromatography. The suitability of protein A as an affinity ligand depends on the species and isotype of any immunoglobulin Fc domain. Protein A can be used to purify an IL-2-Fc fusion proteins. The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered Following any preliminary purification step(s), the mixture comprising the modified IL-2 protein and contaminants may be subjected to low pH hydrophobic interaction chromatography using an elution buffer at a pH between about 2.5-4.5, preferably performed at low salt concentrations (e.g., from about 0-0.25M salt).

Conjugation of a PEG Moiety to an Engineered Q Residue

In one aspect, the present application provides methods of making modified IL-2 protein-PEG conjugates described herein using wildtype (wt) or engineered transglutaminase (TGase). In some embodiments, the engineered TGases (e.g., any engineered TGase described in WO2015191883) can specifically conjugate a PEG moiety to an acceptor glutamine residue on the modified IL-2 protein that is flanked by a glycosylation site. Contrary to previous belief that a glutamine residue flanked by a glycosylation site would be inaccessible to the action of TGase, the inventor has surprisingly found that, by utilizing a specific reaction condition (for example a specific concentration of the TGase enzyme), wildtype TGases are also able to conjugate a PEG moiety to an acceptor glutamine residue on the modified IL-2 protein that is flanked by a glycosylation site in a site-specific and stoichiometric manner.

A variety of means have been used to attach polymer moieties such as PEG and related polymers to reactive groups found on the protein. See e.g., U.S. Pat. Nos. 4,179,337; 4,002,531; Abuchowski et al., 1981, in "Enzymes as Drugs," J. S. Holcerberg and J. Roberts, (Eds.), pp. 367-383; Zalipsky, S., 1995, *Bioconjugate Chemistry,* 6:150-165. The use of PEG and other polymers to modify proteins has been discussed. See e.g., Cheng, T.-L. et al., 1999, *Bioconjugate Chem.,* 10:520-528; Belcheva, N. et al., 1999, *Bioconjugate Chem.,* 10:932-937; Bettinger, T. et al., 1998, *Bioconjugate Chem.,* 9:842-846; Huang, S.-Y, et al., 1998, *Bioconjugate Chem.,* 9:612-617; Xu, B. et al. 1998, *Langmuir,* 13:2447-2456; Schwarz, J. B. et al., 1999, *J. Amer. Chem. Soc.,* 121:2662-2673; Reuter, J. D. et al., 1999, *Bioconjugate Chem.,* 10:271-278; Chan, T.-H. et al., 1997, *J. Org. Chem.,* 62:3500-3504. Typical attachment sites in proteins include primary amino groups, such as those on lysine residues or at the N-terminus, thiol groups, such as those on cysteine side-chains, and carboxyl groups, such as those on glutamate or aspartate residues or at the C-terminus. Common sites of attachment are to the sugar residues of glycoproteins, cysteines or to the N-terminus and lysines of the target polypeptide.

Figure 8:
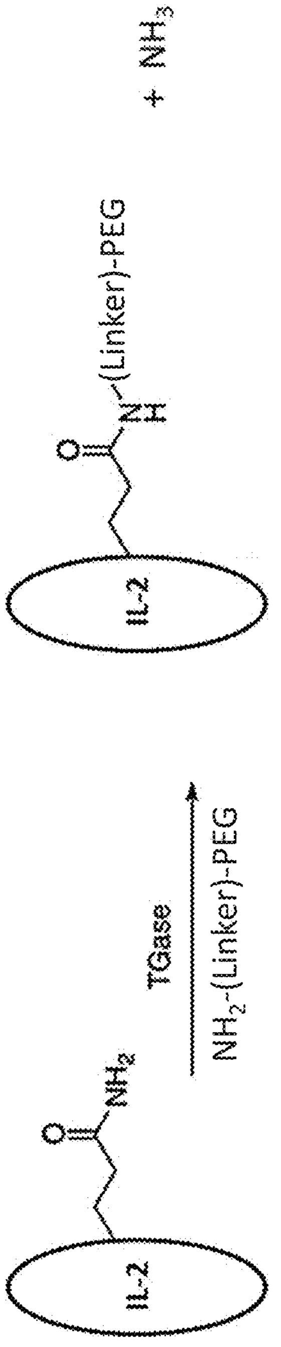
FIG. 8 depicts a diagram showing a one-step modified IL-2 protein-PEG conjugation method.

The methods described herein in some embodiments involve a single conjugation step (see, e.g., FIG. 8). Such method is particularly suitable, for example, when a conjugation yield of between about 20-98% is sufficient to generate a substantial amount of the modified IL-2 protein-PEG conjugate. The one-step method is also useful when there is plenty of supply of the modified IL-2 protein, and when time saving is a bigger concern than getting a high yield.

Figure 9:
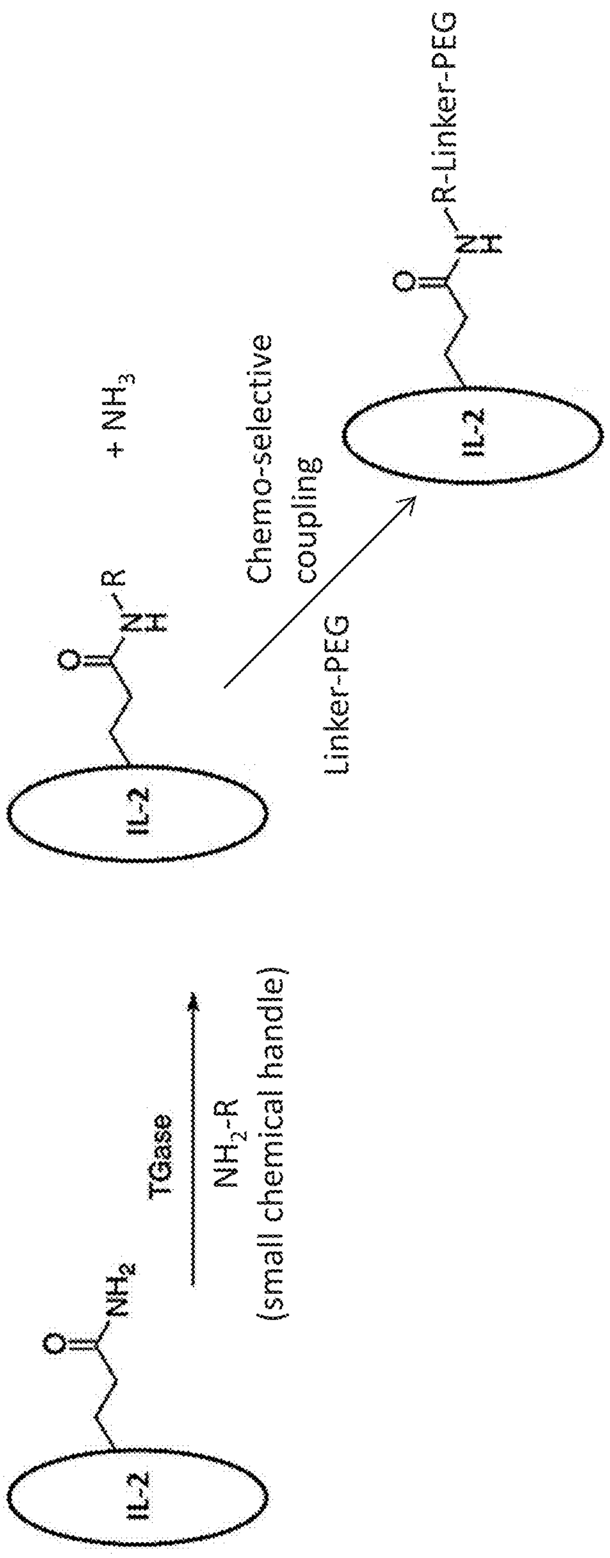
FIG. 9 depicts a diagram showing a two-step modified IL-2 protein-PEG conjugation method.

In some embodiments, the method involves two steps (see, e.g., FIG. 9). First, a small molecule handle is conjugated to the engineered Q residue of the modified IL-2 protein via a TGase to create an intermediate conjugate. Subsequently, a PEG moiety is coupled to the intermediate conjugate via the small molecule handle, either covalently or noncovalently. The small molecule handle can be specifically designed to tailor the coupling of the PEG moiety. The two-step method is particularly useful when the supply of the modified IL-2 protein and/or PEG moiety is limited, and when the PEG moiety induces aggregation of the polypeptide. By using a small molecule handle, the first enzymatic coupling step can allow the achievement of high yield in conjugation. The second chemoselective coupling step then only requires a reactant ratio of PEG moiety: modified IL-2 protein between about 1.2 to about 1.5. This may lead to a higher overall conjugation yield than a one-step process.

Thus, in some embodiments, there is provided a method of making a modified IL-2 protein-PEG conjugate comprising a modified IL-2 protein comprising an engineered Q residue specifically conjugated to a PEG moiety, wherein the method comprises: contacting the modified IL-2 protein with the PEG moiety in the presence of a TGase (wt or engineered TGase) under a condition that is sufficient to generate the modified IL-2 protein-PEG conjugate, wherein the PEG moiety is conjugated to the modified IL-2 protein via the engineered Q residue. In some embodiments, there is provided a method of making a modified IL-2 protein-PEG conjugate comprising a modified IL-2 protein comprising an engineered Q residue specifically conjugated to a PEG moiety, wherein the method comprises: contacting a composition comprising a plurality of modified IL-2 proteins with the PEG moiety in the presence of a TGase under a condition that is sufficient to generate the modified IL-2 protein-PEG conjugate, wherein at least about 30% (such as at least about any of 40%, 50%, 60%, 70%, 75%, 80%, 85%, 90%, 95%, 96%, 97%, 98%, or 99%, or about 100%) of the modified IL-2 protein within the composition is conjugated with the PEG moiety via the engineered Q residue. In some embodiments, the method further comprises generating the modified IL-2 protein comprising the engineered Q residue (see e.g., recombinant production methods described above, also see Examples 1-2). In some embodiments, at least about 70% (such as at least about any of 75%, 80%, 85%, 90%, 95%, 96%, 97%, 98%, or 99%, or about 100%) of the modified IL-2 protein within the composition is conjugated with the PEG moiety via the engineered Q residue (i.e., at least one of the engineered Q residue within the modified IL-2 protein is conjugated with one PEG moiety, or each engineered Q residue within the modified IL-2 protein is each conjugated with one PEG moiety, such PEG conjugated modified IL-2 protein accounts for at least about 70% of the total modified IL-2 protein composition). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one PEG moiety. In some embodiments, all engineered Q residues within the modified IL-2 protein are each conjugated with one PEG moiety. In some embodiments, the modified IL-2 proteins within the composition are the same. In some embodiments, the modified IL-2 proteins within the composition are different, e.g., comprising different engineered Q residues described herein. In some embodiments, modified IL-2 proteins within the composition are PEGylated at different positions of the engineered Q residue, for example, when there are multiple engineered Q residues within the modified IL-2 protein. In some embodiments, modified IL-2 proteins within the composition are PEGylated at the same position of the engineered Q residue, for example, when there are multiple engineered Q residues within the modified IL-2 protein, or when there is only one engineered Q residue within the modified IL-2 protein. In some embodiments, various PEG moieties are used in the methods described herein. Thus in some embodiments, the modified IL-2 protein-PEG conjugates obtained by methods described herein are homogenous, e.g., comprising the same modified IL-2 protein conjugated with the same PEG moiety at the same engineered Q residue. In some embodiments, the modified IL-2 protein-PEG conjugates obtained by methods described herein are heterogeneous, e.g., comprising unPEGylated and PEGylated modified IL-2, comprising the same modified IL-2 protein conjugated with the same PEG moiety at different Q residues, comprising the same modified IL-2 protein conjugated with different PEG moieties at different Q residues, comprising the same modified IL-2 protein conjugated with different PEG moieties at the same Q residue(s), comprising different modified IL-2 proteins conjugated with the same PEG moiety, or comprising different modified IL-2 proteins conjugated with different PEG moieties. In some embodiments, the PEG moiety comprises an —$NH_2$ group. In some embodiments, the PEG moiety is methoxy-PEG-amine. In some embodiments, the PEG moiety comprises a linker, e.g., the PEG moiety is $NH_2$-linker-PEG.

In some embodiments, there is provided a method of making a modified IL-2 protein-PEG conjugate comprising a modified IL-2 protein comprising an engineered Q residue specifically conjugated to a PEG moiety, wherein the PEG moiety and the engineered Q residue are conjugated via a small molecule handle, wherein the method comprises: a) contacting the modified IL-2 protein with the small molecule handle in the presence of a TGase (wt or engineered TGase) under a condition that is sufficient to generate an intermediate conjugate comprising a modified IL-2 protein specifically conjugated to the small molecule handle via the engineered Q residue, and b) contacting the intermediate conjugate with the PEG moiety thereby obtaining the modified IL-2-PEG conjugate, wherein the PEG moiety is conjugated via the small molecule handle. In some embodiments, there is provided a method of making a modified IL-2 protein-PEG conjugate comprising a modified IL-2 protein comprising an engineered Q residue specifically conjugated to a PEG moiety, wherein the PEG moiety and the engineered Q residue are conjugated via a small molecule handle, wherein the method comprises: a) contacting a composition comprising a plurality of modified IL-2 proteins with the small molecule handle in the presence of a TGase (wt or engineered TGase) under a condition that is sufficient to generate an intermediate conjugate comprising a modified IL-2 protein specifically conjugated to the small molecule handle, wherein at least about 30% (such as at least about any of 40%, 50%, 60%, 70%, 75%, 80%, 85%, 90%, 95%, 96%, 97%, 98%, or 99%, or about 100%) of the modified IL-2 protein within the composition is conjugated with the small molecule handle via the engineered Q residue, and b) contacting the intermediate conjugate with the PEG moiety thereby obtaining the modified IL-2-PEG conjugate, wherein at least about 30% (such as at least about any of 40%, 50%, 60%, 70%, 75%, 80%, 85%, 90%, 95%, 96%, 97%, 98%, or 99%, or about 100%) of the intermediate conjugate within the composition is conjugated with the PEG moiety via the small molecule handle. In some embodiments, the method further comprises generating the modified IL-2 protein comprising the engineered Q residue (see e.g., recombinant production methods described above, also see Examples 1-2). In some embodiments, at least about 70% (such as at least about any of 75%, 80%, 85%, 90%, 95%, 96%, 97%, 98%, or 99%, or about 100%) of the modified IL-2 protein within the composition is conjugated with the small molecule handle via the engineered Q residue (i.e., at least one of the engineered Q residue within the modified IL-2 protein is conjugated with one small molecule handle, or each engineered Q residue within the modified IL-2 protein is each conjugated with one small molecule handle, such small molecule handle-conjugated modified IL-2 protein accounts for at least about 70% of the total modified IL-2 protein composition). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one small molecule handle. In some embodiments, all engineered Q residues within the modified IL-2 protein are each conjugated with one small molecule handle. In some embodiments, at least about 70% (such as at least about any of 75%, 80%, 85%, 90%, 95%, 96%, 97%, 98%, or 99%, or about 100%) of the intermediate conjugate within the composition is conjugated with the PEG moiety via the small molecule handle (i.e., at least one of the small molecule handles within the intermediate conjugate is conjugated with one PEG moiety, or each small molecule handle within the intermediate conjugate is each conjugated with one PEG moiety, such PEG-small molecule handle-conjugated modified IL-2 protein accounts for at least about 70% of the intermediate conjugate composition). In some embodiments, at least about 20% (such as at least about any of 30%, 40%, 50%, 60%, 70%, 75%, 80%, 85%, 90%, 95%, 96%, 97%, 98%, or 99%, or about 100%) of the small molecule handles within the intermediate conjugate is each conjugated with one PEG moiety. In some embodiments, all small molecule handles within the intermediate conjugate are each conjugated with one PEG moiety. In some embodiments, at least about 50% (such as at least about any of 60%, 70%, 80%, 90%, 95%, 96%, 97%, 98%, or 99%, or about 100%) of the modified IL-2 protein within the composition is conjugated with the small molecule handle and PEG moiety via the engineered Q residue (i.e., at least one of the engineered Q residue within the modified IL-2 protein is conjugated with one small molecule handle and PEG moiety, or each engineered Q residue within the modified IL-2 protein is each conjugated with one small molecule handle and one PEG moiety, such PEG-small molecule handle-conjugated modified IL-2 protein accounts for at least about 50% (such as at least about any of 60%, 70%, 80%, 90%, 95%, 96%, 97%, 98%, or 99%, or about 100%) of the total modified IL-2 protein composition). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one small molecule handle and one PEG moiety. In some embodiments, all engineered Q residues within the modified IL-2 protein are each conjugated with one small molecule handle and one PEG moiety. In some embodiments, the modified IL-2 proteins within the composition are the same. In some embodiments, the modified IL-2 proteins within the composition are different, e.g., comprising different engineered Q residues described herein. In some embodiments, modified IL-2 proteins within the composition are PEGylated at different positions of the engineered Q residue, for example, when there are multiple engineered Q residues within the modified IL-2 protein. In some embodiments, modified IL-2 proteins within the composition are PEGylated at the same position of the engineered Q residue, for example, when there are multiple engineered Q residues within the modified IL-2 protein, or when there is only one engineered Q residue within the modified IL-2 protein. In some embodiments, various PEG moieties are used in the methods described herein. In some embodiments, various small molecule handles are used in the methods described herein. Thus in some embodiments, the modified IL-2 protein-PEG conjugates obtained by methods described herein are homogenous, e.g., comprising the same modified IL-2 protein conjugated with the same PEG moiety and same small molecule handle at the same engineered Q residue. In some embodiments, the modified IL-2 protein-PEG conjugates obtained by methods described herein are heterogeneous, e.g., comprising unPEGylated and PEGylated modified IL-2, comprising the same modified IL-2 protein conjugated with the same PEG moiety (and same or different small molecule handles) at different Q residues, comprising the same modified IL-2 protein conjugated with different PEG moieties (and same or different small molecule handles) at different Q residues, comprising the same modified IL-2 protein conjugated with different PEG moieties (and same or different small molecule handles) at the same Q residue(s), comprising different modified IL-2 proteins conjugated with the same PEG moiety (and same or different small molecule handles), or comprising different modified IL-2 proteins conjugated with different PEG moieties (and same or different small molecule handles). In some embodiments, the PEG moiety comprises an —$NH_2$ group. In some embodiments, the PEG moiety is methoxy-PEG-amine. In some embodiments, the PEG moiety comprises a linker, e.g., the PEG moiety is $NH_2$-linker-PEG. In some embodiments, the small molecule handle can be any of the small molecule handles described herein (see below "small molecule handle" subsection).

PEG moiety may improve the pharmacokinetic or biological characteristics of polypeptides, e.g., to increase serum half-life and bioactivity, to enhance $AUC_{0-inf}$, and/or to extend in vivo half-lives. Thus, the present invention also provided a method of increasing the circulating half-life (or overall exposure $AUC_{0-inf}$) of an IL-2 protein (e.g., wt IL-2, or any modified IL-2 proteins described herein). In some embodiments, there is provided a method of increasing the circulating half-life (or overall exposure $AUC_{0-inf}$) of an IL-2 protein, comprising: a) introducing an engineered Q residue into an IL-2 protein (e.g., wt IL-2, or IL-2 Aldesleukin) to generate a modified IL-2 protein comprising an engineered Q residue (such as any modified IL-2 proteins described herein); b) contacting the modified IL-2 protein with a PEG moiety in the presence of a TGase under a condition sufficient to generate a modified IL-2 protein-PEG conjugate, wherein the PEG moiety is conjugated to the modified IL-2 protein via the engineered Q residue, and wherein the PEG moiety is of a length sufficient to increase the circulating half-life (or overall exposure $AUC_{0-inf}$) of the PEG conjugated modified IL-2 protein compared to the IL-2 protein (or compared to the same modified IL-2 protein without the PEG moiety). In some embodiments, there is provided a method of increasing the circulating half-life (or overall exposure $AUC_{0-inf}$) of an IL-2 protein (e.g., wt IL-2, or IL-2 Aldesleukin), comprising: a) introducing an engineered Q residue into the IL-2 protein to generate a composition comprising a plurality of modified IL-2 protein comprising an engineered Q residue (such as any modified IL-2 proteins described herein); b) contacting the composition with a PEG moiety in the presence of a TGase under a condition sufficient to generate a modified IL-2 protein-PEG conjugates; wherein at least about 30% (such as at least about any of 40%, 50%, 60%, 70%, 75%, 80%, 85%, 90%, 95%, 96%, 97%, 98%, or 99%, or about 100%) of the modified IL-2 protein within the composition is conjugated with the PEG moiety via the engineered Q residue; and wherein the PEG moiety is of a length sufficient to increase the circulating half-life (or overall exposure $AUC_{0-inf}$) of the PEG conjugated modified IL-2 protein compared to the IL-2 protein (or compared to the same modified IL-2 protein without the PEG moiety). In some embodiments, at least about 70% (such as at least about any of 75%, 80%, 85%, 90%, 95%, 96%, 97%, 98%, or 99%, or about 100%) of the modified IL-2 protein within the composition is conjugated with the PEG moiety via the engineered Q residue (i.e., at least one of the engineered Q residue within the modified IL-2 protein is conjugated with one PEG moiety, or each engineered Q residue within the modified IL-2 protein is each conjugated with one PEG moiety, such PEG-conjugated modified IL-2 protein accounts for at least about 70% of the total modified IL-2 protein composition). In some embodiments, the circulating half-life of the PEG conjugated modified IL-2 protein is at least about 1.5 times (such as at least about any of 2 times, 3 times, 4 times, 5 times, 6 times, 7 times, 8 times, 9 times, 10 times, 15 times, 20 times, 30 times, or more) longer than the IL-2 protein (e.g., wt IL-2, or IL-2 Aldesleukin), and/or longer than the same modified IL-2 protein without the PEG moiety. In some embodiments, the circulating half-life of the PEG conjugated modified IL-2 protein is about 1.5 to about 2 times, about 1.5 to about 5 times, about 3 to about 20 times, about 3 to about 10 times, about 4 to about 18 times, about 5 to about 16 times, about 8 to about 13 times, about 8 times to about 20 times, about 10 to about 20 times, about 15 to about 20 times, about 15 to about 30 times, about 10 to about 15 times, about 6 to about 18 times, about 8 to about 15 times, or about 10 to about 12 times, longer than the IL-2 protein, and/or longer than the same modified IL-2 protein without the PEG moiety. In some embodiments, the modified IL-2 protein-PEG conjugates described herein has a half-life (e.g., elimination half-life or distribution half-life) of about 1 hr to about 30 hrs, such as about 1 hr to about 10 hrs, about 4 hrs to about 30 hrs, about 5 hrs to about 20 hrs, about 10 hrs to about 30 hrs, about 8 hrs to about 25 hrs, about 2 hrs to about 10 hrs, about 20 hrs to about 30 hrs, or about 10 hrs to about 20 hrs. In some embodiments, the modified IL-2 protein-PEG conjugates when administered in a single intravenous injection or a single subcutaneous injection (e.g., at about 2 mg/kg) provides for an $AUC_{0\text{-}last}$ or $AUC_{0\text{-}inf}$ of between about 1 hr·μg/mL to about 500 hr·μg/mL, such as about 1 hr·μg/mL to about 50 hr·μg/mL, about 10 hr·μg/mL to about 100 hr·μg/mL, about 5 hr·μg/mL to about 20 hr·μg/mL, about 50 hr·μg/mL to about 200 hr·μg/mL, about 100 hr·μg/mL to about 500 hr·μg/mL, or about 100 hr·μg/mL to about 300 hr·μg/mL. In some embodiments, the overall exposure ($AUC_{0\text{-}last}$ or $AUC_{0\text{-}inf}$) of the modified IL-2 protein-PEG conjugate is at least about 1.5 times higher, such as at least about any of 2 times, 3 times, 4 times, 5 times, 6 times, 7 times, 8 times, 9 times, 10 times, 15 times, 20 times, 30 times, 40 times, 50 times, 60 times, 100 times, or higher than that of the same modified IL-2 protein without the PEG moiety and/or a parent IL-2 protein (e.g., wild-type IL-2, or IL-2 Aldesleukin). In some embodiments, the overall exposure ($AUC_{0\text{-}last}$ or $AUC_{0\text{-}inf}$) of the modified IL-2 protein-PEG conjugate is about 1.5 to about 5 times, about 2 to about 10 times, about 5 to about 20 times, about 10 to about 100 times, about 20 to about 50 times, or about 43 times, higher than that of the same modified IL-2 protein without the PEG moiety and/or a parent IL-2 protein (e.g., wild-type IL-2, or IL-2 Aldesleukin). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one PEG moiety. In some embodiments, all engineered Q residues within the modified IL-2 protein are each conjugated with one PEG moiety. In some embodiments, the modified IL-2 proteins within the composition are the same. In some embodiments, the modified IL-2 proteins within the composition are different, e.g., comprising different engineered Q residues described herein. In some embodiments, modified IL-2 proteins within the composition are conjugated with PEG moiety at different positions of the engineered Q residue, for example, when there are multiple engineered Q residues within the modified IL-2 protein. In some embodiments, modified IL-2 proteins within the composition are conjugated with PEG moiety at the same position of the engineered Q residue, for example, when there are multiple engineered Q residues within the modified IL-2 protein, or when there is only one engineered Q residue within the modified IL-2 protein. In some embodiments, various PEG moieties are used in the methods described herein. Thus in some embodiments, the modified IL-2 protein-PEG conjugates obtained by methods described herein are homogenous, e.g., comprising the same modified IL-2 protein conjugated with the same PEG moiety at the same engineered Q residue. In some embodiments, the modified IL-2 protein-PEG conjugates obtained by methods described herein are heterogeneous, e.g., comprising unPEGylated and PEGylated modified IL-2, comprising the same modified IL-2 protein conjugated with the same PEG moiety at different Q residues, comprising the same modified IL-2 protein conjugated with different PEG moieties at different Q residues, comprising the same modified IL-2 protein conjugated with different PEG moieties at the same Q residue(s), comprising different modified IL-2 proteins conjugated with the same PEG moiety, or comprising different modified IL-2 proteins conjugated with different PEG moieties. Thus of a composition of a plurality of modified IL-2 proteins described herein, the method described herein increases the circulating half-life (or overall exposure $AUC_{0\text{-}inf}$) of the PEG conjugated modified IL-2 proteins, but not those without PEG conjugation. In some embodiments, the PEG moiety comprises an $-NH_2$ group. In some embodiments, the PEG moiety is methoxy-PEG-amine. In some embodiments, the PEG moiety comprises a linker, e.g., the PEG moiety is $NH_2$-linker-PEG.

In some embodiments, there is provided a method of increasing the circulating half-life (or overall exposure $AUC_{0\text{-}inf}$) of an IL-2 protein, comprising: a) introducing an engineered Q residue into an IL-2 protein (e.g., wt IL-2, or IL-2 Aldesleukin) to generate a modified IL-2 protein comprising an engineered Q residue (such as any modified IL-2 proteins described herein); b) contacting the modified IL-2 protein with a small molecule handle in the presence of a TGase (wt or engineered TGase) under a condition that is sufficient to generate an intermediate conjugate comprising a modified IL-2 protein specifically conjugated to the small molecule handle via the engineered Q residue, and c) contacting the intermediate conjugate with a PEG moiety thereby obtaining a modified IL-2-PEG conjugate, wherein the PEG moiety is conjugated via the small molecule handle, and wherein the PEG moiety is of a length sufficient to increase the circulating half-life (or overall exposure $AUC_{0\text{-}inf}$) of the PEG-conjugated modified IL-2 protein compared to the IL-2 protein (or compared to the same modified IL-2 protein without the PEG moiety). In some embodiments, there is provided a method of increasing the circulating half-life (or overall exposure $AUC_{0\text{-}inf}$) of an IL-2 protein, comprising: a) introducing an engineered Q residue into the IL-2 protein (e.g., wt IL-2, or IL-2 Aldesleukin) to generate a composition comprising a plurality of modified IL-2 protein comprising an engineered Q residue (such as any modified IL-2 proteins described herein); b) contacting the composition with a small molecule handle in the presence of a TGase (wt or engineered TGase) under a condition that is sufficient to generate an intermediate conjugate comprising a modified IL-2 protein specifically conjugated to the small molecule handle via the engineered Q residue, wherein at least about 30% (such as at least about any of 40%, 50%, 60%, 70%, 75%, 80%, 85%, 90%, 95%, 96%, 97%, 98%, or 99%, or about 100%) of the modified IL-2 protein within the composition is conjugated with the small molecule handle via the engineered Q residue, and c) contacting the composition comprising the intermediate conjugate with a PEG moiety thereby obtaining a modified IL-2-PEG conjugate, wherein the PEG moiety is conjugated via the small molecule handle, wherein at least about 30% (such as at least about any of 40%, 50%, 60%, 70%, 75%, 80%, 85%, 90%, 95%, 96%, 97%, 98%, or 99%, or about 100%) of the intermediate conjugate within the composition is conjugated with the PEG moiety via the small molecule handle, and wherein the PEG moiety is of a length sufficient to increase the circulating half-life (or overall exposure $AUC_{0\text{-}inf}$) of the PEG-conjugated modified IL-2 protein compared to the IL-2 protein (or compared to the same modified IL-2 protein without the PEG moiety). In some embodiments, at least about 70% (such as at least about any of 75%, 80%, 85%, 90%, 95%, 96%, 97%, 98%, or 99%, or about 100%) of the modified IL-2 protein within the composition is conjugated with the small molecule handle via the engineered Q residue (i.e., at least one of the engineered Q residue within the modified IL-2 protein is conjugated with one small molecule handle, or each engineered Q residue within the modified IL-2 protein is each conjugated with one small molecule handle, such small molecule handle-conjugated modified IL-2 protein accounts for at least about 70% of the total modified IL-2 protein composition). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one small molecule handle. In some embodiments, all engineered Q residues within the modified IL-2 protein are each conjugated with one small molecule handle. In some embodiments, at least about 70% (such as at least about any of 75%, 80%, 85%, 90%, 95%, 96%, 97%, 98%, or 99%, or about 100%) of the intermediate conjugate within the composition is conjugated with the PEG moiety via the small molecule handle (i.e., at least one of the small molecule handles within the intermediate conjugate is conjugated with one PEG moiety, or each small molecule handle within the intermediate conjugate is each conjugated with one PEG moiety, such PEG-small molecule handle-conjugated modified IL-2 protein accounts for at least about 70% of the intermediate conjugate composition). In some embodiments, at least about 20% (such as at least about any of 30%, 40%, 50%, 60%, 70%, 75%, 80%, 85%, 90%, 95%, 96%, 97%, 98%, or 99%, or about 100%) of the small molecule handles within the intermediate conjugate is each conjugated with one PEG moiety. In some embodiments, all small molecule handles within the intermediate conjugate are each conjugated with one PEG moiety. In some embodiments, at least about 50% (such as at least about any of 60%, 70%, 75%, 80%, 85%, 90%, 95%, 96%, 97%, 98%, or 99%, or about 100%) of the modified IL-2 protein within the composition is conjugated with the small molecule handle and PEG moiety via the engineered Q residue (i.e., at least one of the engineered Q residue within the modified IL-2 protein is conjugated with one small molecule handle and PEG moiety, or each engineered Q residue within the modified IL-2 protein is each conjugated with one small molecule handle and one PEG moiety, such PEG-small molecule handle-conjugated modified IL-2 protein accounts for at least about 50% of the total modified IL-2 protein composition). In some embodiments, at least about 20% (such as at least about any of 30%, 40%, 50%, 60%, 70%, 75%, 80%, 85%, 90%, 95%, 96%, 97%, 98%, or 99%, or about 100%) of the engineered Q residues within the modified IL-2 protein is each conjugated with one small molecule handle and one PEG moiety. In some embodiments, all engineered Q residues within the modified IL-2 protein are each conjugated with one small molecule handle and one PEG moiety. In some embodiments, at least about 70% (such as at least about any of 75%, 80%, 85%, 90%, 95%, 96%, 97%, 98%, or 99%, or about 100%) of the modified IL-2 protein within the composition is conjugated with the PEG moiety and the small molecule handle via the engineered Q residue (i.e., at least one of the engineered Q residue within the modified IL-2 protein is conjugated with one PEG moiety and one small molecule handle, or each engineered Q residue within the modified IL-2 protein is each conjugated with one PEG moiety and one small molecule handle, such PEG-conjugated modified IL-2 protein accounts for at least about 70% of the total modified IL-2 protein composition). In some embodiments, the circulating half-life of the PEG conjugated modified IL-2 protein is at least about 1.5 times (such as at least about any of 2 times, 3 times, 4 times, 5 times, 6 times, 7 times, 8 times, 9 times, 10 times, 15 times, 20 times, 30 times, or more) longer than the IL-2 protein (e.g., wt IL-2, or IL-2 Aldesleukin), and/or longer than the same modified IL-2 protein without the PEG moiety. In some embodiments, the circulating half-life of the PEG conjugated modified IL-2 protein is about 1.5 to about 2 times, about 1.5 to about 5 times, about 3 to about 20 times, about 3 to about 10 times, about 4 to about 18 times, about 5 to about 16 times, about 8 to about 13 times, about 8 times to about 20 times, about 10 to about 20 times, about 15 to about 20 times, about 15 to about 30 times, about 10 to about 15 times, about 6 to about 18 times, about 8 to about 15 times, or about 10 to about 12 times, longer than the IL-2 protein, and/or longer than the same modified IL-2 protein without the PEG moiety. In some embodiments, the modified IL-2 protein-PEG conjugates described herein has a half-life (e.g., elimination half-life or distribution half-life) of about 1 hr to about 30 hrs, such as about 1 hr to about 10 hrs, about 4 hrs to about 30 hrs, about 5 hrs to about 20 hrs, about 10 hrs to about 30 hrs, about 8 hrs to about 25 hrs, about 2 hrs to about 10 hrs, about 20 hrs to about 30 hrs, or about 10 hrs to about 20 hrs. In some embodiments, the modified IL-2 protein-PEG conjugates when administered in a single intravenous injection or a single subcutaneous injection (e.g., at about 2 mg/kg) provides for an $AUC_{0\text{-}last}$ or $AUC_{0\text{-}inf}$ of between about 1 hr·µg/mL to about 500 hr·µg/mL, such as about 1 hr·µg/mL to about 50 hr·µg/mL, about 10 hr·µg/mL to about 100 hr·µg/mL, about 5 hr·µg/mL to about 20 hr·µg/mL, about 50 hr·µg/mL to about 200 hr·µg/mL, about 100 hr·µg/mL to about 500 hr·µg/mL, or about 100 hr·µg/mL to about 300 hr·µg/mL. In some embodiments, the overall exposure ($AUC_{0\text{-}last}$ or $AUC_{0\text{-}inf}$) of the modified IL-2 protein-PEG conjugate is at least about 1.5 times higher, such as at least about any of 2 times, 3 times, 4 times, 5 times, 6 times, 7 times, 8 times, 9 times, 10 times, 15 times, 20 times, 30 times, 40 times, 50 times, 60 times, 100 times, or higher than that of the same modified IL-2 protein without the PEG moiety and/or a parent IL-2 protein (e.g., wild-type IL-2, or IL-2 Aldesleukin). In some embodiments, the overall exposure ($AUC_{0\text{-}last}$ or $AUC_{0\text{-}inf}$) of the modified IL-2 protein-PEG conjugate is about 1.5 to about 5 times, about 2 to about 10 times, about 5 to about 20 times, about 10 to about 100 times, about 20 to about 50 times, or about 43 times, higher than that of the same modified IL-2 protein without the PEG moiety and/or a parent IL-2 protein (e.g., wild-type IL-2, or IL-2 Aldesleukin). In some embodiments, the modified IL-2 proteins within the composition are the same. In some embodiments, the modified IL-2 proteins within the composition are different, e.g., comprising different engineered Q residues described herein. In some embodiments, modified IL-2 proteins within the composition are PEGylated at different positions of the engineered Q residue, for example, when there are multiple engineered Q residues within the modified IL-2 protein. In some embodiments, modified IL-2 proteins within the composition are PEGylated at the same position of the engineered Q residue, for example, when there are multiple engineered Q residues within the modified IL-2 protein, or when there is only one engineered Q residue within the modified IL-2 protein. In some embodiments, various PEG moieties are used in the methods described herein. In some embodiments, various small molecule handles are used in the methods described herein. Thus in some embodiments, the modified IL-2 protein-PEG conjugates obtained by methods described herein are homogenous, e.g., comprising the same modified IL-2 protein conjugated with the same PEG moiety and same small molecule handle at the same engineered Q residue. In some embodiments, the modified IL-2 protein-PEG conjugates obtained by methods described herein are heterogeneous, e.g., comprising unPEGylated and PEGylated modified IL-2, comprising the same modified IL-2 protein conjugated with the same PEG moiety (and same or different small molecule handles) at different Q residues, comprising the same modified IL-2 protein conjugated with different PEG moieties (and same or different small molecule handles) at different Q residues, comprising the same modified IL-2 protein conjugated with different PEG moieties (and same or different small molecule handles) at the same Q residue(s), comprising different modified IL-2 proteins conjugated with the same PEG moiety (and same or different small molecule handles), or comprising different modified IL-2 proteins conjugated with different PEG moieties (and same or different small molecule handles). In some embodiments, the PEG moiety comprises an —$NH_2$ group. In some embodiments, the PEG moiety is methoxy-PEG-amine. In some embodiments, the PEG moiety comprises a linker, e.g., the PEG moiety is $NH_2$-linker-PEG. In some embodiments, the small molecule handle can be any of the small molecule handles described herein (see below "small molecule handle" subsection).

The TGase-catalyzed reaction can be carried out from several hours to a day (e.g. overnight). The PEG moiety and/or the small molecule handle is allowed to react with the modified IL-2 protein (e.g., 1 mg/mL) comprising an engineered Q residue at concentrations between about 400 and about 600 μmol/L, providing an about 2 to about 20 folds excess of the PEG moiety (and/or small molecule handle) over the modified IL-2 protein, or optionally at lower excess of PEG moiety (and/or small molecule handle), e.g. about 3 to about 10 folds, or about 10 to about 20 folds. The reactions can be performed in potassium-free phosphate buffered saline (PBS; pH 8) at 10-37° C. After 1 h to several days, steady-state conditions are achieved. Excess protein, PEG moiety, and TGase are then removed using common methods, such as chromatography, e.g., HPLC. Reactions may be monitored by HPLC.

The resulting modified IL-2 protein-PEG conjugate can be analyzed using any suitable method. For example, the stoichiometry of the conjugated polypeptide can be characterized by liquid chromatography mass spectrometry (LC/MS) using a top-down approach in order to assess the number of PEG moiety and/or small molecule handle conjugated to the modified IL-2 proteins, and in particular the homogeneity of the composition. Conjugates can be reduced before LC/MS analysis. Peptide mapping assays with trypsin digestion and/or Glu-C digestion can be used to examine the primary structure of the protein. Location of PEGylation and/or PEG loading can be determined by comparing the signal intensity of peptides from digested PEGylated sample and digested unPEGylated sample (e.g., trypsin digestion or Glu-C digestion), based on the principle that the addition of PEG conjugation shifts both the mass-to-charge ratio and retention time of a peptide, resulting in much lower intensity or loss of signal at its retention time. Therefore, by comparing to peptide mapping profile of the unPEGylated protein, the peptide with lower intensity or lost signal in the peptide mapping profile of the PEGylated protein is the PEGylated peptide. By comparing between PEGylated peptides identified in trypsin digestion and/or Glu-C digestion, PEGylation location and/or PEG loading can be found and determined. Further investigation by examining extracted ion chromatogram, MS1 and/or MS/MS spectra can be carried out to verify the exact PEGylation site and PEG loading. Also see Example 9 for exemplary methods.

In some embodiments, the product is analyzed for PEG loading (e.g. number of PEG moiety in the modified IL-2 protein-PEG conjugate). In some embodiments, the product is analyzed for small molecule handle loading (e.g. number of small molecule handle in the intermediate conjugate). Such methods can be used to determine the mean number of PEG moiety (and/or small molecule handle) per modified IL-2 protein as well as the distribution of number of PEG moiety (and/or small molecule handle) per modified IL-2 protein in a composition, i.e. the percentage of total modified IL-2 proteins with any given level of PEG loading (and/or small molecule handle loading). The portion of modified IL-2 proteins having a number (n) of engineered Q residue (e.g. n=1, 2, 3, 4, 5, 6, etc.) can be determined. One technique adapted to such determination and more generally PEG loading is hydrophobic interaction chromatography (HIC), HIC can be carried out as described for example in Hamblett et al. (2004) Cancer Res. 10: 7063-7070; Wakankar et al. (2011) mAbs 3(2): 161-172; and Lyon et al (2012) Methods in Enzymology, Vol. 502: 123-138, the disclosure of which are incorporated herein by reference.

The molar ratio between the TGase and the modified IL-2 protein in the PEG conjugation reaction can be controlled to allow efficient transglutamination reaction. For example, in some embodiments, the molar ratio of the TGase and the modified IL-2 protein is about 1:10 to about 1:800, such as any of about 1:10 to about 1:500, about 1:50 to about 1:300, about 1:100 to about 1:800, about 1:100 to about 1:500, about 1:200 to about 1:700, or about 1:10 to about 1:100.

The amount of the transglutaminase in the reaction mixture can be controlled to allow efficient transglutaminase reaction, e.g., PEG conjugation or small molecule handle conjugation. For example, in some embodiments, the concentration of the transglutaminase in the reaction mixture is about 0.001 mg/ml to about 1 mg/ml, such as any of about 0.001 mg/ml to about 0.01 mg/ml, about 0.01 mg/ml to about 0.1 mg/ml, about 0.005 mg/ml to about 0.5 mg/ml, about 0.01 mg/ml to about 0.3 mg/ml, about 0.5 mg/ml to about 1 mg/ml, about 0.001 mg/ml to about 0.1 mg/ml, about 0.003 mg/ml to about 1 mg/ml, or about 0.1 mg/ml to about 1 mg/ml.

In some embodiments, the concentration ratio between the PEG moiety (and/or the small molecule handle) and the modified IL-2 protein is from about 2:1 to about 100:1, including but not limited to any of about 2:1 to about 1:1, about 1:1 to about 100:1, about 5:1 to about 80:1, about 10:1 to about 100:1, about 10:1 to about 50:1, about 50:1 to about 100:1, about 1:1 to about 10:1, about 20:1 to about 80:1, or about 40:1 to about 60:1.

In some embodiments, the conjugation efficiency of the modified IL-2 protein and the PEG moiety (and/or small molecule handle) is at least about 20% (such as at lease about any of 30%, 40%, 50%, 60%, 70%, 80%, 85%, 90%, 95%, 96%, 97%, 98%, or 99%, or about 100%). As used herein, the term "conjugation efficiency", or "crosslinking efficiency" is the ratio between the experimentally measured amount of modified IL-2 protein-PEG conjugate divided by the maximum expected modified IL-2 protein-PEG conjugate amount, or the ratio between the experimentally measured amount of intermediate conjugate comprising a small molecule handle divided by the maximum expected intermediate conjugate comprising a small molecule handle amount. The term "PEGylation efficacy" is the ratio between the experimentally measured amount of modified IL-2 protein-PEG conjugate divided by the maximum expected modified IL-2 protein-PEG conjugate amount. Conjugation efficiency, PEGylation efficacy, or crosslinking efficiency can be measured by various techniques well known to persons skilled in the art, such as hydrophobic interaction chromatography. PEGylation efficacy can also be measured at different temperature, such as room temperature or 37° C. In some embodiments, the conjugation efficacy of the modified IL-2 protein and the small molecule handle is at least about any of 20%-25%, 25%-30%, 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the conjugation efficacy of the intermediate conjugate comprising a small molecule handle and a PEG moiety is at least about any of 20%-25%, 25%-30%, 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the PEGylation efficacy of the modified IL-2 protein and the PEG moiety is at least about any of 20%-25%, 25%-30%, 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the conjugation efficiency of the modified IL-2 protein and the PEG moiety is at least about any of 25%, 30%, 32%, 34%, 36%, 38%, 40%, 42%, 44%, 46%, 48%, 50%, 55%, 60%, 65%, 70%, 75%, 80%, 85%, 90%, 95%, or 99%.

Small Molecule Handle

The small molecule handle described herein generally has the structure of $—NH_2—R$, wherein R is a moiety that allows the attachment of the PEG moiety. The introduction of the small molecule handle in the methods described herein significantly increases the flexibility of the methods. Specifically, the structure of the small molecule handle can be tailored to the attachment of any desired PEG moiety. For example, in some embodiments, R is a ligand which specifically binds to a binding partner. This allows attachment of any PEG moiety that contains the binding partner. Suitable ligand/binding partner pairs include, but are not limited to, antibody/antigen, antigen/antibody, avidin/biotin, biotin/avidin, streptavidin/biotin, biotin/streptavidin, glutathione/GST, GST/glutathione, maltose binding protein/amylose, amylose/maltose binding protein, cellulose binding protein and cellulose, cellulose/cellulose binding protein, etc. When a two-step conjugation method is performed as described herein, the PEG moiety comprises a linker and a PEG molecule, wherein the linker is a binding partner to the R ligand within the small molecule handle.

Other suitable small molecule handles described herein include, but are not limited to, $NH_2—CH_2—CH(OH)—CH_2—NH_2$, $NH_2—R—(OR')_2$, $NH_2—R{=}O$, $NH_2—R—SH$, $NH_2$—R-Azide. These small molecule handles allow the attachment of the PEG moiety through suitable linkers such as $NH_2—O—R$-PEG, Maleimide-R-PEG, and Cyclooctyne-R—(R'-PEG)$_2$, wherein R and R' are independently linker groups, such as linker groups comprising alkyl.

Transglutaminases (TGase)

Transglutaminases (TGase) transfers a moiety having an amine donor group (e.g., a PEG moiety or a small molecule handle containing a primary amine or a lysine donor residue) to an acceptor glutamine residue (e.g., the engineered Q residue of the modified IL-2 protein) through transglutamination, so that a covalent protein crosslinking is formed between the amine donor group and the acceptor Q residue, accompanied by the release of ammonia. After the glutamine-containing first substrate (acceptor or Q-substrate) binds to the enzyme, it forms a gamma-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nepsilon (gamma-glutamyl)lysine isopeptide bridge) is formed and released. This re-establishes the active-center Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-center Cys. In contrast, bacterial TGases isolated from Streptoverticillium sp (vide supra) has an atypical catalytic triad and shows no sequence homology with the papain-like catalytic triad of other TGases. Any TGase described in WO2015191883 can be used in the present invention, the contents of which are incorporated by reference herein in their entirety.

Several types of transglutaminases have been reported in various living organisms including microbials. Examples are TGase from guinea pig liver (GTGase), fish liver (FTGase) and microorganisms (mTGase) and any recombinant TGase (rTGase). Other TGases than the ones listed here can also be used according to the invention. Examples of useful TGases include microbial transglutaminases, such as e.g. from *Streptomyces mobaraense, Streptomyces cinnamoneum* and *Streptomyces griseocarneum* disclosed in U.S. Pat. No. 5,156,956, and *Streptomyces lavendulae* disclosed in U.S. Pat. No. 5,252,469, and *Streptomyces ladakanum* disclosed in JP2003199569. Other useful microbial transglutaminases have been isolated from *Bacillus subtilis* (disclosed in U.S. Pat. No. 5,731,183) and from various Myxomycetes. Other examples of useful microbial transglutaminases are those disclosed in WO 96/06931 (e.g. transglutaminase from *Bacillus lydicus*) and WO 96/22366. Useful non-microbial transglutaminases include guinea-pig liver transglutaminase, and transglutaminases from various marine sources like the flat fish *Pagrus major* (disclosed in EP-0555649), and the Japanese oyster *Crassostrea gigas* (disclosed in U.S. Pat. No. 5,736,356). An exemplary TGase is bacterial transglutaminase (BTG) (see, e.g. EC 2.3.2.13, protein-glutamine-gamma-glutamyltransferase). In another exemplary embodiment, the TGase is from *S. mobaraense*. In another embodiment, the TGase is a mutant (e.g., engineered) TGase having at least 80% sequence homology with native TGase. An example is recombinant bacterial transglutaminase derived from *Streptomyces mobaraensis* (available from Zedira, Darmstadt, Germany).

*Streptomyces ladakanum* ATCC 27441 or NRRL3191 mTgase is expressed as Pre-Pro-mTgase (GenBank access number AY241675). There are 410 amino acid residues in pre-pro-mTGase, 331 in mature enzyme plus 30 of pre and 49 of pro. Pro peptide is a strong inhibitor of mature enzyme. Primers designed according to AY241675 were used to clone the pro-mTgase and mature mTgase from ATCC 27441DNA into pET29b(+) vector's Nde I and Xho I sites. Active mTgase can be obtained either from enterokinase light chain (EKL) digestion of Pro-mTgase or refolding of mature mTgase. mTgase from Strep *Ladakanum* (TG_SL) is very similar to mTgase from Strep. *mobaraensis* (TG_SM, sold by Ajinomoto as ACTIVA®) with a few amino acid differences.

The transglutaminase used in methods described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and allow enzyme activity. In some embodiments, the transglutaminase is a microbial transglutaminase derived from a microbial genome, such as transglutaminase from *Streptoverticillium* or *Streptomices* (e.g., *Streptomyces mobarensis* or *Streptoverticillium mobarensis*). In some embodiments, the transglutaminase is a mammalian protein (e.g., human transglutaminase), a bacterial protein, a plant protein, a fungi protein (e.g., Oomycetes and Actinomicetes transglutaminases), or a prokaryotic protein. In some embodiments, the transglutaminase is from *Micrococcus, Clostridium, Turolpsis, Rhizopus, Monascus*, or *Bacillus.*

Suitable TGase include, but is not limited to, bacterial transglutaminase (BTG) such as the enzyme having EC reference EC 2.3.2.13 (protein-glutamine-7-glutamyltransferase). In some embodiments, the TGase is from Strep *Ladakanum* (TG_SL, SEQ ID NO: 20). In some embodiments, the TGase is from Strep *Mobaraensis* (TG_SM, SEQ ID NO: 22). In some embodiments, the TGase is a recombinant TGase based on the TGase from Strep *Ladakanum* (TG_SL, SEQ ID NO: 21)

In some embodiments, the transglutaminase used in the methods described herein is a recombinant protein produced using recombinant techniques.

In some embodiments, the transglutaminase is wildtype, for example the TGase having the sequence of SEQ ID NO: 20. In some embodiments, the transglutaminase is a recombinant wildtype TGase comprising the wildtype TGase having the sequence of SEQ ID NO: 20, wherein the recombinant wildtype TGase further comprises an additional proline at the N-terminus and optionally a purification tag (such as a polyhistidine tag). In some embodiments, the transglutaminase is a recombinant wildtype TGase having a sequence of SEQ ID NO: 21. Contrary to the general understanding in the art that wildtype transglutaminase is unable to catalyze transglutamination reaction to an acceptor glutamine flanked by a glycosylation site, it was surprisingly found that such reaction can be carried out with substantial efficacy and specificity under certain conditions as described herein.

In some embodiments, the transglutaminase is a purified protein. For example, in some embodiments, the transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is at least about any of 50%, 55%, 60%, 65%, 70%, 75%, 80%, 85%, 90%, 95%, 96%, 97%, 98%, 99%, or 100% pure. In some embodiments, the TGase has a purity of at least about 90%.

In some embodiments, the transglutaminase is engineered. In some embodiments, the TGase is an engineered TGase specifically designed to carry out transglutamination reactions to an acceptor glutamine proximal to a glycosylation site. In some embodiments, the engineered TGase is based on the wildtype TGase from Strep *ladalanum* (SEQ ID NO: 20 or SEQ ID NO: 21). In some embodiments, the engineered TGase is based on the wildtype TGase from Strep *Mobaraensis* (SEQ ID NO: 22). The sequence of a TGase isolated from Strep *ladakanum* has an amino acid sequence which is identical to the sequence from Strep *mobaraensis* except for a total of 22 amino acid differences between the two sequences (Yi-Sin Lin et al., Process Biochemistry 39(5), 591-598 (2004).

In some embodiments, the engineered TGase comprises an amino acid sequence having at least about 80% (such as at least about any of 81%, 82%, 83%, 84%, 85%, 86%, 87%, 88%, 89%, 90%, 91%, 92%, 93%, 94%, 95%, 96%, 97%, 98%, or 99%) identity to a wild-type TGase, such as a wild-type TGase comprising an amino acid sequence of SEQ ID NO: 20, wherein the transglutaminase comprises a deletion selected from the group consisting of: D1-E4; P244-P247; and H279-H289 compared to a wild-type TGase comprising an amino acid sequence of SEQ ID NO: 20. In some embodiments, the engineered transglutaminase comprising an amino acid sequence that is 100% identical to SEQ ID NO: 20 except for one or more deletions selected from the group consisting of: D1-E4; P244-P247; and H279-H289.

In some embodiments, the engineered transglutaminase comprises an amino acid sequence having at least about 80% (such as at least about any of 81%, 82%, 83%, 84%, 85%, 86%, 87%, 88%, 89%, 90%, 91%, 92%, 93%, 94%, 95%, 96%, 97%, 98%, or 99%) identity to SEQ ID NO: 21, wherein the transglutaminase comprises a deletion selected from the group consisting of: P1-E5; P245-P248; and H280-H290. In some embodiments, the engineered transglutaminase comprises an amino acid sequence that is 100% identical to SEQ ID NO: 21 except for one or more deletions selected from the group consisting of: P1-E5; P245-P248; and H280-H290.

In some embodiments, the engineered transglutaminase comprises an amino acid sequence having at least about 80% (such as at least about any of 81%, 82%, 83%, 84%, 85%, 86%, 87%, 88%, 89%, 90%, 91%, 92%, 93%, 94%, 95%, 96%, 97%, 98%, or 99%) identity to SEQ ID NO: 20, wherein the transglutaminase comprises a mutation selected from the group consisting of: deletion of D1-E4; deletion of P244-P247; deletion of N282-L285; substitution of H279-A287 with a G; and substitution of A280-H289 with a G; or a combination thereof. In some embodiments, the engineered transglutaminase comprises an amino acid sequence that is 100% identical to SEQ ID NO: 20 except for one or more deletions selected from the group consisting of: a mutation selected from the group consisting of: deletion of D1-E4; deletion of P244-P247; deletion of N282-L285; substitution of H279-A287 with a G; and substitution of A280-H289 with a G; or a combination thereof.

In some embodiments, the engineered transglutaminase comprising an amino acid sequence having at least about 80% (such as at least about any of 81%, 82%, 83%, 84%, 85%, 86%, 87%, 88%, 89%, 90%, 91%, 92%, 93%, 94%, 95%, 96%, 97%, 98%, or 99%) identity to SEQ ID NO: 21, wherein the transglutaminase comprises a mutation selected from the group consisting of: deletion of P1-E5; deletion of P245-P248; deletion of N283-L286; substitution of H280-A288 with a G; and substitution of A281-H290 with a G; or a combination thereof. In some embodiments, the engineered transglutaminase comprising an amino acid sequence that is 100% identical to SEQ ID NO: 21 except for one or more deletions selected from the group consisting of: a mutation selected from the group consisting of: deletion of P1-E5; deletion of P245-P248; deletion of N283-L286; substitution of H280-A288 with a G; and substitution of A281-H290 with a G; or a combination thereof.

The terms "sequence identity" or "identify" as used interchangeably herein refers the degree of sequence relatedness between peptides, as determined by the number of matches between strings of two or more amino acid residues. Sequence identity can be measured, for example, by the percent of identical matches between the smaller of two or more sequences with gap alignments (if any) addressed by a particular mathematical model or computer program (i.e., "algorithms"). Some methods to determine identity are designed to give the largest match between the sequences tested. Methods to determine identity are described in publicly available computer programs. Exemplary computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In some embodiments, the engineered transglutaminase has a higher transglutaminase activity than that of the TGase encoded by SEQ ID NO: 20 or SEQ ID NO: 21. In some embodiments, conjugation by an engineered TGase described herein is at least about 10% more active than a wildtype transglutaminase under the same reaction conditions. In some embodiments, the specificity activity of the engineered transglutaminase is at least about 1.25×, 1.5×, 2.0×, 2.5×, 3.0×, 3.5×, 4.0×, 4.5×, 5.0×, 5.5×, 6.0×, 6.5×, 7.0×, 7.5×, 8.0×, 8.5×, 9.0×, 9.5×, or 10.5× higher than that of the wildtype TGase (such as the TGase of SEQ ID NO: 20 or SEQ ID NO: 22).

In some embodiments, the engineered TGase of the present invention exhibit an activity which is more than 30%, such as more than 50%, such as more than 70%, such as more than 90% of that of a TGase from *S. ladakanum* having an amino acid sequence of SEQ ID No. 20.

In some embodiments, the TGase is a microbial TGase (mTGase). In some embodiments, the TGase is a wild-type TGase. In some embodiments, the wild-type TGase has an amino acid sequence of SEQ ID NO: 20. In some embodiments, the TGase is an engineered TGase capable of carrying out transglutamination reactions to a Q residue. In some embodiments, the engineered TGase comprises an amino acid sequence having at least about 80% identity to SEQ ID NO: 20. In some embodiments, the TGase has a purity of at least about 90%.

IV. Pharmaceutical Compositions

Further provided by the present application are pharmaceutical compositions comprising any one of the modified IL-2 proteins described herein, or any one of the modified IL-2 protein-PEG conjugates described herein; and an optional pharmaceutically acceptable carrier.

In some embodiments, there is provided a pharmaceutical composition comprising any of the modified IL-2 proteins described herein, and an optional pharmaceutically acceptable carrier (hereinafter also referred to as "modified IL-2 protein pharmaceutical composition"). In some embodiments, the modified IL-2 proteins within the pharmaceutical compositions are the same. In some embodiments, the modified IL-2 proteins within the pharmaceutical compositions are different, e.g., with different engineered Q residues (e.g., insertion, replacement), different amount of engineered Q residues. In some embodiments, the pharmaceutical composition comprises no unmodified IL-2 protein, i.e., all IL-2 proteins bear an engineered Q residue. In some embodiments, the pharmaceutical composition comprises some modified IL-2 protein comprising an engineered Q residue (such as about any of 70%, 75%, 80%, 85%, 90%, 95%, 96%, 97%, 98%, 99%, or 100%), and some IL-2 protein without engineered Q residue.

In some embodiments, there is provided a pharmaceutical composition comprising any of the modified IL-2 protein-PEG conjugates described herein, and an optional pharmaceutically acceptable carrier (hereinafter also referred to as "modified IL-2 protein-PEG conjugate pharmaceutical composition"). In some embodiments, at least about 50% (such as at least about any of 60%, 70%, 80%, 90%, 95%, or 99%, or 100%) of the modified IL-2 protein-PEG conjugates in the pharmaceutical composition comprise one PEG moiety conjugated to the modified IL-2 protein via the engineered Q residue. In some embodiments, the modified IL-2 protein comprises two or more (such as two) engineered Q residues. In some embodiments, at least about 50% (such as at least about any of 60%, 70%, 80%, 90%, 95%, or 99%, or 100%) of the modified IL-2 protein-PEG conjugates in the pharmaceutical composition comprise two or more (such as two) PEG moieties, wherein each PEG moiety is conjugated to one of the two or more (such as two) engineered Q residues of the modified IL-2 protein. In some embodiments, at least about 50% (such as at least about any of 60%, 70%, 80%, 90%, 95%, or 99%, or 100%) of the modified IL-2 protein-PEG conjugates in the pharmaceutical composition comprise one PEG moiety conjugated to each of the engineered Q residues of the modified IL-2 protein. In some embodiments, the pharmaceutical composition comprising the modified IL-2 protein-PEG conjugates comprises no more than about 30% (such as no more than about any of 25%, 20%, 15%, 10%, 9%, 8%, 7%, 6%, 5%, 4%, 3%, 2%, or 1%) modified IL-2 protein without PEG conjugation. In some embodiments, the pharmaceutical composition comprising the modified IL-2 protein-PEG conjugates is homogenous, i.e., all modified IL-2 protein-PEG conjugates comprise the same modified IL-2 protein conjugated with the same PEG moiety on the same engineered Q residue. In some embodiments, the pharmaceutical composition comprising the modified IL-2 protein-PEG conjugates is heterogeneous, e.g., comprising different modified IL-2 protein conjugated with the same PEG moiety, different modified IL-2 protein conjugated with different PEG moieties, the same modified IL-2 protein conjugated with the same PEG moiety on different engineered Q residues, or the same modified IL-2 protein conjugated with different PEG moieties.

The term "pharmaceutically acceptable carrier" is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable carrier" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the modified IL-2 protein or modified IL-2 protein-PEG conjugates described herein.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from about 0.2% to about 1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight, preferably about 1% to about 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/mL to about 1.0 mg/mL, preferably about 0.07 mg/mL to about 0.2 mg/mL.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In some embodiments, the modified IL-2 protein and modified IL-2 protein-PEG conjugates described herein can be deimmunized to reduce immunogenicity upon administration to a subject using known techniques such as those described, e.g., in PCT Publication WO98/52976 and WO00/34317.

The pharmaceutical compositions described herein may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the modified IL-2 protein and modified IL-2 protein-PEG conjugates described herein.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The pharmaceutical compositions described herein in some embodiments are suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or engineered release. Engineered release formulations include controlled, delayed, sustained, pulsed, targeted and programmed release formulations. For example, in one aspect, sterile injectable solutions can be prepared by incorporating the modified IL-2 protein or modified IL-2 protein-PEG conjugates described herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the exemplary methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

An exemplary, non-limiting pharmaceutical composition of the modified IL-2 protein or modified IL-2 protein-PEG conjugate described herein is a formulation as a sterile aqueous solution having a pH that ranges from about 5.0 to about 6.5 and comprising from about 0.5 mg/mL to about 20 mg/mL of a modified IL-2 protein or modified IL-2 protein-PEG conjugate described herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dehydrate.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the PEG moiety and the particular therapeutic or prophylactic effect to be achieved, and (b) the limitations inherent in the art of IL-2 for the treatment of sensitivity in individuals.

The skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

V. Methods of Treatment

The present application further provides methods of treating a disease (such as cancer) in an individual (e.g., human) comprising administering to the individual an effective amount of any one of the pharmaceutical compositions described herein, or the modified IL-2 protein-PEG conjugates (or modified IL-2 proteins) described herein. In some embodiments, the methods of treating a disease (such as cancer) in an individual (e.g., human) described herein comprises preferentially stimulating IL-2Rβ subunit over IL-2Rα subunit compared to a parent IL-2 (e.g., wt IL-2 protein, or IL-2 Aldesleukin). In some embodiments, the pharmaceutical composition is administered intravenously, intratumorally, intraperitoneally, or subcutaneously. In some embodiments, the pharmaceutical composition (e.g., modified IL-2 protein pharmaceutical composition or modified IL-2 protein-PEG conjugate pharmaceutical composition) is administered at about 1 μg/kg to about 100 μg/kg (e.g., about 1 μg/kg to about 50 μg/kg). In some embodiments, the pharmaceutical composition is administered once per month, once every 3 weeks, once every 2 weeks, once a week, twice a week, once every other day, or daily. In some embodiments, the disease is cancer, such as renal cell carcinoma, metastatic melanoma, acute myeloid leukemia (AML), non-Hodgkin's lymphoma (NHL), cutaneous T-cell lymphoma (CTCL), breast cancer, or bladder cancer.

Thus in some embodiments, there is also provided a method of treating a disease (e.g., cancer) in an individual (e.g. human), comprising administering to the individual an effective amount of a pharmaceutical composition comprising (a) a modified IL-2 protein comprising an engineered Q residue; and (b) optionally a pharmaceutically acceptable carrier. In some embodiments, there is provided a method of treating a disease (e.g., cancer) in an individual (e.g. human), comprising administering to the individual an effective amount of a pharmaceutical composition comprising (a) a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue; and (b) optionally a pharmaceutically acceptable carrier. In some embodiments, there is also provided a method of preferentially stimulating IL-2Rβ subunit over IL-2Rα subunit in an individual (e.g. human), comprising administering to the individual an effective amount of a pharmaceutical composition comprising (a) a modified IL-2 protein comprising an engineered Q residue; and (b) optionally a pharmaceutically acceptable carrier. In some embodiments, there is also provided a method of preferentially stimulating IL-2Rβ subunit over IL-2Rα subunit in an individual (e.g. human), comprising administering to the individual an effective amount of a pharmaceutical composition comprising (a) a modified IL-2 protein-PEG conjugate comprising a modified IL-2 protein comprising an engineered Q residue and a PEG moiety (e.g., methoxy-PEG-amine), wherein the PEG moiety is conjugated to the modified IL-2 protein via the engineered Q residue; and (b) optionally a pharmaceutically acceptable carrier. In some embodiments, the pharmaceutical composition is administered once per month, once every 3 weeks, once every 2 weeks, once a week, twice a week, once every other day, or daily. In some embodiments, the disease is cancer, such as renal cell carcinoma, metastatic melanoma, acute myeloid leukemia (AML), non-Hodgkin's lymphoma (NHL), cutaneous T-cell lymphoma (CTCL), breast cancer, or bladder cancer. In some embodiments, the pharmaceutical composition is administered at about 1 μg/kg to about 100 μg/kg (e.g., about 1 μg/kg to about 50 g/kg). In some embodiments, the pharmaceutical composition is administered intravenously, intratumorally, intraperitoneally, or subcutaneously. In some embodiments, the engineered Q residue is within the IL-2Rα subunit binding domain. In some embodiments, the engineered Q residue is between about 1 and about 3 amino acid residues (such as any of 1, 2, or 3 amino acid residues) outside of the IL-2Rα subunit binding domain. In some embodiments, the modified IL-2 protein comprises one engineered Q residue. In some embodiments, the modified IL-2 protein comprises two or more (such as two) engineered Q residues. In some embodiments, the engineered Q residue is (e.g., results from) a single amino acid mutation (e.g., insertion, substitution) relative to a parent IL-2 protein (e.g., wild-type IL-2, or IL-2 Aldesleukin). In some embodiments, the parent IL-2 protein (e.g., IL-2 Aldesleukin) comprises an amino acid sequence of SEQ ID NO: 1. In some embodiments, the single amino acid mutation (e.g., substitution) is selected from the group consisting of F43Q, R37Q, F41Q, K42Q, Y44Q, T36Q, M38Q, and any combinations thereof, wherein the amino acid position is relative to a parent IL-2 protein (e.g., IL-2 Aldesleukin) comprising an amino acid sequence of SEQ ID NO: 1. In some embodiments, the modified IL-2 protein comprises an amino acid sequence of any of SEQ ID NOs: 2 and 4-8. In some embodiments, the engineered Q residue is part of an exogenous patch sequence suitable for TGase reaction. In some embodiments, the exogenous patch sequence replaces a portion of a parent IL-2 protein (e.g., wild-type IL-2, or IL-2 Aldesleukin). In some embodiments, the parent IL-2 protein comprises an amino acid sequence of SEQ ID NO: 1. In some embodiments, the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof. In some embodiments, the modified IL-2 protein comprises an amino acid sequence of any of SEQ ID NOs:

3 and 15-19. In some embodiments, the modified IL-2 protein further comprises one or more additional amino acid mutations that are not engineered Q residues. In some embodiments, the modified IL-2 protein comprises an amino acid sequence having at least about 95% (such as at least about any of 96%, 97%, 98%, 99%, or 100%) identity to a parent IL-2 protein (e.g., wild-type IL-2, or IL-2 Aldesleukin). In some embodiments, the PEG moiety is linear. In some embodiments, the PEG moiety is branched. In some embodiments, the PEG moiety has a molecular weight of between about 10 kDa and about 40 kDa, such as about 20 kDa, about 30 kDa, or about 40 kDa. In some embodiments, the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy. In some embodiments, the PEG moiety is methoxy-PEG-amine. In some embodiments, the modified IL-2 protein-PEG conjugate comprises a modified IL-2 protein comprising one engineered Q residue, and one PEG moiety conjugated to the modified IL-2 protein via the one engineered Q residue. In some embodiments, the modified IL-2 protein comprises two or more engineered Q residues, wherein each of the two or more engineered Q residues is each conjugated with one PEG moiety. In some embodiments, the modified IL-2 protein comprises two or more engineered Q residues, and at least one of the two or more engineered Q residues is each conjugated with one PEG moiety. In some embodiments, the conjugation of the PEG moiety is mediated via a TGase, such as a microbial TGase (mTGase). In some embodiments, the TGase is a wild-type TGase, such as comprising an amino acid sequence of SEQ ID NO: 20. In some embodiments, the TGase is an engineered TGase. In some embodiments, the engineered TGase comprises an amino acid sequence having at least about 80% (such as at least about any of 85%, 90%, 95%, 96%, 97%, 98%, or 99%) identity to SEQ ID NO: 20. In some embodiments, the TGase has a purity of at least about 90% (such as at least about any of 90%, 91%, 92%, 93%, 94%, 95%, 96%, 97%, 98%, 99%, or 100%). In some embodiments, the $K_D$ of the binding between the modified IL-2 protein and an IL-2Rα subunit is about 2 to about 800 times (e.g., about 2 to about 50 times, about 400 to about 500 times, about 476 times, about 5-6 times, about 38-39 times) of the $K_D$ of the binding between a parent IL-2 protein (e.g., wild-type IL-2, human IL-2, or IL-2 Aldesleukin) and the IL-2Rα subunit. In some embodiments, the $K_D$ of the binding between the modified IL-2 protein and an IL-2Rβ subunit is similar to (e.g., equal to) or about 1 to about 30 times (e.g., about 1 to about 10 times, about 10 to about 20 times, about 16 times, about 1.4 times, or about 6.7 times) of the $K_D$ of the binding between parent IL-2 (e.g., wild-type IL-2, human IL-2, or IL-2 Aldesleukin) and IL-2Rβ subunit. In some embodiments, the $K_D$ of the binding between the modified IL-2 protein-PEG conjugate and an IL-2Rα subunit is about 10 to about 2000 times (e.g., about 10 to about 50 times) of the $K_D$ of the binding between a parent IL-2 protein (e.g., wild-type IL-2, human IL-2, or IL-2 Aldesleukin) and an IL-2Rα subunit. In some embodiments, the modified IL-2 protein-PEG conjugate does not bind or cannot be detected (e.g., by SPR) to bind an IL-2Rα subunit. In some embodiments, the $K_D$ of the binding between the modified IL-2 protein-PEG conjugate and an IL-2Rβ subunit is similar to (e.g., equal to) or about 1 to about 30 times (e.g., about 1 to about 10 times, or about 8 to about 11 times) of the $K_D$ of the binding between a parent IL-2 protein (e.g., wild-type IL-2, or IL-2 Aldesleukin) and an IL-2Rβ subunit. In some embodiments, the $K_D$ of the binding between the modified IL-2 protein-PEG conjugate and an IL-2Rβ subunit is similar to (e.g., equal to) or about 1 to about 10 times of the $K_D$ of the binding between the same modified IL-2 protein without PEGylation and the IL-2Rβ subunit. In some embodiments, the $K_D$ of the binding between the modified IL-2 protein and an IL-2Rβ subunit is similar to (e.g., equal to) or about 1 to about 10 times of the $K_D$ of the binding between the same modified IL-2 protein with PEGylation (i.e., modified IL-2 protein-PEG conjugate) and the IL-2Rβ subunit. In some embodiments, the modified IL-2 protein-PEG conjugate is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell. In some embodiments, the modified IL-2 proteins have reduced ability (such as about 2 to about 50 folds or about 2 to about 15 folds reduced ability) in activating a Treg compared to a parent IL-2 protein (e.g., wild-type IL-2, human IL-2, or IL-2 Aldesleukin). In some embodiments, the modified IL-2 protein has similar (e.g., equal to) or about 1 to about 5 folds reduced ability to activate a CTL or a NK cell compared to a parent IL-2 protein (e.g., wild-type IL-2, human IL-2, or IL-2 Aldesleukin). In some embodiments, the modified IL-2 protein has similar (e.g., equal) or preferential activation on CTL and/or NK cells over Treg cells, compared to a parent IL-2 protein (e.g., wild-type IL-2, human IL-2, or IL-2 Aldesleukin), such as similar (e.g., equal) or about 1 to 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin). In some embodiments, the modified IL-2 protein-PEG conjugate has about 2 to about 5000 folds reduced ability to activate a Treg cell compared to a parent IL-2 protein (e.g., wild-type IL-2, human IL-2, or IL-2 Aldesleukin). In some embodiments, the modified IL-2 protein-PEG conjugate has similar (e.g., equal) or about 1 to about 50 folds reduced ability to activate a CTL (or NK) cell compared to a parent IL-2 protein (e.g., wild-type IL-2, human IL-2, or IL-2 Aldesleukin). In some embodiments, the modified IL-2 protein and/or the modified IL-2 protein-PEG conjugate preferentially activates IL-2Rβ subunit over IL-2Rα subunit, compared to parent IL-2 protein (e.g., wild-type IL-2, human IL-2, or IL-2 Aldesleukin). In some embodiments, the modified IL-2 protein-PEG conjugate has similar (e.g., equal) or preferential activation on CTL and/or NK cells over Treg cells, compared to a parent IL-2 protein (e.g., wild-type IL-2, human IL-2, or IL-2 Aldesleukin), such as similar (e.g., equal) or about 1 to about 20 folds (e.g., about 1 to about 10 folds) higher ability to increase the ratio of CTL to Treg or the ratio of NK cell to Treg compared to a parent IL-2 protein (e.g., wild-type IL-2, human IL-2, or IL-2 Aldesleukin).

In some embodiments, the method of treating cancer described herein has one or more of the following biological activities: (1) killing cancer cells; (2) inhibiting proliferation of cancer cells; (3) reducing tumor size; (4) alleviating one or more symptoms in an individual having cancer; (5) inhibiting tumor metastasis (e.g., metastasis to lymph nodes, lung); (6) prolonging survival; (7) prolonging time to cancer progression; (8) preventing, inhibiting, or reducing the likelihood of the recurrence of a cancer; and (9) preferentially stimulating IL-2Rβ subunit over IL-2Rα subunit compared to a parent IL-2 (e.g., wt IL-2 protein, human IL-2, or IL-2 Aldesleukin). In some embodiments, the method of killing cancer cells mediated by the modified IL-2 protein-PEG conjugates (or modified IL-2 protein) described herein or pharmaceutical composition thereof can achieve a tumor cell death rate of at least about any of 40%, 50%, 60%, 70%, 80%, 90%, 95%, or more. In some embodiments, the method of reducing tumor size mediated by the modified IL-2 protein-PEG conjugates (or modified IL-2 protein) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes, lung) mediated by the modified IL-2 protein-PEG conjugates (or modified IL-2 protein) described herein or pharmaceutical composition thereof can inhibit at least about 10% (including for example at least about any of 20%, 30%, 40%, 60%, 70%, 80%, 90%, or 100%) of the metastasis. Metastasis can be assessed by any known methods in the art, such as by blood tests, bone scans, x-ray scans, CT scans, PET scans, and biopsy. In some embodiments, the method of prolonging survival of an individual (such as a human) mediated by the modified IL-2 protein-PEG conjugates (or modified IL-2 protein) described herein or pharmaceutical composition thereof can prolongs the survival of the individual by at least about any of 1, 2, 3, 4, 5, 6, 7, 8, 9, 10, 11, 12, 18, or 24 months, or more. In some embodiments, the method of prolonging time to cancer progression mediated by the modified IL-2 protein-PEG conjugates (or modified IL-2 protein) described herein or pharmaceutical composition thereof can prolong the time to cancer progression by at least about any of 1, 2, 3, 4, 5, 6, 7, 8, 9, 10, 11, or 12 weeks, or more. In some embodiments, the modified IL-2 protein-PEG conjugates (or modified IL-2 protein) described herein or pharmaceutical composition thereof can increase, enhance, or stimulate an immune response or function in a subject by activating effector cells (e.g., CD8+ T cells, NK cells). In some embodiments, the NK cells/CD8+ T cells in the individual have increased or enhanced priming, activation, proliferation, cytokine release and/or cytolytic activity relative to prior to the administration of the modified IL-2 protein-PEG conjugates (or modified IL-2 protein) described herein or pharmaceutical composition thereof. In some embodiments, the treatment effect comprises causing an objective clinical response in the individual. In some embodiments, Stringent Clinical Response (sCR) is obtained in the individual. In some embodiments, the treatment effect comprises causing disease remission (partial or complete) in the individual. In some the clinical remission is obtained after no more than about any one of 6 months, 5 months, 4 months, 3 months, 2 months, 1 months or less after the individual receives the pharmaceutical composition. In some embodiments, the treatment effect comprises preventing relapse or disease progression of the cancer in the individual. In some embodiments, the relapse or disease progression is prevented for at least about 6 months, 1 year, 2 years, 3 years, 4 years, 5 years or more. In some embodiments, the treatment effect comprises inhibiting growth or reducing the size of a solid or lymphatic tumor.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting.

In some embodiments, the methods described herein are suitable for treating a solid cancer selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), cutaneous T-cell lymphoma (CTCL), cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In some embodiments, the methods described herein are suitable for treating a hematologic cancer chosen from one or more of acute myeloid leukemia (AML), chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

Administration of the pharmaceutical compositions may be carried out in any convenient manner, including by injection, ingestion, transfusion, implantation or transplantation. The compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, the modified IL-2 protein described herein, modified IL-2 protein-PEG conjugates described herein, or pharmaceutical composition thereof is administered via a parenteral route, such as any of intramuscular (IM), subcutaneous (SC), intravenous (IV), intra-articular, or intra-peritoneal administration. In some embodiments, the modified IL-2 protein described herein, modified IL-2 protein-PEG conjugates described herein, or pharmaceutical composition thereof is administered subcutaneously. In some embodiments, the modified IL-2 protein described herein, modified IL-2 protein-PEG conjugates described herein, or pharmaceutical composition thereof is administered as an intravenous bolus. In some embodiments, the modified IL-2 protein described herein, modified IL-2 protein-PEG conjugates described herein, or pharmaceutical composition thereof is administered by intravenous infusion. In some embodiments, the modified IL-2 protein described herein, modified IL-2 protein-PEG conjugates described herein, or pharmaceutical composition thereof is administered (e.g., infused) to the individual over a period of time no more than about any of 24 hours, 20 hours, 15 hours, 10 hours, 8 hours, 6 hours, 3 hours, 2 hours, 1 hours, 30 minutes, or less. In some embodiments, the modified IL-2 protein described here, modified IL-2 protein-PEG conjugates described herein, or pharmaceutical composition thereof is administered (e.g., infused) to the individual over a period of time of any one of about 30 minutes to about 1 hour, about 1 hour to about 2 hours, about 2 hours to about 4 hours, about 4 hours to about 6 hours, about 6 hours to about 8 hours, about 8 hours to about 10 hours, about 10 hours to about 12 hours, about 12 hours to about 18 hours, about 18 hours to about 24 hours, about 30 minutes to about 2 hours, about 2 hours to about 5 hours, about 5 hours to about 10 hours, about 10 hours to about 20 hours, about 30 minutes to about 10 hours, or about 30 minutes to about 20 hours. The modified IL-2 protein described here, modified IL-2 protein-PEG conjugates described herein, or pharmaceutical composition thereof may be administered (e.g., infused) to the individual at any suitable rate. In some embodiments, the modified IL-2 protein described here, modified IL-2 protein-PEG conjugates described herein, or pharmaceutical composition thereof may be administered (e.g., infused) at a rate more than about any of 0.001 μg/kg/hr, 0.002 μg/kg/hr, 0.005 μg/kg/hr, 0.01 μg/kg/hr, 0.02 μg/kg/hr, 0.05 μg/kg/hr, 0.1 μg/kg/hr, 0.2 μg/kg/hr, 0.5 μg/kg/hr, 0.6 μg/kg/hr, 0.7 μg/kg/hr, 0.8 μg/kg/hr, 0.9 μg/kg/hr, 1 μg/kg/hr, 1.5 μg/kg/hr, 2 μg/kg/hr, 3 μg/kg/hr, 4 μg/kg/hr, 5 μg/kg/hr, 10 μg/kg/hr, 15 μg/kg/hr, 20 μg/kg/hr, 25 μg/kg/hr, 50 μg/kg/hr, 75 μg/kg/hr, 100 μg/kg/hr or more.

In some embodiments, the modified IL-2 protein described herein, modified IL-2 protein-PEG conjugates described herein, or pharmaceutical composition thereof is administered for a single time. In some embodiments, the modified IL-2 protein described herein, modified IL-2 protein-PEG conjugates described herein, or pharmaceutical composition thereof is administered for multiple times (such as any of 2, 3, 4, 5, 6, or more times). In some embodiments, the modified IL-2 protein described herein, modified IL-2 protein-PEG conjugates described herein, or pharmaceutical composition thereof is administered once per day (daily), once per 2 days, once per 3 days, once per 4 days, once per 5 days, once per 6 days, once per week, once per 10 days, once every 2 weeks, once every 3 weeks, once every 4 weeks, once per month, once per 2 months, once per 3 months, once per 4 months, once per 5 months, once per 6 months, once per 7 months, once per 8 months, once per 9 months, or once per year. In some embodiments, the modified IL-2 protein described herein, modified IL-2 protein-PEG conjugates described herein, or pharmaceutical composition thereof is administered once per day to once per 3 weeks. In some embodiments, the interval between administrations is about any one of 1 week to 2 weeks, 2 weeks to 1 month, 2 weeks to 2 months, 1 month to 2 months, 1 month to 3 months, 3 months to 6 months, or 6 months to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. In some embodiments, the pharmaceutical composition is administered in split doses, such as about any one of 2, 3, 4, 5, or more doses. In some embodiments, the split doses are administered over about a week. In some embodiments, the dose is equally split. In some embodiments, the split doses are about 20%, about 30% and about 50% of the total dose. In some embodiments, the interval between consecutive split doses is about 1 day, 2 days, 3 days or longer. For repeated administrations over several days or longer, depending on the condition, the treatment is sustained until a desired suppression of disease symptoms occurs. However, other dosage regimens may be useful. The progress of this therapy is easily monitored by conventional techniques and assays.

VI. Kits and Articles of Manufacture

Further provided are kits, unit dosages, and articles of manufacture comprising any one of the modified IL-2 protein-PEG conjugates (or modified IL-2 proteins) described herein. In some embodiments, a kit is provided which contains any one of the pharmaceutical compositions described herein and preferably provides instructions for its use, such as for use in the treatment of the disorders described herein.

Kits of the invention include one or more containers comprising a modified IL-2 protein-PEG conjugate (or modified IL-2 protein) described herein for treating a disease. For example, the instructions comprise a description of administration of the modified IL-2 protein-PEG conjugate (or modified IL-2 protein) to treat a disease, such as cancer (e.g., renal cell carcinoma, metastatic melanoma, acute myeloid leukemia (AML), non-Hodgkin's lymphoma (NHL), cutaneous T-cell lymphoma (CTCL), breast cancer, or bladder cancer). The kit may further comprise a description of selecting an individual (e.g., human) suitable for treatment based on identifying whether that individual has the disease and the stage of the disease. The instructions relating to the use of the modified IL-2 protein-PEG conjugate (or modified IL-2 protein) generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable. The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an engineered polypeptide as described herein. The container may further comprise a second pharmaceutically active agent. The kits may optionally provide additional components such as buffers and interpretive information. Normally, the kit comprises a container and a label or package insert(s) on or associated with the container.

In some embodiments, the kit further comprises a TGase (such as any one of the wild-type or engineered TGase described herein). In some embodiments, the kit further comprises other reagents for carrying out the transglutamination reaction, such as PEG moieties (e.g., methoxy-PEG-amine). In some embodiments, the kit further comprises an instruction on carrying out any one of the conjugation methods described herein. In some embodiments, the kit further comprises a solid support for immobilizing the TGase or the modified IL-2 protein. In some embodiments, the TGase in the kit is immobilized on the solid support.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

EXEMPLARY EMBODIMENTS

Embodiment 1. A modified Interleukin-2 (IL-2) protein comprising an engineered glutamine (Q) residue.

Embodiment 2. The modified IL-2 protein of embodiment 1, wherein the engineered Q residue is within the IL-2 Receptor alpha (IL-2Rα) subunit binding domain.

Embodiment 3. The modified IL-2 protein of embodiment 1, wherein the engineered Q residue is between about 1 and about 3 amino acid residues outside of the IL-2Rα subunit binding domain.

Embodiment 4. The modified IL-2 protein of any one of embodiments 1-3, wherein the modified IL-2 protein comprises one engineered Q residue.

Embodiment 5. The modified IL-2 protein of any one of embodiments 1-3, wherein the modified IL-2 protein comprises two or more engineered Q residues.

Embodiment 6. The modified IL-2 protein of any one of embodiments 1-5, wherein the engineered Q residue is or results from a single amino acid mutation relative to a parent IL-2 protein.

Embodiment 7. The modified IL-2 protein of embodiment 6, wherein the parent IL-2 protein comprises an amino acid sequence of SEQ ID NO: 1.

Embodiment 8. The modified IL-2 protein of embodiment 7, wherein the single amino acid mutation is selected from the group consisting of F43Q, R37Q, F41Q, K42Q, Y44Q, T36Q, M38Q, and any combinations thereof.

Embodiment 9. The modified IL-2 protein of embodiment 8, wherein the modified IL-2 protein comprises an amino acid sequence of any of SEQ ID NOs: 2 and 4-8.

Embodiment 10. The modified IL-2 protein of any one of embodiments 1-5, wherein the engineered Q residue is part of an exogenous patch sequence suitable for Transglutaminase (TGase) reaction.

Embodiment 11. The modified IL-2 protein of embodiment 10, wherein the exogenous patch sequence replaces a portion of a parent IL-2 protein.

Embodiment 12. The modified IL-2 protein of embodiment 11, wherein the parent IL-2 protein comprises an amino acid sequence of SEQ ID NO: 1.

Embodiment 13. The modified IL-2 protein of any one of embodiments 10-12, wherein the exogenous patch sequence is selected from the group consisting of LEEQAA (SEQ ID NO: 9), IFKQTY (SEQ ID NO: 10), PKEQKY (SEQ ID NO: 11), VIQGV (SEQ ID NO: 12), REEQFN (SEQ ID NO: 13), GLLQGA (SEQ ID NO: 14), and any combinations thereof.

Embodiment 14. The modified IL-2 protein of embodiment 13, wherein the modified IL-2 protein comprises an amino acid sequence of any of SEQ ID NOs: 3 and 15-19.

Embodiment 15. The modified IL-2 protein of any one of embodiments 1-8 and 10-13, wherein the modified IL-2 protein further comprises one or more additional amino acid mutations that are not engineered Q residues.

Embodiment 16. The modified IL-2 protein of any one of embodiments 1-15, wherein the modified IL-2 protein comprises an amino acid sequence having at least about 95% identity to a parent IL-2 protein comprising an amino acid sequence of SEQ ID NO: 1.

Embodiment 17. The modified IL-2 protein of any one of embodiments 1-16, wherein the $K_D$ of the binding between the modified IL-2 protein and an IL-2Rα subunit is about 2 to about 800 times of the $K_D$ of the binding between a parent IL-2 protein and an IL-2Rα subunit.

Embodiment 18. The modified IL-2 protein of any one of embodiments 1-17, wherein the $K_D$ of the binding between the modified IL-2 protein and an IL-2Rβ subunit is similar to or about 1 to about 30 times of the $K_D$ of the binding between a parent IL-2 protein and an IL-2Rβ subunit.

Embodiment 19. The modified IL-2 protein of any one of embodiments 1-18, wherein the modified IL-2 protein is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell.

Embodiment 20. The modified IL-2 protein of embodiment 19, wherein the modified IL-2 protein has about 2 to about 50 folds reduced ability to activate a Treg cell compared to a parent IL-2 protein.

Embodiment 21. The modified IL-2 protein of embodiment 19 or 20, wherein the modified IL-2 protein has similar or about 1 to about 20 folds higher ability to increase the ratio of CTL to Treg or the ratio of NK cell to Treg compared to a parent IL-2 protein.

Embodiment 22. A modified IL-2 protein-polyethylene glycol (PEG) conjugate comprising a modified IL-2 protein of any one of embodiments 1-21 and a PEG moiety, wherein the PEG moiety is conjugated to the modified IL-2 protein via the engineered Q residue.

Embodiment 23. The modified IL-2 protein-PEG conjugate of embodiment 22, wherein the PEG moiety is linear.

Embodiment 24. The modified IL-2 protein-PEG conjugate of embodiment 22, wherein the PEG moiety is branched.

Embodiment 25. The modified IL-2 protein-PEG conjugate of any one of embodiments 22-24, wherein the PEG moiety has a molecular weight of between about 10 kDa and about 40 kDa.

Embodiment 26. The modified IL-2 protein-PEG conjugate of any one of embodiments 22-25, wherein the PEG moiety has a molecular weight of about 20 kDa.

Embodiment 27. The modified IL-2 protein-PEG conjugate of any one of embodiments 22-26, wherein the PEG moiety is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy.

Embodiment 28. The modified IL-2 protein-PEG conjugate of any one of embodiments 22-27, wherein the PEG moiety is methoxy-PEG-amine.

Embodiment 29. The modified IL-2 protein-PEG conjugate of any one of embodiments 22-28, wherein the modified IL-2 protein comprises two or more engineered Q residues, and wherein at least one of the two or more engineered Q residues is each conjugated with a PEG moiety.

Embodiment 30. The modified IL-2 protein-PEG conjugate of any one of embodiments 22-29, wherein the conjugation of the PEG moiety is mediated via a TGase.

Embodiment 31. The modified IL-2 protein-PEG conjugate of embodiment 30, wherein the TGase is a microbial TGase (mTGase).

Embodiment 32. The modified IL-2 protein-PEG conjugate of embodiment 30 or 31, wherein the TGase is a wild-type TGase.

Embodiment 33. The modified IL-2 protein-PEG conjugate of embodiment 32, wherein the wild-type TGase has an amino acid sequence of SEQ ID NO: 20.

Embodiment 34. The modified IL-2 protein-PEG conjugate of embodiment 30 or 31, wherein the TGase is an engineered TGase.

Embodiment 35. The modified IL-2 protein-PEG conjugate of embodiment 34, wherein the engineered TGase comprises an amino acid sequence having at least about 80% identity to SEQ ID NO: 20.

Embodiment 36. The modified IL-2 protein-PEG conjugate of any one of embodiments 30-35, wherein the TGase has a purity of at least about 90%.

Embodiment 37. The modified IL-2 protein-PEG conjugate of any one of embodiments 22-36, wherein the $K_D$ of the binding between the modified IL-2 protein-PEG conjugate and an IL-2Rα subunit is about 10 to about 2000 times of the $K_D$ of the binding between a parent IL-2 protein and an IL-2Rα subunit.

Embodiment 38. The modified IL-2 protein-PEG conjugate of any one of embodiments 22-37, wherein the $K_D$ of the binding between the modified IL-2 protein-PEG conjugate and an IL-2Rβ subunit is similar to or about 1 to about 30 times of the $K_D$ of the binding between a parent IL-2 protein and an IL-2Rβ subunit.

Embodiment 39. The modified IL-2 protein-PEG conjugate of any one of embodiments 22-38, wherein the modified IL-2 protein-PEG conjugate is capable of activating an immune cell selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell.

Embodiment 40. The modified IL-2 protein-PEG conjugate of embodiment 39, wherein the modified IL-2 protein-PEG conjugate has about 2 to about 5000 folds reduced ability to activate a Treg cell compared to a parent IL-2 protein.

Embodiment 41. The modified IL-2 protein-PEG conjugate of embodiment 39 or 40, wherein the modified IL-2 protein-PEG conjugate has similar or about 1 to 20 folds higher ability to increase the ratio of CTL to Treg or the ratio of NK cell to Treg compared to a parent IL-2 protein.

Embodiment 42. An isolated nucleic acid encoding the modified IL-2 protein of any one of embodiments 1-21.

Embodiment 43. A vector comprising the isolated nucleic acid of embodiment 42.

Embodiment 44. A host cell comprising the isolated nucleic acid of embodiment 42, or the vector of embodiment 43.

Embodiment 45. A pharmaceutical composition comprising the modified IL-2 protein of any one of embodiments 1-21, or the modified IL-2 protein-PEG conjugate of any one of embodiments 22-41, and an optional pharmaceutically acceptable carrier.

Embodiment 46. A method of treating a disease in an individual, comprising administering to the individual an effective amount of the pharmaceutical composition of embodiment 45.

Embodiment 47. The method of embodiment 46, wherein the pharmaceutical composition is administered intravenously, intratumorally, intraperitoneally, or subcutaneously.

Embodiment 48. The method of embodiment 46 or 47, wherein the pharmaceutical composition is administered at about 1 μg/kg to about 100 μg/kg.

Embodiment 49. The method of any one of embodiments 46-48, wherein the pharmaceutical composition is administered once per month, once every 3 weeks, once every 2 weeks, once a week, twice a week, once every other day, or daily.

Embodiment 50. The method of any one of embodiments 46-49, wherein the disease is a cancer.

Embodiment 51. The method of embodiment 50, wherein the cancer is renal cell carcinoma, metastatic melanoma, acute myeloid leukemia (AML), non-Hodgkin's lymphoma (NHL), cutaneous T-cell lymphoma (CTCL), breast cancer, or bladder cancer.

Embodiment 52. A method of making a modified IL-2 protein-PEG conjugate comprising a modified IL-2 protein comprising an engineered Q residue specifically conjugated to a PEG moiety, wherein the method comprises: contacting the modified IL-2 protein of any one of embodiments 1-21 with the PEG moiety in the presence of a TGase under a condition that is sufficient to generate the modified IL-2 protein-PEG conjugate, wherein the PEG moiety is conjugated to the modified IL-2 protein via the engineered Q residue.

Embodiment 53. A method of making a modified IL-2 protein-PEG conjugate comprising a modified IL-2 protein comprising an engineered Q residue specifically conjugated to a PEG moiety, wherein the method comprises: a) contacting the modified IL-2 protein of any one of embodiments 1-21 with a small molecule handle in the presence of a TGase under a condition that is sufficient to generate an intermediate conjugate comprising the modified IL-2 protein specifically conjugated to the small molecule handle via the engineered Q residue, and b) contacting the intermediate conjugate with the PEG moiety thereby obtaining the modified IL-2 protein-PEG conjugate, wherein the PEG moiety is conjugated via the small molecule handle.

Embodiment 54. The method of embodiment 52 or 53, further comprising generating the modified IL-2 protein comprising the engineered Q residue.

Embodiment 55. A method of making a modified IL-2 protein-PEG conjugate comprising a modified IL-2 protein comprising an engineered Q residue specifically conjugated to a PEG moiety, wherein the method comprises: contacting a composition comprising a plurality of modified IL-2 proteins of any one of embodiments 1-21 with the PEG moiety in the presence of a TGase under a condition that is sufficient to generate the modified IL-2 protein-PEG conjugate, wherein at least about 30% of the modified IL-2 protein within the composition is conjugated with the PEG moiety via the engineered Q residue.

Embodiment 56. A method of making a modified IL-2 protein-PEG conjugate comprising a modified IL-2 protein comprising an engineered Q residue specifically conjugated to a PEG moiety, wherein the method comprises: a) contacting a composition comprising a plurality of modified IL-2 proteins of any one of embodiments 1-21 with a small molecule handle in the presence of a TGase under a condition that is sufficient to generate an intermediate conjugate comprising the modified IL-2 protein specifically conjugated to the small molecule handle, wherein at least about 30% of the modified IL-2 protein within the composition is conjugated with the small molecule handle via the engineered Q residue, and b) contacting the intermediate conjugate with the PEG moiety thereby obtaining the modified IL-2 protein-PEG conjugate, wherein at least about 30% of the intermediate conjugate within the composition is conjugated with the PEG moiety via the small molecule handle.

Embodiment 57. The method of embodiment 55 or 56, further comprising generating the composition comprising the plurality of modified IL-2 protein comprising the engineered Q residue.

Embodiment 58. The method of any one of embodiments 55-57, wherein at least about 70% of the modified IL-2 protein within the composition is conjugated with the PEG moiety via the engineered Q residue.

Embodiment 59. A method of increasing the circulating half-life or overall exposure $AUC_{0\text{-}inf}$ of an IL-2 protein, comprising: a) introducing an engineered Q residue into the IL-2 protein to generate a modified IL-2 protein of any one of embodiments 1-21; b) contacting the modified IL-2 protein with a PEG moiety in the presence of a TGase under a condition sufficient to conjugate the PEG moiety to the modified IL-2 protein via the engineered Q residue; and wherein the PEG moiety is of a length sufficient to increase the circulating half-life or overall exposure $AUC_{0\text{-}inf}$ of the PEG conjugated modified IL-2 protein compared to the IL-2 protein.

Embodiment 60. A method of increasing the circulating half-life or overall exposure $AUC_{0\text{-}inf}$ of an IL-2 protein, comprising: a) introducing an engineered Q residue into the IL-2 protein to generate a modified IL-2 protein of any one of embodiments 1-21; b) contacting the modified IL-2 protein with a small molecule handle in the presence of a TGase under a condition that is sufficient to generate an intermediate conjugate comprising the modified IL-2 protein specifically conjugated to the small molecule handle via the engineered Q residue; and c) contacting the intermediate conjugate with a PEG moiety under a condition sufficient to conjugate the PEG moiety to the intermediate conjugate via the small molecule handle; and wherein the PEG moiety is of a length sufficient to increase the circulating half-life or overall exposure $AUC_{0\text{-}inf}$ of the PEG conjugated modified IL-2 protein compared to the IL-2 protein.

Embodiment 61. A method of increasing the circulating half-life or overall exposure $AUC_{0\text{-}inf}$ of an IL-2 protein, comprising: a) introducing an engineered Q residue into the IL-2 protein to generate a composition comprising a plurality of modified IL-2 protein of any one of embodiments 1-21; b) contacting the composition with a PEG moiety in the presence of a TGase under a condition sufficient to conjugate the PEG moiety to the modified IL-2 protein via the engineered Q residue; wherein at least about 30% of the modified IL-2 protein within the composition is conjugated with the PEG moiety via the engineered Q residue; and wherein the PEG moiety is of a length sufficient to increase the circulating half-life or overall exposure $AUC_{0\text{-}inf}$ of the PEG conjugated modified IL-2 protein compared to the IL-2 protein.

Embodiment 62. A method of increasing the circulating half-life or overall exposure $AUC_{0\text{-}inf}$ of an IL-2 protein, comprising: a) introducing an engineered Q residue into the IL-2 protein to generate a composition comprising a plurality of modified IL-2 protein of any one of embodiments 1-21; b) contacting the composition with a small molecule handle in the presence of a TGase under a condition sufficient to conjugate the small molecule handle to the modified IL-2 protein via the engineered Q residue, wherein at least about 30% of the modified IL-2 protein within the composition is conjugated with the small molecule handle via the engineered Q residue; and c) contacting the composition comprising the intermediate conjugate with a PEG moiety thereby obtaining a modified IL-2-protein-PEG conjugate, wherein at least about 30% of the intermediate conjugate within the composition is conjugated with the PEG moiety via the small molecule handle; and wherein the PEG moiety is of a length sufficient to increase the circulating half-life or overall exposure $AUC_{0-inf}$ of the PEG conjugated modified IL-2 protein compared to the IL-2 protein.

Embodiment 63. The method of embodiment 61 or 62, wherein at least about 70% of the modified IL-2 protein within the composition is conjugated with the PEG moiety via the engineered Q residue.

Embodiment 64. The method of any one of embodiments 59-63, wherein the circulating half-life or overall exposure $AUC_{0-inf}$ of the PEG conjugated modified IL-2 protein is at least about 1.5 times longer or bigger than the IL-2 protein.

EXAMPLES

The examples and exemplary embodiments below are intended to be purely exemplary of the invention and should therefore not be considered to limit the invention in any way. The following examples and detailed description are offered by way of illustration and not by way of limitation.

Example 1. Exemplary Modified IL-2 Proteins and Modified IL-2 Protein-PEG Conjugates This example describes the design and preparation of exemplary modified IL-2 protein, modified IL-2 protein-PEG conjugates, and test of their bioactivities.

1. Construction of IL-2 Expression Plasmid

Human IL-2 (IL-2 Aldesleukin) cDNA sequence and nucleic acid sequences encoding modified IL-2 proteins described herein were chemically synthesized, then cloned into pET24a vector using standard molecular cloning methods. Recombinant plasmids were verified by sequencing. IL-2A1 plasmid encodes a modified IL-2 protein (IL-2A1, hereinafter also referred to as "DP006A") comprising an engineered Q residue of F43Q relative to a IL-2 Aldesleukin protein of SEQ ID NO: 1. IL-2A2 plasmids encodes a modified IL-2 protein (IL-2A2) comprising an engineered Q residue within an exogenous patch sequence of IFKQTY, which replaces a portion of the parent IL-2 Aldesleukin of SEQ ID NO: 1 (FIG. 2).

2. Expression of IL-2 Constructs and Purification

Recombinant plasmids were transformed into chemically competent *E. coli* BL21 (DE3) cells. Colonies were selected on an LB plate supplemented with 100 μg/ml Ampicillin.

The pET24a vector resulted in the protein being expressed as inclusion bodies in *E. coli*. Typical recipes used for expression can be found in the literature and in Protein Production by Auto-Induction in High-Density Shaking Cultures, by F. William Studier, Biology Department, Brookhaven National Laboratory, Upton, N.Y. 11973 (Dec. 20, 2007).

Following fermentation, the cells were harvested by centrifugation. The cell mass pellet was stored at −80° C. for future homogenization. The frozen cell mass pellet was re-suspended in cell homogenization buffer (50 mM Tris-HCl, 150 mM NaCl, 5 mM EDTA, pH 8.0) to a concentration of 10% (W/V) and homogenized by a homogenizer (Panda Plus, GEA Niro Soavi) at 4-15° C. for two passes. The homogenate was centrifuged at 10,000×g for 30 minutes. The supernatant was discarded. The inclusion body pellet was washed in three steps sequentially using (1) 50 mM Tris-HCl, 150 mM NaCl, 5 mM EDTA, 2M urea, pH 8.0; (2) 50 mM Tris-HCl, 150 mM NaCl, 5 mM EDTA, 2M urea, pH 8.0; and (3) water. After washing, the crude IL-2 inclusion bodies were obtained.

The crude IL-2 inclusion bodies were dissolved into 6M guanidine, 100 mM Tris, pH 8 buffer. EDTA was added to final concentration 2 mM. Dithiothreitol (DTT) was then added to final concentration 50 mM. The mixture was incubated at 50° C. for 30 minutes. After reduction, water was added to the mixture to reduce guanidine concentration to 4.8M. After one hour of centrifuging at 10000×g, the resulting gel-like pellet was discarded. The guanidine concentration in the supernatant was further reduced to 3.5M by adding water. The mixture was incubated at room temperature for 30 minutes and centrifuged at 10000×g for 30 minutes. The resulting pellet was suspended into 50 mM Tris-HCl, 150 mM NaCl, 5 mM EDTA, 3.5M GdnHCl, pH 8.0, and centrifuged at 10000×g for 30 minutes. This washing step was repeated one more time using water.

The clean and reduced IL-2 inclusion bodies were dissolved into 6M guanidine, 100 mM Tris pH 8 buffer. 100 mM $CuCl_2$ stock was added to reach a final $Cu_{2+}$ concentration 0.1 mM. The mixture was incubated at 4° C. overnight.

The expressed IL-2 solution was put into dialysis bags (having a molecular weight pore size of 3.5 kDa). The dialysis bags were put into a reservoir containing 4.8M guanidine, 0.1M Tris, pH 8 buffer at 4° C. After 4 hours equilibration, the dialysis bags were put into a reservoir containing 1M guanidine, 0.1M Tris, pH 8 buffer at 4° C. After 4 hours equilibration, the dialysis bags were put into a reservoir containing 20 mM citrate, pH 6.0 buffer at 4° C. for 16 hours.

The refolded IL-2 was centrifuged at 10000×g for 40 minutes to remove precipitates.

The refolded and concentrated IL-2 was loaded on a cation column packed with SP-Sepharose HP resin equilibrated with loading buffer 20 mM citrate, pH 6.0. IL-2 construct was eluted by gradient of NaCl in loading buffer. The fractions containing IL-2 were pooled. It should be noted that other suitable purification methods may also be employed, such as size exclusion chromatography and hydrophobic interaction chromatography (HIC chromatography).

The refolded and purified IL-2 constructs were checked with SDS-PAGE and RP-HPLC.

SDS-PAGE Analysis

Samples were analyzed by sodium dodecyl sulfate-polyacrylamide gel electrophoresis (SDS-PAGE) using the Bio-Rad Mini-PROTEAN Tetra System and 4-20% Mini-PROTEAN®TGX™ Precast Protein Gels. Samples were prepared, loaded on the gel and electrophoresis performed at 180 voltage for about 25 minutes.

RP-HPLC

Refolded and purified IL-2 protein was analyzed by analytical HPLC using an Agilent HPLC 1100 system. A RP C4 column (250×4.6 mm, Vydac 214TP54) was used. Elution was carried out at a flow rate of 1 mL/min at 50° C. with a linear gradient of ACN (40-70%) in 0.1% TFA for 30 min. Absorbance was measured at 280 nm.

FIG. 3 shows SDS-PAGE analysis of different IL-2 expression and purification samples. 5 g of IL-2 sample was loaded into each lane. Lane 1 contains IL-2A1 (DP006A) supernatant from *E. coli* expression. Lane 2 contains purified IL-2A1 expressed as insoluble form of inclusion body, which was expressed at high level in *E. coli*. Lanes 3 and 4 contain refolded and purified IL-2A1 and IL-2A2, respectfully. The SDS-PAGE result shows that exemplary modified IL-2 proteins IL-2A1 and IL-2A2 have been refolded into soluble form and purified to high purity. The modified IL-2 protein has a size of approximately 153-155 kDa.

3. Binding Affinity

The affinity of modified IL-2 proteins to IL-2Rα and IL-2Rβ is measured directly by surface plasmon resonance (Biacore T-200) and compared to that of parent IL-2 protein (e.g., IL-2 Aldesleukin). Anti-human antibody is coupled to the surface of a CM-5 sensor chip using EDC/NHS chemistry. Then either human IL-2Rα-Fc or IL-2Rβ-Fc fusion protein is used as the captured ligand over this surface. Serial dilutions of modified IL-2 proteins are made in acetate buffer pH 4.5, starting at 5 mM. These dilutions are allowed to bind to the IL-2R ligands for 5 minutes, and the response unit (RU) bound is plotted against concentration to determine EC50 values. The affinities of each isoform to each IL-2 receptor subtype are calculated as fold changes relative to those of parent IL-2 (e.g., IL-2 Aldesleukin) to the same IL-2R subtype.

Example 2. Conjugate Modified IL-2 Protein with Methoxy-PEG-Amine by mTGase Catalysis Purified modified IL-2 proteins (purified IL-2A1 and IL-2A2; 4 mg/ml) were dissolved in Tris-buffer (pH 7.0). 20 kDa methoxy-PEG-amine (JenKem Technology) was added to IL-2 solution to final concentrations of 0.5-1 mM. Purified wildtype TGase (TG_SL) was added to the IL-2 and PEG solution mixture with a final concentration of 0.02-0.4 mg/ml. The reactions were incubated at 25° C. Reactions were followed by IEX-HPLC and SDS-PAGE analysis. IL-2A1 conjugated with 20 kDa methoxy-PEG-amine is hereinafter also referred to as "PEG-20K-IL-2A 1" or "DP006-A-20."

Cation Exchange Chromatography

A SP-HP Sepharose (GE Healthcare) cation exchange column with a bed volume of approximately 100 ml was prepared using standard methods. The column was connected to a GE Healthcare (Chalfont St. Giles, UK) AKTA AVANT to purify the prepared modified IL-2 protein-PEG conjugates (PEG-20K-IL-2A1, PEG-20K-IL-2A2). Details for the purification process are described below.

Modified IL-2 protein-PEG conjugate was loaded on a cation column packed with SP-Sepharose HP resin equilibrated with loading buffer 20 mM citrate, pH 6.0. Modified IL-2 protein-PEG conjugate was eluted by gradient of NaCl in loading buffer. The fractions under the modified IL-2 protein-PEG conjugate peak were pooled. It should be noted that other suitable purification methods may also be employed, such as size exclusion chromatography and hydrophobic interaction chromatography (HIC chromatography).

Various modified IL-2 protein and PEG conjugates samples were analyzed by SDS-PAGE using the BioRad Mini-PROTEAN Tetra System and 4-20% Mini-PROTEAN®TGX™ Precast Protein Gels. Samples were prepared, 5 μg loaded on the gel and electrophoresis performed at 180 voltage for 25 minutes. The protein bands were visualized by staining with Coomassie staining. PEG-conjugates were stained with a barium iodide solution. The gel was soaked in water for 30 min and then immersed in a 5% $BaCl_2$ solution for 15 min. Then, iodine solution (1.3% 12+4% KI) was added and incubated for 5 min. Finally, the gel was left to destain in water for 30 min.

Figure 4A:
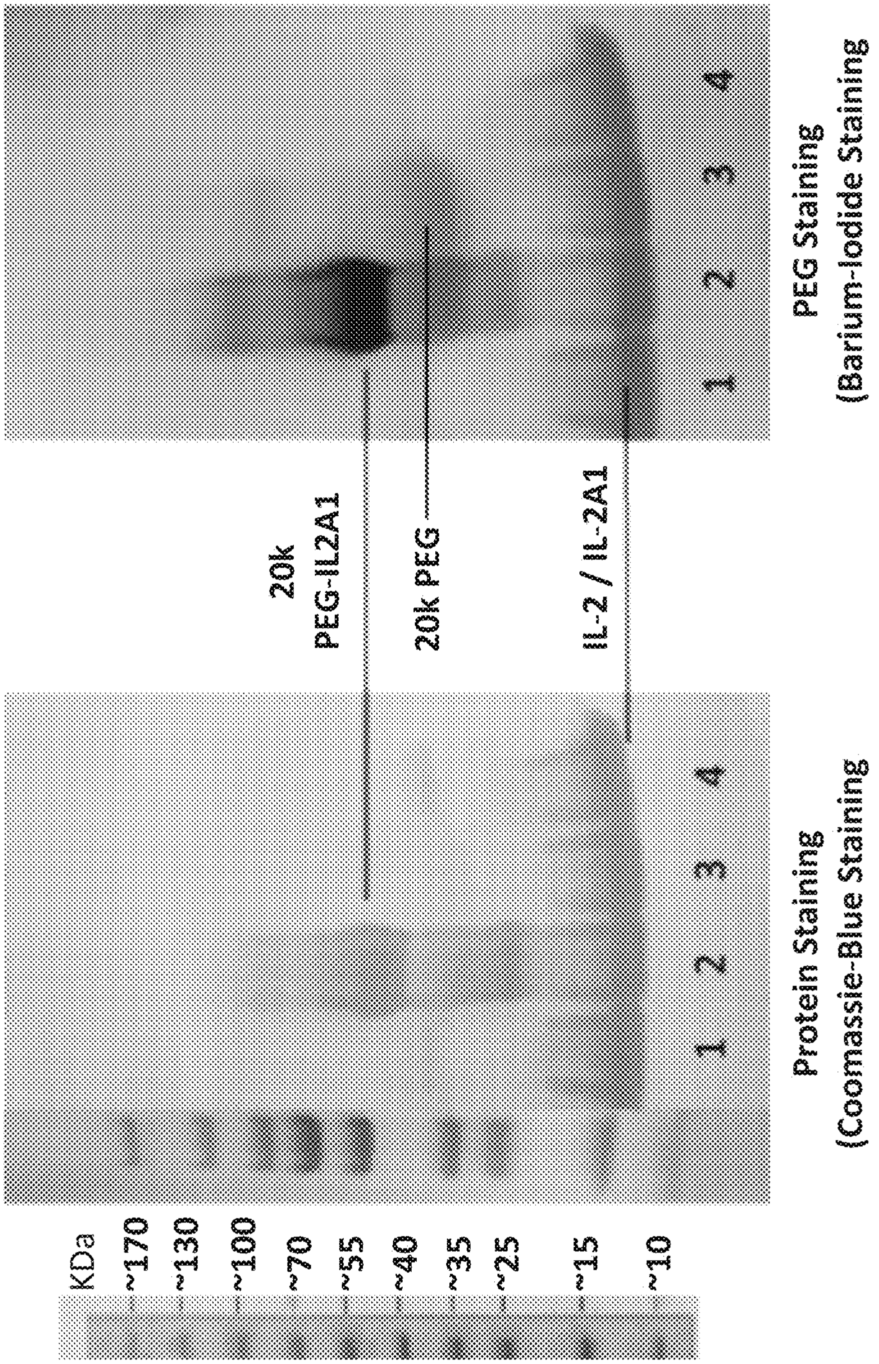
FIGS. 4A-4B show SDS-PAGE analysis of PEGylation of exemplary modified IL-2 proteins (IL-2A1, IL-2A2), with parent IL-2 protein (Aldesleukin) as control. The left panels show Coomassie-blue protein staining, the right panels show PEG staining with Barium-Iodide.
Figure 4B:
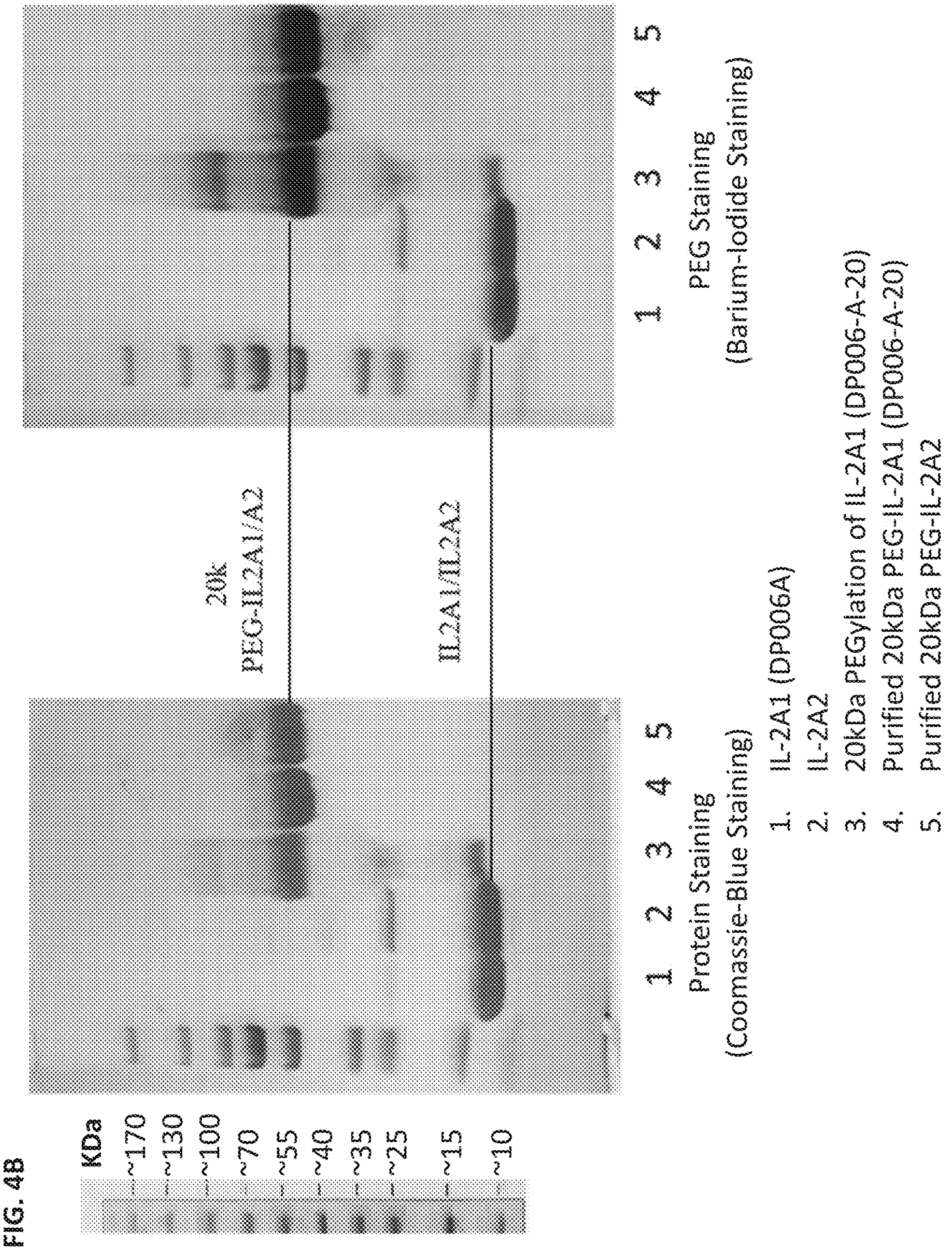

As can be seen from FIG. 4A, after conjugating with a 20 kDa methoxy-PEG-amine, the modified IL-2 protein-PEG conjugate (PEG-20K-IL-2A1, DP006-A-20) had a size of approximately 62 kDa, compared to the 14.8 kDa parent modified IL-2 protein (IL-2A1). Parent IL-2 (IL-2 Aldesleukin) without the engineered Q residue was not conjugated with the PEG moiety, indicating that endogenous Q residues within IL-2 protein are not responsive to TGase-mediated transglutamination. FIG. 4B demonstrates great purity of modified IL-2 protein-PEG conjugate after cation exchange chromatography purification.

The binding affinity of modified IL-2 protein-PEG conjugates can be measured by the method described in "3. Binding affinity" subsection of Example 1.

Similarly, IL-2A1 conjugated with 30 kDa methoxy-PEG-amine (hereinafter also referred to as "PEG-30K-IL-2A1" or "DP006-A-30") and IL-2A1 conjugated with 40 kDa methoxy-PEG-amine (hereinafter also referred to as "PEG-40K-IL-2A1" or "DP006-A-40") were also constructed and purified (data not shown).

Example 3. Examination of Bioactivity of Modified IL-2 Proteins and Modified IL-2 Protein-PEG Conjugates by In Vitro Cell-Based Assay The activity of IL-2A1, IL-2A2, PEG-20K-IL-2A1, and PEG-20K-IL-2A2 were evaluated in a cell proliferation assay using CTLL-2 cells. IL-2 Aldesleukin served as control. CTLL-2 is C57BL/6 mouse cytotoxic T lymphocyte cell line with high expression of CD25 and IL-2Rα on cell surface.

CTLL-2 cells were maintained in complete RPMI 1640 medium supplemented with 2 mM L-glutamine, 1 mM sodium pyruvate, 10% fetal bovine serum, and 50-100 units/mL of IL-2 Aldesleukin, at 37° C. under a 5% $CO_2$ atmosphere and 85% humidity. The cells were cultured in suspension until they reached a cell density of $1\times10^6$ cells/mL before splitting.

For the bioactivity assay, cells were split so that the cell numbers would be at least $3\times10^5$/mL before treating with test IL-2 constructs. The cells were washed three times in Dulbecco's phosphate buffered saline, then re-suspended in supplemented media without IL-2 (Aldesleukin) at a cell density of $3\times10^5$-$4\times10^5$ cells/mL, and plated in a 96-well black walled clear bottom microplates at 100 μL/well. A serial dilution of 6× concentrations of test samples was prepared with supplemented media without IL-2 (Aldesleukin) in a 96-well plate, then 20 μL of 6× concentrations of test samples was added into all wells with 100 μL of cells except for negative control wells, which were supplied with 20 μL supplemented media without IL-2 (Aldesleukin). CTLL-2 cells were incubated at 37° C. in a 5% $CO_2$ atmosphere with 85% humidity for 44 hours. Following 44-hour incubation, 20 μL of 0.03% Resazurin was added to each well. The plate was mixed for two minutes on an orbital shaker then incubated at 37° C. in a 5% $CO_2$ atmosphere with 85% humidity for additional 4 hours. The testing plate was then read using a SpectraMax Geminixs (Molecular Device) microplate reader at $\lambda^{ex}$ 555 nm/$\lambda^{em}$ 585 nm (570 nm cut-off).

The EC50 values (concentration of test compound required to exhibit 50% of maximal response) for cell proliferation were calculated from analysis of dose-response curves, using Software XLFit Excel Version (4.3.2 Build 11) (ID Business Solutions Limited) Fit model 201.

Figure 5:
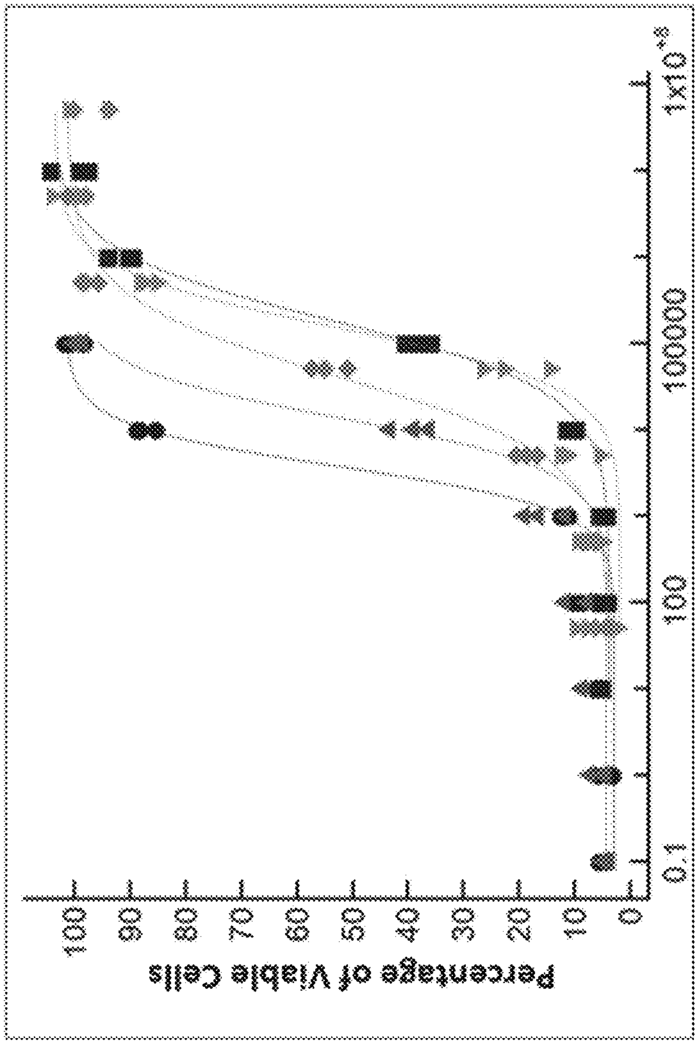
FIG. 5 demonstrates CTLL-2 cell growth assay in response to parent IL-2 protein (Aldesleukin), exemplary modified IL-2 proteins (IL-2A1, IL-2A2), and exemplary modified IL-2 protein-PEG conjugates (PEG-20K-IL-2A1, PEG-20K-IL-2A2). X-axis shows protein concentration.

The bioactivities of exemplary modified IL-2 proteins and modified IL-2 protein-PEG conjugates measured using the cell proliferation assay was demonstrated in FIG. 5. FIG. 5 shows that all test IL-2 constructs induced growth of CTLL-2 cells in a dose-dependent manner. IL-2A1 and IL-2A2 were able to stimulate the growth of CTLL-2, indicating that they have been refolded into proper conformation. Compared to parent IL-2 Aldesleukin, the bioactivity of IL-2A1 in inducing CTLL-2 cell growth reduced about 4 folds, and that of IL-2A2 reduced about 49 folds. 20 kDa PEG-IL-2A1 (DP006-A-20) exhibited slightly reduced bioactivity (about 3 folds) compared to its parent protein IL-2A1 (DP006A), while the bioactivity of 20 kDa PEG-IL-2A2 was similar as its parent protein IL-2A2.

Since the engineered Q residue and resulting PEG conjugation position was designed within the IL-2Rα subunit binding domain, the bioactivity variation of modified IL-2 proteins and their PEGylated forms may reflect different binding ability to IL-2Rα subunit on T cells. As shown in FIG. 5, Q residue mutation led to reduced binding of modified IL-2 proteins to IL-2Rα subunit. The bioactivity of IL-2A2 was more severely affected compared to IL-2A1, probably because more amino acid mutations were introduced (IFKQTY patch replacement) in IL-2A2 compared to single amino acid mutation (F43Q single amino acid substitution) in IL-2A1. The results also demonstrated that PEG conjugation at the IL-2Rα subunit binding domain could further reduce the binding to IL-2Rα subunit, compared to unPEGylated parent modified IL-2 forms. For example, PEG conjugation caused about 3-fold bioactivity reduction for 20 kDa PEG-IL-2A1 (DP006-A-20) compared to unPEGylated parent protein IL-2A1 (DP006A). The reason that PEG conjugation did not further reduce the bioactivity of PEG-IL-2A2 was probably because the patch replacement mutation in IL-2A2 already significantly abolished its binding to IL-2Rα subunit, to the extent that PEG conjugation would not further reduce PEG-IL-2A2 binding to IL-2Rα subunit.

Example 4. In Vivo Bioactivity of Modified IL-2 Proteins and Modified IL-2 Protein-PEG Conjugates in Inducing Lymphocyte Proliferation Modified IL-2A1, modified IL-2A2, their 20 kDa PEGylated forms, and parent IL-2 Aldesleukin were compared for their ability to induce the expansion of NK cells, CD8+ T cells and Treg cells in C57BL/6 mice. C57BL/6 mice (male, 6 weeks of age, Harlan, Indianapolis, Ind.) were randomly divided into six treatment groups (5 mice per group): a daily PBS group, a daily IL-2 Aldesleukin group, a daily IL-2A1 group (DP006A), a daily IL-2A2 group and two single-dose groups of 20k PEG-IL-2A1 (DP006-A-20) and 20k PEG-IL-2A2. Mice in the daily groups received daily intraperitoneal (i.p.) of parent IL-2 (Aldesleukin, unmodified IL-2), modified IL-2A1, or modified IL-2A2 at a dose of 20 μg/animal (or PBS as negative control) for 5 days. The single-dose groups received a single subcutaneous (s.c.) injections of 20k PEG-IL-2A1 or 20k PEG-IL-2A2 at a dose of 100 μg/animal on day 0.

Five days after treatment, blood and splenocytes were collected. PBMCs were isolated from the blood using histopaque (Sigma, St. Louis, Mo.). PBMC and splenocytes were then stained with PE-labeled anti-CD19 to identify B cells, PE-labeled anti-CD335 (NKD46) to identify NK cells, FITC-labeled anti-CD4 to identify Treg cells, and FITC-labeled anti-CD8 antibodies to identify cytotoxic T cells/CTLs (BioLegend, San Diego, Calif.). Stained cells were analyzed on a FACScan flow cytometer (BD Bioscience, San Jose, Calif.).

Figure 6A:
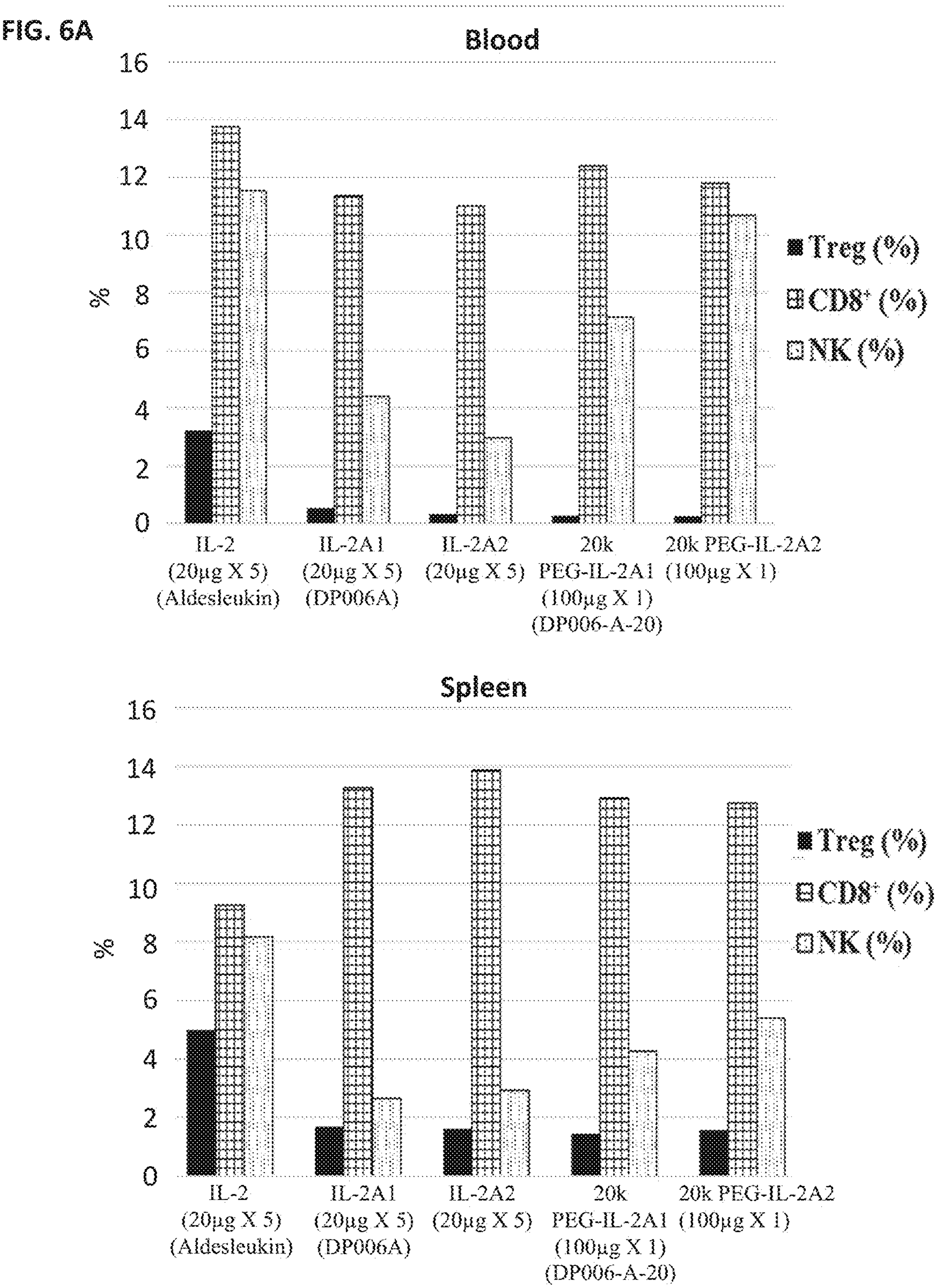

As can be seen from FIG. 6A, modified IL-2A1 (DP006A) had much lower induction on the expansion of Treg cells compared to parent IL-2 Aldesleukin; while IL-2A2, PEG-20K-IL-2A1 (DP006-A-20) or PEG-20K-IL-2A2 had little effect on the expansion of Treg cells. The percentage of Treg cells in blood after incubating with IL-2 test samples was as below: 3.23% (IL-2 Aldesleukin), 0.52% (IL-2A1, DP006A), 0.32% (IL-2A2), 0.28% (20k PEG-IL-2A1, DP006-A-20), and 0.25% (20k PEG-IL-2A2). The binding of IL-2 to IL-2Rα (CD25) on the cell surface of Treg cells may lead to their proliferation. The significantly reduced effect in inducing Treg cell proliferation of IL-2A1 (DP006A) and IL-2A2 was likely due to their mutations within the IL-2Rα (CD25) binding domain, leading to reduced IL-2/IL-2Rα binding. The ability to induce Treg proliferation of IL-2A2 was more severely affected compared to IL-2A1, probably because more amino acid mutations were introduced (IFKQTY patch replacement) in IL-2A2 compared to single amino acid mutation (F43Q single amino acid substitution) in IL-2A1. Further introducing 20 kDa PEG moiety to these two modified IL-2 proteins further diminished their ability in inducing Treg proliferation, likely due to complete abolishment of PEG-20K-IL-2/IL-2Rα binding.

As can be seen from FIG. 6B, modified IL-2 proteins and modified IL-2 protein-PEG 20 kDa conjugates tremendously induced CD8+ T cell proliferation relative to Treg cells, both in blood and in spleen, with 20 kDa PEGylated modified IL-2 proteins demonstrating even stronger induction of CD8+ T cell proliferation relative to Treg cells in blood compared to unPEGylated parent modified IL-2 proteins. NK cell proliferation relative to that of Treg cell was enhanced by modified IL-2 proteins in blood; PEGylation of the modified IL-2 protein significantly enhanced the proliferation induction effect on NK cells relative to Treg cells compared to unPEGylated parent modified IL-2 proteins, both in blood and in spleen.

FIGS. 6A-6B demonstrated that reduced induction in the proliferation of Treg cells by modified IL-2 proteins and 20 kDa PEG conjugates thereof compared to IL-2 Aldesleukin lead to higher ratio of CD8+ killer T cells: Treg cells and higher ratio of NK cells: Treg cells in the blood; while both reduced induction in the proliferation of Treg cells and higher induction in the proliferation of CD8+ cells by modified IL-2 proteins and 20 kDa PEG conjugates thereof compared to IL-2 Aldesleukin lead to higher ratio of CD8+ killer T cells: Treg cells and higher ratio of NK cells: Treg cells in the spleen. Such preferential induction of CD8+ T cells and NK cells over Treg cells was likely due to the higher binding affinity of modified IL-2 proteins and PEG conjugates thereof to IL-2Rβ and/or IL-2Rγ, and lacking or diminished binding affinity towards CD25+ cells (IL-2Rα expressing cells, e.g., Treg). This indicated that modified IL-2 proteins and their PEG conjugates descried herein could significantly alter the overall lymphocyte composition of peripheral blood or associated with tumor. Considering the single s.c. injection of PEGylated modified IL-2 protein compared to multiple i.p. injections of unPEGylated parent modified IL-2 protein, the results demonstrated prolonged effects of PEGylated form.

These results were consistent with those in below examples: anti-tumor animal study (Example 5) and pharmacokinetics study (Example 6).

Example 5. In Vivo Bioactivity of Modified IL-2 Proteins and Modified IL-2 Protein-PEG Conjugates in Reducing Tumor Volume in a Mouse Melanoma Xenograft Model The anti-tumor activity of exemplary modified IL-2 proteins and modified IL-2 protein-PEG conjugates was assessed in B16-F10 melanoma tumor model.

B16-F10 melanoma cells were purchased from ATCC and cultured at 37° C., 5% $CO_2$ in high-glucose DMEM (Gibco) containing 10% FBS (Gibco), and 2 mM L-glutamine. Viability of cells at 85% or more were used for inoculation. Cell viability was checked by Trypan blue staining and counted under microscope. B16-F10 cells (70%-80% confluent) were reconstituted in PBS and injected subcutaneously into the left flanks of C57BL/6 mice (6 weeks old, $8\times10^4$ cells/mouse).

Tumors were allowed to grow to a size of about 50 $mm^3$, then 30 xenograft mice were randomly divided into 6 treatment groups (5 mice per group): a daily PBS group (negative control), a daily IL-2 (Aldesleukin) group by intraperitoneal dose, a daily IL-2A1 (DP006A) group by i.p. dose, a daily IL-2A2 group by i.p. dose, and two single-dose groups of 20k PEG-IL-2A1 (DP006-A-20) and 20k PEG-IL-2A2 by subcutaneous (sc) dose. Xenograft mice in the daily groups received daily intraperitoneal (i.p.) injections of IL-2 Aldesleukin, modified IL-2A1, or modified IL-2A2 at a dose of 20 μg/animal (or PBS as negative control) for 5 days. The single-dose groups received a single subcutaneous (s.c.) injection of 20k PEG-IL-2A1 or 20k PEG-IL-2A2 at a dose of 100 μg/animal on day 0. Body weights of the xenograft mice and tumor volumes ($mm^3$) were measured every two days.

Figure 7:
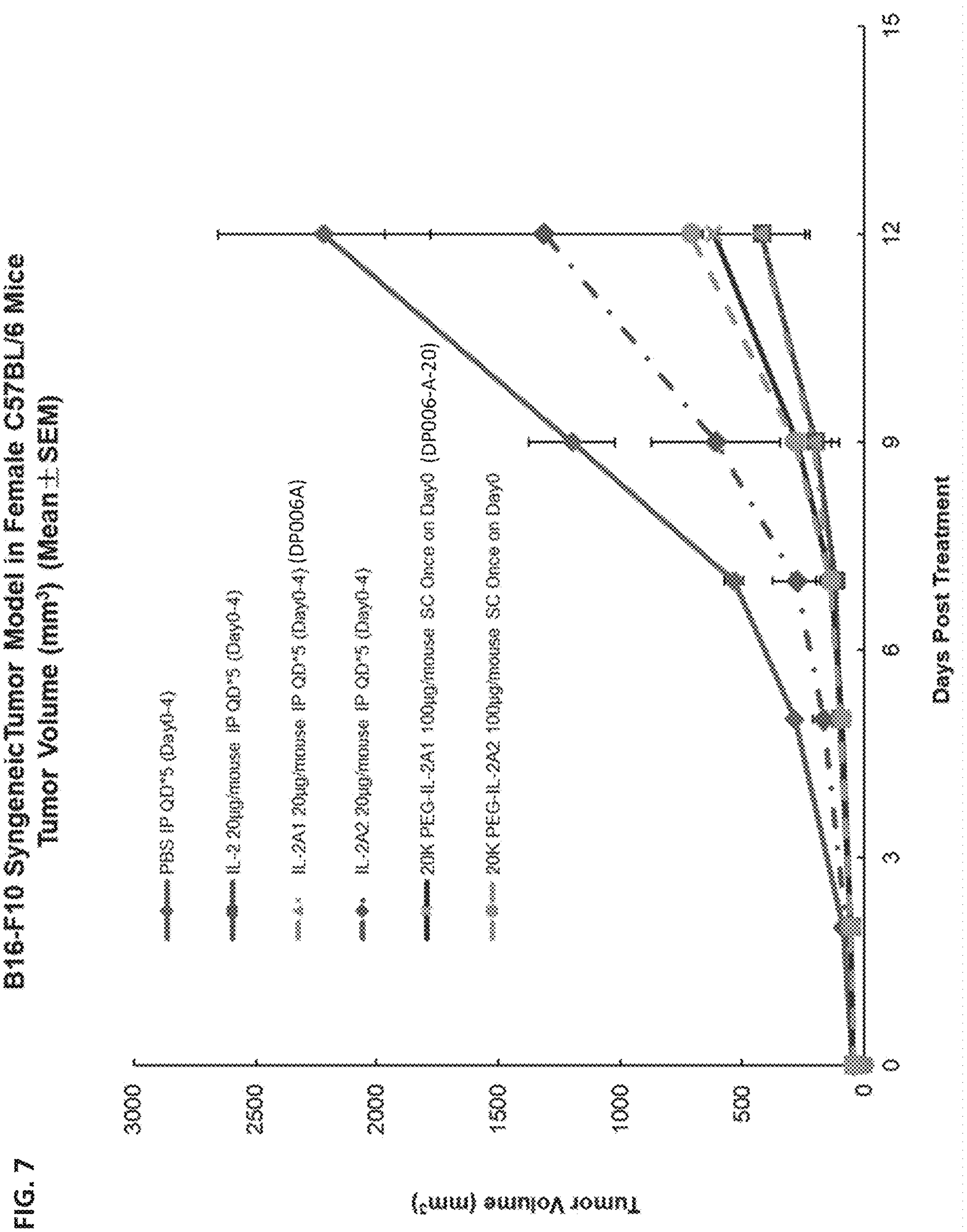
FIG. 7 demonstrates in vivo effects of parent IL-2 (Aldesleukin, unmodified IL-2), exemplary modified IL-2 proteins (IL-2A1, IL-2A2), and exemplary modified IL-2 protein-PEG conjugates (PEG-20K-IL-2A1, PEG-20K-IL-2A2) on B16-F10 mouse melanoma xenograft tumor volume. PBS injection served as negative control. Parent IL-2 and modified IL-2 proteins (IL-2A1, IL-2A2) were intraperitoneally (i.p.) injected, once per day for 5 days, 20 g/mouse/day. Modified IL-2 protein-PEG conjugates were subcutaneously (s.c.) injected for a single dose, 100 μg/mouse.

As can be seen from FIG. 7, modified IL-2 proteins exhibited tumor growth inhibition effects in melanoma xenograft mice model, with IL-2A1 (DP006A) showing similar therapeutic effect as Aldesleukin IL-2, while the therapeutic effect of IL-2A2 was less potent than that of IL-2A1. PEGylated IL2-A1 and PEGylated IL-2A2, following a single dose injection, showed prolonged tumor growth inhibition effect. At equivalent molar dose, 20 kDa PEGylated IL2-A1 (DP006-A-20) and kDa PEGylated IL-2A2 demonstrated similar (only slightly less) therapeutic efficacy following a single dose treatment compared to that of IL-2 Aldesleukin and IL-2A1 following five daily doses, demonstrating prolonged effects of PEGylated form.

Figures 10A, 10B:
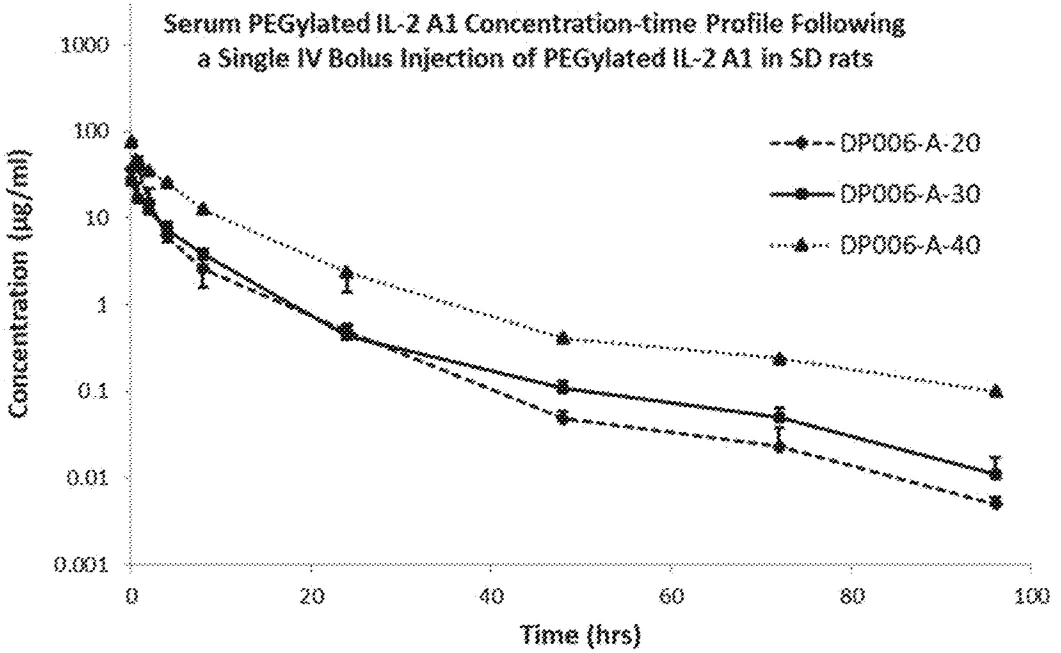
FIG. 10A depicts serum concentration of PEG-IL-2A1 (with 20 kDa, 30 kDa, or 40 kDa PEG moiety) over time following a single i.v. bolus injection in SD rats.
FIG. 10B depicts PK metrics of PEG-IL-2A1 following a single i.v. bolus injection in SD rats.

Example 6. Examination of Half-Life of Modified IL-2 Proteins and Modified IL-2 Protein-PEG Conjugates Pharmacokinetic (PK) study of modified IL-2 protein-PEG conjugates (PEG-20K-IL-2A1 (DP006-A-20), PEG-30K-IL-2A1 (DP006-A-30), and PEG-40K-IL-2A1 (DP006-A-40)) following a single intravenous dose in rats was performed. Male Sprague-Dawley rats (three groups, n=3/group; 7-8 weeks old young adult) were intravenously administered 2 mg/kg of test PEG-IL-2 constructs. Blood samples were taken at designated time points post-administration (0, 5 min, 15 min, 45 min, 2, 6, 24, 48, 72 and 96 hrs) and processed to obtain serum. Serum samples were stored at −20° C. before ELISA analysis. For ELISA assay, an anti-IL-2 antibody (R17003M2F9; Yurogen Biosystem) was used as the capture antibody, and an anti-PEG antibody (AGP4-PABM-B; IBMS Sinica) was used as the detection antibody. Plasma concentrations of modified IL-2 protein-PEG conjugates at each time point were calculated based on a standard curve plotted with corresponding modified IL-2 protein-PEG conjugate solutions ranging from about 0.1 ng/ml to about 10 ng/ml. Modified IL-2 protein-PEG conjugates were found to have longer serum circulating half-life compared to IL-2 Aldesleukin under intravenous dosing setting. The mean half-life for PEG-20K-IL-2A1 (DP006-A-20), PEG-30K-IL-2A1 (DP006-A-30), and PEG-40K-IL-2A1 (DP006-A-40) were 11.9 hours, 14.0 hours, and 19.4 hours, respectively (see FIGS. 10A-10B), while the half-life of IL-2 Aldesleukin is only 80 minutes based on literature (e.g., PROLEUKIN® (aldesleukin) FDA label). PK metrics of modified IL-2 protein-PEG conjugates are shown in FIG. 10B. The results demonstrate that the bigger size the PEG conjugate, the longer the half-life and higher $C_{last}$ of the modified IL-2 protein-PEG conjugates.

Figures 11A, 11B:
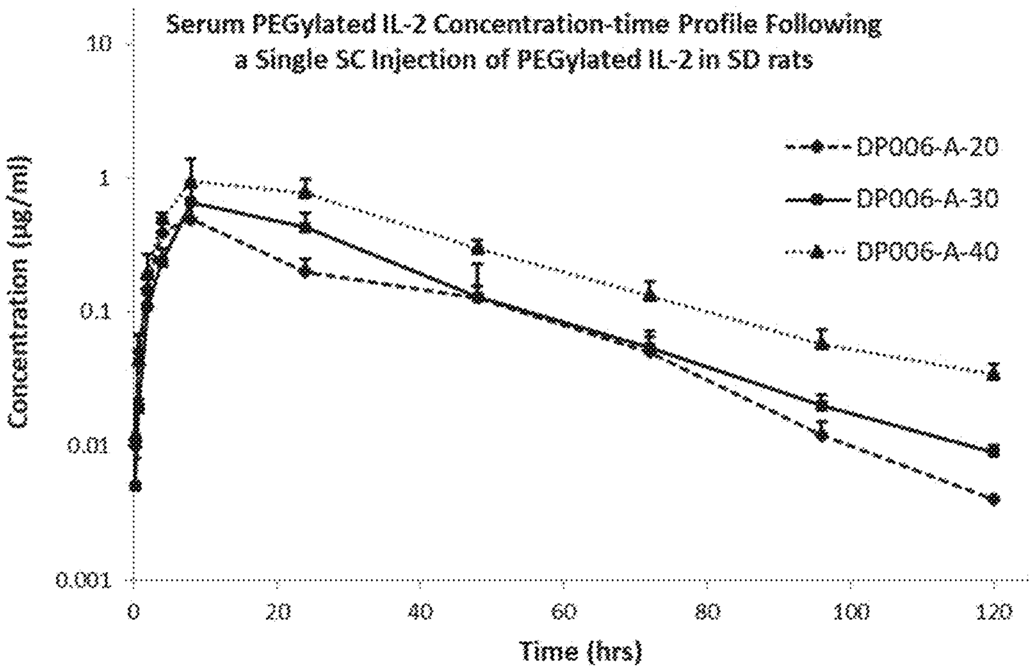
FIG. 11A depicts serum concentration of PEG-IL-2A1 (with 20 kDa, 30 kDa, or 40 kDa PEG moiety) over time following a single s.c. injection in SD rats.
FIG. 11B depicts PK metrics of PEG-IL-2A1 following a single s.c. injection in SD rats.

PK study of modified IL-2 protein-PEG conjugates following a single subcutaneous dose in rats was performed. Male Sprague-Dawley rats (three groups, n=3/group; 7-8 weeks old young adult) were subcutaneously administered with 2.0 mg/kg of test PEG-IL-2 constructs. Blood samples were taken at designated time points post-administration (0, 30 min, 1, 2, 6, 8, 24, 48, 72, and 96 hrs) and processed to obtain serum. Serum samples were stored at −20° C. before ELISA analysis. For ELISA assay, an anti-IL-2 antibody (R17003M2F9; Yurogen Biosystem) was used as the capture antibody, and an anti-PEG antibody (AGP4-PABM-B; IBMS Sinica) was used as the detection antibody. Plasma concentrations of modified IL-2 protein-PEG conjugates at each time point were calculated based on a standard curve plotted with corresponding modified IL-2 protein-PEG conjugate solutions ranging from about 0.1 ng/ml to about 10 ng/ml. Modified IL-2 protein-PEG conjugates were found to have longer serum circulating half-life compared to IL-2 Aldesleukin under subcutaneous dosing setting. The mean half-life for PEG-20K-IL-2A1 (DP006-A-20), PEG-30K-IL-2A1 (DP006-A-30), and PEG-40K-IL-2A1 (DP006-A-40) were 15.6 hours, 17.2 hours, and 22.0 hours, respectively (see FIGS. 11A-11B), while the half-life of IL-2 Aldesleukin is only 80 minutes based on literature. PK metrics of modified IL-2 protein-PEG conjugates are shown in FIG. 11B. The results demonstrate that the bigger size the PEG conjugate, the longer the half-life and higher $C_{max}$/$C_{last}$/AUC of the modified IL-2 protein-PEG conjugates.

Concentration of modified IL-2 proteins in bio matrices such as plasma can be determined using an ELISA method which uses anti-modified IL-2 protein derived in house. The concentration of modified IL-2 protein in plasma is determined from a standard curve using corresponding modified IL-2 protein solutions ranging from about 0.1 ng/ml to about 200 ng/ml.

Example 7. Surface Plasmon Resonance (SPR) Binding Analysis of Modified IL-2 Proteins and Modified IL-2 Protein-PEG Conjugates The binding affinities of modified IL-2 protein or modified IL-2 protein-PEG conjugates to IL-2Rα or IL-2Rβ were measured by SPR (Biacore T-200) and compared to that of Aldesleukin IL-2 protein. Anti-histidine antibody was coupled to the surface of a CM-5 sensor chip using EDC/NHS chemistry. For IL-2Rα binding test, human IL-2Rα-His was used as the captured ligand over the surface. For IL-2Rβ binding test, human IL-2Rβ-His was used as the captured ligand over the surface. Serial dilutions of modified IL-2 protein or modified IL-2 protein-PEG conjugates were made with Running Buffer (1×HEPES, with 0.005% Tween-20, pH 7.4). These serial dilutions were allowed to bind to the IL-2Rα-His or IL-2Rβ-His ligands for 60 seconds. Binding responses were measured in response unit (RU) and plotted against protein concentration to determine Kd values (see Table 1). The binding affinities of each construct to IL-2Rα or IL-2Rβ were further calculated as fold changes relative to those of Aldesleukin IL-2 protein to the same IL-2R subtype (see Table 1).

Figure 12A:
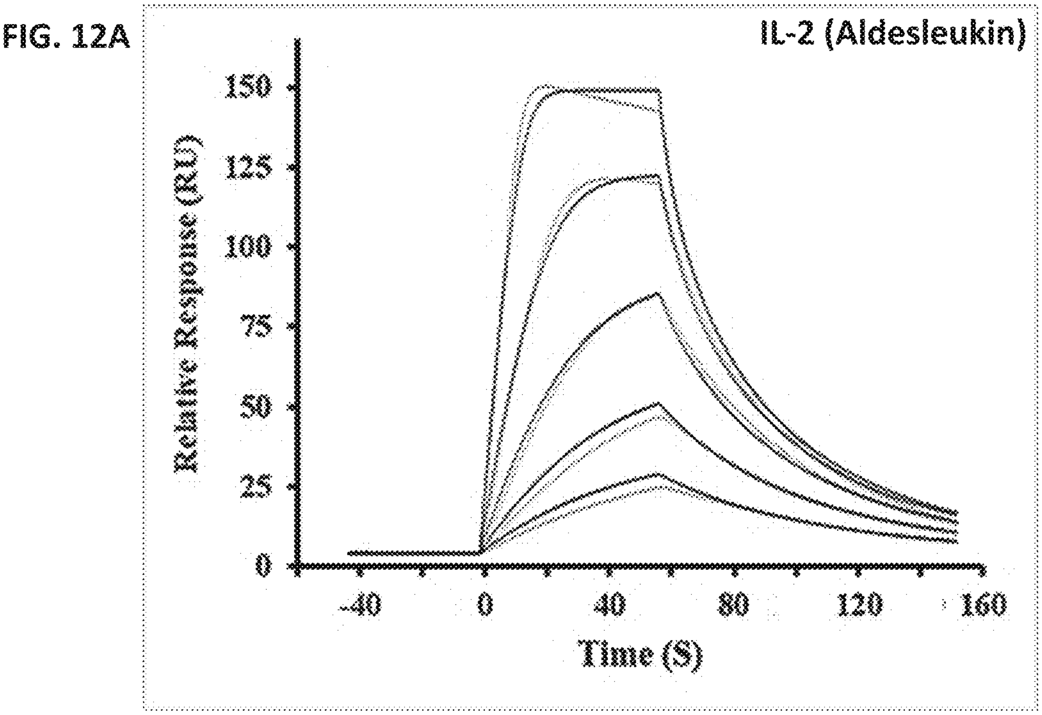
FIGS. 12A-12E depict SPR binding curves of Aldesleukin IL-2 (FIG. 12A), IL-2A1 (DP006A, FIG. 12B), PEG-20K-IL-2A1 (DP006-A-20, FIG. 12C), PEG-30K-IL-2A1 (DP006-A-30, FIG. 12D), or PEG-40K-IL-2A1 (DP006-A-40, FIG. 12E) to IL-2Rα subunit. X-axis shows time, y-axis shows response unit (RU).
Figure 12B:
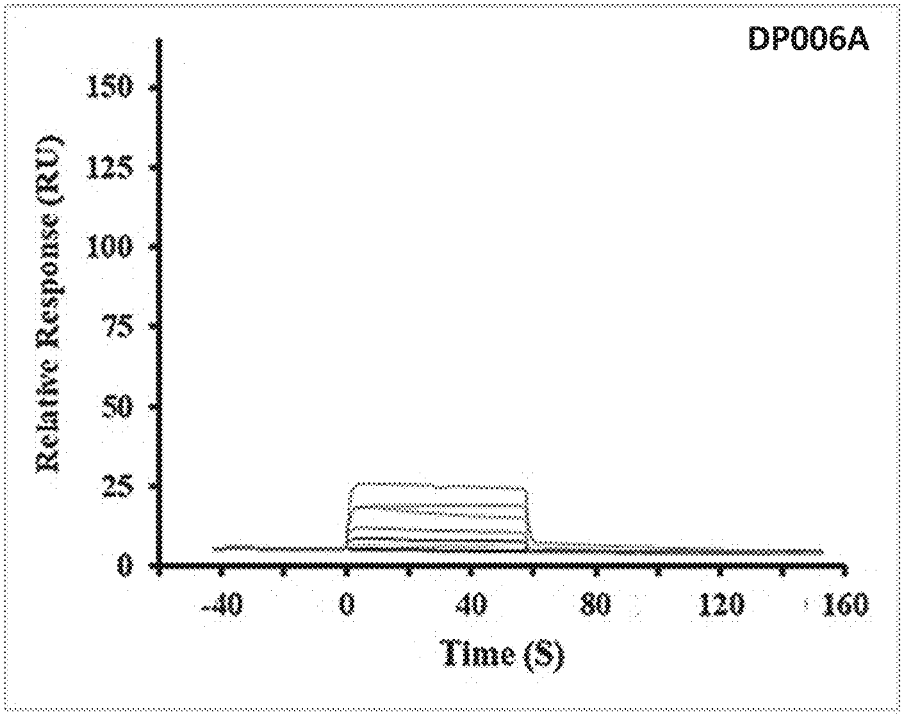
Figure 12C:
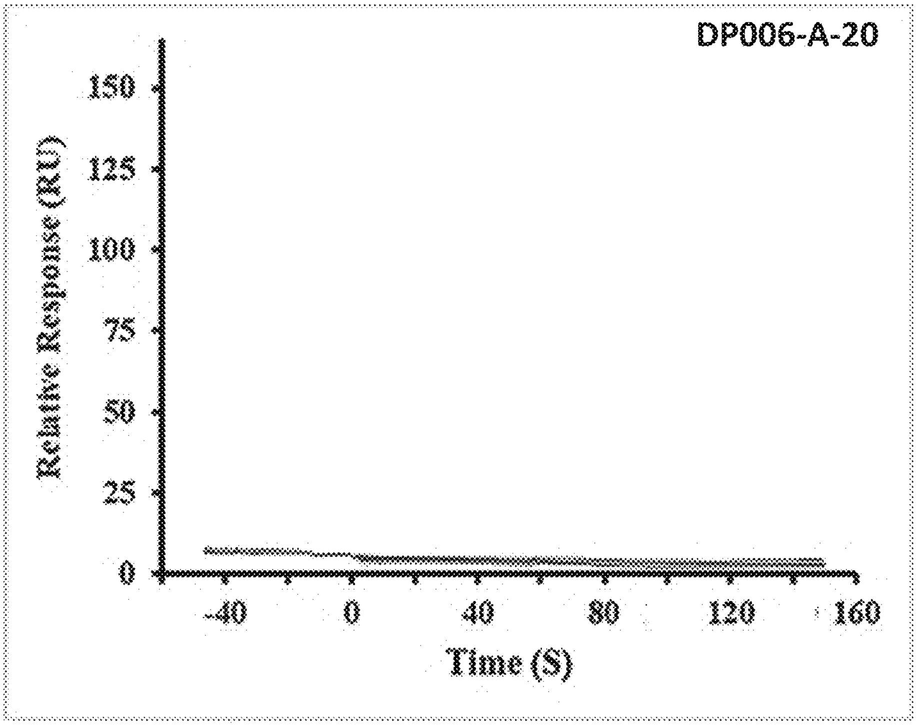
Figure 12D:
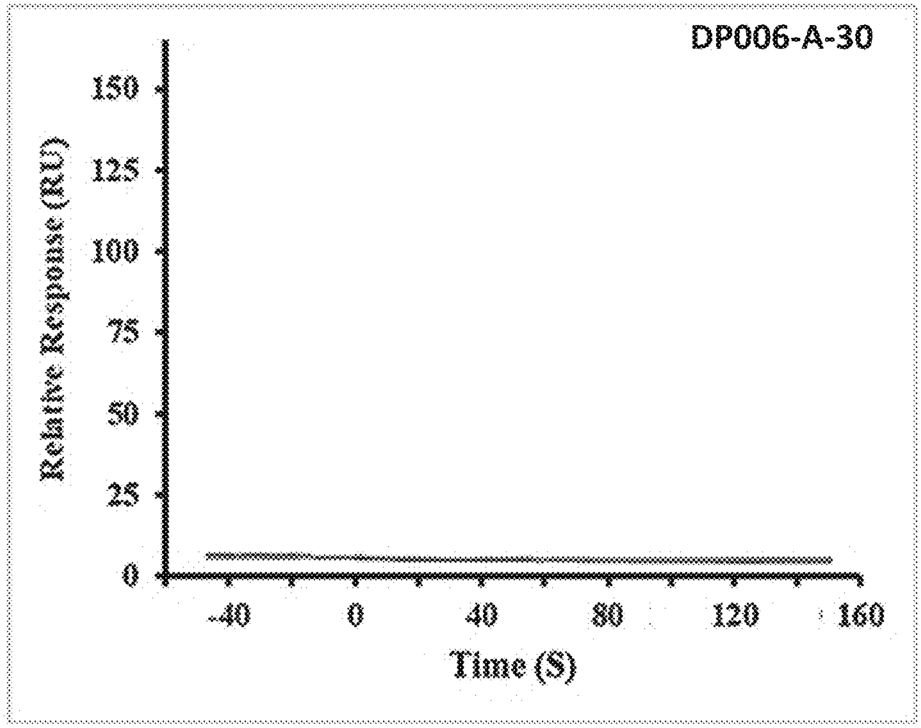
Figure 12E:
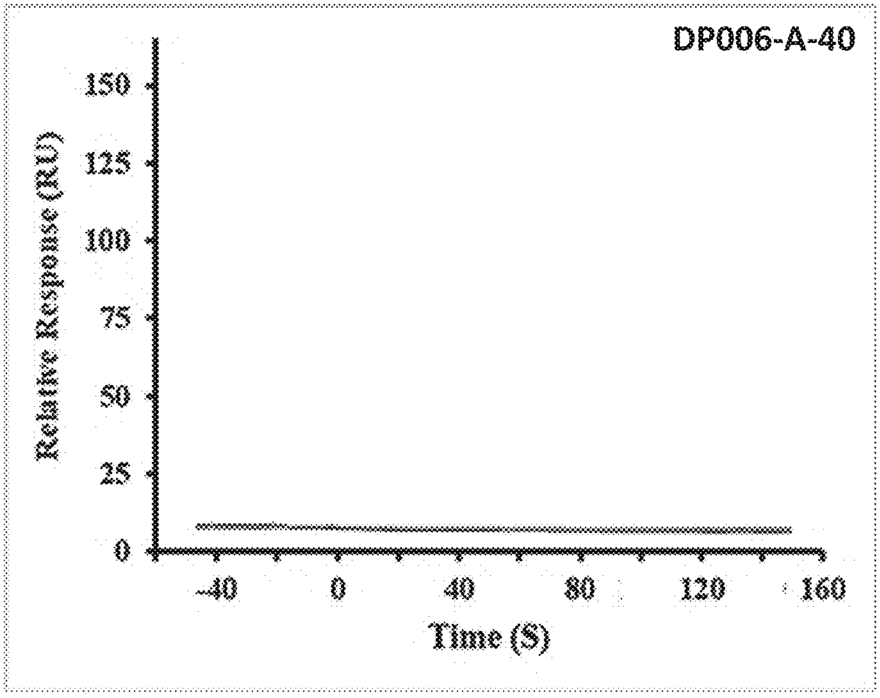
Figure 13A:
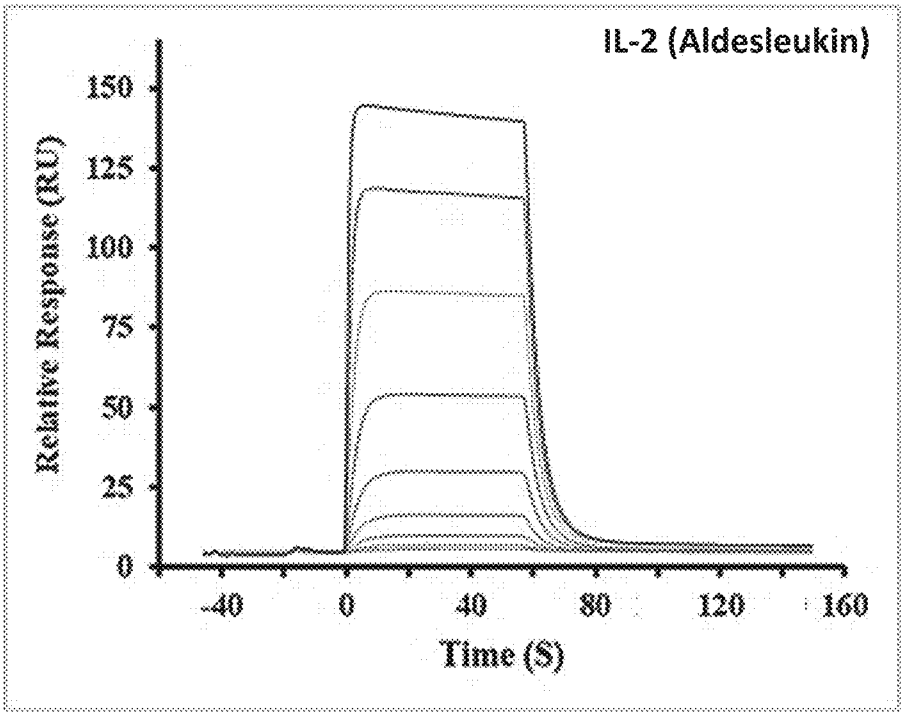
FIGS. 13A-13E depict SPR binding curves of Aldesleukin IL-2 (FIG. 13A), IL-2A1 (DP006A, FIG. 13B), PEG-20K-IL-2A1 (DP006-A-20, FIG. 13C), PEG-30K-IL-2A1 (DP006-A-30, FIG. 13D), or PEG-40K-IL-2A1 (DP006-A-40, FIG. 13E) to IL-2Rβ subunit. X-axis shows time, y-axis shows response unit (RU).
Figure 13B:
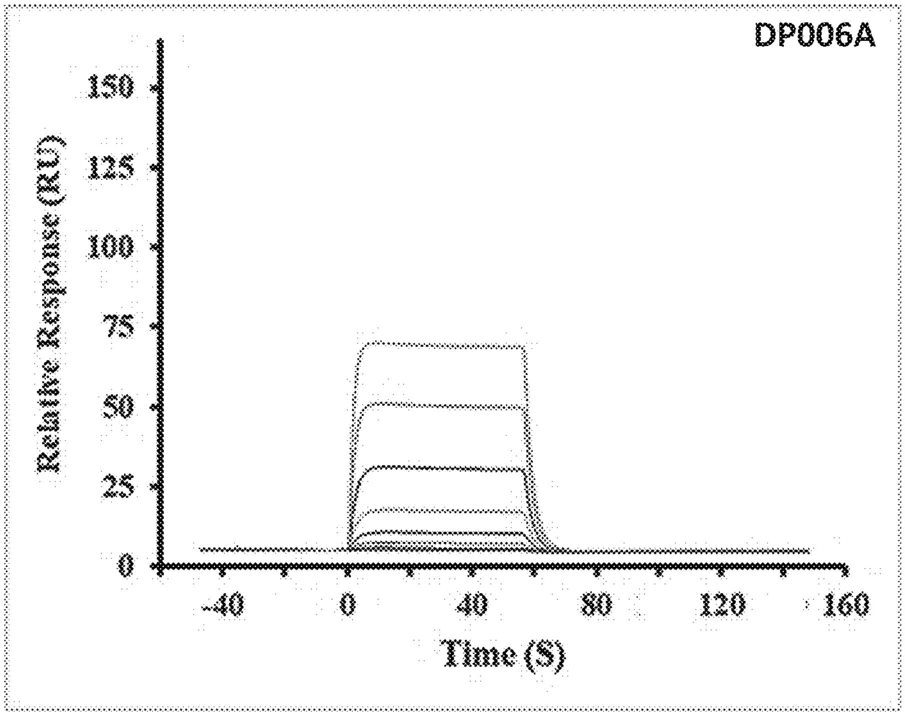
Figure 13C:
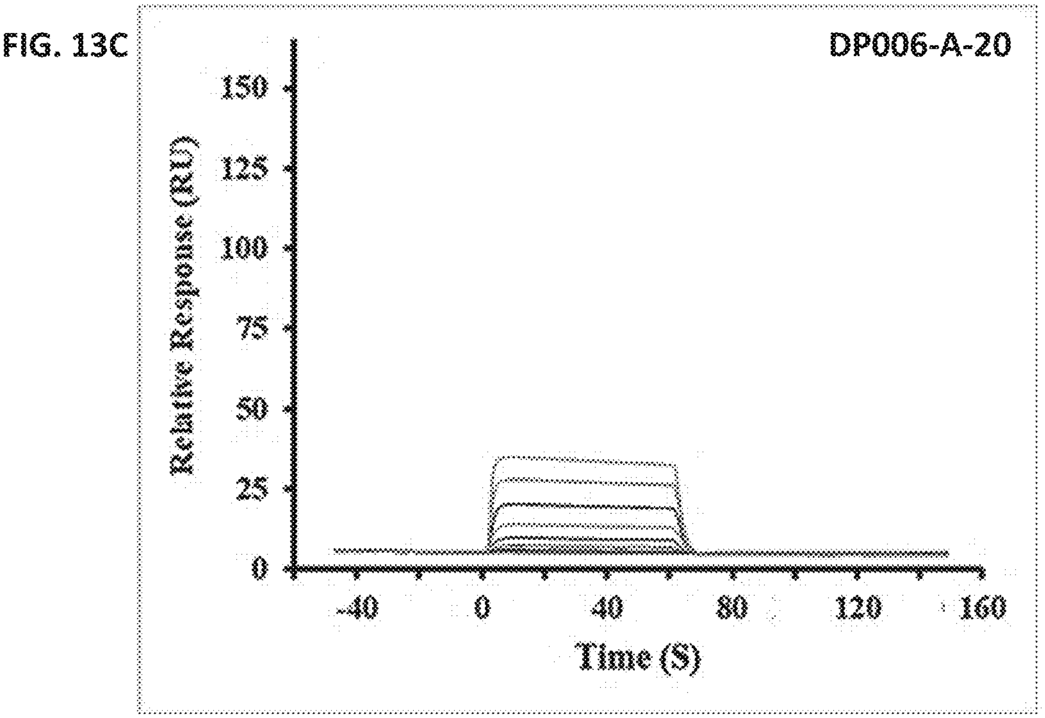
Figure 13D:
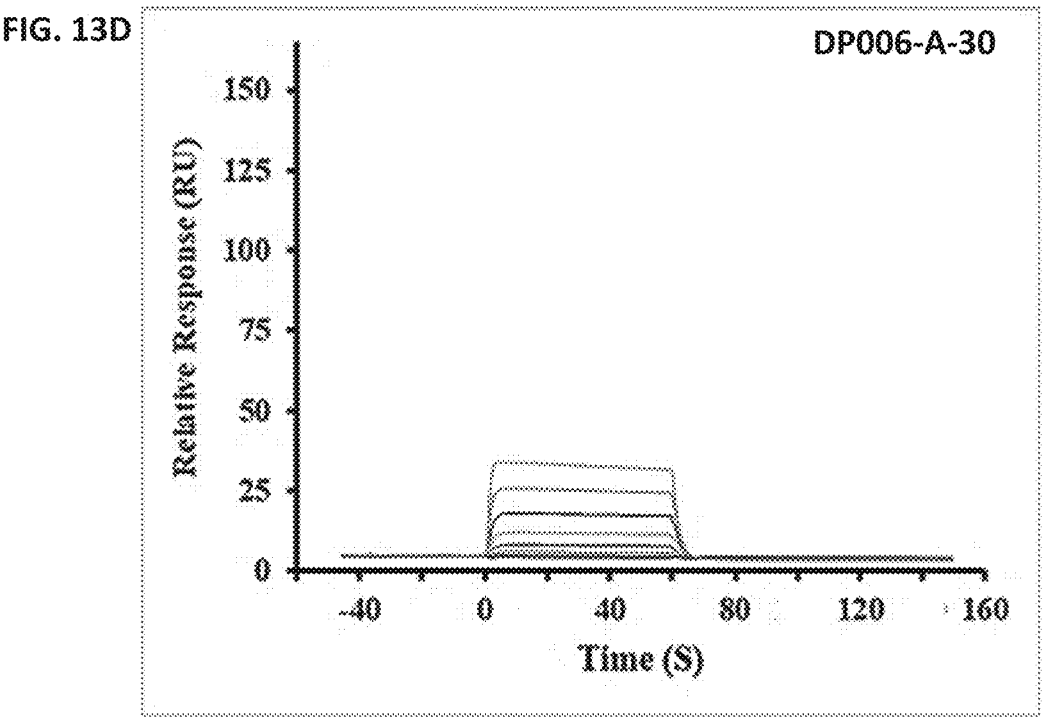
Figure 13E:
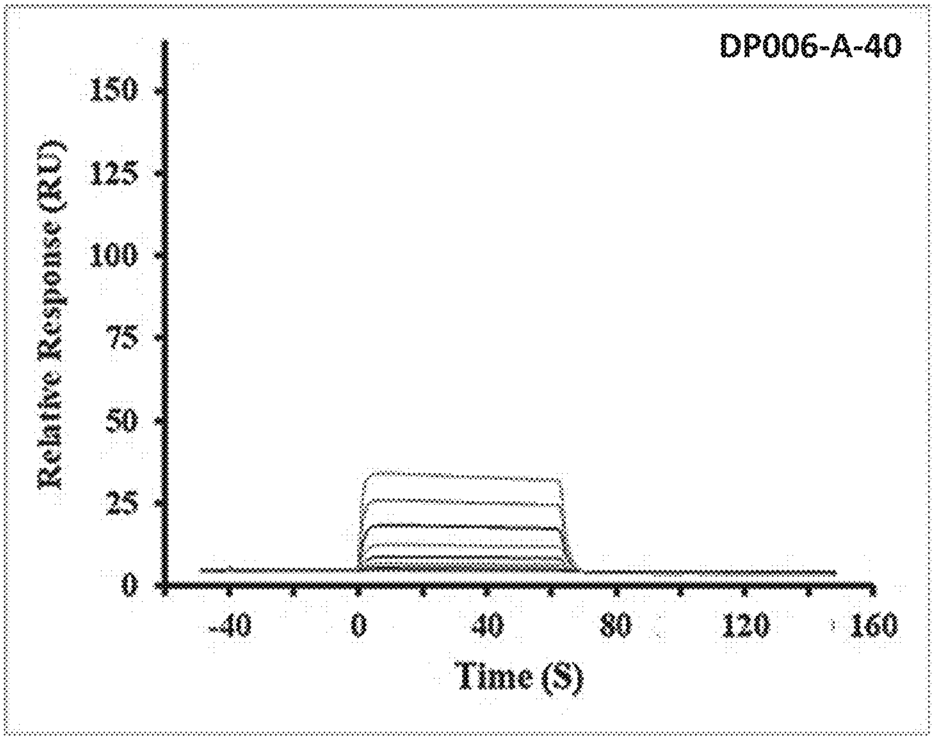

As shown in Table 1, modified IL-2A1 (DP006A) carrying an F43Q mutation in the IL-2Rα subunit binding domain dramatically reduced (~476.45 folds reduction) binding to IL-2Rα compared to Aldesleukin IL-2 protein (FIGS. 12A-12B). Conjugating PEG moiety to IL-2A1 further reduced binding to IL-2Rα to the extent that no binding was detected by SPR in this experiment (FIGS. 12C-12E). The binding affinity of IL-2A1 (DP006A) to IL-2Rβ also reduced (~15.65 folds reduction) compared to that of Aldesleukin IL-2 protein (FIGS. 13A-13B), suggesting that F43Q mutation in the IL-2Rα subunit binding domain also had some influence on IL-2Rβ binding, likely due to effects on protein folding. Surprisingly, conjugating PEG to IL-2A1 (DP006A) strengthened its binding to IL-2Rβ subunit compared to that of unconjugated IL-2A1 (compare FIGS. 13C-13E with FIG. 13B, and Kd in Table 1), although the binding of modified IL-2 protein-PEG conjugates to IL-2Rβ subunit was still less (~8.34-10.91 folds reduction) compared to that of Aldesleukin IL-2 protein (compare FIGS. 13C-13E with FIG. 13A, and Kd in Table 1). The stronger binding to IL-2Rβ of PEGylated DP006A compared to unpegylated DP006A was probably because PEGylation stabilized DP006A or reduced protein loss during the experiment (IL-2 protein is very hydrophobic and easy to stick to most surface it contacts). The results also showed that the bigger size the PEG moiety, the lower the binding of modified IL-2 protein-PEG conjugates to IL-2Rβ subunit. As shown in Table 1, although modified IL-2 (DP006A) and modified IL-2 protein-PEG conjugates both exhibited reduced binding to IL-2R subunit compared to Aldesleukin IL-2 protein, they showed more binding reduction to IL-2Rα subunit compared to IL-2Rβ subunit, reflecting desired bioactivities.

TABLE 1

| SPR binding data | | | | |
|---|---|---|---|---|
| | Binding to IL-2Rα (CD25) | | Binding to IL-2Rβ (CD122) | |
| Construct | Kd (μM) | Fold change relative to IL-2 (wt) | Kd (μM) | Fold change relative to IL-2 (wt) |
| IL-2 (Aldesleukin) | 0.0361 | 1 | 0.536 | 1 |
| DP006A | 17.2 | 476.45 | 8.39 | 15.65 |

TABLE 1-continued

| SPR binding data | | | | |
|---|---|---|---|---|
| | Binding to IL-2Rα (CD25) | | Binding to IL-2Rβ (CD122) | |
| Construct | Kd (μM) | Fold change relative to IL-2 (wt) | Kd (μM) | Fold change relative to IL-2 (wt) |
| DP006-A-20 | No binding | | 4.47 | 8.34 |
| DP006-A-30 | No binding | | 5.41 | 10.09 |
| DP006-A-40 | No binding | | 5.85 | 10.91 |

Example 8. Pharmacokinetic Study of DP630a (DP006-A-30) and DP006-A in Rats Following a Single I.V. Or S.C. Injection of DP630a (DP006-A-30) or DP006-A 1. Objective The objective of this study was to determine the serum pharmacokinetics (PK) of modified IL-2 protein-PEG conjugate PEG-30K-IL-2A1 (“DP630a” or “DP006-A-30”) following a single intravenous or subcutaneous administration. DP630a (DP006-A-30) was produced by conjugation of 30 kDa PEG with IL-2A1 (DP006-A). The serum pharmacokinetics of DP006-A was also determined following a single intravenous of DP006-A compared with DP630a (DP006-A-30). Based on obtained serum pharmacokinetics results, their PK profiles, including half-life and overall exposure ($AUC_{0\text{-}last}$), were compared.

2. Study Summary

Three groups of rats with three males per group (total N=9) received a single bolus intravenous injection or subcutaneous injection of DP006-A or DP630a (DP006-A-30) at dose level of 2 mg/kg. Blood was collected from each animal at designated timepoints (see Table 2) and processed for serum. Then all serum samples were analyzed by ELISA.

TABLE 2

| Groups and dosing | | | | | |
|---|---|---|---|---|---|
| Group | No. of Animals | Test Article | Administration | Dose Level (mg/kg) | Blood Collection Timepoint |
| 1 | 3 males | DP006-A | I.V. | 2.0 | pre-dose (0 min), 5 min, 15 min, 30 min, 1 hr, 2 hrs. 3 hrs. 4 hrs. 6 hrs. 8 hrs post-dosing |
| 2 | 3 males | DP630a (DP006-A-30) | I.V. | 2.0 | pre-dose (0 min), 5 min, 30 min, 1 hr, 2 hrs, 4 hrs, 8 hrs, day 1 (24 hrs), day 2 (48 hrs), day 3 (72 hrs) |
| 3 | 3 males | DP630a (DP006-A-30) | S.C. | 2.0 | pre-dose (0 min), 30 min, 1 hr, 2 hrs, 4 hrs, 8 hrs, day 1 (24 hrs), day 2 (48 hrs), day 3 (72 hrs), day 4 |

3. Testing Facility

The animal experiment and sample collection were conducted at BTS Research (10635 Roselle Street, Suite D-H, San Diego, Calif. 92121).

4. Test Articles

Table 3 shows the test article information. The test articles were stored at −20° C. and moved to room temperature 30 minutes before dosing.

TABLE 3

| Test articles | | |
|---|---|---|
| Test Article | Batch | Concentration (mg/mL)* |
| DP630a (DP006-A-30) | A-30-02262020 | 1.0 |
| DP006-A | A-02172020 | 1.0 |

*Concentration is protein content

5. In-Life Phase 5.1 Animals

Table 4 shows information of animals used in the study. Animal housing and lab procedures followed BTS Research's study protocol #20P-DCP-002. No animal death or adverse effects were observed according to BTS Research.

TABLE 4

| Animals | | | |
|---|---|---|---|
| Species | Rats | Age | 9-11 weeks at dose |
| Strain | Sprague Dawley (SD) | Number and gender | 9 males |
| Source | Envigo (Livermore, CA) | Identification | Ear tag, tail mark, and cage card |

5.2 Sample Collection

Blood was collected from each animal at designated timepoints (see Table 2) and processed for serum. Serum was stored at −20° C. at both BTS Research and CSPC Dophen. Serum was shipped to CSPC Dophen on dry ice.

5.5.3 Sample Analysis 5.3.1 ELISA Analysis for DP630a (DP006-A-30)

In the ELISA assay for DP630a (DP006-A-30), DP630a was used as reference standard, which was prepared in-house at CSPC Dophen in a batch produced on Feb. 26, 2020. Nunc Maxisorp plates (Cat #43711, black) were coated with Rabbit anti-IL-2 antibody (Clone 2F9) (YUROGEN, Cat #R17003M2F9, Lot #201708062F9) at a concentration of 1.0 μg/mL in coating buffer (10 mM Tris pH 8.5) (100 μl/well) and incubated for 0.5 hours at room temperature with shaking and then at 4° C. overnight. Following incubation, 100 μl of 2% milk in PBS was added to each well and incubated for 2 hours at room temperature with shaking to block non-specific binding sites. Plates were then washed, serum samples or standards (eight standards ranging from 0 to 10 ng/mL) diluted in dilution buffer (1% non-fat milk in PBS and 0.00005-0.2% rat serum) were added to wells and incubated for 2 hours at room temperature with shaking. After washing, mouse AGP4-biotin anti-PEG IgM antibody (IBMS Sinica, Product No. AGP4-PABM-B Lot #Mae-A3, 550 μg/ml) prepared in dilution buffer (0.1% BSA in PBS) was added to each well and incubated at room temperature for 1 hour with shaking. Following incubation, plates were washed and Streptavidin-HRP (R&D System Lot 321894, Part No. 890803) diluted in dilution buffer (0.1% BSA in PBS) was added and incubated for 1 hour with shaking. Substrate was prepared by diluting 100 μl of Amplex Red (in DMF), 100 μl of 5 mM 4-Iodophenol and 10 μl of 3% $H_2O_2$ in 11 mL of 10 mM Tris pH 8.5. Plates were washed, and 100 μl of prepared substrate was added into each well. Fluorescence measurements were made using SpectraMax Gemini XS (Molecular Devices, Sunnyvale, Calif.) microplate reader with excitation at 555 nm and emission at 585 nm (570 nm emission cut-off). The ELISA method detection range was from 0.041 ng/mL to 10 ng/mL of DP630a (DP006-A-30).

5.3.2 ELISA Analysis for DP006-A

In the ELISA assay for DP006-A, DP006-A was used as reference standard, which was prepared in-house at CSPC Dophen. Similar procedures of ELISA assay as described in Section 5.3.1 was used except that the plates were coated with rabbit anti-IL-2 antibody (Clone 2F9) at a concentration of 2.0 μg/mL (200 μl/well), and human IL-2 Duoset® ELISA detection antibody (DY202; R&D system) was used instead of mouse AGP4-biotin anti-PEG IgM antibody. The ELISA method detection range was from 3 ng/mL to 200 ng/mL of DP006-A.

5.3.3 Pharmacokinetic Analysis

All pharmacokinetics analysis was conducted on concentration-time profiles of DP630a (DP006-A-30) and DP006-A by non-compartmental analysis using PKSolver V2 software (Zhang Y. et al., "PKSolver: An add-in program for pharmacokinetic and pharmacodynamic data analysis in Microsoft Excel," Comput Methods Programs Biomed. 2010; 99(3):306-1).

Figure 14:
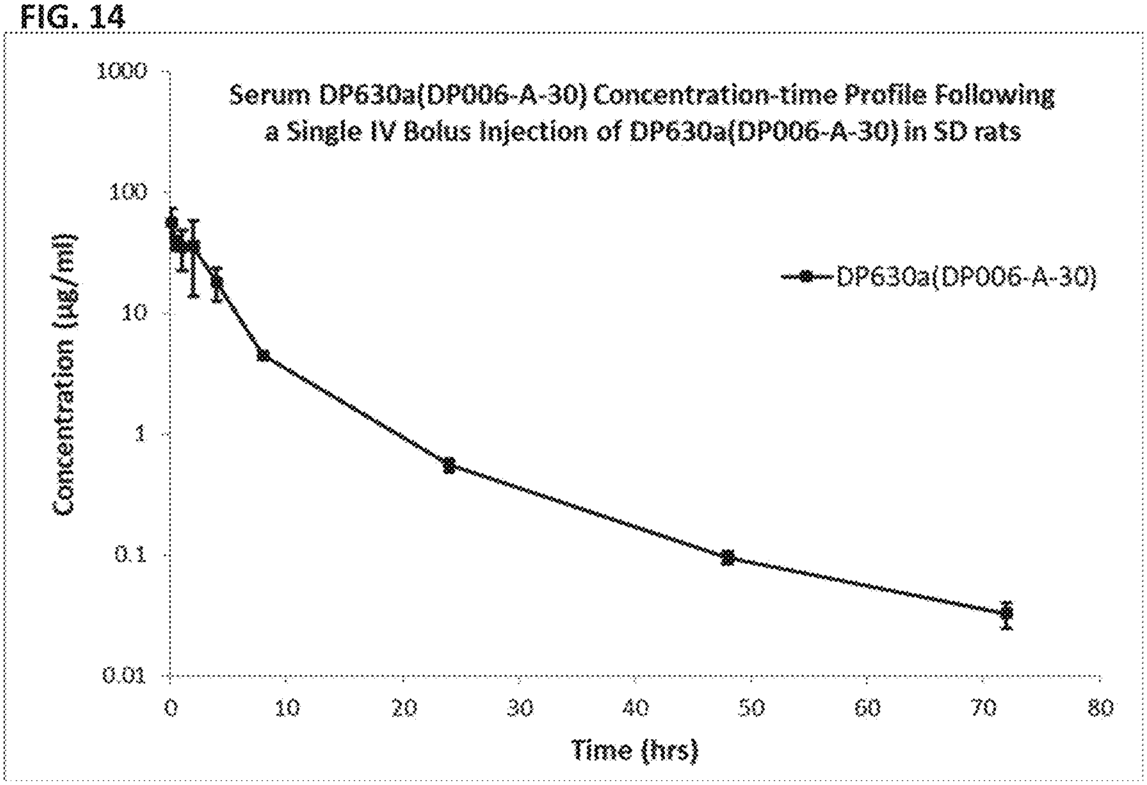
FIG. 14 shows PEG-30K-IL-2A1 DP630a (DP006-A-30) serum concentration-time profile following a single intravenous bolus injection of 2 mg/kg DP630a (DP006-A-30) in SD rats. Data are represented with average of 3 animals (males) and standard deviation.

6. Results 6.1 Serum DP630a (DP006-A-30) Pharmacokinetics Following a Single IV Injection Serum concentrations of DP630a (DP006-A-30) over time following a single intravenous injection at 2 mg/kg are summarized in Table 5, and the average concentration-time (3 animals per time point) profile is shown in FIG. 14. PK parameters are summarized in Table 6. The data demonstrate that after IV administration of DP630a (DP006-A-30), there was a slow elimination phase with a half-life of around 12 hours. The peak concentration of DP630a (DP006-A-30) was at 56.7 μg/mL. The overall exposure ($AUC_{0\text{-}3\ day}$) was 227.5 μg*hr/mL.

TABLE 5

Concentrations of DP630a (DP006-A-30) (μg/mL) in SD rat serum following a single intravenous injection of DP630a (DP006-A-30) Group 2: Dose of DP630a at 2 mg/kg, single IV

| | Male, Concentration (μg/mL) | | | | |
|---|---|---|---|---|---|
| Time (hr) | 2001 | 2002 | 2003 | Average | Stdev |
| 0 | ND | ND | ND | NA | NA |
| 0.08 | 40.61 | 55.74 | 73.79 | 56.71 | 16.61 |
| 0.5 | 32.51 | 38.90 | 42.43 | 37.95 | 5.03 |
| 1 | 28.62 | 27.50 | 50.63 | 35.58 | 13.04 |
| 2 | 25.52 | 20.80 | 60.82 | 35.71 | 21.87 |
| 4 | 12.05 | 22.91 | 19.38 | 18.12 | 5.54 |
| 8 | 4.42 | 4.38 | 4.71 | 4.50 | 0.18 |
| 24 | 0.55 | 0.49 | 0.63 | 0.56 | 0.07 |
| 48 | 0.08 | 0.10 | 0.10 | 0.10 | 0.01 |
| 72 | 0.02 | 0.03 | 0.04 | 0.03 | 0.01 |

Note:
ND = not detected;
NA = not applicable

TABLE 6

PK parameters of SD rats with I.V. administered DP630a (DP006-A-30)

| Group | PEGylated DP006-A | | $C_{max}$ (μg/mL) | $T_{max}$ (hr) [a] | $C_{last}$ (μg/mL) | $T_{last}$ (hr) | $AUC_{0-t}$ (μg*hr/mL) | $t_{1/2}$ (hr) |
|---|---|---|---|---|---|---|---|---|
| 2 | 30K | Mean | 56.7 | 0.08 | 0.03 | 72 | 227.5 | 11.73 |
| | | SD | 16.62 | 0.00 | 0.01 | NA | 57.19 | 1.03 |
| | | N | 3 | 3 | 3 | 3 | 3 | 3 |

Figure 15:
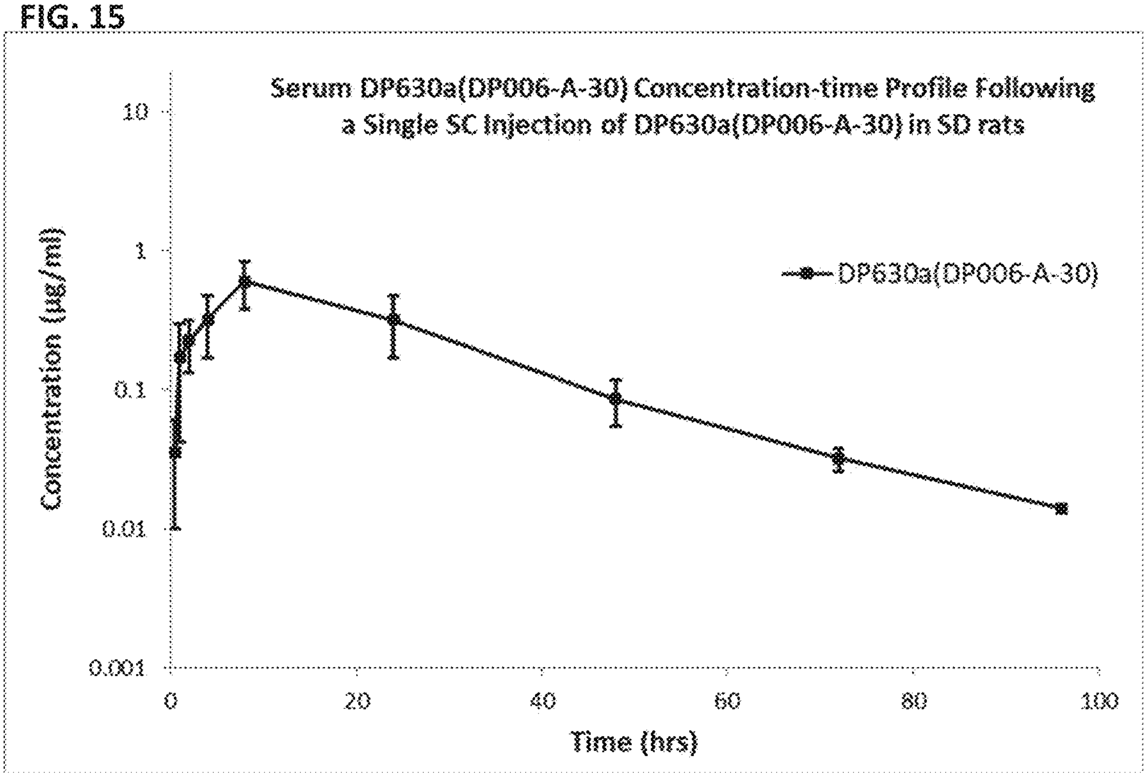
FIG. 15 shows PEG-30K-IL-2A1 DP630a (DP006-A-30) serum concentration-time profile following a single subcutaneous injection of 2 mg/kg DP630a (DP006-A-30) in SD rats. Data are represented with average of 3 animals (males) and standard deviation.

Note:
NA = not applicable; DN = dose normalized to 1 mg/kg; [a] median value is used 6.2 Serum DP630a (DP006-A-30) Pharmacokinetics Following a Single SC Injection Serum concentrations of DP630a (DP006-A-30) over time following a single subcutaneous injection at 2 mg/kg are summarized in Table 7, and the average concentration-time (3 animals per time point) profile is shown in FIG. 15. PK parameters are summarized in Table 8. The data demonstrate that after SC administration of DP630a (DP006-A-30), the serum concentration of DP630a (DP006-A-30) peaked within ~7 hours post-dosing, followed by a slow elimination phase with a half-life of around 18 hours. The peak concentration of DP630a was 0.6 μg/mL. The overall exposure ($AUC_{0\text{-}4\ day}$) of DP630a (DP006-A-30) was 16.9 μg*hr/mL.

TABLE 7

Concentrations of DP630a (DP006-A-30) (μg/mL) in SD rat serum following a single subcutaneous injection of DP630a (DP006-A-30)
Group 3: Dose of DP630a at 2 mg/kg, single SC

| | Male, Concentration (μg/mL) | | | | |
|---|---|---|---|---|---|
| Time (hr) | 3001 | 3002 | 3003 | Average | Stdev |
| 0 | ND | ND | ND | NA | NA |
| 0.5 | 0.035 | 0.01 | 0.059 | 0.035 | 0.025 |
| 1 | 0.063 | 0.137 | 0.311 | 0.17 | 0.128 |
| 2 | 0.146 | 0.206 | 0.329 | 0.227 | 0.093 |
| 4 | 0.184 | 0.293 | 0.485 | 0.321 | 0.153 |
| 8 | 0.863 | 0.495 | 0.454 | 0.604 | 0.225 |
| 24 | 0.494 | 0.225 | 0.24 | 0.319 | 0.151 |
| 48 | 0.121 | 0.075 | 0.063 | 0.086 | 0.031 |
| 72 | 0.039 | 0.029 | 0.028 | 0.032 | 0.006 |
| 96 | 0.015 | 0.015 | 0.013 | 0.014 | 0.001 |

Note:
ND = not detected;
NA = not applicable

TABLE 8

PK parameters of SD rats with S.C. administered DP630a (DP006-A-30)

| Group | PEGylated DP006-A | | $C_{max}$ (μg/mL) | $T_{max}$ (hr) [a] | $C_{last}$ (μg/mL) | $T_{last}$ (hr) | $AUC_{0-t}$ (μg*hr/mL) | $t_{1/2}$ (hr) |
|---|---|---|---|---|---|---|---|---|
| 3 | 30K | Mean | 0.60 | 6.7 | 0.014 | 96 | 16.9 | 18.1 |
| | | SD | 0.20 | 2.3 | 0.001 | NA | 5.6 | 2.9 |
| | | N | 3 | 3 | 3 | 3 | 3 | 3 |

Figure 16:
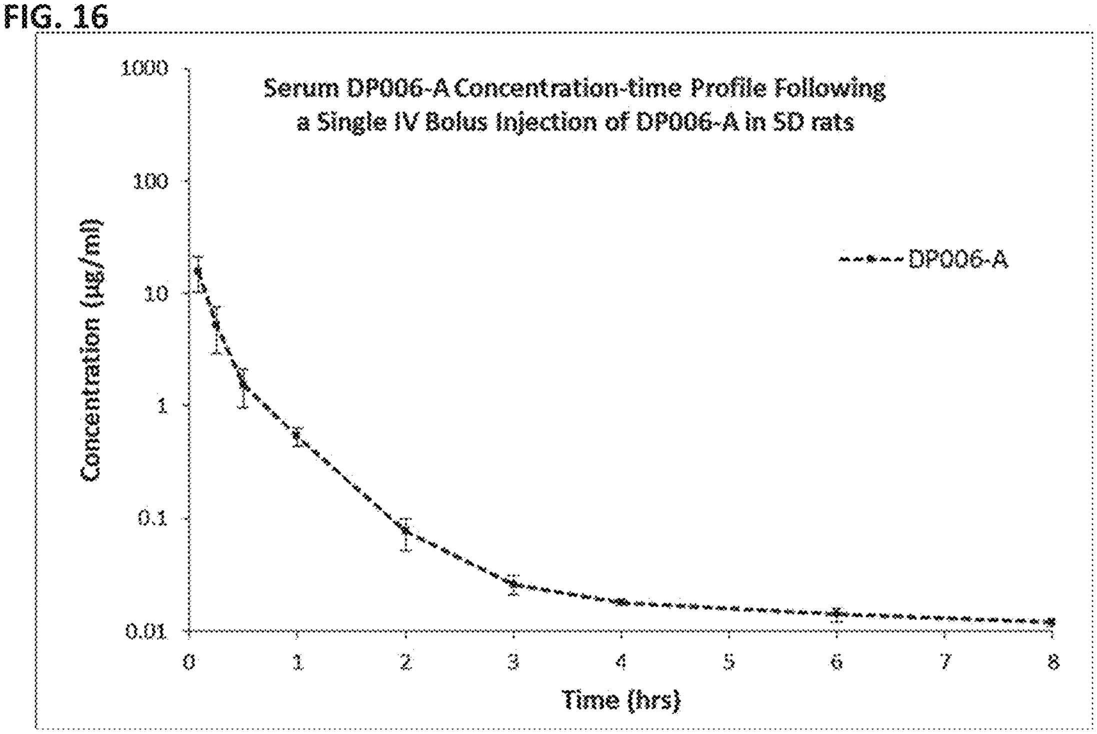
FIG. 16 shows DP006-A serum concentration-time profile following a single intravenous bolus injection of 2 mg/kg DP006-A in SD rats. Data are represented with average of 3 animals (males) and standard deviation.

Note:
NA = not applicable; DN = dose normalized to 1 mg/kg; [a] median value is used 6.3 Serum DP006-A Pharmacokinetics Following a Single IV Injection Serum concentrations of DP006-A over time following a single intravenous injection at 2 mg/kg are summarized in Table 9, and the average concentration-time (3 animals per time point) profile is shown in FIG. 16. PK parameters are summarized in Table 10. The data demonstrate that after IV administration of DP006-A, there was a slow elimination phase with a half-life of around 7.3 hours. The peak concentration of DP006-A was 15.6 μg/mL. The overall exposure ($AUC_{0\text{-}8\ hr}$) was 5.3 μg*hr/mL.

TABLE 9

Concentrations of DP006-A (μg/mL) in SD rat serum following a single intravenous injection of DP006-A
Group 1: Dose of DP006-A at 2 mg/kg, single IV

| | Male, Concentration (μg/mL) | | | | |
|---|---|---|---|---|---|
| Time (hr) | 1001 | 1002 | 1003 | Average | Stdev |
| 0 | ND | ND | ND | NA | NA |
| 0.08 | 10.26 | 20.88 | 15.59 | 15.58 | 5.31 |
| 0.25 | 3.56 | 7.97 | 4.35 | 5.29 | 2.35 |
| 0.5 | 1.19 | 2.2 | 1.22 | 1.53 | 0.57 |
| 1 | 0.49 | 0.66 | 0.47 | 0.54 | 0.1 |
| 2 | 0.104 | 0.061 | 0.064 | 0.076 | 0.024 |
| 3 | 0.031 | 0.021 | 0.026 | 0.026 | 0.005 |
| 4 | 0.018 | 0.016 | 0.018 | 0.018 | 0.001 |
| 6 | 0.013 | 0.012 | 0.016 | 0.014 | 0.002 |
| 8 | 0.012 | 0.011 | 0.013 | 0.012 | 0.001 |

Note:
ND = not detected;
NA = not applicable

TABLE 10

PK parameters of SD rats with I.V. administered DP006-A

| Group | DP006-A | | $C_{max}$ (μg/mL) | $T_{max}$ (hr) [a] | $C_{last}$ (μg/mL) | $T_{last}$ (hr) | $AUC_{0-t}$ (μg*hr/mL) | $t_{1/2}$ (hr) |
|---|---|---|---|---|---|---|---|---|
| 1 | | Mean | 15.6 | 0.1 | 0.012 | 8 | 5.3 | 7.3 |
| | | SD | 5.3 | 0.0 | 0.001 | NA | 1.7 | 1.4 |
| | | N | 3 | 3 | 3 | 3 | 3 | 3 |

Figure 17:
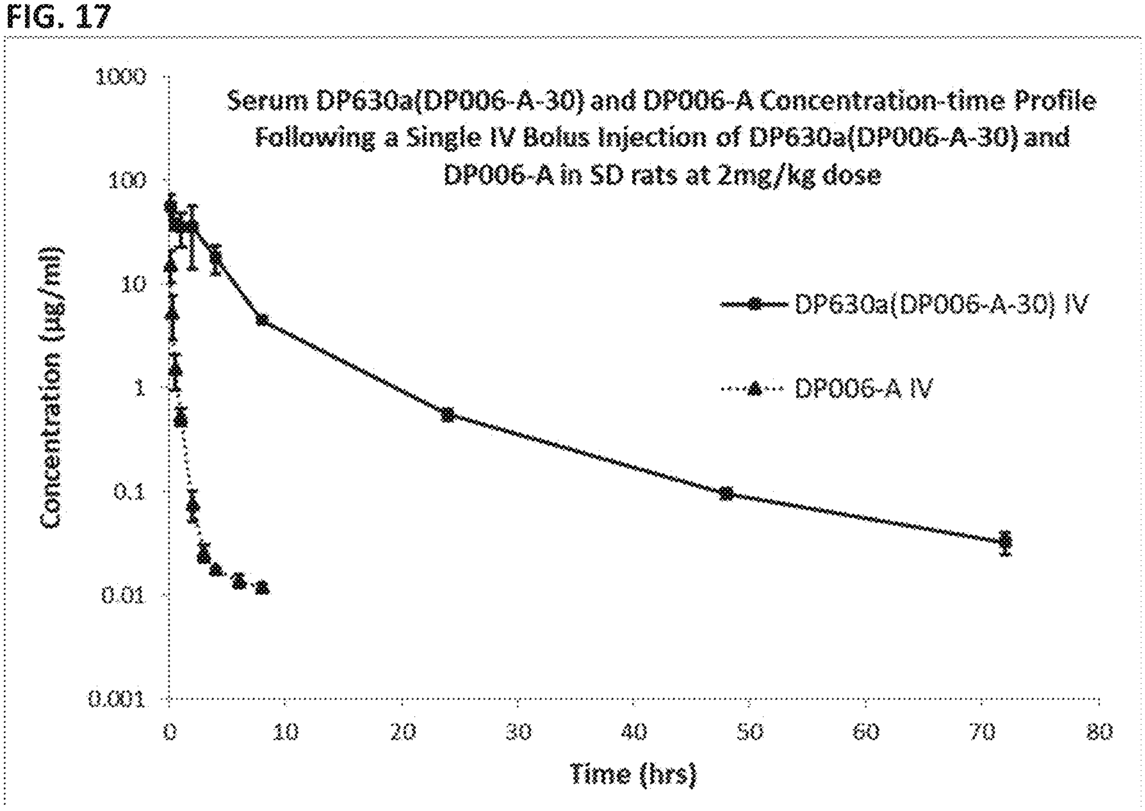
FIG. 17 shows comparison of serum DP630a (DP006-A-30) and DP006-A concentration-time profiles following a single intravenous bolus injection of DP630a (DP006-A-30) or DP006-A in SD rats at 2 mg/kg. Data are represented with average of 3 animals (males) and standard deviation. The end timepoint was 72 hours for DP630a (DP006-A-30), and 8 hours for DP006-A.

Note:
NA = not applicable; DN = dose normalized to 1 mg/kg; [a] median value is used 7. Discussion As can be seen from FIG. 17, following intravenous dosing at 2 mg/kg, DP006-A quickly dropped in levels in blood and distributed into the body, while DP630a (DP006-A-30) carrying a 30 kDa PEG moiety was mainly confined in the circulating blood and slowly eliminated. The improved stability of pegylated form of modified IL-2 is also demonstrated by pharmacokinetic profiles: the elimination half-life increased 60.3% for DP603a (DP006-A-30; 11.7 hours) compared to DP006-A (7.3 hours); and the overall exposure ($AUC_{0\text{-}last}$) increased about 42 folds for DP630a (DP006-A-30; 227.5 μg*hr/mL) compared to DP006-A (5.3 μg*hr/mL).

Figure 18:
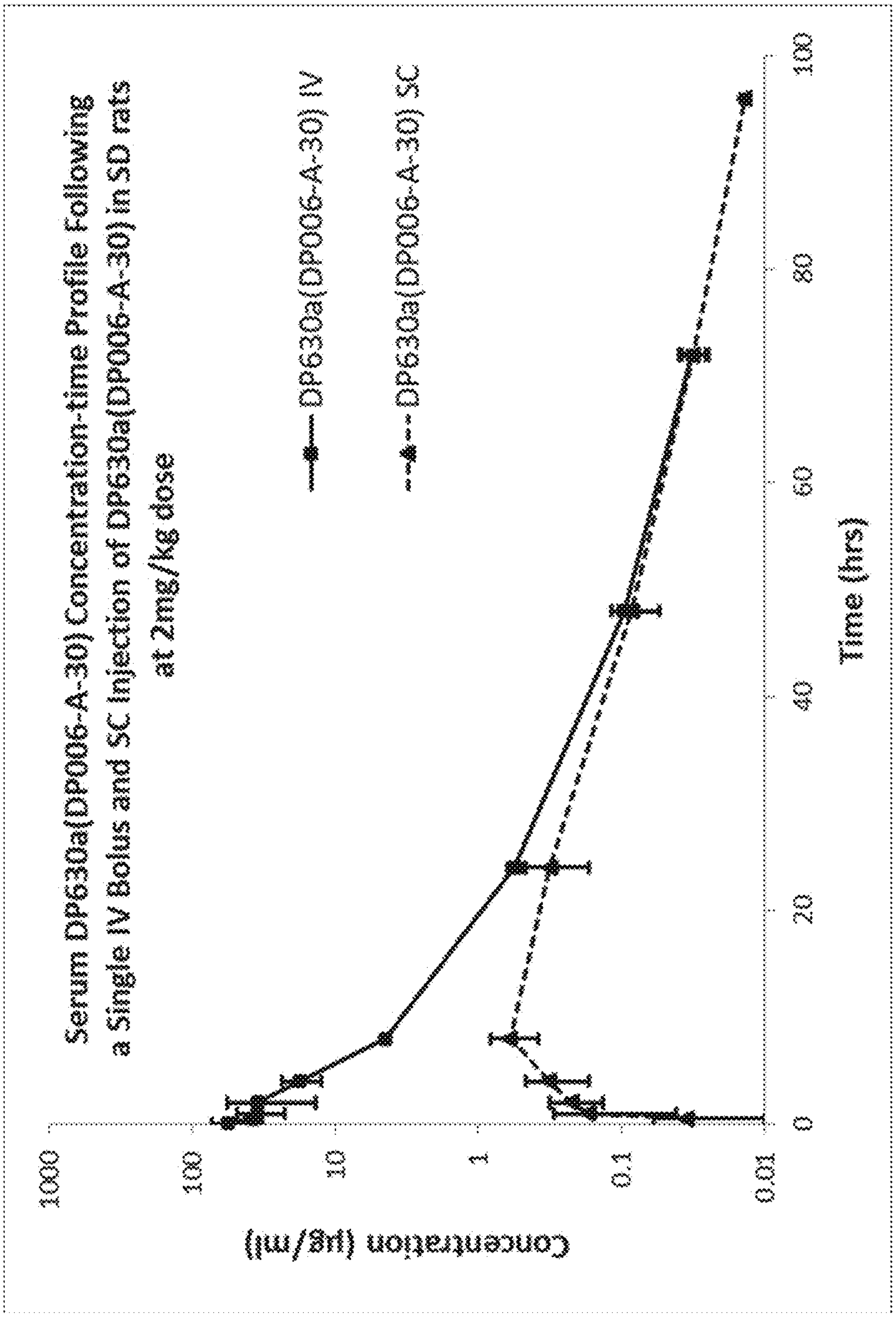
FIG. 18 shows comparison of serum DP630a (DP006-A-30) concentration-time profiles following a single intravenous bolus injection or a single subcutaneous injection in SD rats at 2 mg/kg. Data are represented with average of 3 animals (males) and standard deviation.

The bioavailability of DP630a (DP006-A-30) following a single subcutaneous dose at 2 mg/kg was low at 7.4% calculated by comparing the AUC of subcutaneous dose to that of the intravenous dosing (see FIG. 18).

The elimination half-life of DP006-A (~7.3 hrs) following IV dose at 2 mg/kg assessed using noncompartmental analysis here is much longer than the reported IL-2 half-life in humans (e.g., half-life of IL-2 Aldesleukin is about 80 minutes based on literature; see, e.g., PROLEUKIN® (aldesleukin) FDA label). This is likely due to the dosing level differences. In this study, the dose level was 2 mg/kg; whereas in human, the clinical dose is about 0.037 mg/kg. Due to the detection limit of ELISA method, the elimination phase might not be observed in human studies when such a low dose (0.037 mg/kg) of IL-2 is administered, hence the half-life time in the distribution phase was reported as the elimination half-life time in human. In this study, if the distribution phase of DP006-A was treated as the elimination phase (i.e., the duration of 1-4 hours following dosing), the observed half-life time would have been less than 0.5 hours (see Table 9 and FIG. 16), much shorter than the elimination half-life time observed (4 to 8 hours; see FIG. 16). Therefore, considering about the much lower clinical dose of IL-2, the half-life time in the distribution phase could serve as the functional half-life time. Then the improved stability and PK profiles of pegylated modified IL-2 (DP630a or DP006-A-30) shown above would be even more prominent compared to non-pegylated modified IL-2 (DP006-A).

8. Conclusion

This study demonstrates that DP630a (DP006-A-30) has prolonged stability and exposure compared to DP006-A following intravenous or subcutaneous administration, suggesting that pegylation can improve protein stability and help achieve preferred PK profiles for modified IL-2 proteins.

Example 9. Determination of PEG Conjugation Site for DP006-A-30 Using LC-MS/MS The purpose of this study was to determine the site of polyethylene glycol (PEG) conjugation in DP006-A-30 (PEG-30K-IL-2A1) by liquid chromatography tandem mass spectrometry (LC-MS/MS). Peptide mapping assay with trypsin and Glu-C digestion was used to examine the primary structure of the protein. Location of PEGylation was determined by comparing the signal intensity of peptides from digested PEGylated sample and digested unPEGylated sample, based on the principle that the addition of PEG conjugation shifts both the mass-to-charge ratio and retention time of a peptide, resulting in much lower intensity or loss of signal at its retention time. Therefore, by comparing to peptide mapping profile of the unPEGylated protein, the peptide with lower intensity or lost signal in the peptide mapping profile of the PEGylated protein is the PEGylated peptide. By comparing between PEGylated peptides identified in trypsin digestion and Glu-C digestion, PEGylation and its location were found and determined. Further investigation by examining MS/MS spectra of PEGylated peptides also confirmed the existence of and the conjugation site of the PEG conjugation. The results from this study demonstrate that, for DP006-A-30, the PEG conjugation site is at Q43.

1. Study Design

In order to determine the site of PEG conjugation in DP006-A-30 (DP006-A is about 15 kDa, DP006-A-30 is about 45 kDa), peptide mapping assays with trypsin digestion and Glu-C digestion were performed on DP006-A (IL-2A1) and DP006-A-30 (PEG-30K-IL-2A1). The signal intensities of digested peptides were compared between PEGylated sample digest and unPEGylated sample digest. Lower signal intensity of a certain peptide indicates that this peptide is PEGylated. Since it is known that Glutamine (Q) is the designated amino acid for PEGylation, PEGylation was located and assigned to single Glutamine by combining the results from trypsin digestion and Glu-C digestion. MS/MS spectra of PEGylated peptides were also investigated to confirm the existence and location of PEG conjugation.

2. Materials and Methods 2.1 Test Materials

The study was conducted at Alliance Pharma (Malvern, Pa.). DP006-A and DP006-A-30 were provided by CSPC Dophen. See Table 11.

TABLE 11

| Materials | |
|---|---|
| Test materials: | DP006-A UnPEGylated IL-2A1, 0.5 mg/mL<br>DP006-A-30 PEGylated DP006-A, 0.5 mg/mL |
| Storage conditions: | Kept at −80° C. before testing |

2.2 Sample Preparation for Peptide Mapping

An aliquot containing 50 μg of DP006-A or DP006-A-30 was placed in the Speed Vac to reduce the volume to approximately 25 μL. 25 μL of 1% RapiGest in 50 mM ammonium bicarbonate was added to each sample to arrive a final concentration of 1% RapiGest in each sample. Samples were reduced by adding 2.5 μL of 1 M dithiothreitol (DTT) and incubated at 60° C. for 1 hour. Samples were then alkylated by adding 8 μL of 1 M Iodoacetamide (IAA) and incubated at room temperature in dark for 30 minutes. The treated samples were then aliquoted equally into two tubes and subject to trypsin digestion or Glu-C digestion at a ratio of 1:20 of enzyme to protein. Samples were incubated at 37° C. overnight and terminated reaction by acidifying using 10% TFA (trifluoroacetic acid) and centrifugation. The supernatant was collected and analyzed by LC-MS/MS.

2.3 LC-MS/MS Method

Electrospray ionization mass spectrometry (ESI-MS) was performed on an Agilent 6545XT QTOF mass spectrometer operating in the positive ion mode, see Tables 12-14. Full scan MS data was collected over mass to charge (m/z) range of 250-2,000. MS/MS scans were performed for the top three precursors observed (potentially PEGylated peptides).

TABLE 12

| LC-MS/MS Instrumentation and Software | |
|---|---|
| Auto injector/ controller/pumps: | Agilent 1290 Infinity II |
| HPLC column(s): | Waters Acquity UPLC Peptide BEH C18 Column, 300 Å, 1.7 μm, 2.1 mm × 150 mm |
| Mass spectrometer: | Agilent 6545XT AdvanceBio QTOF mass spectrometer |

TABLE 13

| Elution Program | | |
|---|---|---|
| | Mobile Phase | |
| Time (minutes) | % A | % B |
| 0 | 98 | 2 |
| 1 | 98 | 2 |
| 30 | 55 | 45 |
| 40 | 5 | 95 |
| 42 | 5 | 95 |
| 42.1 | 98 | 2 |
| 52 | 98 | 2 |

Mobile phase A: 0.1% formic acid (FA) in water
Mobile phase B: 0.1% FA in acetonitrile
HPLC flow rate: 0.2 mL/min

TABLE 14

| Source and Ion Lens Parameters | | | |
|---|---|---|---|
| MS Ion Source | Dual AJS ESI | VCap | 4000 V |
| Gas Temperature | 290 °C | Fragmentor | 175 V |
| Gas Flow Rate | 13 L/min. | Skimmer | 65 V |
| Nebulizer | 35 psi | Octopole RF Peak | 750 V |

2.4 Data Analysis

Peptide mapping data were subject to database searching using Protein Metrics. A database containing sequences of DP006-A was used. See Table 15 for database searching parameters. The remaining unidentified sequences were then confirmed by full scan mass spectrometry (MS1) accurate mass extraction to achieve full sequence coverage.

TABLE 15

| Database searching parameters | |
|---|---|
| Software | Protein Metrics-Byonic |
| Cleavage site(s) | RK for Trypsin or DE for GluC |
| Cleavage side | C-terminal |
| Digestion specificity | Fully specific (fastest) |

TABLE 15-continued

| Database searching parameters | |
|---|---|
| Missed cleavages | 2 |
| Precursor mass tolerance | 20 ppm |
| Fragmentation type | QTOF/HCD |
| Fragment mass tolerance | 20 ppm |
| Recalibration (from Preview) | None |
| Recalibration (lock mass) | None |
| Fixed and Variable modifications | Carbamidomethyl / +57.021464 @ C ǀ fixed<br>Deamidated / +0.984016 @ N, Q ǀ rare1<br>Oxidation / +15.994915 @ C, M, W ǀ rare1 |
| Total common max | 2 |
| Total rare max | 1 |
| Maximum precursor mass | 10000 |
| Precursor & charge assignments | Compute from MS1 |

3. Results and Discussion 3.1 Peptide Mapping of DP006-A and DP006-A-30 with Trypsin Digestion FIG. 19 shows sequence coverage of DP006-A and DP006-A-30 with trypsin digestion by database searching. Combined with MS1 accurate mass extraction (Table 16), 100% sequence coverage was achieved.

TABLE 16

List of Peptides and their Retention Times, Masses, and Peak Intensities for DP006-A and DP006-A-30 with Trypsin Digestion

| From-to (aa residue) | Sequence | Retention Time (min) | Observed Mass (Da) | Theoretical Mass (Da) | ppm | Peak Intensity DP006A | Peak Intensity DP006A-30 |
|---|---|---|---|---|---|---|---|
| 1-7 | PTSSSTK (SEQ ID NO: 31) | 2.6 | 706.3515 | 706.3497 | 2.5 | 8.79E+04 | 1.85E+05 |
| 9-34 | TQLQLEHLLLDLQ MILNGINNYKNPK (SEQ ID NO: 32) | 28.6 | 3062.6577 | 3062.6587 | -0.3 | 1.49E+04 | 1.01E+05 |
| 35-37 | LTR (SEQ ID NO: 33) | 3.7 | 388.2428 | 388.2434 | -1.5 | 2.30E+05 | 8.34E+05 |
| 38-42 | MLTFK (SEQ ID NO: 34) | 14.0 | 638.3484 | 638.3462 | 3.4 | 8.42E+05 | 7.81E+05 |
| 43-47 | **QYMPK** (SEQ ID NO: 35) | 8.5 | 665.3228 | 665.3207 | 3.1 | 1.42E+06 | 4.00E+04 |
| 48-53 | KATELK (SEQ ID NO: 36) | 5.0 | 688.4152 | 688.4119 | 4.8 | 7.16E+05 | 1.23E+06 |
| 54-75 | HLQCLEEELKPLE EVLNLAQSK (SEQ ID NO: 37) | 24.2 | 2619.3644 | 2619.3578 | 2.5 | 1.51E+06 | 1.62E+06 |
| 76-82 | NFHLRPR (SEQ ID NO: 38) | 9.5 | 938.5229 | 938.5199 | 3.1 | 1.62E+06 | 1.63E+06 |
| 83-96 | DLISNINVIVLELK (SEQ ID NO: 39) | 26.6 | 1581.9372 | 1581.9342 | 1.9 | 2.42E+05 | 3.54E+05 |
| 97-119 | GSETTFMCEYADE TATIVEFLNR (SEQ ID NO: 40) | 26.4 | 2683.1637 | 2683.1782 | -5.4 | 3.34E+04 | 1.89E+04 |
| 120-132 | WITFSQSIISTLT (SEQ ID NO: 41) | 25.5 | 1495.7896 | 1495.7922 | -1.8 | 2.25E+05 | 6.66E+05 |

FIG. 20 shows base peak chromatography of DP006-A and DP006-A-30 with trypsin digestion. The missing peak in DP006-A-30 chromatography at ~8.5 minutes (see arrow) corresponds to P43-47 peptide, showing that this peptide had much lower intensity in the PEGylated protein digest than in the unPEGylated protein digest. This suggests that there are potential PEGylation sites in this P43-47 peptide, which should be located on the designated amino acid Glutamine (Q43). The detailed intensity comparison for each tryptic peptide is listed in Table 16. Only P43-47 peptide showed lower intensity in the PEGylated sample digest, confirming that PEG was conjugated to this P43-47 peptide in the PEGylated sample and the conjugation was only present in this peptide.

The PEGylated form of P43-47 was also identified by manual investigation. A series of ions with mass differences of 44 Da (mass of one PEG unit) were observed. As shown in FIG. 21, they were only present in the PEGylated sample, and were in low intensity because the PEGylated peptides were heterogeneous. Examples of their MS1 and MS/MS spectra are shown in FIG. 22 and FIG. 23, in which 44 Da spacing in the spectra indicates the presence of PEGylation. Based on fragments identified in the MS/MS spectra, the location of PEGylation was confirmed to be located on the Glutamine (Q43) in P43-47.

3.2 Peptide Mapping of DP006-A and DP006-A-30 with Glu-C Digestion

FIG. 24 shows sequence coverage of DP006-A and DP006-A-30 with Glu-C digestion by database searching. Combined with MS1 accurate mass extraction (Table 17), 100% sequence coverage was achieved.

TABLE 17

List of Peptides and their Retention Times, Masses, and Peak Intensities for DP006-A and DP006-A-30 with Glu-C Digestion

| From-to (aa residue) | Sequence | Retention Time (min) | Observed Mass (Da) | Theoretical Mass (Da) | ppm | Peak Intensity DP006A | DP006A-30 |
|---|---|---|---|---|---|---|---|
| 1-14 | PTSSSTKKTQLQLE (SEQ ID NO: 42) | 10.9 | 1546.8225 | 1546.8203 | 1.4 | 5.12E+05 | 7.14E+05 |
| 15-51 | **HLLLDLQMILNGIN NYKNPKLTRMLTFK QYMPKKATE** (SEQ ID NO: 43) | 23.3 | 4417.4152 | 4417.3840 | 7.1 | 4.51E+03 | ND |
| 52-61 | LKHLQCLEEE (SEQ ID NO: 44) | 11.4 | 1297.6386 | 1297.6336 | 3.8 | 1.65E+06 | 1.65E+06 |
| 62-67 | LKPLEE (SEQ ID NO: 45) | 11.0 | 727.4167 | 727.4116 | 7.0 | 1.63E+06 | 1.67E+06 |
| 68-94 | VLNLAQSKNFHLRPR DLISNINVIVLE (SEQ ID NO: 46) | 21.5 | 3114.7705 | 3114.7666 | 1.3 | 1.51E+05 | 1.63E+06 |
| 95-99 | LKGSE (SEQ ID NO: 47) | 3.8 | 532.2844 | 532.2857 | −2.4 | 8.84E+04 | 1.16E+05 |
| 100-105 | TTFMCE (SEQ ID NO: 48) | 13.1 | 787.2912 | 787.2881 | 3.9 | 3.25E+04 | 4.28E+04 |
| 106-109 | YADE (SEQ ID NO: 49) | 5.3 | 1265.4608 | 1265.4580 | 2.2 | 8.57E+05 | 1.06E+06 |
| 110-115 | TATIVE (SEQ ID NO: 50) | 10.8 | 632.3395 | 632.3381 | 2.2 | 1.67E+06 | 1.66E+06 |
| 116-132 | FLNRWITFSQSIISTLT (SEQ ID NO: 51) | 27.2 | 2026.0891 | 2026.0888 | 0.1 | 4.57E+05 | 1.65E+06 |

FIG. 25 shows base peak chromatography (BPC) of DP006-A and DPOO6-A-30 with Glu-C digestion. Although there was no obvious missing peak in the BPC, the detailed intensity comparison for each Glu-C digested peptide (Table 17) shows that P15-51 was not identified in the PEGylated sample digest, while other peptides had similar intensity in both PEGylated and unPEGylated sample digests. This indicates that there were potential PEGylation sites in this P15-51 peptide, in line with the location of PEGylation identified from trypsin digestion.

4. Conclusion

Based on peptide mapping data for DP006-A and DP006-A30 with trypsin and Glu-C digestion, and investigation on extracted ion chromatogram, MS1, and MS/MS spectra, PEG conjugation was located to a single Glutamine (Q43) for DP006-A-30 as listed in Table 18.

TABLE 18

| PEGylation site of DP006-A-30 | |
|---|---|
| DP006-A-30 | PTSSSTKKTQLQLE**HLLLDLQMILNGINNYKNPKLTRML TFKQYMPKKATE**LKHLQCLEEELKPLEEVLNLAQSKNFH LRPRDLISNINVIVLELKGSETTFMCEYADETATIVEFL NRWITFSQSIISTLT (SEQ ID NO: 2) |

Q: PEGylation site
Underline: PEGylated tryptic peptide
Bold: PEGylated Glu-C peptide

SEQUENCE LISTING

SEQ ID NO: 1 (Aldesleukin human recombinant IL-2 amino acid sequence)
PTSSSTKKTQLQLEHLLLDLQMILNGINNYKNPKLTRMLTFKFYMPKKATELKHLQCLEEELKPL
EEVLNLAQSKNFHLRPRDLISNINVIVLELKGSETTFMCEYADETATIVEFLNRWITFSQSIISTLT SEQ ID NO: 2 (IL-2 (A1) Mutation (F43Q) amino acid sequence)
PTSSSTKKTQLQLEHLLLDLQMILNGINNYKNPKLTRMLTFKQYMPKKATELKHLQCLEEELKPL
EEVLNLAQSKNFHLRPRDLISNINVIVLELKGSETTFMCEYADETATIVEFLNRWITFSQSIISTLT SEQ ID NO: 3 (IL-2 (A2) Mutation (IFKQTY) amino acid sequence)
PTSSSTKKTQLQLEHLLLDLQMILNGINNYKNPKLTRMLIFKQTYPKKATELKHLQCLEEELKPLE
EVLNLAQSKNFHLRPRDLISNINVIVLELKGSETTFMCEYADETATIVEFLNRWITFSQSIISTLT SEQ ID NO: 4 (IL-2 (A3) Mutation (R37Q) amino acid sequence)
PTSSSTKKTQLQLEHLLLDLQMILNGINNYKNPKLTQMLTFKFYMPKKATELKHLQCLEEELKPL
EEVLNLAQSKNFHLRPRDLISNINVIVLELKGSETTFMCEYADETATIVEFLNRWITFSQSIISTLT SEQ ID NO: 5 (IL-2 (A4) Mutation (F41Q) amino acid sequence)
PTSSSTKKTQLQLEHLLLDLQMILNGINNYKNPKLTRMLTQKFYMPKKATELKHLQCLEEELKPL
EEVLNLAQSKNFHLRPRDLISNINVIVLELKGSETTFMCEYADETATIVEFLNRWITFSQSIISTLT SEQ ID NO: 6 (IL-2 (A5) Mutation (K42Q) amino acid sequence)
PTSSSTKKTQLQLEHLLLDLQMILNGINNYKNPKLTRMLTFQFYMPKKATELKHLQCLEEELKPL
EEVLNLAQSKNFHLRPRDLISNINVIVLELKGSETTFMCEYADETATIVEFLNRWITFSQSIISTLT SEQ ID NO: 7 (IL-2 (A6) Mutation (Y44Q) amino acid sequence)
PTSSSTKKTQLQLEHLLLDLQMILNGINNYKNPKLTRMLTFKFQMPKKATELKHLQCLEEELKPL
EEVLNLAQSKNFHLRPRDLISNINVIVLELKGSETTFMCEYADETATIVEFLNRWITFSQSIISTLT SEQ ID NO: 8 (IL-2 (A8) Mutations (R37Q, Y44Q) amino acid sequence)
PTSSSTKKTQLQLEHLLLDLQMILNGINNYKNPKLTQMLTFKFQMPKKATELKHLQCLEEELKPL
EEVLNLAQSKNFHLRPRDLISNINVIVLELKGSETTFMCEYADETATIVEFLNRWITFSQSIISTLT SEQ ID NO: 9 (exogenous patch amino acid sequence)
LEEQAA SEQ ID NO: 10 (exogenous patch amino acid sequence)
IFKQTY SEQ ID NO: 11 (exogenous patch amino acid sequence)
PKEQKY SEQ ID NO: 12 (exogenous patch amino acid sequence)
VIQGV SEQ ID NO: 13 (exogenous patch amino acid sequence)
REEQFN SEQ ID NO: 14 (exogenous patch amino acid sequence)
GLLQGA SEQ ID NO: 15 (IL-2 (A9) Mutation (LEEQAA) amino acid sequence)
PTSSSTKKTQLQLEHLLLDLQMILNGINNYKNPKLTRMLLEEQAAPKKATELKHLQCLEEELKPL
EEVLNLAQSKNFHLRPRDLISNINVIVLELKGSETTFMCEYADETATIVEFLNRWITFSQSIISTLT SEQ ID NO: 16 (IL-2 (A10) Mutation (PKEQKY) amino acid sequence)
PTSSSTKKTQLQLEHLLLDLQMILNGINNYKNPKLTRMLTFKFYMPKEQKYLKHLQCLEEELKPL
EEVLNLAQSKNFHLRPRDLISNINVIVLELKGSETTFMCEYADETATIVEFLNRWITFSQSIISTLT SEQ ID NO: 17 (IL-2 (A11) Mutation (VIQGV) amino acid sequence)
PTSSSTKKTQLQLEHLLLDLQMILNGINNYKNPKLTRMLTVIQGVPKKATELKHLQCLEEELKPLE
EVLNLAQSKNFHLRPRDLISNINVIVLELKGSETTFMCEYADETATIVEFLNRWITFSQSIISTLT -continued

SEQUENCE LISTING

SEQ ID NO: 18 (IL-2 (A12) Mutation (REEQFN) amino acid sequence)
PTSSSTKKTQLQLEHLLLDLQMILNGINNYKNPKLTRMLREEQFNPKKATELKHLQCLEEELKPLE
EVLNLAQSKNFHLRPRDLISNINVIVLELKGSETTFMCEYADETATIVEFLNRWITFSQSIISTLT SEQ ID NO: 19 (IL-2 (A13) Mutation (GLLQGA) amino acid sequence)
PTSSSTKKTQLQLEHLLLDLQMILNGINNYKNPKLTRMLGLLQGAPKKATELKHLQCLEEELKPL
EEVLNLAQSKNFHLRPRDLISNINVIVLELKGSETTFMCEYADETATIVEFLNRWITFSQSIISTLT SEQ ID NO: 20 (*Strep Ladakanum* TGase (TG_SL) amino acid sequence)
DSDERVTPPAEPLDRMPDPYRPSYGRAETIVNNYIRKWQQVYSHRDGRKQQMTEEQREWLSYG
CVGVTWVNSGQYPTNRLAFAFFDEDKYKNELKNGRPRSGETRAEFEGRVAKDSFDEAKGFQRA
RDVASVMNKALENAHDEGAYLDNLKKELANGNDALRNEDARSPFYSALRNTPSFKDRNGGNH
DPSKMKAVIYSKHFWSGQDRSGSSDKRKYGDPEAFRPDRGTGLVDMSRDRNIPRSPTSPGESFVN
FDYGWFGAQTEADADKTVWTHGNHYHAPNGSLGAMHVYESKFRNWSDGYSDFDRGAYVVTF
VPKSWNTAPDKVTQGWP SEQ ID NO: 21 (recombinant TGase based on *Strep Ladakanum* (TG_SL) amino acid sequence)
PDSDERVTPPAEPLDRMPDPYRPSYGRAETIVNNYIRKWQQVYSHRDGRKQQMTEEQREWLSY
GCVGVTWVNSGQYPTNRLAFAFFDEDKYKNELKNGRPRSGETRAEFEGRVAKDSFDEAKGFQR
ARDVASVMNKALENAHDEGAYLDNLKKELANGNDALRNEDARSPFYSALRNTPSFKDRNGGN
HDPSKMKAVIYSKHFWSGQDRSGSSDKRKYGDPEAFRPDRGTGLVDMSRDRNIPRSPTSPGESFV
NFDYGWFGAQTEADADKTVWTHGNHYHAPNGSLGAMHVYESKFRNWSDGYSDFDRGAYVVT
FVPKSWNTAPDKVTQGWPLEHHHHHHHH SEQ ID NO: 22 (*Strep Mobaraensis* TGase (TG_SM) amino acid sequence)
DSDDRVTPPAEPLDRMPDPYRPSYGRAETVVNNYIRKWQQVYSHRDGRKQQMTEEQREWLSYG
CVGVTWVNSGQYPTNRLAFASFDEDRFKNELKNGRPRSGETRAEFEGRVAKESFDEEKGFQRAR
EVASVMNRALENAHDESAYLDNLKKELANGNDALRNEDARSPFYSALRNTPSFKERNGGNHDP
SRMKAVIYSKHFWSGQDRSSSADKRKYGDPDAFRPAPGTGLVDMSRDRNIPRSPTSPGEGFVNFD
YGWFGAQTEADADKTVWTHGNHYHAPNGSLGAMHVYESKFRNWSEGYSDFDRGAYVITFIPK
SWNTAPDKVKQGWP SEQ ID NO: 23 (human precursor IL-2 protein amino acid sequence)
MYRMQLLSCIALSLALVTNSAPTSSSTKKTQLQLEHLLLDLQMILNGINNYKNPKLTRMLTFKFY
MPKKATELKHLQCLEEELKPLEEVLNLAQSKNFHLRPRDLISNINVIVLELKGSETTFMCEYADET
ATIVEFLNRWITFCQSIISTLT SEQ ID NO: 24 (human mature IL-2 protein amino acid sequence)
APTSSSTKKTQLQLEHLLLDLQMILNGINNYKNPKLTRMLTFKFYMPKKATELKHLQCLEEELKP
LEEVLNLAQSKNFHLRPRDLISNINVIVLELKGSETTFMCEYADETATIVEFLNRWITFCQSIISTLT SEQ ID NO: 25 (X can be any amino acid residue)
XXXXQX SEQ ID NO: 26 (X can be any amino acid residue)
QXXXXX

SEQ ID NO: 27
NYKNPK

SEQ ID NO: 28 (X can be any amino acid residue)
XXX

SEQ ID NO: 29 (X can be any amino acid residue)
QXX

SEQ ID NO: 30 (X can be any amino acid residue)
QXXXQX

SEQ ID NO: 31
PTSSSTK

SEQ ID NO: 32
TQLQLEHLLLDLQMILNGINNYKNPK

SEQ ID NO: 33
LTR

SEQ ID NO: 34
MLTFK

SEQ ID NO: 35
QYMPK

SEQ ID NO: 36
KATELK

-continued

SEQUENCE LISTING

SEQ ID NO: 37
HLQCLEEELKPLEEVLNLAQSK

SEQ ID NO: 38
NFHLRPR

SEQ ID NO: 39
DLISNINVIVLELK

SEQ ID NO: 40
GSETTFMCEYADETATIVEFLNR

SEQ ID NO: 41
WITFSQSIISTLT

SEQ ID NO: 42
PTSSSTKKTQLQLE

SEQ ID NO: 43
HLLLDLQMILNGINNYKNPKLTRMLTFKQYMPKKATE

SEQ ID NO: 44
LKHLQCLEEE

SEQ ID NO: 45
LKPLEE

SEQ ID NO: 46
VLNLAQSKNFHLRPRDLISNINVIVLE

SEQ ID NO: 47
LKGSE

SEQ ID NO: 48
TTFMCE

SEQ ID NO: 49
YADE

SEQ ID NO: 50
TATIVE

SEQ ID NO: 51
FLNRWITFSQSIISTLT

The invention claimed is:

1. A modified Interleukin-2 (IL-2) protein comprising an engineered glutamine (Q) residue, wherein the engineered Q residue is part of an exogenous patch sequence which is IFKQTY (SEQ ID NO: 10), and the modified IL-2 protein comprises an amino acid sequence of SEQ ID NO: 3.

2. The modified IL-2 protein of claim 1, wherein the $K_D$ of the binding between the modified IL-2 protein and an IL-2Rα subunit is 2 to 800 times of the $K_D$ of the binding between a parent IL-2 protein and an IL-2Rα subunit.

3. The modified IL-2 protein of claim 1, wherein the $K_D$ of the binding between the modified IL-2 protein and an IL-2Rβ subunit is 1 to 30 times of the $K_D$ of the binding between a parent IL-2 protein and an IL-2Rβ subunit.

4. A modified IL-2 protein-polyethylene glycol (PEG) conjugate comprising a modified IL-2 protein of claim 1 and a PEG moiety, wherein the PEG moiety is conjugated to the modified IL-2 protein via the engineered Q residue.

5. The modified IL-2 protein-PEG conjugate of claim 4, wherein the PEG moiety is linear or branched, wherein the PEG moiety is methoxy-PEG-amine.

6. The modified IL-2 protein-PEG conjugate of claim 4, wherein the PEG moiety has a molecular weight of between 10 kDa and 40 kDa.

7. The modified IL-2 protein-PEG conjugate of claim 4, wherein the conjugation of the PEG moiety is mediated via a TGase.

8. The modified IL-2 protein-PEG conjugate of claim 7, wherein the TGase is a microbial TGase (mTGase).

9. The modified IL-2 protein-PEG conjugate of claim 7, wherein the TGase is a wild-type TGase, and the wild-type TGase has an amino acid sequence of SEQ ID NO: 20.

10. The modified IL-2 protein-PEG conjugate of claim 4, wherein the $K_D$ of the binding between the modified IL-2 protein-PEG conjugate and an IL-2Rα subunit is 10 to 2000 times of the $K_D$ of the binding between a parent IL-2 protein and an IL-2Rα subunit, or $K_D$ of the binding between the modified IL-2 protein-PEG conjugate and an IL-2Rβ subunit is 1 to 30 times of the $K_D$ of the binding between a parent IL-2 protein and an IL-2Rβ subunit.

11. A method for activating an immune cell using the modified IL-2 protein-PEG conjugate of claim 4, wherein the immune cell is selected from the group consisting of a killer T cell ($T_c$, cytotoxic T lymphocyte, or CTL), a helper T cell ($T_h$), a regulatory T cells (Treg), a γδ T cell, a natural killer T (NKT) cell, and a natural killer (NK) cell.

12. The method of claim 11, wherein the modified IL-2 protein-PEG conjugate has 2 to 5000 fold reduced ability to activate a Treg cell compared to a parent IL-2 protein, or the modified IL-2 protein-PEG conjugate has 1 to 20 fold higher ability to increase the ratio of CTL to Treg or the ratio of NK cell to Treg compared to a parent IL-2 protein.

13. A pharmaceutical composition comprising the modified IL-2 protein of claim 1, or a modified IL-2 protein-PEG conjugate thereof, and an optional pharmaceutically acceptable carrier.

14. A method of treating a disease, comprising administering to a subject in need thereof an effective amount of a pharmaceutical composition, and the pharmaceutical composition comprising the modified IL-2 protein of claim 1 and an optional pharmaceutically acceptable carrier, wherein the disease is a cancer.

15. The method of claim 14, wherein the cancer is renal cell carcinoma, metastatic melanoma, acute myeloid leukemia (AML), non-Hodgkin's lymphoma (NHL), cutaneous T-cell lymphoma (CTCL), breast cancer, or bladder cancer.

* * * * *